United States Patent
Shelton, IV et al.

(10) Patent No.: US 9,730,692 B2
(45) Date of Patent: Aug. 15, 2017

(54) SURGICAL STAPLING DEVICE WITH A CURVED STAPLE CARTRIDGE

(71) Applicant: Ethicon Endo-Surgery, Inc., Cincinnati, OH (US)

(72) Inventors: Frederick E. Shelton, IV, Hillsboro, OH (US); Jerome R. Morgan, Cincinnati, OH (US)

(73) Assignee: Ethicon LLC, Guaynabo, PR (US)

( * ) Notice: Subject to any disclaimer, the term of this patent is extended or adjusted under 35 U.S.C. 154(b) by 1016 days.

(21) Appl. No.: 13/795,963

(22) Filed: Mar. 12, 2013

(65) Prior Publication Data

US 2013/0186934 A1 Jul. 25, 2013

Related U.S. Application Data

(63) Continuation of application No. 11/652,169, filed on Jan. 11, 2007, now abandoned.

(51) Int. Cl.
| | |
|---|---|
| *A61B 17/068* | (2006.01) |
| *A61B 17/072* | (2006.01) |
| *A61B 17/34* | (2006.01) |

(52) U.S. Cl.
CPC ...... *A61B 17/068* (2013.01); *A61B 17/07207* (2013.01); *A61B 17/07292* (2013.01); *A61B 2017/0725* (2013.01); *A61B 2017/07214* (2013.01); *A61B 2017/07221* (2013.01); *A61B 2017/07228* (2013.01); *A61B 2017/07278* (2013.01); *A61B 2017/3456* (2013.01)

(58) Field of Classification Search
CPC .... A61B 17/07207; A61B 2017/07278; A61B 2017/2933; A61B 17/068

USPC .......................................... 227/175.1, 176.1
See application file for complete search history.

(56) References Cited

U.S. PATENT DOCUMENTS

| 66,052 A | 6/1867 | Smith |
|---|---|---|
| 662,587 A | 11/1900 | Blake |

(Continued)

FOREIGN PATENT DOCUMENTS

| AU | 2008207624 A1 | 3/2009 |
|---|---|---|
| AU | 2010214687 A1 | 9/2010 |

(Continued)

OTHER PUBLICATIONS

Disclosed Anonymously, "Motor-Driven Surgical Stapler Improvements," Research Disclosure Database No. 526041, Published: Feb. 2008.

(Continued)

*Primary Examiner* — Michelle Lopez

(57) ABSTRACT

In various embodiments, an end effector for use with a surgical instrument is disclosed. The end effector comprises a staple cartridge comprising a plurality of staple cavities arranged in staple cavity rows, a plurality of staples ejectably stored in the staple cavities, and a slot comprising a longitudinal curvature. The end effector further comprises a staple-ejecting sled configured to translate along the slot during a firing stroke, wherein the staple-ejecting sled comprises a ramp and an irreversibly curved guide, wherein the irreversibly curved guide is connected to the ramp within the staple cartridge and wherein the irreversibly curved guide comprises a longitudinal curvature that matches the longitudinal curvature of the slot.

21 Claims, 36 Drawing Sheets

(56) References Cited

U.S. PATENT DOCUMENTS

| | | |
|---|---|---|
| 670,748 A | 3/1901 | Weddeler |
| 951,393 A | 3/1910 | Hahn |
| 1,306,107 A | 6/1919 | Elliott |
| 1,314,601 A | 9/1919 | McCaskey |
| 1,677,337 A | 7/1928 | Grove |
| 1,794,907 A | 3/1931 | Kelly |
| 2,037,727 A | 4/1936 | La Chapelle |
| 2,132,295 A | 10/1938 | Hawkins |
| 2,161,632 A | 6/1939 | Nattenheimer |
| 2,211,117 A | 8/1940 | Hess |
| 2,214,870 A | 9/1940 | West |
| 2,318,379 A | 5/1943 | Davis et al. |
| 2,441,096 A | 5/1948 | Happe |
| 2,526,902 A | 10/1950 | Rublee |
| 2,578,686 A | 12/1951 | Fish |
| 2,674,149 A | 4/1954 | Benson |
| 2,711,461 A | 6/1955 | Happe |
| 2,804,848 A | 9/1957 | O'Farrell et al. |
| 2,808,482 A | 10/1957 | Zanichkowsky et al. |
| 2,853,074 A | 9/1958 | Olson |
| 2,959,974 A | 11/1960 | Emrick |
| 3,032,769 A | 5/1962 | Palmer |
| 3,075,062 A | 1/1963 | Iaccarino |
| 3,078,465 A | 2/1963 | Bobrov |
| 3,079,606 A | 3/1963 | Bobrov et al. |
| 3,166,072 A | 1/1965 | Sullivan, Jr. |
| 3,196,869 A | 7/1965 | Scholl |
| 3,204,731 A | 9/1965 | Bent et al. |
| 3,266,494 A | 8/1966 | Brownrigg et al. |
| 3,269,630 A | 8/1966 | Fleischer |
| 3,275,211 A | 9/1966 | Hirsch et al. |
| 3,317,103 A | 5/1967 | Cullen et al. |
| 3,317,105 A | 5/1967 | Astafjev et al. |
| 3,357,296 A | 12/1967 | Lefever |
| 3,490,675 A | 1/1970 | Green et al. |
| 3,494,533 A | 2/1970 | Green et al. |
| 3,499,591 A | 3/1970 | Green |
| 3,503,396 A | 3/1970 | Pierie et al. |
| 3,551,987 A | 1/1971 | Wilkinson |
| 3,568,675 A | 3/1971 | Harvey |
| 3,572,159 A | 3/1971 | Tschanz |
| 3,598,943 A | 8/1971 | Barrett |
| 3,608,549 A | 9/1971 | Merrill |
| 3,640,317 A | 2/1972 | Panfili |
| 3,643,851 A | 2/1972 | Green et al. |
| 3,661,666 A | 5/1972 | Foster et al. |
| 3,662,939 A | 5/1972 | Bryan |
| 3,695,646 A | 10/1972 | Mommsen |
| 3,709,221 A | 1/1973 | Riely |
| 3,717,294 A | 2/1973 | Green |
| 3,734,207 A | 5/1973 | Fishbein |
| 3,740,994 A | 6/1973 | DeCarlo, Jr. |
| 3,744,495 A | 7/1973 | Johnson |
| 3,746,002 A | 7/1973 | Haller |
| 3,751,902 A | 8/1973 | Kingsbury et al. |
| 3,819,100 A | 6/1974 | Noiles et al. |
| 3,821,919 A | 7/1974 | Knohl |
| 3,841,474 A | 10/1974 | Maier |
| 3,851,196 A | 11/1974 | Hinds |
| 3,885,491 A | 5/1975 | Curtis |
| 3,892,228 A | 7/1975 | Mitsui |
| 3,894,174 A | 7/1975 | Cartun |
| 3,940,844 A | 3/1976 | Colby et al. |
| 3,950,686 A | 4/1976 | Randall |
| 3,955,581 A | 5/1976 | Spasiano et al. |
| RE28,932 E | 8/1976 | Noiles et al. |
| 3,981,051 A | 9/1976 | Brumlik |
| 4,054,108 A | 10/1977 | Gill |
| 4,060,089 A | 11/1977 | Noiles |
| 4,106,446 A | 8/1978 | Yamada et al. |
| 4,111,206 A | 9/1978 | Vishnevsky et al. |
| 4,129,059 A | 12/1978 | Van Eck |
| 4,169,990 A | 10/1979 | Lerdman |
| 4,180,285 A | 12/1979 | Reneau |
| 4,198,734 A | 4/1980 | Brumlik |
| 4,198,982 A | 4/1980 | Fortner et al. |
| 4,207,898 A | 6/1980 | Becht |
| 4,213,562 A | 7/1980 | Garrett et al. |
| 4,226,242 A | 10/1980 | Jarvik |
| 4,244,372 A | 1/1981 | Kapitanov et al. |
| 4,250,436 A | 2/1981 | Weissman |
| 4,261,244 A | 4/1981 | Becht et al. |
| 4,272,002 A | 6/1981 | Moshofsky |
| 4,272,662 A | 6/1981 | Simpson |
| 4,274,304 A | 6/1981 | Curtiss |
| 4,275,813 A | 6/1981 | Noiles |
| 4,289,133 A | 9/1981 | Rothfuss |
| 4,296,654 A | 10/1981 | Mercer |
| 4,304,236 A | 12/1981 | Conta et al. |
| 4,305,539 A | 12/1981 | Korolkov et al. |
| 4,312,685 A | 1/1982 | Riedl |
| 4,317,451 A | 3/1982 | Cerwin et al. |
| 4,321,002 A | 3/1982 | Froehlich |
| 4,328,839 A | 5/1982 | Lyons et al. |
| 4,331,277 A | 5/1982 | Green |
| 4,340,331 A | 7/1982 | Savino |
| 4,347,450 A | 8/1982 | Colligan |
| 4,349,028 A | 9/1982 | Green |
| 4,353,371 A | 10/1982 | Cosman |
| 4,373,147 A | 2/1983 | Carlson, Jr. |
| 4,379,457 A | 4/1983 | Gravener et al. |
| 4,380,312 A | 4/1983 | Landrus |
| 4,382,326 A | 5/1983 | Rabuse |
| 4,383,634 A | 5/1983 | Green |
| 4,393,728 A | 7/1983 | Larson et al. |
| 4,396,139 A | 8/1983 | Hall et al. |
| 4,397,311 A | 8/1983 | Kanshin et al. |
| 4,402,445 A | 9/1983 | Green |
| 4,408,692 A | 10/1983 | Sigel et al. |
| 4,409,057 A | 10/1983 | Molenda et al. |
| 4,415,112 A | 11/1983 | Green |
| 4,416,276 A | 11/1983 | Newton et al. |
| 4,428,376 A | 1/1984 | Mericle |
| 4,429,695 A | 2/1984 | Green |
| 4,434,796 A | 3/1984 | Karapetian et al. |
| 4,438,659 A | 3/1984 | Desplats |
| 4,442,964 A | 4/1984 | Becht |
| 4,448,194 A | 5/1984 | DiGiovanni et al. |
| 4,451,743 A | 5/1984 | Suzuki et al. |
| 4,454,887 A | 6/1984 | Krüger |
| 4,467,805 A | 8/1984 | Fukuda |
| 4,473,077 A | 9/1984 | Noiles et al. |
| 4,475,679 A | 10/1984 | Fleury, Jr. |
| 4,485,816 A | 12/1984 | Krumme |
| 4,485,817 A | 12/1984 | Swiggett |
| 4,486,928 A | 12/1984 | Tucker et al. |
| 4,488,523 A | 12/1984 | Shichman |
| 4,489,875 A | 12/1984 | Crawford et al. |
| 4,499,895 A | 2/1985 | Takayama |
| 4,500,024 A | 2/1985 | DiGiovanni et al. |
| 4,505,272 A | 3/1985 | Utyamyshev et al. |
| 4,505,273 A | 3/1985 | Braun et al. |
| 4,505,414 A | 3/1985 | Filipi |
| 4,506,671 A | 3/1985 | Green |
| 4,512,038 A | 4/1985 | Alexander et al. |
| 4,520,817 A | 6/1985 | Green |
| 4,522,327 A | 6/1985 | Korthoff et al. |
| 4,526,174 A | 7/1985 | Froehlich |
| 4,527,724 A | 7/1985 | Chow et al. |
| 4,530,453 A | 7/1985 | Green |
| 4,531,522 A | 7/1985 | Bedi et al. |
| 4,532,927 A | 8/1985 | Miksza, Jr. |
| 4,548,202 A | 10/1985 | Duncan |
| 4,565,109 A | 1/1986 | Tsay |
| 4,565,189 A | 1/1986 | Mabuchi |
| 4,566,620 A | 1/1986 | Green et al. |
| 4,569,469 A | 2/1986 | Mongeon et al. |
| 4,571,213 A | 2/1986 | Ishimoto |
| 4,573,468 A | 3/1986 | Conta et al. |
| 4,573,469 A | 3/1986 | Golden et al. |
| 4,573,622 A | 3/1986 | Green et al. |
| 4,576,167 A | 3/1986 | Noiles et al. |
| 4,580,712 A | 4/1986 | Green |
| 4,585,153 A | 4/1986 | Failla et al. |

(56) References Cited

U.S. PATENT DOCUMENTS

| | | |
|---|---|---|
| 4,589,416 A | 5/1986 | Green |
| 4,591,085 A | 5/1986 | Di Giovanni |
| 4,597,753 A | 7/1986 | Turley |
| 4,600,037 A | 7/1986 | Hatten |
| 4,604,786 A | 8/1986 | Howie, Jr. |
| 4,605,001 A | 8/1986 | Rothfuss et al. |
| 4,605,004 A | 8/1986 | Di Giovanni et al. |
| 4,606,343 A | 8/1986 | Conta et al. |
| 4,607,638 A | 8/1986 | Crainich |
| 4,608,981 A | 9/1986 | Rothfuss et al. |
| 4,610,250 A | 9/1986 | Green |
| 4,610,383 A | 9/1986 | Rothfuss et al. |
| 4,619,262 A | 10/1986 | Taylor |
| 4,619,391 A | 10/1986 | Sharkany et al. |
| 4,628,459 A | 12/1986 | Shinohara et al. |
| 4,629,107 A | 12/1986 | Fedotov et al. |
| 4,632,290 A | 12/1986 | Green et al. |
| 4,633,874 A | 1/1987 | Chow et al. |
| 4,634,419 A | 1/1987 | Kreizman et al. |
| 4,641,076 A | 2/1987 | Linden |
| 4,643,731 A | 2/1987 | Eckenhoff |
| 4,646,722 A | 3/1987 | Silverstein et al. |
| 4,655,222 A | 4/1987 | Florez et al. |
| 4,662,555 A | 5/1987 | Thornton |
| 4,663,874 A | 5/1987 | Sano et al. |
| 4,664,305 A | 5/1987 | Blake, III et al. |
| 4,665,916 A | 5/1987 | Green |
| 4,667,674 A | 5/1987 | Korthoff et al. |
| 4,669,647 A | 6/1987 | Storace |
| 4,671,445 A | 6/1987 | Barker et al. |
| 4,676,245 A | 6/1987 | Fukuda |
| 4,684,051 A | 8/1987 | Akopov et al. |
| 4,691,703 A | 9/1987 | Auth et al. |
| 4,693,248 A | 9/1987 | Failla |
| 4,700,703 A | 10/1987 | Resnick et al. |
| 4,708,141 A | 11/1987 | Inoue et al. |
| 4,709,120 A | 11/1987 | Pearson |
| 4,715,520 A | 12/1987 | Roehr, Jr. et al. |
| 4,719,917 A | 1/1988 | Barrows et al. |
| 4,727,308 A | 2/1988 | Huljak et al. |
| 4,728,020 A | 3/1988 | Green et al. |
| 4,728,876 A | 3/1988 | Mongeon et al. |
| 4,729,260 A | 3/1988 | Dudden |
| 4,730,726 A | 3/1988 | Holzwarth |
| 4,741,336 A | 5/1988 | Failla et al. |
| 4,743,214 A | 5/1988 | Tai-Cheng |
| 4,747,820 A | 5/1988 | Hornlein et al. |
| 4,750,902 A | 6/1988 | Wuchinich et al. |
| 4,752,024 A | 6/1988 | Green et al. |
| 4,754,909 A | 7/1988 | Barker et al. |
| 4,767,044 A | 8/1988 | Green |
| 4,773,420 A | 9/1988 | Green |
| 4,777,780 A | 10/1988 | Holzwarth |
| 4,787,387 A | 11/1988 | Burbank, III et al. |
| 4,790,225 A | 12/1988 | Moody et al. |
| 4,805,617 A | 2/1989 | Bedi et al. |
| 4,805,823 A | 2/1989 | Rothfuss |
| 4,809,695 A | 3/1989 | Gwathmey et al. |
| 4,815,460 A | 3/1989 | Porat et al. |
| 4,817,847 A | 4/1989 | Redtenbacher et al. |
| 4,819,853 A | 4/1989 | Green |
| 4,821,939 A | 4/1989 | Green |
| 4,827,911 A | 5/1989 | Broadwin et al. |
| 4,830,855 A | 5/1989 | Stewart |
| 4,834,720 A | 5/1989 | Blinkhorn |
| 4,844,068 A | 7/1989 | Arata et al. |
| 4,848,637 A | 7/1989 | Pruitt |
| 4,865,030 A | 9/1989 | Polyak |
| 4,869,414 A | 9/1989 | Green et al. |
| 4,869,415 A | 9/1989 | Fox |
| 4,873,977 A | 10/1989 | Avant et al. |
| 4,880,015 A | 11/1989 | Nierman |
| 4,890,613 A | 1/1990 | Golden et al. |
| 4,892,244 A | 1/1990 | Fox et al. |
| 4,893,622 A | 1/1990 | Green et al. |
| 4,896,678 A | 1/1990 | Ogawa |
| 4,900,303 A | 2/1990 | Lemelson |
| 4,903,697 A | 2/1990 | Resnick et al. |
| 4,915,100 A | 4/1990 | Green |
| 4,930,503 A | 6/1990 | Pruitt |
| 4,930,674 A | 6/1990 | Barak |
| 4,931,047 A | 6/1990 | Broadwin et al. |
| 4,932,960 A | 6/1990 | Green et al. |
| 4,938,408 A | 7/1990 | Bedi et al. |
| 4,941,623 A | 7/1990 | Pruitt |
| 4,944,443 A | 7/1990 | Oddsen et al. |
| 4,951,860 A | 8/1990 | Peters et al. |
| 4,955,959 A | 9/1990 | Tompkins et al. |
| 4,965,709 A | 10/1990 | Ngo |
| 4,973,274 A | 11/1990 | Hirukawa |
| 4,978,049 A | 12/1990 | Green |
| 4,978,333 A | 12/1990 | Broadwin et al. |
| 4,986,808 A | 1/1991 | Broadwin et al. |
| 4,988,334 A | 1/1991 | Hornlein et al. |
| 5,002,543 A | 3/1991 | Bradshaw et al. |
| 5,002,553 A | 3/1991 | Shiber |
| 5,005,754 A | 4/1991 | Van Overloop |
| 5,009,661 A | 4/1991 | Michelson |
| 5,014,899 A | 5/1991 | Presty et al. |
| 5,015,227 A | 5/1991 | Broadwin et al. |
| 5,018,515 A | 5/1991 | Gilman |
| 5,018,657 A | 5/1991 | Pedlick et al. |
| 5,024,671 A | 6/1991 | Tu et al. |
| 5,027,834 A | 7/1991 | Pruitt |
| 5,031,814 A | 7/1991 | Tompkins et al. |
| 5,035,040 A | 7/1991 | Kerrigan et al. |
| 5,038,109 A | 8/1991 | Goble et al. |
| 5,040,715 A | 8/1991 | Green et al. |
| 5,042,707 A | 8/1991 | Taheri |
| 5,061,269 A | 10/1991 | Muller |
| 5,062,563 A | 11/1991 | Green et al. |
| 5,065,929 A | 11/1991 | Schulze et al. |
| 5,071,052 A | 12/1991 | Rodak et al. |
| 5,071,430 A | 12/1991 | de Salis et al. |
| 5,074,454 A | 12/1991 | Peters |
| 5,079,006 A | 1/1992 | Urquhart |
| 5,080,556 A | 1/1992 | Carreno |
| 5,083,695 A | 1/1992 | Foslien et al. |
| 5,084,057 A | 1/1992 | Green et al. |
| 5,088,979 A | 2/1992 | Filipi et al. |
| 5,088,997 A | 2/1992 | Delahuerga et al. |
| 5,094,247 A | 3/1992 | Hernandez et al. |
| 5,100,420 A | 3/1992 | Green et al. |
| 5,104,025 A | 4/1992 | Main et al. |
| 5,104,397 A | 4/1992 | Vasconcelos et al. |
| 5,106,008 A | 4/1992 | Tompkins et al. |
| 5,108,368 A | 4/1992 | Hammerslag et al. |
| 5,111,987 A | 5/1992 | Moeinzadeh et al. |
| 5,116,349 A | 5/1992 | Aranyi |
| 5,122,156 A | 6/1992 | Granger et al. |
| 5,129,570 A | 7/1992 | Schulze et al. |
| 5,137,198 A | 8/1992 | Nobis et al. |
| 5,139,513 A | 8/1992 | Segato |
| 5,141,144 A | 8/1992 | Foslien et al. |
| 5,142,932 A | 9/1992 | Moya et al. |
| 5,155,941 A | 10/1992 | Takahashi et al. |
| 5,156,315 A | 10/1992 | Green et al. |
| 5,156,609 A | 10/1992 | Nakao et al. |
| 5,156,614 A | 10/1992 | Green et al. |
| 5,158,567 A | 10/1992 | Green |
| D330,699 S | 11/1992 | Gill |
| 5,163,598 A | 11/1992 | Peters et al. |
| 5,171,247 A | 12/1992 | Hughett et al. |
| 5,171,249 A | 12/1992 | Stefanchik et al. |
| 5,171,253 A | 12/1992 | Klieman et al. |
| 5,188,111 A | 2/1993 | Yates et al. |
| 5,190,517 A | 3/1993 | Zieve et al. |
| 5,190,544 A | 3/1993 | Chapman et al. |
| 5,190,560 A | 3/1993 | Woods et al. |
| 5,192,288 A | 3/1993 | Thompson et al. |
| 5,195,968 A | 3/1993 | Lundquist et al. |
| 5,197,648 A | 3/1993 | Gingold |
| 5,197,649 A | 3/1993 | Bessler et al. |
| 5,197,966 A | 3/1993 | Sommerkamp |

(56) References Cited

U.S. PATENT DOCUMENTS

| | | |
|---|---|---|
| 5,200,280 A | 4/1993 | Karasa |
| 5,205,459 A | 4/1993 | Brinkerhoff et al. |
| 5,207,697 A | 5/1993 | Carusillo et al. |
| 5,209,747 A | 5/1993 | Knoepfler |
| 5,211,649 A | 5/1993 | Kohler et al. |
| 5,211,655 A | 5/1993 | Hasson |
| 5,217,457 A | 6/1993 | Delahuerga et al. |
| 5,217,478 A | 6/1993 | Rexroth |
| 5,219,111 A | 6/1993 | Bilotti et al. |
| 5,221,036 A | 6/1993 | Takase |
| 5,221,281 A | 6/1993 | Klicek |
| 5,222,963 A | 6/1993 | Brinkerhoff et al. |
| 5,222,975 A | 6/1993 | Crainich |
| 5,222,976 A | 6/1993 | Yoon |
| 5,223,675 A | 6/1993 | Taft |
| 5,234,447 A | 8/1993 | Kaster et al. |
| 5,236,440 A | 8/1993 | Hlavacek |
| 5,239,981 A | 8/1993 | Anapliotis |
| 5,240,163 A | 8/1993 | Stein et al. |
| 5,242,457 A | 9/1993 | Akopov et al. |
| 5,244,462 A | 9/1993 | Delahuerga et al. |
| 5,246,156 A | 9/1993 | Rothfuss et al. |
| 5,246,443 A | 9/1993 | Mai |
| 5,253,793 A | 10/1993 | Green et al. |
| 5,258,009 A | 11/1993 | Conners |
| 5,258,012 A | 11/1993 | Luscombe et al. |
| 5,259,366 A | 11/1993 | Reydel et al. |
| 5,260,637 A | 11/1993 | Pizzi |
| 5,263,629 A | 11/1993 | Trumbull et al. |
| 5,263,973 A | 11/1993 | Cook |
| 5,264,218 A | 11/1993 | Rogozinski |
| 5,268,622 A | 12/1993 | Philipp |
| 5,271,543 A | 12/1993 | Grant et al. |
| 5,271,544 A | 12/1993 | Fox et al. |
| RE34,519 E | 1/1994 | Fox et al. |
| 5,275,323 A | 1/1994 | Schulze et al. |
| 5,275,608 A | 1/1994 | Forman et al. |
| 5,279,416 A | 1/1994 | Malec et al. |
| 5,281,216 A | 1/1994 | Klicek |
| 5,282,806 A | 2/1994 | Haber et al. |
| 5,282,829 A | 2/1994 | Hermes |
| 5,284,128 A | 2/1994 | Hart |
| 5,285,945 A | 2/1994 | Brinkerhoff et al. |
| 5,289,963 A | 3/1994 | McGarry et al. |
| 5,290,271 A | 3/1994 | Jernberg |
| 5,292,053 A | 3/1994 | Bilotti et al. |
| 5,297,714 A | 3/1994 | Kramer |
| 5,304,204 A | 4/1994 | Bregen |
| 5,307,976 A | 5/1994 | Olson et al. |
| 5,309,927 A | 5/1994 | Welch |
| 5,312,023 A | 5/1994 | Green et al. |
| 5,312,024 A | 5/1994 | Grant et al. |
| 5,312,329 A | 5/1994 | Beaty et al. |
| 5,314,424 A | 5/1994 | Nicholas |
| 5,314,445 A | 5/1994 | Heidmueller née Degwitz et al. |
| 5,314,466 A | 5/1994 | Stern et al. |
| 5,318,221 A | 6/1994 | Green et al. |
| 5,330,487 A | 7/1994 | Thornton et al. |
| 5,330,502 A | 7/1994 | Hassler et al. |
| 5,332,142 A | 7/1994 | Robinson et al. |
| 5,333,422 A | 8/1994 | Warren et al. |
| 5,333,772 A | 8/1994 | Rothfuss et al. |
| 5,333,773 A | 8/1994 | Main et al. |
| 5,334,183 A | 8/1994 | Wuchinich |
| 5,336,232 A | 8/1994 | Green et al. |
| 5,339,799 A | 8/1994 | Kami et al. |
| 5,341,724 A | 8/1994 | Vatel |
| 5,341,810 A | 8/1994 | Dardel |
| 5,342,381 A | 8/1994 | Tidemand |
| 5,342,395 A | 8/1994 | Jarrett et al. |
| 5,342,396 A | 8/1994 | Cook |
| 5,344,060 A | 9/1994 | Gravener et al. |
| 5,344,454 A | 9/1994 | Clarke et al. |
| 5,346,504 A | 9/1994 | Ortiz et al. |
| 5,348,259 A | 9/1994 | Blanco et al. |
| 5,350,388 A | 9/1994 | Epstein |
| 5,350,391 A | 9/1994 | Iacovelli |
| 5,350,400 A | 9/1994 | Esposito et al. |
| 5,352,229 A | 10/1994 | Goble et al. |
| 5,352,235 A | 10/1994 | Koros et al. |
| 5,352,238 A | 10/1994 | Green et al. |
| 5,354,303 A | 10/1994 | Spaeth et al. |
| 5,356,006 A | 10/1994 | Alpern et al. |
| 5,358,506 A | 10/1994 | Green et al. |
| 5,358,510 A | 10/1994 | Luscombe et al. |
| 5,359,231 A | 10/1994 | Flowers et al. |
| D352,780 S | 11/1994 | Glaeser et al. |
| 5,360,305 A | 11/1994 | Kerrigan |
| 5,360,428 A | 11/1994 | Hutchinson, Jr. |
| 5,364,001 A | 11/1994 | Bryan |
| 5,364,003 A | 11/1994 | Williamson, IV |
| 5,366,133 A | 11/1994 | Geiste |
| 5,366,134 A | 11/1994 | Green et al. |
| 5,366,479 A | 11/1994 | McGarry et al. |
| 5,368,015 A | 11/1994 | Wilk |
| 5,368,592 A | 11/1994 | Stern et al. |
| 5,370,645 A | 12/1994 | Klicek et al. |
| 5,372,124 A | 12/1994 | Takayama et al. |
| 5,372,596 A | 12/1994 | Klicek et al. |
| 5,372,602 A | 12/1994 | Burke |
| 5,374,277 A | 12/1994 | Hassler |
| 5,376,095 A | 12/1994 | Ortiz |
| 5,379,933 A * | 1/1995 | Green ............... A61B 17/07207 227/176.1 |
| 5,381,649 A | 1/1995 | Webb |
| 5,381,782 A | 1/1995 | DeLaRama et al. |
| 5,382,247 A | 1/1995 | Cimino et al. |
| 5,383,880 A | 1/1995 | Hooven |
| 5,383,881 A | 1/1995 | Green et al. |
| 5,383,888 A | 1/1995 | Zvenyatsky et al. |
| 5,383,895 A | 1/1995 | Holmes et al. |
| 5,389,098 A | 2/1995 | Tsuruta et al. |
| 5,389,104 A | 2/1995 | Hahnen et al. |
| 5,391,180 A | 2/1995 | Tovey et al. |
| 5,392,979 A | 2/1995 | Green et al. |
| 5,395,030 A | 3/1995 | Kuramoto et al. |
| 5,395,033 A | 3/1995 | Byrne et al. |
| 5,395,034 A | 3/1995 | Allen et al. |
| 5,395,312 A | 3/1995 | Desai |
| 5,395,384 A | 3/1995 | Duthoit |
| 5,397,046 A | 3/1995 | Savage et al. |
| 5,397,324 A | 3/1995 | Carroll et al. |
| 5,403,312 A | 4/1995 | Yates et al. |
| 5,405,072 A | 4/1995 | Zlock et al. |
| 5,405,073 A | 4/1995 | Porter |
| 5,405,344 A | 4/1995 | Williamson et al. |
| 5,405,360 A | 4/1995 | Tovey |
| 5,407,293 A | 4/1995 | Crainich |
| 5,409,498 A | 4/1995 | Braddock et al. |
| 5,411,508 A | 5/1995 | Bessler et al. |
| 5,413,107 A | 5/1995 | Oakley et al. |
| 5,413,267 A | 5/1995 | Solyntjes et al. |
| 5,413,268 A | 5/1995 | Green et al. |
| 5,413,272 A | 5/1995 | Green et al. |
| 5,413,573 A | 5/1995 | Koivukangas |
| 5,415,334 A | 5/1995 | Williamson, IV et al. |
| 5,415,335 A | 5/1995 | Knodell, Jr. |
| 5,417,203 A | 5/1995 | Tovey et al. |
| 5,417,361 A | 5/1995 | Williamson, IV |
| 5,421,829 A | 6/1995 | Olichney et al. |
| 5,422,567 A | 6/1995 | Matsunaga |
| 5,423,471 A | 6/1995 | Mastri et al. |
| 5,423,809 A | 6/1995 | Klicek |
| 5,425,745 A | 6/1995 | Green et al. |
| 5,431,322 A | 7/1995 | Green et al. |
| 5,431,654 A | 7/1995 | Nic |
| 5,431,668 A | 7/1995 | Burbank, III et al. |
| 5,433,721 A | 7/1995 | Hooven et al. |
| 5,437,681 A | 8/1995 | Meade et al. |
| 5,438,302 A | 8/1995 | Goble |
| 5,439,155 A | 8/1995 | Viola |
| 5,439,156 A | 8/1995 | Grant et al. |
| 5,439,479 A | 8/1995 | Schichman et al. |
| 5,441,191 A | 8/1995 | Linden |

(56) References Cited

U.S. PATENT DOCUMENTS

| | | |
|---|---|---|
| 5,441,193 A | 8/1995 | Gravener |
| 5,441,483 A | 8/1995 | Avitall |
| 5,441,494 A | 8/1995 | Ortiz |
| 5,444,113 A | 8/1995 | Sinclair et al. |
| 5,445,155 A | 8/1995 | Sieben |
| 5,445,304 A | 8/1995 | Plyley et al. |
| 5,445,644 A | 8/1995 | Pietrafitta et al. |
| 5,447,265 A | 9/1995 | Vidal et al. |
| 5,447,417 A | 9/1995 | Kuhl et al. |
| 5,447,513 A | 9/1995 | Davison et al. |
| 5,449,355 A | 9/1995 | Rhum et al. |
| 5,449,365 A | 9/1995 | Green et al. |
| 5,449,370 A | 9/1995 | Vaitekunas |
| 5,452,836 A | 9/1995 | Huitema et al. |
| 5,452,837 A | 9/1995 | Williamson, IV et al. |
| 5,454,378 A | 10/1995 | Palmer et al. |
| 5,454,827 A | 10/1995 | Aust et al. |
| 5,456,401 A | 10/1995 | Green et al. |
| 5,458,579 A | 10/1995 | Chodorow et al. |
| 5,462,215 A | 10/1995 | Viola et al. |
| 5,464,013 A | 11/1995 | Lemelson |
| 5,464,144 A | 11/1995 | Guy et al. |
| 5,464,300 A | 11/1995 | Crainich |
| 5,465,894 A | 11/1995 | Clark et al. |
| 5,465,895 A | 11/1995 | Knodel et al. |
| 5,465,896 A | 11/1995 | Allen et al. |
| 5,466,020 A | 11/1995 | Page et al. |
| 5,467,911 A | 11/1995 | Tsuruta et al. |
| 5,468,253 A | 11/1995 | Bezwada et al. |
| 5,470,006 A | 11/1995 | Rodak |
| 5,470,007 A | 11/1995 | Plyley et al. |
| 5,470,009 A | 11/1995 | Rodak |
| 5,470,010 A | 11/1995 | Rothfuss et al. |
| 5,472,132 A | 12/1995 | Savage et al. |
| 5,472,442 A | 12/1995 | Klicek |
| 5,473,204 A | 12/1995 | Temple |
| 5,474,057 A | 12/1995 | Makower et al. |
| 5,474,223 A | 12/1995 | Viola et al. |
| 5,474,566 A | 12/1995 | Alesi et al. |
| 5,476,206 A | 12/1995 | Green et al. |
| 5,476,479 A | 12/1995 | Green et al. |
| 5,478,003 A | 12/1995 | Green et al. |
| 5,478,354 A | 12/1995 | Tovey et al. |
| 5,480,089 A | 1/1996 | Blewett |
| 5,480,409 A | 1/1996 | Riza |
| 5,482,197 A | 1/1996 | Green et al. |
| 5,484,095 A | 1/1996 | Green et al. |
| 5,484,398 A | 1/1996 | Stoddard |
| 5,484,451 A | 1/1996 | Akopov et al. |
| 5,485,947 A | 1/1996 | Olson et al. |
| 5,485,952 A | 1/1996 | Fontayne |
| 5,487,499 A | 1/1996 | Sorrentino et al. |
| 5,487,500 A | 1/1996 | Knodel et al. |
| 5,489,058 A | 2/1996 | Plyley et al. |
| 5,489,256 A | 2/1996 | Adair |
| 5,496,312 A | 3/1996 | Klicek |
| 5,496,317 A | 3/1996 | Goble et al. |
| 5,497,933 A | 3/1996 | DeFonzo et al. |
| 5,501,654 A | 3/1996 | Failla et al. |
| 5,503,320 A | 4/1996 | Webster et al. |
| 5,503,635 A | 4/1996 | Sauer et al. |
| 5,503,638 A | 4/1996 | Cooper et al. |
| 5,505,363 A | 4/1996 | Green et al. |
| 5,507,426 A | 4/1996 | Young et al. |
| 5,509,596 A | 4/1996 | Green et al. |
| 5,509,916 A | 4/1996 | Taylor |
| 5,511,564 A | 4/1996 | Wilk |
| 5,514,129 A | 5/1996 | Smith |
| 5,514,157 A | 5/1996 | Nicholas et al. |
| 5,518,163 A | 5/1996 | Hooven |
| 5,518,164 A | 5/1996 | Hooven |
| 5,520,678 A | 5/1996 | Heckele et al. |
| 5,520,700 A | 5/1996 | Beyar et al. |
| 5,522,817 A | 6/1996 | Sander et al. |
| 5,522,831 A | 6/1996 | Sleister et al. |
| 5,527,320 A | 6/1996 | Carruthers et al. |
| 5,529,235 A | 6/1996 | Boiarski et al. |
| D372,086 S | 7/1996 | Grasso et al. |
| 5,531,305 A | 7/1996 | Roberts et al. |
| 5,531,744 A | 7/1996 | Nardella et al. |
| 5,533,521 A | 7/1996 | Granger |
| 5,533,581 A | 7/1996 | Barth et al. |
| 5,533,661 A | 7/1996 | Main et al. |
| 5,535,934 A | 7/1996 | Boiarski et al. |
| 5,535,935 A | 7/1996 | Vidal et al. |
| 5,535,937 A | 7/1996 | Boiarski et al. |
| 5,540,375 A | 7/1996 | Bolanos et al. |
| 5,541,376 A | 7/1996 | Ladtkow et al. |
| 5,542,594 A | 8/1996 | McKean et al. |
| 5,542,949 A | 8/1996 | Yoon |
| 5,543,119 A | 8/1996 | Sutter et al. |
| 5,547,117 A | 8/1996 | Hamblin et al. |
| 5,549,583 A | 8/1996 | Sanford et al. |
| 5,549,621 A | 8/1996 | Bessler et al. |
| 5,549,627 A | 8/1996 | Kieturakis |
| 5,549,628 A | 8/1996 | Cooper et al. |
| 5,549,637 A | 8/1996 | Crainich |
| 5,551,622 A | 9/1996 | Yoon |
| 5,553,675 A | 9/1996 | Pitzen et al. |
| 5,553,765 A | 9/1996 | Knodel et al. |
| 5,554,148 A | 9/1996 | Aebischer et al. |
| 5,554,169 A | 9/1996 | Green et al. |
| 5,556,416 A | 9/1996 | Clark et al. |
| 5,558,665 A | 9/1996 | Kieturakis |
| 5,558,671 A | 9/1996 | Yates |
| 5,560,530 A | 10/1996 | Bolanos et al. |
| 5,560,532 A | 10/1996 | DeFonzo et al. |
| 5,562,239 A | 10/1996 | Boiarski et al. |
| 5,562,241 A | 10/1996 | Knodel et al. |
| 5,562,682 A | 10/1996 | Oberlin et al. |
| 5,562,690 A | 10/1996 | Green et al. |
| 5,562,701 A | 10/1996 | Huitema et al. |
| 5,562,702 A | 10/1996 | Huitema et al. |
| 5,564,615 A | 10/1996 | Bishop et al. |
| 5,569,161 A | 10/1996 | Ebling et al. |
| 5,569,270 A | 10/1996 | Weng |
| 5,569,284 A | 10/1996 | Young et al. |
| 5,571,090 A | 11/1996 | Sherts |
| 5,571,100 A | 11/1996 | Goble et al. |
| 5,571,116 A | 11/1996 | Bolanos et al. |
| 5,571,285 A | 11/1996 | Chow et al. |
| 5,573,543 A | 11/1996 | Akopov et al. |
| 5,574,431 A | 11/1996 | McKeown et al. |
| 5,575,054 A | 11/1996 | Klinzing et al. |
| 5,575,789 A | 11/1996 | Bell et al. |
| 5,575,799 A | 11/1996 | Bolanos et al. |
| 5,575,803 A | 11/1996 | Cooper et al. |
| 5,575,805 A | 11/1996 | Li |
| 5,577,654 A | 11/1996 | Bishop |
| 5,579,978 A | 12/1996 | Green et al. |
| 5,580,067 A | 12/1996 | Hamblin et al. |
| 5,582,611 A * | 12/1996 | Tsuruta ............ A61B 17/00234 606/142 |
| 5,582,617 A | 12/1996 | Klieman et al. |
| 5,584,425 A | 12/1996 | Savage et al. |
| 5,586,711 A | 12/1996 | Plyley et al. |
| 5,588,579 A | 12/1996 | Schnut et al. |
| 5,588,580 A | 12/1996 | Paul et al. |
| 5,588,581 A | 12/1996 | Conlon et al. |
| 5,591,170 A | 1/1997 | Spievack et al. |
| 5,591,187 A | 1/1997 | Dekel |
| 5,597,107 A | 1/1997 | Knodel et al. |
| 5,599,151 A | 2/1997 | Daum et al. |
| 5,599,279 A | 2/1997 | Slotman et al. |
| 5,599,344 A | 2/1997 | Paterson |
| 5,599,350 A | 2/1997 | Schulze et al. |
| 5,599,852 A | 2/1997 | Scopelianos et al. |
| 5,601,224 A | 2/1997 | Bishop et al. |
| 5,603,443 A | 2/1997 | Clark et al. |
| 5,605,272 A | 2/1997 | Witt et al. |
| 5,605,273 A | 2/1997 | Hamblin et al. |
| 5,607,094 A | 3/1997 | Clark et al. |
| 5,607,095 A | 3/1997 | Smith et al. |
| 5,607,433 A | 3/1997 | Polla et al. |

(56) References Cited

U.S. PATENT DOCUMENTS

| | | |
|---|---|---|
| 5,607,450 A | 3/1997 | Zvenyatsky et al. |
| 5,609,285 A | 3/1997 | Grant et al. |
| 5,609,601 A | 3/1997 | Kolesa et al. |
| 5,611,709 A | 3/1997 | McAnulty |
| 5,613,966 A | 3/1997 | Makower et al. |
| 5,615,820 A | 4/1997 | Viola |
| 5,618,294 A | 4/1997 | Aust et al. |
| 5,618,303 A | 4/1997 | Marlow et al. |
| 5,618,307 A | 4/1997 | Donlon et al. |
| 5,619,992 A | 4/1997 | Guthrie et al. |
| 5,620,289 A | 4/1997 | Curry |
| 5,620,452 A | 4/1997 | Yoon |
| 5,624,398 A | 4/1997 | Smith et al. |
| 5,624,452 A | 4/1997 | Yates |
| 5,626,587 A | 5/1997 | Bishop et al. |
| 5,626,595 A | 5/1997 | Sklar et al. |
| 5,628,446 A | 5/1997 | Geiste et al. |
| 5,628,743 A | 5/1997 | Cimino |
| 5,628,745 A | 5/1997 | Bek |
| 5,630,539 A | 5/1997 | Plyley et al. |
| 5,630,540 A | 5/1997 | Blewett |
| 5,630,541 A | 5/1997 | Williamson, IV et al. |
| 5,630,782 A | 5/1997 | Adair |
| 5,632,432 A | 5/1997 | Schulze et al. |
| 5,632,433 A | 5/1997 | Grant et al. |
| 5,634,584 A | 6/1997 | Okorocha et al. |
| 5,636,779 A | 6/1997 | Palmer |
| 5,636,780 A | 6/1997 | Green et al. |
| 5,639,008 A | 6/1997 | Gallagher et al. |
| 5,643,291 A | 7/1997 | Pier et al. |
| 5,645,209 A | 7/1997 | Green et al. |
| 5,647,526 A | 7/1997 | Green et al. |
| 5,647,869 A | 7/1997 | Goble et al. |
| 5,649,937 A | 7/1997 | Bito et al. |
| 5,649,956 A | 7/1997 | Jensen et al. |
| 5,651,491 A | 7/1997 | Heaton et al. |
| 5,653,373 A | 8/1997 | Green et al. |
| 5,653,374 A | 8/1997 | Young et al. |
| 5,653,677 A | 8/1997 | Okada et al. |
| 5,653,721 A | 8/1997 | Knodel et al. |
| 5,655,698 A | 8/1997 | Yoon |
| 5,657,429 A | 8/1997 | Wang et al. |
| 5,657,921 A | 8/1997 | Young et al. |
| 5,658,238 A | 8/1997 | Suzuki et al. |
| 5,658,281 A | 8/1997 | Heard |
| 5,658,300 A | 8/1997 | Bito et al. |
| 5,658,307 A | 8/1997 | Exconde |
| 5,662,258 A | 9/1997 | Knodel et al. |
| 5,662,260 A | 9/1997 | Yoon |
| 5,662,662 A | 9/1997 | Bishop et al. |
| 5,665,085 A | 9/1997 | Nardella |
| 5,667,517 A | 9/1997 | Hooven |
| 5,667,526 A | 9/1997 | Levin |
| 5,667,527 A | 9/1997 | Cook |
| 5,669,544 A | 9/1997 | Schulze et al. |
| 5,669,904 A | 9/1997 | Platt, Jr. et al. |
| 5,669,907 A | 9/1997 | Platt, Jr. et al. |
| 5,669,918 A | 9/1997 | Balazs et al. |
| 5,673,840 A | 10/1997 | Schulze et al. |
| 5,673,841 A | 10/1997 | Schulze et al. |
| 5,673,842 A | 10/1997 | Bittner et al. |
| 5,674,286 A | 10/1997 | D'Alessio et al. |
| 5,678,748 A | 10/1997 | Plyley et al. |
| 5,680,981 A | 10/1997 | Mililli et al. |
| 5,680,982 A | 10/1997 | Schulze et al. |
| 5,680,983 A | 10/1997 | Plyley et al. |
| 5,683,349 A | 11/1997 | Makower et al. |
| 5,685,474 A | 11/1997 | Seeber |
| 5,686,090 A | 11/1997 | Schilder et al. |
| 5,688,270 A | 11/1997 | Yates et al. |
| 5,690,269 A | 11/1997 | Bolanos et al. |
| 5,692,668 A | 12/1997 | Schulze et al. |
| 5,693,020 A | 12/1997 | Rauh |
| 5,693,042 A | 12/1997 | Boiarski et al. |
| 5,693,051 A | 12/1997 | Schulze et al. |
| 5,695,494 A | 12/1997 | Becker |
| 5,695,502 A | 12/1997 | Pier et al. |
| 5,695,504 A | 12/1997 | Gifford, III et al. |
| 5,695,524 A | 12/1997 | Kelley et al. |
| 5,697,542 A | 12/1997 | Knodel et al. |
| 5,697,543 A | 12/1997 | Burdorff |
| 5,697,909 A | 12/1997 | Eggers et al. |
| 5,697,943 A | 12/1997 | Sauer et al. |
| 5,700,270 A | 12/1997 | Peyser et al. |
| 5,702,387 A | 12/1997 | Arts et al. |
| 5,702,408 A | 12/1997 | Wales et al. |
| 5,702,409 A | 12/1997 | Rayburn et al. |
| 5,704,087 A | 1/1998 | Strub |
| 5,704,534 A | 1/1998 | Huitema et al. |
| 5,706,997 A | 1/1998 | Green et al. |
| 5,706,998 A | 1/1998 | Plyley et al. |
| 5,707,392 A | 1/1998 | Kortenbach |
| 5,709,334 A | 1/1998 | Sorrentino et al. |
| 5,709,680 A | 1/1998 | Yates et al. |
| 5,709,706 A | 1/1998 | Kienzle et al. |
| 5,711,472 A | 1/1998 | Bryan |
| 5,713,128 A | 2/1998 | Schrenk et al. |
| 5,713,505 A | 2/1998 | Huitema |
| 5,713,895 A | 2/1998 | Lontine et al. |
| 5,713,896 A | 2/1998 | Nardella |
| 5,713,920 A | 2/1998 | Bezwada et al. |
| 5,715,987 A | 2/1998 | Kelley et al. |
| 5,715,988 A | 2/1998 | Palmer |
| 5,716,366 A | 2/1998 | Yates |
| 5,718,359 A | 2/1998 | Palmer et al. |
| 5,718,360 A | 2/1998 | Green et al. |
| 5,718,548 A | 2/1998 | Costellessa |
| 5,720,744 A | 2/1998 | Eggleston et al. |
| D393,067 S | 3/1998 | Geary et al. |
| 5,725,536 A | 3/1998 | Oberlin et al. |
| 5,725,554 A | 3/1998 | Simon et al. |
| 5,728,110 A | 3/1998 | Vidal et al. |
| 5,728,121 A | 3/1998 | Bimbo et al. |
| 5,730,758 A | 3/1998 | Allgeyer |
| 5,732,821 A | 3/1998 | Stone et al. |
| 5,732,871 A | 3/1998 | Clark et al. |
| 5,732,872 A | 3/1998 | Bolduc et al. |
| 5,733,308 A | 3/1998 | Daugherty et al. |
| 5,735,445 A | 4/1998 | Vidal et al. |
| 5,735,848 A | 4/1998 | Yates et al. |
| 5,735,874 A | 4/1998 | Measamer et al. |
| 5,738,474 A | 4/1998 | Blewett |
| 5,738,648 A | 4/1998 | Lands et al. |
| 5,743,456 A | 4/1998 | Jones et al. |
| 5,747,953 A | 5/1998 | Philipp |
| 5,749,889 A | 5/1998 | Bacich et al. |
| 5,749,893 A | 5/1998 | Vidal et al. |
| 5,752,644 A | 5/1998 | Bolanos et al. |
| 5,752,965 A | 5/1998 | Francis et al. |
| 5,755,717 A | 5/1998 | Yates et al. |
| 5,758,814 A | 6/1998 | Gallagher et al. |
| 5,762,255 A | 6/1998 | Chrisman et al. |
| 5,762,256 A | 6/1998 | Mastri et al. |
| 5,766,188 A | 6/1998 | Igaki |
| 5,766,205 A | 6/1998 | Zvenyatsky et al. |
| 5,769,748 A | 6/1998 | Eyerly et al. |
| 5,769,892 A | 6/1998 | Kingwell |
| 5,772,379 A | 6/1998 | Evensen |
| 5,772,578 A | 6/1998 | Heimberger et al. |
| 5,772,659 A | 6/1998 | Becker et al. |
| 5,776,130 A | 7/1998 | Buysse et al. |
| 5,778,939 A | 7/1998 | Hok-Yin |
| 5,779,130 A | 7/1998 | Alesi et al. |
| 5,779,131 A | 7/1998 | Knodel et al. |
| 5,779,132 A | 7/1998 | Knodel et al. |
| 5,782,396 A | 7/1998 | Mastri et al. |
| 5,782,397 A | 7/1998 | Koukline |
| 5,782,749 A | 7/1998 | Riza |
| 5,782,859 A | 7/1998 | Nicholas et al. |
| 5,784,934 A | 7/1998 | Izumisawa |
| 5,785,232 A | 7/1998 | Vidal et al. |
| 5,785,647 A | 7/1998 | Tompkins et al. |
| 5,787,897 A | 8/1998 | Kieturakis |
| 5,792,135 A | 8/1998 | Madhani et al. |

(56) References Cited

U.S. PATENT DOCUMENTS

| | | |
|---|---|---|
| 5,792,165 A | 8/1998 | Klieman et al. |
| 5,794,834 A | 8/1998 | Hamblin et al. |
| 5,796,188 A | 8/1998 | Bays |
| 5,797,536 A | 8/1998 | Smith et al. |
| 5,797,537 A | 8/1998 | Oberlin et al. |
| 5,797,538 A | 8/1998 | Heaton et al. |
| 5,797,906 A | 8/1998 | Rhum et al. |
| 5,797,959 A | 8/1998 | Castro et al. |
| 5,799,857 A | 9/1998 | Robertson et al. |
| 5,800,379 A | 9/1998 | Edwards |
| 5,800,423 A | 9/1998 | Jensen |
| 5,806,676 A | 9/1998 | Wasgien |
| 5,807,376 A | 9/1998 | Viola et al. |
| 5,807,378 A | 9/1998 | Jensen et al. |
| 5,807,393 A | 9/1998 | Williamson, IV et al. |
| 5,809,441 A | 9/1998 | McKee |
| 5,810,721 A | 9/1998 | Mueller et al. |
| 5,810,811 A | 9/1998 | Yates et al. |
| 5,810,846 A | 9/1998 | Virnich et al. |
| 5,810,855 A | 9/1998 | Rayburn et al. |
| 5,813,813 A | 9/1998 | Daum et al. |
| 5,814,055 A | 9/1998 | Knodel et al. |
| 5,814,057 A | 9/1998 | Oi et al. |
| 5,816,471 A | 10/1998 | Plyley et al. |
| 5,817,084 A | 10/1998 | Jensen |
| 5,817,091 A | 10/1998 | Nardella et al. |
| 5,817,093 A | 10/1998 | Williamson, IV et al. |
| 5,817,109 A | 10/1998 | McGarry et al. |
| 5,817,119 A | 10/1998 | Klieman et al. |
| 5,820,009 A | 10/1998 | Melling et al. |
| 5,823,066 A | 10/1998 | Huitema et al. |
| 5,824,333 A | 10/1998 | Scopelianos et al. |
| 5,826,776 A | 10/1998 | Schulze et al. |
| 5,827,271 A | 10/1998 | Buysse et al. |
| 5,827,298 A | 10/1998 | Hart et al. |
| 5,829,662 A | 11/1998 | Allen et al. |
| 5,833,690 A | 11/1998 | Yates et al. |
| 5,833,695 A | 11/1998 | Yoon |
| 5,833,696 A | 11/1998 | Whitfield et al. |
| 5,836,503 A | 11/1998 | Ehrenfels et al. |
| 5,836,960 A | 11/1998 | Kolesa et al. |
| 5,839,639 A | 11/1998 | Sauer et al. |
| 5,843,021 A | 12/1998 | Edwards et al. |
| 5,843,096 A | 12/1998 | Igaki et al. |
| 5,843,097 A | 12/1998 | Mayenberger et al. |
| 5,843,122 A | 12/1998 | Riza |
| 5,843,132 A | 12/1998 | Ilvento |
| 5,843,169 A | 12/1998 | Taheri |
| 5,846,254 A | 12/1998 | Schulze et al. |
| 5,849,011 A | 12/1998 | Jones et al. |
| 5,849,023 A | 12/1998 | Mericle |
| 5,855,311 A | 1/1999 | Hamblin et al. |
| 5,855,583 A | 1/1999 | Wang et al. |
| 5,860,581 A | 1/1999 | Robertson et al. |
| 5,860,975 A | 1/1999 | Goble et al. |
| 5,865,361 A | 2/1999 | Milliman et al. |
| 5,868,760 A | 2/1999 | McGuckin, Jr. |
| 5,871,135 A | 2/1999 | Williamson, IV et al. |
| 5,873,885 A | 2/1999 | Weidenbenner |
| 5,876,401 A | 3/1999 | Schulze et al. |
| 5,878,193 A | 3/1999 | Wang et al. |
| 5,878,937 A | 3/1999 | Green et al. |
| 5,878,938 A | 3/1999 | Bittner et al. |
| 5,891,160 A | 4/1999 | Williamson, IV et al. |
| 5,893,506 A | 4/1999 | Powell |
| 5,893,835 A | 4/1999 | Witt et al. |
| 5,893,878 A | 4/1999 | Pierce |
| 5,894,979 A | 4/1999 | Powell |
| 5,897,552 A | 4/1999 | Edwards et al. |
| 5,897,562 A | 4/1999 | Bolanos et al. |
| 5,899,914 A | 5/1999 | Zirps et al. |
| 5,901,895 A | 5/1999 | Heaton et al. |
| 5,902,312 A | 5/1999 | Frater et al. |
| 5,904,647 A | 5/1999 | Ouchi |
| 5,904,693 A | 5/1999 | Dicesare et al. |
| 5,904,702 A | 5/1999 | Ek et al. |
| 5,906,625 A | 5/1999 | Bito et al. |
| 5,908,402 A | 6/1999 | Blythe |
| 5,908,427 A | 6/1999 | McKean et al. |
| 5,911,353 A | 6/1999 | Bolanos et al. |
| 5,915,616 A | 6/1999 | Viola et al. |
| 5,916,225 A | 6/1999 | Kugel |
| 5,918,791 A | 7/1999 | Sorrentino et al. |
| 5,919,198 A | 7/1999 | Graves, Jr. et al. |
| 5,921,956 A | 7/1999 | Grinberg et al. |
| 5,928,256 A | 7/1999 | Riza |
| 5,931,847 A | 8/1999 | Bittner et al. |
| 5,931,853 A | 8/1999 | McEwen et al. |
| 5,937,951 A | 8/1999 | Izuchukwu et al. |
| 5,938,667 A | 8/1999 | Peyser et al. |
| 5,941,442 A | 8/1999 | Geiste et al. |
| 5,944,172 A | 8/1999 | Hannula |
| 5,944,715 A | 8/1999 | Goble et al. |
| 5,947,984 A | 9/1999 | Whipple |
| 5,948,030 A | 9/1999 | Miller et al. |
| 5,951,516 A | 9/1999 | Bunyan |
| 5,951,552 A | 9/1999 | Long et al. |
| 5,951,574 A | 9/1999 | Stefanchik et al. |
| 5,951,581 A | 9/1999 | Saadat et al. |
| 5,954,259 A | 9/1999 | Viola et al. |
| 5,964,394 A | 10/1999 | Robertson |
| 5,964,774 A | 10/1999 | McKean et al. |
| 5,971,916 A | 10/1999 | Koren |
| 5,973,221 A | 10/1999 | Collyer et al. |
| 5,977,746 A | 11/1999 | Hershberger et al. |
| 5,984,949 A | 11/1999 | Levin |
| 5,988,479 A | 11/1999 | Palmer |
| 5,997,528 A | 12/1999 | Bisch et al. |
| 5,997,552 A | 12/1999 | Person et al. |
| 6,003,517 A | 12/1999 | Sheffield et al. |
| 6,004,319 A | 12/1999 | Goble et al. |
| 6,004,335 A | 12/1999 | Vaitekunas et al. |
| 6,010,054 A * | 1/2000 | Johnson ............ A61B 17/07207 227/176.1 |
| 6,010,513 A | 1/2000 | Törmälä et al. |
| 6,012,494 A | 1/2000 | Balazs |
| 6,013,076 A | 1/2000 | Goble et al. |
| 6,015,406 A | 1/2000 | Goble et al. |
| 6,015,417 A | 1/2000 | Reynolds, Jr. |
| 6,017,322 A | 1/2000 | Snoke et al. |
| 6,017,354 A | 1/2000 | Culp et al. |
| 6,017,356 A | 1/2000 | Frederick et al. |
| 6,022,352 A | 2/2000 | Vandewalle |
| 6,024,741 A | 2/2000 | Williamson, IV et al. |
| 6,024,748 A | 2/2000 | Manzo et al. |
| 6,027,501 A | 2/2000 | Goble et al. |
| 6,032,849 A | 3/2000 | Mastri et al. |
| 6,033,378 A | 3/2000 | Lundquist et al. |
| 6,033,399 A | 3/2000 | Gines |
| 6,033,427 A | 3/2000 | Lee |
| 6,037,724 A | 3/2000 | Buss et al. |
| 6,039,733 A | 3/2000 | Buysse et al. |
| 6,039,734 A | 3/2000 | Goble |
| 6,042,601 A | 3/2000 | Smith |
| 6,045,560 A | 4/2000 | McKean et al. |
| 6,047,861 A | 4/2000 | Vidal et al. |
| 6,050,472 A | 4/2000 | Shibata |
| 6,050,990 A | 4/2000 | Tankovich et al. |
| 6,050,996 A | 4/2000 | Schmaltz et al. |
| 6,053,390 A | 4/2000 | Green et al. |
| 6,053,922 A | 4/2000 | Krause et al. |
| RE36,720 E | 5/2000 | Green et al. |
| 6,056,735 A | 5/2000 | Okada et al. |
| 6,056,746 A | 5/2000 | Goble et al. |
| 6,062,360 A | 5/2000 | Shields |
| 6,063,097 A | 5/2000 | Oi et al. |
| 6,063,098 A | 5/2000 | Houser et al. |
| 6,065,679 A | 5/2000 | Levie et al. |
| 6,065,919 A | 5/2000 | Peck |
| 6,066,132 A | 5/2000 | Chen et al. |
| 6,068,627 A | 5/2000 | Orszulak et al. |
| 6,071,233 A | 6/2000 | Ishikawa et al. |
| 6,074,386 A | 6/2000 | Goble et al. |
| 6,074,401 A | 6/2000 | Gardiner et al. |

(56) References Cited

U.S. PATENT DOCUMENTS

| | | |
|---|---|---|
| 6,077,286 A | 6/2000 | Cuschieri et al. |
| 6,079,606 A | 6/2000 | Milliman et al. |
| 6,080,181 A | 6/2000 | Jensen et al. |
| 6,082,577 A | 7/2000 | Coates et al. |
| 6,083,191 A | 7/2000 | Rose |
| 6,083,234 A | 7/2000 | Nicholas et al. |
| 6,083,242 A | 7/2000 | Cook |
| 6,086,544 A | 7/2000 | Hibner et al. |
| 6,086,600 A | 7/2000 | Kortenbach |
| 6,090,106 A | 7/2000 | Goble et al. |
| 6,093,186 A | 7/2000 | Goble |
| 6,099,537 A | 8/2000 | Sugai et al. |
| 6,099,551 A | 8/2000 | Gabbay |
| 6,102,271 A | 8/2000 | Longo et al. |
| 6,104,304 A | 8/2000 | Clark et al. |
| 6,109,500 A | 8/2000 | Alli et al. |
| 6,117,148 A | 9/2000 | Ravo et al. |
| 6,117,158 A | 9/2000 | Measamer et al. |
| 6,119,913 A | 9/2000 | Adams et al. |
| 6,120,433 A | 9/2000 | Mizuno et al. |
| 6,123,241 A | 9/2000 | Walter et al. |
| H1904 H | 10/2000 | Yates et al. |
| 6,126,058 A | 10/2000 | Adams et al. |
| 6,126,670 A | 10/2000 | Walker et al. |
| 6,131,789 A | 10/2000 | Schulze et al. |
| 6,131,790 A | 10/2000 | Piraka |
| 6,132,368 A | 10/2000 | Cooper |
| 6,139,546 A | 10/2000 | Koenig et al. |
| 6,149,660 A | 11/2000 | Laufer et al. |
| 6,152,935 A | 11/2000 | Kammerer et al. |
| 6,155,473 A | 12/2000 | Tompkins et al. |
| 6,156,056 A | 12/2000 | Kearns et al. |
| 6,159,146 A | 12/2000 | El Gazayerli |
| 6,159,200 A | 12/2000 | Verdura et al. |
| 6,159,224 A | 12/2000 | Yoon |
| 6,162,208 A | 12/2000 | Hipps |
| 6,162,537 A | 12/2000 | Martin et al. |
| 6,165,175 A | 12/2000 | Wampler et al. |
| 6,165,184 A | 12/2000 | Verdura et al. |
| 6,165,188 A | 12/2000 | Saadat et al. |
| 6,168,605 B1 | 1/2001 | Measamer et al. |
| 6,171,305 B1 | 1/2001 | Sherman |
| 6,171,316 B1 | 1/2001 | Kovac et al. |
| 6,171,330 B1 | 1/2001 | Benchetrit |
| 6,174,308 B1 | 1/2001 | Goble et al. |
| 6,174,309 B1 | 1/2001 | Wrublewski et al. |
| 6,175,290 B1 | 1/2001 | Forsythe et al. |
| 6,179,195 B1 | 1/2001 | Adams et al. |
| 6,179,776 B1 | 1/2001 | Adams et al. |
| 6,181,105 B1 | 1/2001 | Cutolo et al. |
| 6,182,673 B1 | 2/2001 | Kindermann et al. |
| 6,187,003 B1 | 2/2001 | Buysse et al. |
| 6,190,386 B1 | 2/2001 | Rydell |
| 6,193,129 B1 | 2/2001 | Bittner et al. |
| 6,197,042 B1 | 3/2001 | Ginn et al. |
| 6,200,330 B1 | 3/2001 | Benderev et al. |
| 6,202,914 B1 | 3/2001 | Geiste et al. |
| 6,206,897 B1 | 3/2001 | Jamiolkowski et al. |
| 6,206,904 B1 | 3/2001 | Ouchi |
| 6,210,403 B1 | 4/2001 | Klicek |
| 6,213,999 B1 | 4/2001 | Platt, Jr. et al. |
| 6,214,028 B1 | 4/2001 | Yoon et al. |
| 6,220,368 B1 | 4/2001 | Ark et al. |
| 6,223,100 B1 | 4/2001 | Green |
| 6,223,835 B1 | 5/2001 | Habedank et al. |
| 6,224,617 B1 | 5/2001 | Saadat et al. |
| 6,228,081 B1 | 5/2001 | Goble |
| 6,228,083 B1 | 5/2001 | Lands et al. |
| 6,228,084 B1 | 5/2001 | Kirwan, Jr. |
| 6,231,565 B1 | 5/2001 | Tovey et al. |
| 6,234,178 B1 | 5/2001 | Goble et al. |
| 6,241,139 B1 | 6/2001 | Milliman et al. |
| 6,241,140 B1 | 6/2001 | Adams et al. |
| 6,241,723 B1 | 6/2001 | Heim et al. |
| 6,245,084 B1 | 6/2001 | Mark et al. |
| 6,248,117 B1 | 6/2001 | Blatter |
| 6,249,076 B1 | 6/2001 | Madden et al. |
| 6,250,532 B1 | 6/2001 | Green et al. |
| 6,258,107 B1 | 7/2001 | Balázs et al. |
| 6,261,286 B1 | 7/2001 | Goble et al. |
| 6,264,086 B1 | 7/2001 | McGuckin, Jr. |
| 6,264,087 B1 | 7/2001 | Whitman |
| 6,270,508 B1 | 8/2001 | Klieman et al. |
| 6,273,876 B1 | 8/2001 | Klima et al. |
| 6,273,897 B1 | 8/2001 | Dalessandro et al. |
| 6,277,114 B1 | 8/2001 | Bullivant et al. |
| 6,293,942 B1 | 9/2001 | Goble et al. |
| 6,296,640 B1 | 10/2001 | Wampler et al. |
| 6,302,311 B1 | 10/2001 | Adams et al. |
| 6,305,891 B1 | 10/2001 | Burlingame |
| 6,306,134 B1 | 10/2001 | Goble et al. |
| 6,306,149 B1 | 10/2001 | Meade |
| 6,309,403 B1 | 10/2001 | Minor et al. |
| 6,315,184 B1 | 11/2001 | Whitman |
| 6,320,123 B1 | 11/2001 | Reimers |
| 6,322,494 B1 | 11/2001 | Bullivant et al. |
| 6,324,339 B1 | 11/2001 | Hudson et al. |
| 6,325,799 B1 | 12/2001 | Goble |
| 6,325,810 B1 | 12/2001 | Hamilton et al. |
| 6,330,965 B1 | 12/2001 | Milliman et al. |
| 6,331,181 B1 | 12/2001 | Tierney et al. |
| 6,331,761 B1 | 12/2001 | Kumar et al. |
| 6,333,029 B1 | 12/2001 | Vyakarnam et al. |
| 6,334,860 B1 | 1/2002 | Dorn |
| 6,334,861 B1 | 1/2002 | Chandler et al. |
| 6,336,926 B1 | 1/2002 | Goble |
| 6,338,737 B1 | 1/2002 | Toledano |
| 6,343,731 B1 | 2/2002 | Adams et al. |
| 6,346,077 B1 | 2/2002 | Taylor et al. |
| 6,352,503 B1 | 3/2002 | Matsui et al. |
| 6,352,532 B1 | 3/2002 | Kramer et al. |
| 6,355,699 B1 | 3/2002 | Vyakarnam et al. |
| 6,356,072 B1 | 3/2002 | Chass |
| 6,358,224 B1 | 3/2002 | Tims et al. |
| 6,364,877 B1 | 4/2002 | Goble et al. |
| 6,364,888 B1 | 4/2002 | Niemeyer et al. |
| 6,370,981 B2 | 4/2002 | Watarai |
| 6,373,152 B1 | 4/2002 | Wang et al. |
| 6,383,201 B1 | 5/2002 | Dong |
| 6,387,113 B1 | 5/2002 | Hawkins et al. |
| 6,387,114 B2 | 5/2002 | Adams |
| 6,391,038 B2 | 5/2002 | Vargas et al. |
| 6,392,854 B1 | 5/2002 | O'Gorman |
| 6,398,781 B1 | 6/2002 | Goble et al. |
| 6,398,797 B2 | 6/2002 | Bombard et al. |
| 6,402,766 B2 | 6/2002 | Bowman et al. |
| 6,406,440 B1 | 6/2002 | Stefanchik |
| 6,406,472 B1 | 6/2002 | Jensen |
| 6,409,724 B1 | 6/2002 | Penny et al. |
| H2037 H | 7/2002 | Yates et al. |
| 6,413,274 B1 | 7/2002 | Pedros |
| 6,416,486 B1 | 7/2002 | Wampler |
| 6,416,509 B1 | 7/2002 | Goble et al. |
| 6,419,695 B1 | 7/2002 | Gabbay |
| 6,423,079 B1 | 7/2002 | Blake, III |
| RE37,814 E | 8/2002 | Allgeyer |
| 6,428,070 B1 | 8/2002 | Takanashi et al. |
| 6,429,611 B1 | 8/2002 | Li |
| 6,436,097 B1 | 8/2002 | Nardella |
| 6,436,107 B1 | 8/2002 | Wang et al. |
| 6,436,110 B2 | 8/2002 | Bowman et al. |
| 6,436,122 B1 | 8/2002 | Frank et al. |
| 6,439,439 B1 | 8/2002 | Rickard et al. |
| 6,439,446 B1 | 8/2002 | Perry et al. |
| 6,440,146 B2 | 8/2002 | Nicholas et al. |
| 6,443,973 B1 | 9/2002 | Whitman |
| 6,447,518 B1 | 9/2002 | Krause et al. |
| 6,450,391 B1 | 9/2002 | Kayan et al. |
| 6,450,989 B2 | 9/2002 | Dubrul et al. |
| 6,454,781 B1 | 9/2002 | Witt et al. |
| 6,468,275 B1 | 10/2002 | Wampler et al. |
| 6,471,106 B1 | 10/2002 | Reining |
| 6,471,659 B2 | 10/2002 | Eggers et al. |
| 6,478,210 B2 | 11/2002 | Adams et al. |

(56) References Cited

U.S. PATENT DOCUMENTS

| | | |
|---|---|---|
| 6,482,200 B2 | 11/2002 | Shippert |
| 6,485,490 B2 | 11/2002 | Wampler et al. |
| 6,485,667 B1 | 11/2002 | Tan |
| 6,488,196 B1 | 12/2002 | Fenton, Jr. |
| 6,488,197 B1 | 12/2002 | Whitman |
| 6,491,201 B1 | 12/2002 | Whitman |
| 6,491,690 B1 | 12/2002 | Goble et al. |
| 6,491,701 B2 | 12/2002 | Tierney et al. |
| 6,492,785 B1 | 12/2002 | Kasten et al. |
| 6,494,896 B1 | 12/2002 | D'Alessio et al. |
| 6,500,176 B1 | 12/2002 | Truckai et al. |
| 6,500,194 B2 | 12/2002 | Benderev et al. |
| 6,503,257 B2 | 1/2003 | Grant et al. |
| 6,503,259 B2 | 1/2003 | Huxel et al. |
| 6,505,768 B2 | 1/2003 | Whitman |
| 6,510,854 B2 | 1/2003 | Goble |
| 6,511,468 B1 | 1/2003 | Cragg et al. |
| 6,512,360 B1 | 1/2003 | Goto et al. |
| 6,517,528 B1 | 2/2003 | Pantages et al. |
| 6,517,535 B2 | 2/2003 | Edwards |
| 6,517,565 B1 | 2/2003 | Whitman et al. |
| 6,517,566 B1 | 2/2003 | Hovland et al. |
| 6,522,101 B2 | 2/2003 | Malackowski |
| 6,527,782 B2 | 3/2003 | Hogg et al. |
| 6,527,785 B2 | 3/2003 | Sancoff et al. |
| 6,533,157 B1 | 3/2003 | Whitman |
| 6,533,784 B2 | 3/2003 | Truckai et al. |
| 6,535,764 B2 | 3/2003 | Imran et al. |
| 6,543,456 B1 | 4/2003 | Freeman |
| 6,545,384 B1 | 4/2003 | Pelrine et al. |
| 6,547,786 B1 | 4/2003 | Goble |
| 6,550,546 B2 | 4/2003 | Thurler et al. |
| 6,551,333 B2 | 4/2003 | Kuhns et al. |
| 6,554,861 B2 | 4/2003 | Knox et al. |
| 6,555,770 B2 | 4/2003 | Kawase |
| 6,558,378 B2 | 5/2003 | Sherman et al. |
| 6,558,379 B1 | 5/2003 | Batchelor et al. |
| 6,565,560 B1 | 5/2003 | Goble et al. |
| 6,566,619 B2 | 5/2003 | Gillman et al. |
| 6,569,085 B2 | 5/2003 | Kortenbach et al. |
| 6,569,171 B2 | 5/2003 | DeGuillebon et al. |
| 6,578,751 B2 | 6/2003 | Hartwick |
| 6,582,427 B1 | 6/2003 | Goble et al. |
| 6,582,441 B1 | 6/2003 | He et al. |
| 6,583,533 B2 | 6/2003 | Pelrine et al. |
| 6,585,144 B2 | 7/2003 | Adams et al. |
| 6,588,643 B2 | 7/2003 | Bolduc et al. |
| 6,589,164 B1 | 7/2003 | Flaherty |
| 6,592,538 B1 | 7/2003 | Hotchkiss et al. |
| 6,592,597 B2 | 7/2003 | Grant et al. |
| 6,596,296 B1 | 7/2003 | Nelson et al. |
| 6,596,304 B1 | 7/2003 | Bayon et al. |
| 6,596,432 B2 | 7/2003 | Kawakami et al. |
| D478,665 S | 8/2003 | Isaacs et al. |
| D478,986 S | 8/2003 | Johnston et al. |
| 6,601,749 B2 | 8/2003 | Sullivan et al. |
| 6,602,252 B2 | 8/2003 | Mollenauer |
| 6,602,262 B2 | 8/2003 | Griego et al. |
| 6,605,078 B2 | 8/2003 | Adams |
| 6,605,669 B2 | 8/2003 | Awokola et al. |
| 6,607,475 B2 | 8/2003 | Doyle et al. |
| 6,613,069 B2 | 9/2003 | Boyd et al. |
| 6,616,686 B2 | 9/2003 | Coleman et al. |
| 6,619,529 B2 | 9/2003 | Green et al. |
| 6,620,166 B1 | 9/2003 | Wenstrom, Jr. et al. |
| 6,626,834 B2 | 9/2003 | Dunne et al. |
| 6,629,630 B2 | 10/2003 | Adams |
| 6,629,974 B2 | 10/2003 | Penny et al. |
| 6,629,988 B2 | 10/2003 | Weadock |
| 6,635,838 B1 | 10/2003 | Kornelson |
| 6,636,412 B2 | 10/2003 | Smith |
| 6,638,108 B2 | 10/2003 | Tachi |
| 6,638,285 B2 | 10/2003 | Gabbay |
| 6,638,297 B1 | 10/2003 | Huitema |
| RE38,335 E | 11/2003 | Aust et al. |
| 6,641,528 B2 | 11/2003 | Torii |
| 6,644,532 B2 | 11/2003 | Green et al. |
| 6,645,201 B1 | 11/2003 | Utley et al. |
| 6,646,307 B1 | 11/2003 | Yu et al. |
| 6,648,816 B2 | 11/2003 | Irion et al. |
| 6,652,595 B1 | 11/2003 | Nicolo |
| D484,243 S | 12/2003 | Ryan et al. |
| D484,595 S | 12/2003 | Ryan et al. |
| D484,596 S | 12/2003 | Ryan et al. |
| 6,656,177 B2 | 12/2003 | Truckai et al. |
| 6,656,193 B2 | 12/2003 | Grant et al. |
| 6,663,623 B1 | 12/2003 | Oyama et al. |
| 6,663,641 B1 | 12/2003 | Kovac et al. |
| 6,666,854 B1 | 12/2003 | Lange |
| 6,666,875 B1 | 12/2003 | Sakurai et al. |
| 6,667,825 B2 | 12/2003 | Lu et al. |
| 6,669,073 B2 | 12/2003 | Milliman et al. |
| 6,671,185 B2 | 12/2003 | Duval |
| D484,977 S | 1/2004 | Ryan et al. |
| 6,676,660 B2 | 1/2004 | Wampler et al. |
| 6,679,269 B2 | 1/2004 | Swanson |
| 6,679,410 B2 | 1/2004 | Würsch et al. |
| 6,681,978 B2 | 1/2004 | Geiste et al. |
| 6,681,979 B2 | 1/2004 | Whitman |
| 6,682,527 B2 | 1/2004 | Strul |
| 6,682,528 B2 | 1/2004 | Frazier et al. |
| 6,685,727 B2 | 2/2004 | Fisher et al. |
| 6,689,153 B1 | 2/2004 | Skiba |
| 6,692,507 B2 | 2/2004 | Pugsley et al. |
| 6,695,198 B2 | 2/2004 | Adams et al. |
| 6,695,199 B2 | 2/2004 | Whitman |
| 6,695,774 B2 | 2/2004 | Hale et al. |
| 6,698,643 B2 | 3/2004 | Whitman |
| 6,699,235 B2 | 3/2004 | Wallace et al. |
| 6,704,210 B1 | 3/2004 | Myers |
| 6,705,503 B1 | 3/2004 | Pedicini et al. |
| 6,709,445 B2 | 3/2004 | Boebel et al. |
| 6,712,773 B1 | 3/2004 | Viola |
| 6,716,223 B2 | 4/2004 | Leopold et al. |
| 6,716,232 B1 | 4/2004 | Vidal et al. |
| 6,716,233 B1 | 4/2004 | Whitman |
| 6,722,552 B2 | 4/2004 | Fenton, Jr. |
| 6,723,087 B2 | 4/2004 | O'Neill et al. |
| 6,723,091 B2 | 4/2004 | Goble et al. |
| 6,726,697 B2 | 4/2004 | Nicholas et al. |
| 6,726,706 B2 | 4/2004 | Dominguez |
| 6,729,119 B2 | 5/2004 | Schnipke et al. |
| 6,736,825 B2 | 5/2004 | Blatter et al. |
| 6,736,854 B2 | 5/2004 | Vadurro et al. |
| 6,740,030 B2 | 5/2004 | Martone et al. |
| 6,747,121 B2 | 6/2004 | Gogolewski |
| 6,749,560 B1 | 6/2004 | Konstorum et al. |
| 6,752,768 B2 | 6/2004 | Burdorff et al. |
| 6,752,816 B2 | 6/2004 | Culp et al. |
| 6,755,195 B1 | 6/2004 | Lemke et al. |
| 6,755,338 B2 | 6/2004 | Hahnen et al. |
| 6,758,846 B2 | 7/2004 | Goble et al. |
| 6,761,685 B2 | 7/2004 | Adams et al. |
| 6,762,339 B1 | 7/2004 | Klun et al. |
| 6,767,352 B2 | 7/2004 | Field et al. |
| 6,767,356 B2 | 7/2004 | Kanner et al. |
| 6,769,590 B2 | 8/2004 | Vresh et al. |
| 6,769,594 B2 | 8/2004 | Orban, III |
| 6,770,027 B2 | 8/2004 | Banik et al. |
| 6,770,072 B1 | 8/2004 | Truckai et al. |
| 6,773,409 B2 | 8/2004 | Truckai et al. |
| 6,773,438 B2 | 8/2004 | Knodel et al. |
| 6,777,838 B2 | 8/2004 | Miekka et al. |
| 6,780,151 B2 | 8/2004 | Grabover et al. |
| 6,780,180 B1 | 8/2004 | Goble et al. |
| 6,783,524 B2 | 8/2004 | Anderson et al. |
| 6,786,382 B1 | 9/2004 | Hoffman |
| 6,786,864 B2 | 9/2004 | Matsuura et al. |
| 6,786,896 B1 | 9/2004 | Madani et al. |
| 6,790,173 B2 | 9/2004 | Saadat et al. |
| 6,793,652 B1 | 9/2004 | Whitman et al. |
| 6,793,661 B2 | 9/2004 | Hamilton et al. |
| 6,793,663 B2 | 9/2004 | Kneifel et al. |
| 6,802,843 B2 | 10/2004 | Truckai et al. |

(56) References Cited

U.S. PATENT DOCUMENTS

| | | |
|---|---|---|
| 6,805,273 B2 | 10/2004 | Bilotti et al. |
| 6,806,808 B1 | 10/2004 | Watters et al. |
| 6,808,525 B2 | 10/2004 | Latterell et al. |
| 6,814,741 B2 | 11/2004 | Bowman et al. |
| 6,817,508 B1 | 11/2004 | Racenet et al. |
| 6,817,509 B2 | 11/2004 | Geiste et al. |
| 6,817,974 B2 | 11/2004 | Cooper et al. |
| 6,818,018 B1 | 11/2004 | Sawhney |
| 6,820,791 B2 | 11/2004 | Adams |
| 6,821,273 B2 | 11/2004 | Mollenauer |
| 6,821,282 B2 | 11/2004 | Perry et al. |
| 6,821,284 B2 | 11/2004 | Sturtz et al. |
| 6,827,246 B2 | 12/2004 | Sullivan et al. |
| 6,827,712 B2 | 12/2004 | Tovey et al. |
| 6,827,725 B2 | 12/2004 | Batchelor et al. |
| 6,828,902 B2 | 12/2004 | Casden |
| 6,830,174 B2 | 12/2004 | Hillstead et al. |
| 6,831,629 B2 | 12/2004 | Nishino et al. |
| 6,832,998 B2 | 12/2004 | Goble |
| 6,834,001 B2 | 12/2004 | Myono |
| 6,835,173 B2 | 12/2004 | Couvillon, Jr. |
| 6,835,199 B2 | 12/2004 | McGuckin, Jr. et al. |
| 6,835,336 B2 | 12/2004 | Watt |
| 6,837,846 B2 | 1/2005 | Jaffe et al. |
| 6,838,493 B2 | 1/2005 | Williams et al. |
| 6,840,423 B2 | 1/2005 | Adams et al. |
| 6,843,403 B2 | 1/2005 | Whitman |
| 6,843,789 B2 | 1/2005 | Goble |
| 6,843,793 B2 | 1/2005 | Brock et al. |
| 6,846,307 B2 | 1/2005 | Whitman et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| 6,850,817 B1 | 2/2005 | Green |
| 6,853,879 B2 | 2/2005 | Sunaoshi |
| 6,858,005 B2 | 2/2005 | Ohline et al. |
| RE38,708 E | 3/2005 | Bolanos et al. |
| 6,861,142 B1 | 3/2005 | Wilkie et al. |
| 6,863,694 B1 | 3/2005 | Boyce et al. |
| 6,866,178 B2 | 3/2005 | Adams et al. |
| 6,866,671 B2 | 3/2005 | Tierney et al. |
| 6,867,248 B1 | 3/2005 | Martin et al. |
| 6,869,435 B2 | 3/2005 | Blake, III |
| 6,872,214 B2 | 3/2005 | Sonnenschein et al. |
| 6,874,669 B2 | 4/2005 | Adams et al. |
| 6,877,647 B2 | 4/2005 | Green et al. |
| 6,878,106 B1 | 4/2005 | Herrmann |
| 6,889,116 B2 | 5/2005 | Jinno |
| 6,893,435 B2 | 5/2005 | Goble |
| 6,899,538 B2 | 5/2005 | Matoba |
| 6,905,057 B2 | 6/2005 | Swayze et al. |
| 6,905,497 B2 | 6/2005 | Truckai et al. |
| 6,908,472 B2 | 6/2005 | Wiener et al. |
| 6,911,033 B2 | 6/2005 | de Guillebon et al. |
| 6,913,579 B2 | 7/2005 | Truckai et al. |
| 6,913,608 B2 | 7/2005 | Liddicoat et al. |
| 6,913,613 B2 | 7/2005 | Schwarz et al. |
| 6,921,397 B2 | 7/2005 | Corcoran et al. |
| 6,921,412 B1 | 7/2005 | Black et al. |
| 6,923,093 B2 | 8/2005 | Ullah |
| 6,923,803 B2 | 8/2005 | Goble |
| 6,926,716 B2 | 8/2005 | Baker et al. |
| 6,929,641 B2 | 8/2005 | Goble et al. |
| 6,929,644 B2 | 8/2005 | Truckai et al. |
| 6,931,830 B2 | 8/2005 | Liao |
| 6,932,218 B2 | 8/2005 | Kosann et al. |
| 6,932,810 B2 | 8/2005 | Ryan |
| 6,936,042 B2 | 8/2005 | Wallace et al. |
| 6,939,358 B2 | 9/2005 | Palacios et al. |
| 6,942,662 B2 | 9/2005 | Goble et al. |
| 6,945,444 B2 | 9/2005 | Gresham et al. |
| 6,945,981 B2 | 9/2005 | Donofrio et al. |
| 6,953,138 B1 | 10/2005 | Dworak et al. |
| 6,953,139 B2 | 10/2005 | Milliman et al. |
| 6,958,035 B2 | 10/2005 | Friedman et al. |
| 6,959,851 B2 | 11/2005 | Heinrich |
| 6,959,852 B2 | 11/2005 | Shelton, IV et al. |
| 6,960,107 B1 | 11/2005 | Schaub et al. |
| 6,960,163 B2 | 11/2005 | Ewers et al. |
| 6,960,220 B2 | 11/2005 | Marino et al. |
| 6,964,363 B2 | 11/2005 | Wales et al. |
| 6,966,907 B2 | 11/2005 | Goble |
| 6,966,909 B2 | 11/2005 | Marshall et al. |
| 6,971,988 B2 | 12/2005 | Orban, III |
| 6,972,199 B2 | 12/2005 | Lebouitz et al. |
| 6,974,462 B2 | 12/2005 | Sater |
| 6,978,921 B2 | 12/2005 | Shelton, IV et al. |
| 6,978,922 B2 | 12/2005 | Bilotti et al. |
| 6,981,628 B2 | 1/2006 | Wales |
| 6,981,941 B2 | 1/2006 | Whitman et al. |
| 6,981,978 B2 | 1/2006 | Gannoe |
| 6,984,203 B2 | 1/2006 | Tartaglia et al. |
| 6,984,231 B2 | 1/2006 | Goble et al. |
| 6,986,451 B1 | 1/2006 | Mastri et al. |
| 6,988,649 B2 | 1/2006 | Shelton, IV et al. |
| 6,988,650 B2 | 1/2006 | Schwemberger et al. |
| 6,990,796 B2 | 1/2006 | Schnipke et al. |
| 6,993,413 B2 | 1/2006 | Sunaoshi |
| 6,994,708 B2 | 2/2006 | Manzo |
| 6,995,729 B2 | 2/2006 | Govari et al. |
| 6,997,931 B2 | 2/2006 | Sauer et al. |
| 6,998,816 B2 | 2/2006 | Wieck et al. |
| 7,000,818 B2 | 2/2006 | Shelton, IV et al. |
| 7,000,819 B2 | 2/2006 | Swayze et al. |
| 7,001,380 B2 | 2/2006 | Goble |
| 7,001,408 B2 | 2/2006 | Knodel et al. |
| 7,008,435 B2 | 3/2006 | Cummins |
| 7,009,039 B2 | 3/2006 | Yayon et al. |
| 7,011,657 B2 | 3/2006 | Truckai et al. |
| 7,018,357 B2 | 3/2006 | Emmons |
| 7,018,390 B2 | 3/2006 | Turovskiy et al. |
| 7,025,743 B2 | 4/2006 | Mann et al. |
| 7,029,435 B2 | 4/2006 | Nakao |
| 7,032,798 B2 | 4/2006 | Whitman et al. |
| 7,032,799 B2 | 4/2006 | Viola et al. |
| 7,033,356 B2 | 4/2006 | Latterell et al. |
| 7,036,680 B1 | 5/2006 | Flannery |
| 7,037,344 B2 | 5/2006 | Kagan et al. |
| 7,041,102 B2 | 5/2006 | Truckai et al. |
| 7,041,868 B2 | 5/2006 | Greene et al. |
| 7,043,852 B2 | 5/2006 | Hayashida et al. |
| 7,044,352 B2 | 5/2006 | Shelton, IV et al. |
| 7,044,353 B2 | 5/2006 | Mastri et al. |
| 7,048,687 B1 | 5/2006 | Reuss et al. |
| 7,048,745 B2 | 5/2006 | Tierney et al. |
| 7,052,494 B2 | 5/2006 | Goble et al. |
| 7,052,499 B2 | 5/2006 | Steger et al. |
| 7,055,730 B2 | 6/2006 | Ehrenfels et al. |
| 7,055,731 B2 | 6/2006 | Shelton, IV et al. |
| 7,056,284 B2 | 6/2006 | Martone et al. |
| 7,056,330 B2 | 6/2006 | Gayton |
| 7,059,331 B2 | 6/2006 | Adams et al. |
| 7,059,508 B2 | 6/2006 | Shelton, IV et al. |
| 7,063,671 B2 | 6/2006 | Couvillon, Jr. |
| 7,063,712 B2 | 6/2006 | Vargas et al. |
| 7,066,879 B2 | 6/2006 | Fowler et al. |
| 7,066,944 B2 | 6/2006 | Laufer et al. |
| 7,067,038 B2 | 6/2006 | Trokhan et al. |
| 7,070,083 B2 | 7/2006 | Jankowski |
| 7,070,559 B2 | 7/2006 | Adams et al. |
| 7,070,597 B2 | 7/2006 | Truckai et al. |
| 7,071,287 B2 | 7/2006 | Rhine et al. |
| 7,075,770 B1 | 7/2006 | Smith |
| 7,077,856 B2 | 7/2006 | Whitman |
| 7,080,769 B2 | 7/2006 | Vresh et al. |
| 7,081,114 B2 | 7/2006 | Rashidi |
| 7,083,073 B2 | 8/2006 | Yoshie et al. |
| 7,083,075 B2 | 8/2006 | Swayze et al. |
| 7,083,571 B2 | 8/2006 | Wang et al. |
| 7,083,615 B2 | 8/2006 | Peterson et al. |
| 7,083,619 B2 | 8/2006 | Truckai et al. |
| 7,083,620 B2 | 8/2006 | Jahns et al. |
| 7,087,054 B2 | 8/2006 | Truckai et al. |
| 7,087,071 B2 | 8/2006 | Nicholas et al. |

(56) References Cited

U.S. PATENT DOCUMENTS

| | | |
|---|---|---|
| 7,090,637 B2 | 8/2006 | Danitz et al. |
| 7,090,673 B2 | 8/2006 | Dycus et al. |
| 7,090,683 B2 | 8/2006 | Brock et al. |
| 7,090,684 B2 | 8/2006 | McGuckin, Jr. et al. |
| 7,094,202 B2 | 8/2006 | Nobis et al. |
| 7,094,247 B2 | 8/2006 | Monassevitch et al. |
| 7,097,089 B2 | 8/2006 | Marczyk |
| 7,097,644 B2 | 8/2006 | Long |
| 7,097,650 B2 | 8/2006 | Weller et al. |
| 7,098,794 B2 | 8/2006 | Lindsay et al. |
| 7,100,949 B2 | 9/2006 | Williams et al. |
| 7,104,741 B2 | 9/2006 | Krohn |
| 7,108,695 B2 | 9/2006 | Witt et al. |
| 7,108,701 B2 | 9/2006 | Evens et al. |
| 7,108,709 B2 | 9/2006 | Cummins |
| 7,111,769 B2 | 9/2006 | Wales et al. |
| 7,112,214 B2 | 9/2006 | Peterson et al. |
| RE39,358 E | 10/2006 | Goble |
| 7,114,642 B2 | 10/2006 | Whitman |
| 7,118,582 B1 | 10/2006 | Wang et al. |
| 7,121,446 B2 | 10/2006 | Arad et al. |
| 7,122,028 B2 | 10/2006 | Looper et al. |
| 7,125,409 B2 | 10/2006 | Truckai et al. |
| 7,126,303 B2 | 10/2006 | Farritor et al. |
| 7,126,879 B2 | 10/2006 | Snyder |
| 7,128,253 B2 | 10/2006 | Mastri et al. |
| 7,128,254 B2 | 10/2006 | Shelton, IV et al. |
| 7,128,748 B2 | 10/2006 | Mooradian et al. |
| 7,131,445 B2 | 11/2006 | Amoah |
| 7,133,601 B2 | 11/2006 | Phillips et al. |
| 7,134,587 B2 | 11/2006 | Schwemberger et al. |
| 7,137,981 B2 | 11/2006 | Long |
| 7,140,527 B2 | 11/2006 | Ehrenfels et al. |
| 7,140,528 B2 | 11/2006 | Shelton, IV |
| 7,143,923 B2 | 12/2006 | Shelton, IV et al. |
| 7,143,924 B2 | 12/2006 | Scirica et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,147,139 B2 | 12/2006 | Schwemberger et al. |
| 7,147,140 B2 | 12/2006 | Wukusick et al. |
| 7,147,637 B2 | 12/2006 | Goble |
| 7,147,650 B2 | 12/2006 | Lee |
| 7,150,748 B2 | 12/2006 | Ebbutt et al. |
| 7,153,300 B2 | 12/2006 | Goble |
| 7,156,863 B2 | 1/2007 | Sonnenschein et al. |
| 7,159,750 B2 | 1/2007 | Racenet et al. |
| 7,160,299 B2 | 1/2007 | Baily |
| 7,161,036 B2 | 1/2007 | Oikawa et al. |
| 7,168,604 B2 | 1/2007 | Milliman et al. |
| 7,172,104 B2 | 2/2007 | Scirica et al. |
| 7,172,593 B2 | 2/2007 | Trieu et al. |
| 7,179,223 B2 | 2/2007 | Motoki et al. |
| 7,179,267 B2 | 2/2007 | Nolan et al. |
| 7,182,239 B1 | 2/2007 | Myers |
| 7,182,763 B2 | 2/2007 | Nardella |
| 7,183,737 B2 | 2/2007 | Kitagawa |
| 7,188,758 B2 | 3/2007 | Viola et al. |
| 7,189,207 B2 | 3/2007 | Viola |
| 7,195,627 B2 | 3/2007 | Amoah et al. |
| 7,199,537 B2 | 4/2007 | Okamura et al. |
| 7,202,653 B2 | 4/2007 | Pai |
| 7,204,835 B2 | 4/2007 | Latterell et al. |
| 7,207,233 B2 | 4/2007 | Wadge |
| 7,207,471 B2 | 4/2007 | Heinrich et al. |
| 7,207,472 B2 | 4/2007 | Wukusick et al. |
| 7,207,556 B2 | 4/2007 | Saitoh et al. |
| 7,208,005 B2 | 4/2007 | Frecker et al. |
| 7,210,609 B2 | 5/2007 | Leiboff et |
| 7,211,081 B2 | 5/2007 | Goble |
| 7,211,084 B2 | 5/2007 | Goble et al. |
| 7,211,092 B2 | 5/2007 | Hughett |
| 7,213,736 B2 | 5/2007 | Wales et al. |
| 7,214,224 B2 | 5/2007 | Goble |
| 7,215,517 B2 | 5/2007 | Takamatsu |
| 7,217,285 B2 | 5/2007 | Vargas et al. |
| 7,220,260 B2 | 5/2007 | Fleming et al. |
| 7,220,272 B2 | 5/2007 | Weadock |
| 7,225,963 B2 | 6/2007 | Scirica |
| 7,225,964 B2 | 6/2007 | Mastri et al. |
| 7,234,624 B2 | 6/2007 | Gresham et al. |
| 7,235,089 B1 | 6/2007 | McGuckin, Jr. |
| 7,235,302 B2 | 6/2007 | Jing et al. |
| 7,237,708 B1 | 7/2007 | Guy et al. |
| 7,238,195 B2 | 7/2007 | Viola |
| 7,241,288 B2 | 7/2007 | Braun |
| 7,246,734 B2 | 7/2007 | Shelton, IV |
| 7,247,161 B2 | 7/2007 | Johnston et al. |
| 7,252,660 B2 | 8/2007 | Kunz |
| 7,255,696 B2 | 8/2007 | Goble et al. |
| 7,256,695 B2 | 8/2007 | Hamel et al. |
| 7,258,262 B2 | 8/2007 | Mastri et al. |
| 7,258,546 B2 | 8/2007 | Beier et al. |
| 7,260,431 B2 | 8/2007 | Libbus et al. |
| 7,265,374 B2 | 9/2007 | Lee et al. |
| 7,267,679 B2 | 9/2007 | McGuckin, Jr. et al. |
| 7,273,483 B2 | 9/2007 | Wiener et al. |
| 7,278,562 B2 | 10/2007 | Mastri et al. |
| 7,278,563 B1 | 10/2007 | Green |
| 7,278,949 B2 | 10/2007 | Bader |
| 7,278,994 B2 | 10/2007 | Goble |
| 7,282,048 B2 | 10/2007 | Goble et al. |
| 7,286,850 B2 | 10/2007 | Frielink et al. |
| 7,287,682 B1 | 10/2007 | Ezzat et al. |
| 7,293,685 B2 | 11/2007 | Ehrenfels et al. |
| 7,295,893 B2 | 11/2007 | Sunaoshi |
| 7,295,907 B2 | 11/2007 | Lu et al. |
| 7,296,722 B2 | 11/2007 | Ivanko |
| 7,296,724 B2 | 11/2007 | Green et al. |
| 7,297,149 B2 | 11/2007 | Vitali et al. |
| 7,300,373 B2 | 11/2007 | Jinno et al. |
| 7,300,450 B2 | 11/2007 | Vleugels et al. |
| 7,303,106 B2 | 12/2007 | Milliman et al. |
| 7,303,107 B2 | 12/2007 | Milliman et al. |
| 7,303,108 B2 | 12/2007 | Shelton, IV |
| 7,303,502 B2 | 12/2007 | Thompson |
| 7,303,556 B2 | 12/2007 | Metzger |
| 7,306,597 B2 | 12/2007 | Manzo |
| 7,308,998 B2 | 12/2007 | Mastri et al. |
| 7,322,975 B2 | 1/2008 | Goble et al. |
| 7,322,994 B2 | 1/2008 | Nicholas et al. |
| 7,324,572 B2 | 1/2008 | Chang |
| 7,326,203 B2 | 2/2008 | Papineau et al. |
| 7,326,213 B2 | 2/2008 | Benderev et al. |
| 7,328,828 B2 | 2/2008 | Ortiz et al. |
| 7,328,829 B2 | 2/2008 | Arad et al. |
| 7,330,004 B2 | 2/2008 | DeJonge et al. |
| 7,331,340 B2 | 2/2008 | Barney |
| 7,334,717 B2 | 2/2008 | Rethy et al. |
| 7,334,718 B2 | 2/2008 | McAlister et al. |
| 7,335,199 B2 | 2/2008 | Goble et al. |
| 7,336,048 B2 | 2/2008 | Lohr |
| 7,336,184 B2 | 2/2008 | Smith et al. |
| 7,338,513 B2 | 3/2008 | Lee et al. |
| 7,341,591 B2 | 3/2008 | Grinberg |
| 7,343,920 B2 | 3/2008 | Toby et al. |
| 7,344,532 B2 | 3/2008 | Goble et al. |
| 7,348,763 B1 | 3/2008 | Reinhart et al. |
| RE40,237 E | 4/2008 | Bilotti et al. |
| 7,351,258 B2 | 4/2008 | Ricotta et al. |
| 7,354,447 B2 | 4/2008 | Shelton, IV et al. |
| 7,354,502 B2 | 4/2008 | Polat et al. |
| 7,357,287 B2 | 4/2008 | Shelton, IV et al. |
| 7,357,806 B2 | 4/2008 | Rivera et al. |
| 7,361,195 B2 | 4/2008 | Schwartz et al. |
| 7,364,060 B2 | 4/2008 | Milliman |
| 7,364,061 B2 | 4/2008 | Swayze et al. |
| 7,377,918 B2 | 5/2008 | Amoah |
| 7,377,928 B2 | 5/2008 | Zubik et al. |
| 7,380,695 B2 | 6/2008 | Doll et al. |
| 7,380,696 B2 | 6/2008 | Shelton, IV et al. |
| 7,384,417 B2 | 6/2008 | Cucin |
| 7,386,730 B2 | 6/2008 | Uchikubo |
| 7,388,217 B2 | 6/2008 | Buschbeck et al. |

(56) References Cited

U.S. PATENT DOCUMENTS

| | | |
|---|---|---|
| 7,388,484 B2 | 6/2008 | Hsu |
| 7,391,173 B2 | 6/2008 | Schena |
| 7,396,356 B2 | 7/2008 | Mollenauer |
| 7,397,364 B2 | 7/2008 | Govari |
| 7,398,907 B2 | 7/2008 | Racenet et al. |
| 7,398,908 B2 | 7/2008 | Holsten et al. |
| 7,400,752 B2 | 7/2008 | Zacharias |
| 7,401,721 B2 | 7/2008 | Holsten et al. |
| 7,404,508 B2 | 7/2008 | Smith et al. |
| 7,404,509 B2 | 7/2008 | Ortiz et al. |
| 7,404,822 B2 | 7/2008 | Viart et al. |
| 7,407,074 B2 | 8/2008 | Ortiz et al. |
| 7,407,075 B2 | 8/2008 | Holsten et al. |
| 7,407,076 B2 | 8/2008 | Racenet et al. |
| 7,407,077 B2 | 8/2008 | Ortiz et al. |
| 7,407,078 B2 | 8/2008 | Shelton, IV et al. |
| 7,410,086 B2 | 8/2008 | Ortiz et al. |
| 7,413,563 B2 | 8/2008 | Corcoran et al. |
| 7,416,101 B2 | 8/2008 | Shelton, IV et al. |
| 7,418,078 B2 | 8/2008 | Blanz et al. |
| RE40,514 E | 9/2008 | Mastri et al. |
| 7,419,080 B2 | 9/2008 | Smith et al. |
| 7,419,081 B2 | 9/2008 | Ehrenfels et al. |
| 7,419,495 B2 | 9/2008 | Menn et al. |
| 7,422,136 B1 | 9/2008 | Marczyk |
| 7,422,138 B2 | 9/2008 | Bilotti et al. |
| 7,422,139 B2 | 9/2008 | Shelton, IV et al. |
| 7,424,965 B2 | 9/2008 | Racenet et al. |
| 7,427,607 B2 | 9/2008 | Suzuki |
| 7,431,188 B1 | 10/2008 | Marczyk |
| 7,431,189 B2 | 10/2008 | Shelton, IV et al. |
| 7,431,694 B2 | 10/2008 | Stefanchik et al. |
| 7,431,730 B2 | 10/2008 | Viola |
| 7,434,715 B2 | 10/2008 | Shelton, IV et al. |
| 7,434,717 B2 | 10/2008 | Shelton, IV et al. |
| 7,438,209 B1 | 10/2008 | Hess et al. |
| 7,438,718 B2 | 10/2008 | Milliman et al. |
| 7,439,354 B2 | 10/2008 | Lenges et al. |
| 7,441,684 B2 | 10/2008 | Shelton, IV et al. |
| 7,441,685 B1 | 10/2008 | Boudreaux |
| 7,442,201 B2 | 10/2008 | Pugsley et al. |
| 7,448,525 B2 | 11/2008 | Shelton, IV et al. |
| 7,451,904 B2 | 11/2008 | Shelton, IV |
| 7,455,208 B2 | 11/2008 | Wales et al. |
| 7,455,676 B2 | 11/2008 | Holsten et al. |
| 7,455,682 B2 | 11/2008 | Viola |
| 7,461,767 B2 | 12/2008 | Viola et al. |
| 7,462,187 B2 | 12/2008 | Johnston et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,467,740 B2 | 12/2008 | Shelton, IV et al. |
| 7,467,849 B2 | 12/2008 | Silverbrook et al. |
| 7,472,814 B2 | 1/2009 | Mastri et al. |
| 7,472,815 B2 | 1/2009 | Shelton, IV et al. |
| 7,472,816 B2 | 1/2009 | Holsten et al. |
| 7,473,253 B2 | 1/2009 | Dycus et al. |
| 7,473,263 B2 | 1/2009 | Johnston et al. |
| 7,479,608 B2 | 1/2009 | Smith |
| 7,481,347 B2 | 1/2009 | Roy |
| 7,481,348 B2 | 1/2009 | Marczyk |
| 7,481,349 B2 | 1/2009 | Holsten et al. |
| 7,481,824 B2 | 1/2009 | Boudreaux et al. |
| 7,485,133 B2 | 2/2009 | Cannon et al. |
| 7,485,142 B2 | 2/2009 | Milo |
| 7,487,899 B2 | 2/2009 | Shelton, IV et al. |
| 7,490,749 B2 | 2/2009 | Schall et al. |
| 7,494,039 B2 | 2/2009 | Racenet et al. |
| 7,494,499 B2 | 2/2009 | Nagase et al. |
| 7,494,501 B2 | 2/2009 | Ahlberg et al. |
| 7,500,979 B2 | 3/2009 | Hueil et al. |
| 7,501,198 B2 | 3/2009 | Barlev et al. |
| 7,503,474 B2 | 3/2009 | Hillstead et al. |
| 7,506,790 B2 | 3/2009 | Shelton, IV |
| 7,506,791 B2 | 3/2009 | Omaits et al. |
| 7,507,202 B2 | 3/2009 | Schoellhorn |
| 7,510,107 B2 | 3/2009 | Timm et al. |
| 7,510,566 B2 | 3/2009 | Jacobs et al. |
| 7,513,408 B2 | 4/2009 | Shelton, IV et al. |
| 7,517,356 B2 | 4/2009 | Heinrich |
| 7,524,320 B2 | 4/2009 | Tierney et al. |
| 7,530,984 B2 | 5/2009 | Sonnenschein et al. |
| 7,530,985 B2 | 5/2009 | Takemoto et al. |
| 7,533,906 B2 | 5/2009 | Luettgen et al. |
| 7,534,259 B2 | 5/2009 | Lashinski et al. |
| 7,540,867 B2 | 6/2009 | Jinno et al. |
| 7,546,939 B2 | 6/2009 | Adams et al. |
| 7,546,940 B2 | 6/2009 | Milliman et al. |
| 7,547,312 B2 | 6/2009 | Bauman et al. |
| 7,549,563 B2 | 6/2009 | Mather et al. |
| 7,549,564 B2 | 6/2009 | Boudreaux |
| 7,549,998 B2 | 6/2009 | Braun |
| 7,552,854 B2 | 6/2009 | Wixey et al. |
| 7,556,185 B2 | 7/2009 | Viola |
| 7,556,186 B2 | 7/2009 | Milliman |
| 7,556,647 B2 | 7/2009 | Drews et al. |
| 7,559,449 B2 | 7/2009 | Viola |
| 7,559,450 B2 | 7/2009 | Wales et al. |
| 7,559,452 B2 | 7/2009 | Wales et al. |
| 7,559,937 B2 | 7/2009 | de la Torre et al. |
| 7,562,910 B2 | 7/2009 | Kertesz et al. |
| 7,563,862 B2 | 7/2009 | Sieg et al. |
| 7,565,993 B2 | 7/2009 | Milliman et al. |
| 7,566,300 B2 | 7/2009 | Devierre et al. |
| 7,567,045 B2 | 7/2009 | Fristedt |
| 7,568,603 B2 | 8/2009 | Shelton, IV et al. |
| 7,568,604 B2 | 8/2009 | Ehrenfels et al. |
| 7,568,619 B2 | 8/2009 | Todd et al. |
| 7,575,144 B2 | 8/2009 | Ortiz et al. |
| 7,588,174 B2 | 9/2009 | Holsten et al. |
| 7,588,175 B2 | 9/2009 | Timm et al. |
| 7,588,176 B2 | 9/2009 | Timm et al. |
| 7,588,177 B2 | 9/2009 | Racenet |
| 7,591,783 B2 | 9/2009 | Boulais et al. |
| 7,597,229 B2 | 10/2009 | Boudreaux et al. |
| 7,597,230 B2 | 10/2009 | Racenet et al. |
| 7,600,663 B2 | 10/2009 | Green |
| 7,604,150 B2 | 10/2009 | Boudreaux |
| 7,604,151 B2 | 10/2009 | Hess et al. |
| 7,607,557 B2 | 10/2009 | Shelton, IV et al. |
| 7,611,038 B2 | 11/2009 | Racenet et al. |
| 7,611,474 B2 | 11/2009 | Hibner et al. |
| 7,615,003 B2 | 11/2009 | Stefanchik et al. |
| 7,615,067 B2 | 11/2009 | Lee et al. |
| 7,617,961 B2 | 11/2009 | Viola |
| 7,624,902 B2 | 12/2009 | Marczyk et al. |
| 7,624,903 B2 | 12/2009 | Green et al. |
| 7,625,370 B2 | 12/2009 | Hart et al. |
| 7,631,793 B2 | 12/2009 | Rethy et al. |
| 7,631,794 B2 | 12/2009 | Rethy et al. |
| 7,635,074 B2 | 12/2009 | Olson et al. |
| 7,637,409 B2 | 12/2009 | Marczyk |
| 7,637,410 B2 | 12/2009 | Marczyk |
| 7,638,958 B2 | 12/2009 | Philipp et al. |
| 7,641,091 B2 | 1/2010 | Olson et al. |
| 7,641,092 B2 | 1/2010 | Kruszynski et al. |
| 7,641,093 B2 | 1/2010 | Doll et al. |
| 7,641,095 B2 | 1/2010 | Viola |
| 7,644,783 B2 | 1/2010 | Roberts et al. |
| 7,644,848 B2 | 1/2010 | Swayze et al. |
| 7,645,230 B2 | 1/2010 | Mikkaichi et al. |
| 7,648,519 B2 | 1/2010 | Lee et al. |
| 7,650,185 B2 | 1/2010 | Maile et al. |
| 7,651,017 B2 | 1/2010 | Ortiz et al. |
| 7,651,498 B2 | 1/2010 | Shifrin et al. |
| 7,654,431 B2 | 2/2010 | Hueil et al. |
| 7,655,288 B2 | 2/2010 | Bauman et al. |
| 7,656,131 B2 | 2/2010 | Embrey et al. |
| 7,658,311 B2 | 2/2010 | Boudreaux |
| 7,658,312 B2 | 2/2010 | Vidal et al. |
| 7,659,219 B2 | 2/2010 | Biran et al. |
| 7,662,161 B2 | 2/2010 | Briganti et al. |
| 7,665,646 B2 | 2/2010 | Prommersberger |
| 7,665,647 B2 | 2/2010 | Shelton, IV et al. |

(56) References Cited

U.S. PATENT DOCUMENTS

| | | |
|---|---|---|
| 7,669,746 B2 | 3/2010 | Shelton, IV |
| 7,669,747 B2 | 3/2010 | Weisenburgh, II et al. |
| 7,670,334 B2 | 3/2010 | Hueil et al. |
| 7,673,780 B2 | 3/2010 | Shelton, IV et al. |
| 7,673,781 B2 | 3/2010 | Swayze et al. |
| 7,673,782 B2 | 3/2010 | Hess et al. |
| 7,673,783 B2 | 3/2010 | Morgan et al. |
| 7,674,253 B2 | 3/2010 | Fisher et al. |
| 7,674,255 B2 | 3/2010 | Braun |
| 7,674,263 B2 | 3/2010 | Ryan |
| 7,674,270 B2 | 3/2010 | Layer |
| 7,682,307 B2 | 3/2010 | Danitz et al. |
| 7,686,201 B2 | 3/2010 | Csiky |
| 7,686,826 B2 | 3/2010 | Lee et al. |
| 7,688,028 B2 | 3/2010 | Phillips et al. |
| 7,691,098 B2 | 4/2010 | Wallace et al. |
| 7,691,106 B2 | 4/2010 | Schenberger et al. |
| 7,694,865 B2 | 4/2010 | Scirica |
| 7,695,485 B2 | 4/2010 | Whitman et al. |
| 7,699,204 B2 | 4/2010 | Viola |
| 7,699,835 B2 | 4/2010 | Lee et al. |
| 7,699,844 B2 | 4/2010 | Utley et al. |
| 7,699,846 B2 | 4/2010 | Ryan |
| 7,699,856 B2 | 4/2010 | Van Wyk et al. |
| 7,699,859 B2 | 4/2010 | Bombard et al. |
| 7,699,860 B2 | 4/2010 | Huitema et al. |
| 7,703,653 B2 | 4/2010 | Shah et al. |
| 7,708,180 B2 | 5/2010 | Murray et al. |
| 7,708,181 B2 | 5/2010 | Cole et al. |
| 7,708,758 B2 | 5/2010 | Lee et al. |
| 7,714,239 B2 | 5/2010 | Smith |
| 7,717,312 B2 | 5/2010 | Beetel |
| 7,717,313 B2 | 5/2010 | Criscuolo et al. |
| 7,717,846 B2 | 5/2010 | Zirps et al. |
| 7,718,180 B2 | 5/2010 | Karp |
| 7,718,556 B2 | 5/2010 | Matsuda et al. |
| 7,721,930 B2 | 5/2010 | McKenna et al. |
| 7,721,931 B2 | 5/2010 | Shelton, IV et al. |
| 7,721,933 B2 | 5/2010 | Ehrenfels et al. |
| 7,721,934 B2 | 5/2010 | Shelton, IV et al. |
| 7,721,936 B2 | 5/2010 | Shalton, IV et al. |
| 7,722,527 B2 | 5/2010 | Bouchier et al. |
| 7,722,607 B2 | 5/2010 | Dumbauld et al. |
| 7,722,610 B2 | 5/2010 | Viola et al. |
| 7,726,537 B2 | 6/2010 | Olson et al. |
| 7,726,538 B2 | 6/2010 | Holsten et al. |
| 7,726,539 B2 | 6/2010 | Holsten et al. |
| 7,727,954 B2 | 6/2010 | McKay |
| 7,729,742 B2 | 6/2010 | Govari |
| 7,731,072 B2 | 6/2010 | Timm et al. |
| 7,731,073 B2 | 6/2010 | Wixey et al. |
| 7,731,724 B2 | 6/2010 | Huitema et al. |
| 7,735,703 B2 | 6/2010 | Morgan et al. |
| 7,736,374 B2 | 6/2010 | Vaughan et al. |
| 7,738,971 B2 | 6/2010 | Swayze et al. |
| 7,740,159 B2 | 6/2010 | Shelton, IV et al. |
| 7,742,036 B2 | 6/2010 | Grant et al. |
| 7,743,960 B2 | 6/2010 | Whitman et al. |
| 7,744,624 B2 | 6/2010 | Bettuchi |
| 7,744,627 B2 | 6/2010 | Orban, III et al. |
| 7,744,628 B2 | 6/2010 | Viola |
| 7,748,587 B2 | 7/2010 | Haramiishi et al. |
| 7,749,204 B2 | 7/2010 | Dhanaraj et al. |
| 7,751,870 B2 | 7/2010 | Whitman |
| 7,753,245 B2 | 7/2010 | Boudreaux et al. |
| 7,753,904 B2 | 7/2010 | Shelton, IV et al. |
| 7,758,612 B2 | 7/2010 | Shipp |
| 7,766,209 B2 | 8/2010 | Baxter, III et al. |
| 7,766,210 B2 | 8/2010 | Shelton, IV et al. |
| 7,766,821 B2 | 8/2010 | Brunnen et al. |
| 7,766,894 B2 | 8/2010 | Weitzner et al. |
| 7,770,773 B2 | 8/2010 | Whitman et al. |
| 7,770,774 B2 | 8/2010 | Mastri et al. |
| 7,770,775 B2 | 8/2010 | Shelton, IV et al. |
| 7,770,776 B2 | 8/2010 | Chen et al. |
| 7,771,396 B2 | 8/2010 | Stefanchik et al. |
| 7,772,720 B2 | 8/2010 | McGee et al. |
| 7,776,037 B2 | 8/2010 | Odom |
| 7,776,060 B2 | 8/2010 | Mooradian et al. |
| 7,778,004 B2 | 8/2010 | Nerheim et al. |
| 7,780,054 B2 | 8/2010 | Wales |
| 7,780,055 B2 | 8/2010 | Scirica et al. |
| 7,780,663 B2 | 8/2010 | Yates et al. |
| 7,780,685 B2 | 8/2010 | Hunt et al. |
| 7,784,662 B2 | 8/2010 | Wales et al. |
| 7,784,663 B2 | 8/2010 | Shelton, IV |
| 7,787,256 B2 | 8/2010 | Chan et al. |
| 7,789,875 B2 | 9/2010 | Brock et al. |
| 7,789,883 B2 | 9/2010 | Takashino et al. |
| 7,789,889 B2 | 9/2010 | Zubik et al. |
| 7,793,812 B2 | 9/2010 | Moore et al. |
| 7,794,475 B2 | 9/2010 | Hess et al. |
| 7,798,386 B2 | 9/2010 | Schall et al. |
| 7,799,039 B2 | 9/2010 | Shelton, IV et al. |
| 7,799,044 B2 | 9/2010 | Johnston et al. |
| 7,799,965 B2 | 9/2010 | Patel et al. |
| 7,803,151 B2 | 9/2010 | Whitman |
| 7,806,891 B2 | 10/2010 | Nowlin et al. |
| 7,810,690 B2 | 10/2010 | Bilotti et al. |
| 7,810,691 B2 | 10/2010 | Boyden et al. |
| 7,810,692 B2 | 10/2010 | Hall et al. |
| 7,810,693 B2 | 10/2010 | Broehl et al. |
| 7,815,092 B2 | 10/2010 | Whitman et al. |
| 7,815,565 B2 | 10/2010 | Stefanchik et al. |
| 7,819,296 B2 | 10/2010 | Hueil et al. |
| 7,819,297 B2 | 10/2010 | Doll et al. |
| 7,819,298 B2 | 10/2010 | Hall et al. |
| 7,819,299 B2 | 10/2010 | Shelton, IV et al. |
| 7,819,886 B2 | 10/2010 | Whitfield et al. |
| 7,823,592 B2 | 11/2010 | Bettuchi et al. |
| 7,823,760 B2 | 11/2010 | Zemlok et al. |
| 7,824,401 B2 | 11/2010 | Manzo et al. |
| 7,824,426 B2 | 11/2010 | Racenet et al. |
| 7,828,189 B2 | 11/2010 | Holsten et al. |
| 7,828,794 B2 | 11/2010 | Sartor |
| 7,828,808 B2 | 11/2010 | Hinman et al. |
| 7,832,408 B2 | 11/2010 | Shelton, IV et al. |
| 7,832,611 B2 | 11/2010 | Boyden et al. |
| 7,832,612 B2 | 11/2010 | Baxter, III et al. |
| 7,833,234 B2 | 11/2010 | Bailly et al. |
| 7,836,400 B2 | 11/2010 | May et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,837,694 B2 | 11/2010 | Tethrake et al. |
| 7,838,789 B2 | 11/2010 | Stoffers et al. |
| 7,841,503 B2 | 11/2010 | Sonnenschein et al. |
| 7,842,025 B2 | 11/2010 | Coleman et al. |
| 7,842,028 B2 | 11/2010 | Lee |
| 7,845,533 B2 | 12/2010 | Marczyk et al. |
| 7,845,534 B2 | 12/2010 | Viola et al. |
| 7,845,535 B2 | 12/2010 | Scircia |
| 7,845,536 B2 | 12/2010 | Viola et al. |
| 7,845,537 B2 | 12/2010 | Shelton, IV et al. |
| 7,846,149 B2 | 12/2010 | Jankowski |
| 7,850,642 B2 | 12/2010 | Moll et al. |
| 7,850,982 B2 | 12/2010 | Stopek et al. |
| 7,854,736 B2 | 12/2010 | Ryan |
| 7,857,183 B2 | 12/2010 | Shelton, IV |
| 7,857,185 B2 | 12/2010 | Swayze et al. |
| 7,857,186 B2 | 12/2010 | Baxter, III et al. |
| 7,857,813 B2 | 12/2010 | Schmitz et al. |
| 7,861,906 B2 | 1/2011 | Doll et al. |
| 7,862,579 B2 | 1/2011 | Ortiz et al. |
| 7,866,525 B2 | 1/2011 | Scirica |
| 7,866,527 B2 | 1/2011 | Hall et al. |
| 7,866,528 B2 | 1/2011 | Olson et al. |
| 7,870,989 B2 | 1/2011 | Viola et al. |
| 7,871,418 B2 | 1/2011 | Thompson et al. |
| 7,879,070 B2 | 2/2011 | Ortiz et al. |
| 7,883,465 B2 | 2/2011 | Donofrio et al. |
| 7,886,951 B2 | 2/2011 | Hessler |
| 7,886,952 B2 | 2/2011 | Scirica et al. |
| 7,887,530 B2 | 2/2011 | Zemlok et al. |

(56) References Cited

U.S. PATENT DOCUMENTS

| | | |
|---|---|---|
| 7,887,535 B2 | 2/2011 | Lands et al. |
| 7,891,531 B1 | 2/2011 | Ward |
| 7,891,532 B2 | 2/2011 | Mastri et al. |
| 7,892,245 B2 | 2/2011 | Liddicoat et al. |
| 7,893,586 B2 | 2/2011 | West et al. |
| 7,896,214 B2 | 3/2011 | Farascioni |
| 7,896,215 B2 | 3/2011 | Adams et al. |
| 7,896,877 B2 | 3/2011 | Hall et al. |
| 7,896,895 B2 | 3/2011 | Boudreaux et al. |
| 7,900,805 B2 | 3/2011 | Shelton, IV et al. |
| 7,905,380 B2 | 3/2011 | Shelton, IV et al. |
| 7,905,381 B2 | 3/2011 | Baxter, III et al. |
| 7,905,889 B2 | 3/2011 | Catanese, III et al. |
| 7,905,902 B2 | 3/2011 | Huitema et al. |
| 7,909,191 B2 | 3/2011 | Baker et al. |
| 7,909,220 B2 | 3/2011 | Viola |
| 7,909,221 B2 | 3/2011 | Viola et al. |
| 7,913,891 B2 | 3/2011 | Doll et al. |
| 7,913,893 B2 | 3/2011 | Mastri et al. |
| 7,914,543 B2 | 3/2011 | Roth et al. |
| 7,914,551 B2 | 3/2011 | Ortiz et al. |
| 7,918,230 B2 | 4/2011 | Whitman et al. |
| 7,918,376 B1 | 4/2011 | Knodel et al. |
| 7,918,377 B2 | 4/2011 | Measamer et al. |
| 7,918,848 B2 | 4/2011 | Lau et al. |
| 7,922,061 B2 | 4/2011 | Shelton, IV et al. |
| 7,922,063 B2 | 4/2011 | Zemlok et al. |
| 7,922,743 B2 | 4/2011 | Heinrich et al. |
| 7,926,691 B2 | 4/2011 | Viola et al. |
| 7,927,328 B2 | 4/2011 | Orszulak et al. |
| 7,928,281 B2 | 4/2011 | Augustine |
| 7,930,065 B2 | 4/2011 | Larkin et al. |
| 7,931,660 B2 | 4/2011 | Aranyi et al. |
| 7,931,695 B2 | 4/2011 | Ringeisen |
| 7,934,630 B2 | 5/2011 | Shelton, IV et al. |
| 7,934,631 B2 | 5/2011 | Balbierz et al. |
| 7,935,773 B2 | 5/2011 | Hadba et al. |
| 7,938,307 B2 | 5/2011 | Bettuchi |
| 7,941,865 B2 | 5/2011 | Seman, Jr. et al. |
| 7,942,303 B2 | 5/2011 | Shah |
| 7,942,890 B2 | 5/2011 | D'Agostino et al. |
| 7,944,175 B2 | 5/2011 | Mori et al. |
| 7,950,560 B2 | 5/2011 | Zemlok et al. |
| 7,950,561 B2 | 5/2011 | Aranyi |
| 7,951,071 B2 | 5/2011 | Whitman et al. |
| 7,951,166 B2 | 5/2011 | Orban et al. |
| 7,954,682 B2 | 6/2011 | Giordano et al. |
| 7,954,684 B2 | 6/2011 | Boudreaux |
| 7,954,686 B2 | 6/2011 | Baxter, III et al. |
| 7,954,687 B2 | 6/2011 | Zemlok et al. |
| 7,955,257 B2 | 6/2011 | Frasier et al. |
| 7,955,322 B2 | 6/2011 | Devengenzo et al. |
| 7,959,050 B2 | 6/2011 | Smith et al. |
| 7,959,051 B2 | 6/2011 | Smith et al. |
| 7,959,052 B2 | 6/2011 | Sonnenschein et al. |
| 7,963,432 B2 | 6/2011 | Knodel et al. |
| 7,963,433 B2 | 6/2011 | Whitman et al. |
| 7,963,963 B2 | 6/2011 | Francischelli et al. |
| 7,963,964 B2 | 6/2011 | Santilli et al. |
| 7,966,799 B2 | 6/2011 | Morgan et al. |
| 7,967,178 B2 | 6/2011 | Scirica et al. |
| 7,967,179 B2 | 6/2011 | Olson et al. |
| 7,967,180 B2 | 6/2011 | Scirica |
| 7,967,181 B2 | 6/2011 | Viola et al. |
| 7,967,839 B2 | 6/2011 | Flock et al. |
| 7,972,298 B2 | 7/2011 | Wallace et al. |
| 7,980,443 B2 | 7/2011 | Scheib et al. |
| 7,988,026 B2 | 8/2011 | Knodel et al. |
| 7,988,027 B2 | 8/2011 | Olson et al. |
| 7,988,028 B2 | 8/2011 | Farascioni et al. |
| 7,992,757 B2 | 8/2011 | Wheeler et al. |
| 7,997,468 B2 | 8/2011 | Farascioni |
| 7,997,469 B2 | 8/2011 | Olson et al. |
| 8,002,696 B2 | 8/2011 | Suzuki |
| 8,002,784 B2 | 8/2011 | Jinno et al. |
| 8,002,785 B2 | 8/2011 | Weiss et al. |
| 8,002,795 B2 | 8/2011 | Beetel |
| 8,006,365 B2 | 8/2011 | Levin et al. |
| 8,006,885 B2 | 8/2011 | Marczyk |
| 8,006,889 B2 | 8/2011 | Adams et al. |
| 8,007,511 B2 | 8/2011 | Brock et al. |
| 8,011,550 B2 | 9/2011 | Aranyi et al. |
| 8,011,551 B2 | 9/2011 | Marczyk et al. |
| 8,011,553 B2 | 9/2011 | Mastri et al. |
| 8,011,555 B2 | 9/2011 | Tarinelli et al. |
| 8,012,170 B2 | 9/2011 | Whitman et al. |
| 8,016,176 B2 | 9/2011 | Kasvikis et al. |
| 8,016,177 B2 | 9/2011 | Bettuchi et al. |
| 8,016,178 B2 | 9/2011 | Olson et al. |
| 8,016,855 B2 | 9/2011 | Whitman et al. |
| 8,016,858 B2 | 9/2011 | Whitman |
| 8,016,881 B2 | 9/2011 | Furst |
| 8,020,742 B2 | 9/2011 | Marczyk |
| 8,020,743 B2 | 9/2011 | Shelton, IV |
| 8,021,375 B2 | 9/2011 | Aldrich et al. |
| 8,025,199 B2 | 9/2011 | Whitman et al. |
| 8,028,883 B2 | 10/2011 | Stopek |
| 8,028,884 B2 | 10/2011 | Sniffin et al. |
| 8,028,885 B2 | 10/2011 | Smith et al. |
| 8,034,077 B2 | 10/2011 | Smith et al. |
| 8,034,363 B2 | 10/2011 | Li et al. |
| 8,037,591 B2 | 10/2011 | Spivey et al. |
| 8,038,045 B2 | 10/2011 | Bettuchi et al. |
| 8,038,046 B2 | 10/2011 | Smith et al. |
| 8,038,686 B2 | 10/2011 | Huitema et al. |
| 8,043,207 B2 | 10/2011 | Adams |
| 8,043,328 B2 | 10/2011 | Hahnen et al. |
| 8,047,236 B2 | 11/2011 | Perry |
| 8,048,503 B2 | 11/2011 | Farnsworth et al. |
| 8,056,787 B2 | 11/2011 | Boudreaux et al. |
| 8,056,788 B2 | 11/2011 | Mastri et al. |
| 8,057,508 B2 | 11/2011 | Shelton, IV |
| 8,058,771 B2 | 11/2011 | Giordano et al. |
| 8,061,576 B2 | 11/2011 | Cappola |
| 8,062,330 B2 | 11/2011 | Prommersberger et al. |
| 8,066,167 B2 | 11/2011 | Measamer et al. |
| 8,066,168 B2 | 11/2011 | Vidal et al. |
| D650,074 S | 12/2011 | Hunt et al. |
| 8,070,035 B2 | 12/2011 | Holsten et al. |
| 8,070,743 B2 | 12/2011 | Kagan et al. |
| 8,075,571 B2 | 12/2011 | Vitali et al. |
| 8,083,118 B2 | 12/2011 | Milliman et al. |
| 8,083,119 B2 | 12/2011 | Prommersberger |
| 8,083,120 B2 | 12/2011 | Shelton, IV et al. |
| 8,084,001 B2 | 12/2011 | Burns et al. |
| 8,085,013 B2 | 12/2011 | Wei et al. |
| 8,091,756 B2 | 1/2012 | Viola |
| 8,092,443 B2 | 1/2012 | Bischoff |
| 8,092,932 B2 | 1/2012 | Phillips et al. |
| 8,096,458 B2 | 1/2012 | Hessler |
| 8,097,017 B2 | 1/2012 | Viola |
| 8,100,310 B2 | 1/2012 | Zemlok |
| 8,100,872 B2 | 1/2012 | Patel |
| 8,102,278 B2 | 1/2012 | Deck et al. |
| 8,105,350 B2 | 1/2012 | Lee et al. |
| 8,108,072 B2 | 1/2012 | Zhao et al. |
| 8,109,426 B2 | 2/2012 | Milliman et al. |
| 8,110,208 B1 | 2/2012 | Hen |
| 8,113,405 B2 | 2/2012 | Milliman |
| 8,113,410 B2 | 2/2012 | Hall et al. |
| 8,114,100 B2 | 2/2012 | Smith et al. |
| 8,123,103 B2 | 2/2012 | Milliman |
| 8,123,766 B2 | 2/2012 | Bauman et al. |
| 8,123,767 B2 | 2/2012 | Bauman et al. |
| 8,127,975 B2 | 3/2012 | Olson et al. |
| 8,127,976 B2 | 3/2012 | Scirica et al. |
| 8,128,624 B2 | 3/2012 | Couture et al. |
| 8,128,643 B2 | 3/2012 | Aranyi et al. |
| 8,128,645 B2 | 3/2012 | Sonnenschein et al. |
| 8,132,703 B2 | 3/2012 | Milliman et al. |
| 8,132,706 B2 | 3/2012 | Marczyk et al. |
| 8,134,306 B2 | 3/2012 | Drader et al. |
| 8,136,712 B2 | 3/2012 | Zingman |
| 8,136,713 B2 | 3/2012 | Hathaway et al. |

(56) References Cited

U.S. PATENT DOCUMENTS

| | | |
|---|---|---|
| 8,140,417 B2 | 3/2012 | Shibata |
| 8,141,762 B2 | 3/2012 | Bedi et al. |
| 8,141,763 B2 | 3/2012 | Milliman |
| 8,142,425 B2 | 3/2012 | Eggers |
| 8,146,790 B2 | 4/2012 | Milliman |
| 8,147,485 B2 | 4/2012 | Wham et al. |
| 8,152,041 B2 | 4/2012 | Kostrzewski |
| 8,157,145 B2 | 4/2012 | Shelton, IV et al. |
| 8,157,148 B2 | 4/2012 | Scirica |
| 8,157,151 B2 | 4/2012 | Ingmanson et al. |
| 8,157,152 B2 | 4/2012 | Holsten et al. |
| 8,157,153 B2 | 4/2012 | Shelton, IV et al. |
| 8,157,793 B2 | 4/2012 | Omori et al. |
| 8,161,977 B2 | 4/2012 | Shelton, IV et al. |
| 8,162,138 B2 | 4/2012 | Bettenhausen et al. |
| 8,162,197 B2 | 4/2012 | Mastri et al. |
| 8,167,185 B2 | 5/2012 | Shelton, IV et al. |
| 8,167,895 B2 | 5/2012 | D'Agostino et al. |
| 8,167,898 B1 | 5/2012 | Schaller et al. |
| 8,170,241 B2 | 5/2012 | Roe et al. |
| 8,172,120 B2 | 5/2012 | Boyden et al. |
| 8,172,122 B2 | 5/2012 | Kasvikis et al. |
| 8,172,124 B2 | 5/2012 | Shelton, IV et al. |
| 8,177,797 B2 | 5/2012 | Shimoji et al. |
| 8,180,458 B2 | 5/2012 | Kane et al. |
| 8,181,840 B2 | 5/2012 | Milliman |
| 8,186,555 B2 | 5/2012 | Shelton, IV et al. |
| 8,186,560 B2 | 5/2012 | Hess et al. |
| 8,191,752 B2 | 6/2012 | Scirica |
| 8,192,460 B2 | 6/2012 | Orban, III et al. |
| 8,196,795 B2 | 6/2012 | Moore et al. |
| 8,196,796 B2 | 6/2012 | Shelton, IV et al. |
| 8,201,720 B2 | 6/2012 | Hessler |
| 8,201,721 B2 | 6/2012 | Zemlok et al. |
| 8,205,779 B2 | 6/2012 | Ma |
| 8,205,780 B2 | 6/2012 | Sorrentino et al. |
| 8,205,781 B2 | 6/2012 | Baxter, III et al. |
| 8,210,411 B2 | 7/2012 | Yates et al. |
| 8,210,414 B2 | 7/2012 | Bettuchi et al. |
| 8,210,415 B2 | 7/2012 | Ward |
| 8,210,416 B2 | 7/2012 | Milliman et al. |
| 8,211,125 B2 | 7/2012 | Spivey |
| 8,214,019 B2 | 7/2012 | Govari et al. |
| 8,215,531 B2 | 7/2012 | Shelton, IV et al. |
| 8,215,533 B2 | 7/2012 | Viola et al. |
| 8,220,468 B2 | 7/2012 | Cooper et al. |
| 8,220,688 B2 | 7/2012 | Laurent et al. |
| 8,220,690 B2 | 7/2012 | Hess et al. |
| 8,221,424 B2 | 7/2012 | Cha |
| 8,225,799 B2 | 7/2012 | Bettuchi |
| 8,226,715 B2 | 7/2012 | Hwang et al. |
| 8,227,946 B2 | 7/2012 | Kim |
| 8,228,048 B2 | 7/2012 | Spencer |
| 8,231,040 B2 | 7/2012 | Zemlok et al. |
| 8,231,041 B2 | 7/2012 | Marczyk et al. |
| 8,231,042 B2 | 7/2012 | Hessler et al. |
| 8,231,043 B2 | 7/2012 | Tarinelli et al. |
| 8,236,010 B2 | 8/2012 | Ortiz et al. |
| 8,241,271 B2 | 8/2012 | Millman et al. |
| 8,241,308 B2 | 8/2012 | Kortenbach et al. |
| 8,241,322 B2 | 8/2012 | Whitman et al. |
| 8,245,594 B2 | 8/2012 | Rogers et al. |
| 8,245,898 B2 | 8/2012 | Smith et al. |
| 8,245,899 B2 | 8/2012 | Swensgard et al. |
| 8,245,900 B2 | 8/2012 | Scirica |
| 8,245,901 B2 | 8/2012 | Stopek |
| 8,246,637 B2 | 8/2012 | Viola et al. |
| 8,256,654 B2 | 9/2012 | Bettuchi et al. |
| 8,256,655 B2 | 9/2012 | Sniffin et al. |
| 8,256,656 B2 | 9/2012 | Milliman et al. |
| 8,257,251 B2 | 9/2012 | Shelton, IV et al. |
| 8,257,356 B2 | 9/2012 | Bleich et al. |
| 8,257,391 B2 | 9/2012 | Orban, III et al. |
| 8,262,655 B2 | 9/2012 | Ghabrial et al. |
| 8,267,300 B2 | 9/2012 | Boudreaux |
| 8,267,924 B2 | 9/2012 | Zemlok et al. |
| 8,267,946 B2 | 9/2012 | Whitfield et al. |
| 8,267,951 B2 | 9/2012 | Whayne et al. |
| 8,269,121 B2 | 9/2012 | Smith |
| 8,272,553 B2 | 9/2012 | Mastri et al. |
| 8,272,554 B2 | 9/2012 | Whitman et al. |
| 8,273,404 B2 | 9/2012 | Dave et al. |
| 8,276,801 B2 | 10/2012 | Zemlok et al. |
| 8,276,802 B2 | 10/2012 | Kostrzewski |
| 8,281,973 B2 | 10/2012 | Wenchell et al. |
| 8,281,974 B2 | 10/2012 | Hessler et al. |
| 8,286,845 B2 | 10/2012 | Perry et al. |
| 8,287,561 B2 | 10/2012 | Nunez et al. |
| 8,292,151 B2 | 10/2012 | Viola |
| 8,292,155 B2 | 10/2012 | Shelton, IV et al. |
| 8,292,157 B2 | 10/2012 | Smith et al. |
| 8,292,888 B2 | 10/2012 | Whitman |
| 8,298,161 B2 | 10/2012 | Vargas |
| 8,298,677 B2 | 10/2012 | Wiesner et al. |
| 8,302,323 B2 | 11/2012 | Fortier et al. |
| 8,308,040 B2 | 11/2012 | Huang et al. |
| 8,308,042 B2 | 11/2012 | Aranyi |
| 8,308,046 B2 | 11/2012 | Prommersberger |
| 8,308,659 B2 | 11/2012 | Scheibe et al. |
| 8,313,496 B2 | 11/2012 | Sauer et al. |
| 8,313,509 B2 | 11/2012 | Kostrzewski |
| 8,317,070 B2 | 11/2012 | Hueil et al. |
| 8,317,071 B1 | 11/2012 | Knodel |
| 8,317,074 B2 | 11/2012 | Ortiz et al. |
| 8,317,790 B2 | 11/2012 | Bell et al. |
| 8,319,002 B2 | 11/2012 | Daniels et al. |
| 8,322,455 B2 | 12/2012 | Shelton, IV et al. |
| 8,322,589 B2 | 12/2012 | Boudreaux |
| 8,322,590 B2 | 12/2012 | Patel et al. |
| 8,323,789 B2 | 12/2012 | Rozhin et al. |
| 8,328,061 B2 | 12/2012 | Kasvikis |
| 8,328,062 B2 | 12/2012 | Viola |
| 8,328,063 B2 | 12/2012 | Milliman et al. |
| 8,328,064 B2 | 12/2012 | Racenet et al. |
| 8,328,802 B2 | 12/2012 | Deville et al. |
| 8,328,823 B2 | 12/2012 | Aranyi et al. |
| 8,333,313 B2 | 12/2012 | Boudreaux et al. |
| 8,333,764 B2 | 12/2012 | Francischelli et al. |
| 8,336,753 B2 | 12/2012 | Olson et al. |
| 8,336,754 B2 | 12/2012 | Cappola et al. |
| 8,342,378 B2 | 1/2013 | Marczyk et al. |
| 8,342,379 B2 | 1/2013 | Whitman et al. |
| 8,348,123 B2 | 1/2013 | Scirica et al. |
| 8,348,126 B2 | 1/2013 | Olson et al. |
| 8,348,127 B2 | 1/2013 | Marczyk |
| 8,348,129 B2 | 1/2013 | Bedi et al. |
| 8,348,130 B2 | 1/2013 | Shah et al. |
| 8,348,131 B2 | 1/2013 | Omaits et al. |
| 8,348,972 B2 | 1/2013 | Soltz et al. |
| 8,353,437 B2 | 1/2013 | Boudreaux |
| 8,353,438 B2 | 1/2013 | Baxter, III et al. |
| 8,353,439 B2 | 1/2013 | Baxter, III et al. |
| 8,357,144 B2 | 1/2013 | Whitman et al. |
| 8,360,296 B2 | 1/2013 | Zingman |
| 8,360,297 B2 | 1/2013 | Shelton, IV et al. |
| 8,360,298 B2 | 1/2013 | Farascioni et al. |
| 8,360,299 B2 | 1/2013 | Zemlok et al. |
| 8,361,501 B2 | 1/2013 | DiTizio et al. |
| 8,365,973 B1 | 2/2013 | White et al. |
| 8,365,975 B1 | 2/2013 | Manoux et al. |
| 8,365,976 B2 | 2/2013 | Hess et al. |
| 8,366,559 B2 | 2/2013 | Papenfuss et al. |
| 8,371,491 B2 | 2/2013 | Huitema et al. |
| 8,371,492 B2 | 2/2013 | Aranyi et al. |
| 8,371,493 B2 | 2/2013 | Aranyi et al. |
| 8,372,094 B2 | 2/2013 | Bettuchi et al. |
| 8,376,865 B2 | 2/2013 | Forster et al. |
| 8,377,044 B2 | 2/2013 | Coe et al. |
| 8,388,633 B2 | 3/2013 | Rousseau et al. |
| 8,393,513 B2 | 3/2013 | Jankowski |
| 8,393,514 B2 | 3/2013 | Shelton, IV et al. |
| 8,397,971 B2 | 3/2013 | Yates et al. |
| 8,398,633 B2 | 3/2013 | Mueller |
| 8,398,673 B2 | 3/2013 | Hinchliffe et al. |

(56) References Cited

U.S. PATENT DOCUMENTS

| | | |
|---|---|---|
| 8,403,138 B2 | 3/2013 | Weisshaupt et al. |
| 8,403,198 B2 | 3/2013 | Sorrentino et al. |
| 8,403,832 B2 | 3/2013 | Cunningham et al. |
| 8,403,945 B2 | 3/2013 | Whitfield et al. |
| 8,408,439 B2 | 4/2013 | Huang et al. |
| 8,408,442 B2 | 4/2013 | Racenet et al. |
| 8,409,079 B2 | 4/2013 | Oakamoto et al. |
| 8,409,174 B2 | 4/2013 | Omori |
| 8,409,222 B2 | 4/2013 | Whitfield et al. |
| 8,409,223 B2 | 4/2013 | Sorrentino et al. |
| 8,413,870 B2 | 4/2013 | Pastorelli et al. |
| 8,413,871 B2 | 4/2013 | Racenet et al. |
| 8,413,872 B2 | 4/2013 | Patel |
| 8,414,577 B2 | 4/2013 | Boudreaux et al. |
| 8,418,909 B2 | 4/2013 | Kostrzewski |
| 8,424,737 B2 | 4/2013 | Scirica |
| 8,424,739 B2 | 4/2013 | Racenet et al. |
| 8,424,740 B2 | 4/2013 | Shelton, IV et al. |
| 8,424,741 B2 | 4/2013 | McGuckin, Jr. et al. |
| 8,425,600 B2 | 4/2013 | Maxwell |
| 8,430,292 B2 | 4/2013 | Patel et al. |
| 8,430,892 B2 | 4/2013 | Bindra et al. |
| 8,430,898 B2 | 4/2013 | Wiener et al. |
| 8,439,246 B1 | 5/2013 | Knodel et al. |
| 8,444,036 B2 | 5/2013 | Shelton, IV |
| 8,444,549 B2 | 5/2013 | Viola et al. |
| 8,453,904 B2 | 6/2013 | Eskaros et al. |
| 8,453,906 B2 | 6/2013 | Huang et al. |
| 8,453,907 B2 | 6/2013 | Laurent et al. |
| 8,453,908 B2 | 6/2013 | Bedi et al. |
| 8,453,912 B2 | 6/2013 | Mastri et al. |
| 8,453,914 B2 | 6/2013 | Laurent et al. |
| 8,454,628 B2 | 6/2013 | Smith et al. |
| 8,457,757 B2 | 6/2013 | Cauller et al. |
| 8,459,520 B2 | 6/2013 | Giordano et al. |
| 8,459,525 B2 | 6/2013 | Yates et al. |
| 8,464,922 B2 | 6/2013 | Marczyk |
| 8,464,923 B2 | 6/2013 | Shelton, IV |
| 8,464,924 B2 | 6/2013 | Gresham et al. |
| 8,464,925 B2 | 6/2013 | Hull et al. |
| 8,465,502 B2 | 6/2013 | Zergiebel |
| 8,469,973 B2 | 6/2013 | Meade et al. |
| 8,474,677 B2 | 7/2013 | Woodard, Jr. et al. |
| 8,475,453 B2 | 7/2013 | Marczyk et al. |
| 8,475,474 B2 | 7/2013 | Bombard et al. |
| 8,479,969 B2 | 7/2013 | Shelton, IV |
| 8,480,703 B2 | 7/2013 | Nicholas et al. |
| 8,485,412 B2 | 7/2013 | Shelton, IV et al. |
| 8,485,413 B2 | 7/2013 | Scheib et al. |
| 8,490,853 B2 | 7/2013 | Criscuolo et al. |
| 8,491,581 B2 | 7/2013 | Deville et al. |
| 8,496,156 B2 | 7/2013 | Sniffin et al. |
| 8,496,683 B2 | 7/2013 | Prommersberger et al. |
| 8,499,992 B2 | 8/2013 | Whitman et al. |
| 8,499,993 B2 | 8/2013 | Shelton, IV et al. |
| 8,500,762 B2 | 8/2013 | Sholev et al. |
| 8,506,557 B2 | 8/2013 | Zemlok et al. |
| 8,506,580 B2 | 8/2013 | Zergiebel et al. |
| 8,506,581 B2 | 8/2013 | Wingardner, III et al. |
| 8,512,359 B2 | 8/2013 | Whitman et al. |
| 8,517,239 B2 | 8/2013 | Scheib et al. |
| 8,517,241 B2 | 8/2013 | Nicholas et al. |
| 8,517,243 B2 | 8/2013 | Giordano et al. |
| 8,517,244 B2 | 8/2013 | Shelton, IV et al. |
| 8,521,273 B2 | 8/2013 | Kliman |
| 8,523,043 B2 | 9/2013 | Ullrich et al. |
| 8,523,881 B2 | 9/2013 | Cabiri et al. |
| 8,523,900 B2 | 9/2013 | Jinno et al. |
| 8,529,588 B2 | 9/2013 | Ahlberg et al. |
| 8,529,600 B2 | 9/2013 | Woodard, Jr. et al. |
| 8,529,819 B2 | 9/2013 | Ostapoff et al. |
| 8,534,528 B2 | 9/2013 | Shelton, IV |
| 8,535,304 B2 | 9/2013 | Sklar et al. |
| 8,540,128 B2 | 9/2013 | Shelton, IV et al. |
| 8,540,129 B2 | 9/2013 | Baxter, III et al. |
| 8,540,130 B2 | 9/2013 | Moore et al. |
| 8,540,131 B2 | 9/2013 | Swayze |
| 8,540,133 B2 | 9/2013 | Bedi et al. |
| 8,540,733 B2 | 9/2013 | Whitman et al. |
| 8,551,076 B2 | 10/2013 | Duval et al. |
| 8,556,151 B2 | 10/2013 | Viola |
| 8,556,918 B2 | 10/2013 | Bauman et al. |
| 8,561,870 B2 | 10/2013 | Baxter, III et al. |
| 8,561,873 B2 | 10/2013 | Ingmanson et al. |
| 8,567,656 B2 | 10/2013 | Shelton, IV et al. |
| 8,573,461 B2 | 11/2013 | Shelton, IV et al. |
| 8,573,465 B2 | 11/2013 | Shelton, IV et al. |
| 8,579,176 B2 | 11/2013 | Smith et al. |
| 8,579,178 B2 | 11/2013 | Holsten et al. |
| 8,579,937 B2 | 11/2013 | Gresham |
| 8,584,919 B2 | 11/2013 | Hueil et al. |
| 8,585,721 B2 | 11/2013 | Kirsch |
| 8,590,762 B2 | 11/2013 | Hess et al. |
| 8,602,287 B2 | 12/2013 | Yates et al. |
| 8,602,288 B2 | 12/2013 | Shelton, IV et al. |
| 8,603,135 B2 | 12/2013 | Mueller |
| 8,608,044 B2 | 12/2013 | Hueil et al. |
| 8,608,045 B2 | 12/2013 | Smith et al. |
| 8,608,046 B2 | 12/2013 | Laurent et al. |
| 8,608,745 B2 | 12/2013 | Guzman et al. |
| 8,613,383 B2 | 12/2013 | Beckman et al. |
| 8,616,431 B2 | 12/2013 | Timm et al. |
| 8,622,274 B2 | 1/2014 | Yates et al. |
| 8,622,275 B2 | 1/2014 | Baxter, III et al. |
| 8,628,518 B2 | 1/2014 | Blumenkranz et al. |
| 8,631,987 B2 | 1/2014 | Shelton, IV et al. |
| 8,632,462 B2 | 1/2014 | Yoo et al. |
| 8,632,525 B2 | 1/2014 | Kerr et al. |
| 8,632,535 B2 | 1/2014 | Shelton, IV et al. |
| 8,632,563 B2 | 1/2014 | Nagase et al. |
| 8,636,187 B2 | 1/2014 | Hueil et al. |
| 8,636,736 B2 | 1/2014 | Yates et al. |
| 8,640,788 B2 | 2/2014 | Dachs, II et al. |
| 8,647,258 B2 | 2/2014 | Aranyi et al. |
| 8,652,120 B2 | 2/2014 | Giordano et al. |
| 8,652,151 B2 | 2/2014 | Lehman et al. |
| 8,657,174 B2 | 2/2014 | Yates et al. |
| 8,657,176 B2 | 2/2014 | Shelton, IV et al. |
| 8,657,177 B2 | 2/2014 | Scirica et al. |
| 8,657,178 B2 | 2/2014 | Hueil et al. |
| 8,662,370 B2 | 3/2014 | Takei |
| 8,663,192 B2 | 3/2014 | Hester et al. |
| 8,668,129 B2 | 3/2014 | Olson |
| 8,668,130 B2 | 3/2014 | Hess et al. |
| 8,672,206 B2 | 3/2014 | Aranyi et al. |
| 8,672,207 B2 | 3/2014 | Shelton, IV et al. |
| 8,672,208 B2 | 3/2014 | Hess et al. |
| 8,678,263 B2 | 3/2014 | Viola |
| 8,679,093 B2 | 3/2014 | Farra |
| 8,679,137 B2 | 3/2014 | Bauman et al. |
| 8,679,454 B2 | 3/2014 | Guire et al. |
| 8,684,250 B2 | 4/2014 | Bettuchi et al. |
| 8,684,253 B2 | 4/2014 | Giordano et al. |
| 8,685,020 B2 | 4/2014 | Weizman et al. |
| 8,695,866 B2 | 4/2014 | Leimbach et al. |
| 8,696,665 B2 | 4/2014 | Hunt et al. |
| 8,701,958 B2 | 4/2014 | Shelton, IV et al. |
| 8,701,959 B2 | 4/2014 | Shah |
| 8,708,211 B2 | 4/2014 | Zemlok et al. |
| 8,708,213 B2 | 4/2014 | Shelton, IV et al. |
| 8,720,766 B2 | 5/2014 | Hess et al. |
| 8,721,630 B2 | 5/2014 | Ortiz et al. |
| 8,721,666 B2 | 5/2014 | Schroeder et al. |
| 8,727,197 B2 | 5/2014 | Hess et al. |
| 8,728,119 B2 | 5/2014 | Cummins |
| 8,733,613 B2 | 5/2014 | Huitema et al. |
| 8,733,614 B2 | 5/2014 | Ross et al. |
| 8,734,478 B2 | 5/2014 | Widenhouse et al. |
| 8,739,033 B2 | 5/2014 | Rosenberg |
| 8,740,034 B2 | 6/2014 | Morgan et al. |
| 8,740,037 B2 | 6/2014 | Shelton, IV et al. |
| 8,740,038 B2 | 6/2014 | Shelton, IV et al. |
| 8,746,529 B2 | 6/2014 | Shelton, IV et al. |
| 8,746,530 B2 | 6/2014 | Giordano et al. |

(56) References Cited

U.S. PATENT DOCUMENTS

| | | |
|---|---|---|
| 8,746,535 B2 | 6/2014 | Shelton, IV et al. |
| 8,747,238 B2 | 6/2014 | Shelton, IV et al. |
| 8,752,264 B2 | 6/2014 | Ackley et al. |
| 8,752,699 B2 | 6/2014 | Morgan et al. |
| 8,752,747 B2 | 6/2014 | Shelton, IV et al. |
| 8,752,749 B2 | 6/2014 | Moore et al. |
| 8,757,465 B2 | 6/2014 | Woodard, Jr. et al. |
| 8,758,235 B2 | 6/2014 | Jaworek |
| 8,758,391 B2 | 6/2014 | Swayze et al. |
| 8,758,438 B2 | 6/2014 | Boyce et al. |
| 8,763,875 B2 | 7/2014 | Morgan et al. |
| 8,763,877 B2 | 7/2014 | Schall et al. |
| 8,763,879 B2 | 7/2014 | Shelton, IV et al. |
| 8,771,169 B2 | 7/2014 | Whitman et al. |
| 8,777,004 B2 | 7/2014 | Shelton, IV et al. |
| 8,783,541 B2 | 7/2014 | Shelton, IV et al. |
| 8,783,542 B2 | 7/2014 | Riestenberg et al. |
| 8,783,543 B2 | 7/2014 | Shelton, IV et al. |
| 8,784,404 B2 | 7/2014 | Doyle et al. |
| 8,784,415 B2 | 7/2014 | Malackowski et al. |
| 8,789,737 B2 | 7/2014 | Hodgkinson et al. |
| 8,789,739 B2 | 7/2014 | Swensgard |
| 8,789,740 B2 | 7/2014 | Baxter, III et al. |
| 8,789,741 B2 | 7/2014 | Baxter, III et al. |
| 8,790,684 B2 | 7/2014 | Dave et al. |
| 8,794,496 B2 | 8/2014 | Scirica |
| 8,794,497 B2 | 8/2014 | Zingman |
| 8,795,276 B2 | 8/2014 | Dietz et al. |
| 8,800,838 B2 | 8/2014 | Shelton, IV |
| 8,800,841 B2 | 8/2014 | Ellerhorst et al. |
| 8,801,734 B2 | 8/2014 | Shelton, IV et al. |
| 8,801,735 B2 | 8/2014 | Shelton, IV et al. |
| 8,801,752 B2 | 8/2014 | Fortier et al. |
| 8,808,294 B2 | 8/2014 | Fox et al. |
| 8,808,311 B2 | 8/2014 | Heinrich et al. |
| 8,813,866 B2 | 8/2014 | Suzuki |
| 8,814,024 B2 | 8/2014 | Woodard, Jr. et al. |
| 8,814,025 B2 | 8/2014 | Miller et al. |
| 8,820,603 B2 | 9/2014 | Shelton, IV et al. |
| 8,820,605 B2 | 9/2014 | Shelton, IV |
| 8,820,606 B2 | 9/2014 | Hodgkinson |
| 8,827,133 B2 | 9/2014 | Shelton, IV et al. |
| 8,827,903 B2 | 9/2014 | Shelton, IV et al. |
| 8,833,632 B2 | 9/2014 | Swensgard |
| 8,840,003 B2 | 9/2014 | Morgan et al. |
| 8,840,603 B2 | 9/2014 | Shelton, IV et al. |
| 8,844,789 B2 | 9/2014 | Shelton, IV et al. |
| 8,851,354 B2 | 10/2014 | Swensgard et al. |
| 8,852,199 B2 | 10/2014 | Deslauriers et al. |
| 8,857,693 B2 | 10/2014 | Schuckmann et al. |
| 8,857,694 B2 | 10/2014 | Shelton, IV et al. |
| 8,858,571 B2 | 10/2014 | Shelton, IV et al. |
| 8,858,590 B2 | 10/2014 | Shelton, IV et al. |
| 8,864,007 B2 | 10/2014 | Widenhouse et al. |
| 8,864,009 B2 | 10/2014 | Shelton, IV et al. |
| 8,870,050 B2 | 10/2014 | Hodgkinson |
| 8,875,971 B2 | 11/2014 | Hall et al. |
| 8,875,972 B2 | 11/2014 | Weisenburgh, II et al. |
| 8,876,857 B2 | 11/2014 | Burbank |
| 8,893,946 B2 | 11/2014 | Boudreaux et al. |
| 8,893,949 B2 | 11/2014 | Shelton, IV et al. |
| 8,899,463 B2 | 12/2014 | Schall et al. |
| 8,899,464 B2 | 12/2014 | Hueil et al. |
| 8,899,465 B2 | 12/2014 | Shelton, IV et al. |
| 8,899,466 B2 | 12/2014 | Baxter, III et al. |
| 8,911,426 B2 | 12/2014 | Coppeta et al. |
| 8,911,471 B2 | 12/2014 | Spivey et al. |
| 8,920,438 B2 | 12/2014 | Aranyi et al. |
| 8,925,782 B2 | 1/2015 | Shelton, IV |
| 8,925,783 B2 | 1/2015 | Zemlok et al. |
| 8,925,788 B2 | 1/2015 | Hess et al. |
| 8,926,598 B2 | 1/2015 | Mollere et al. |
| 8,931,682 B2 | 1/2015 | Timm et al. |
| 8,936,614 B2 | 1/2015 | Allen, IV |
| 8,939,343 B2 | 1/2015 | Milliman et al. |
| 8,939,344 B2 | 1/2015 | Olson et al. |
| 8,960,520 B2 | 2/2015 | McCuen |
| 8,960,521 B2 | 2/2015 | Kostrzewski |
| 8,967,443 B2 | 3/2015 | McCuen |
| 8,967,446 B2 | 3/2015 | Beardsley et al. |
| 8,968,312 B2 | 3/2015 | Marczyk et al. |
| 8,968,337 B2 | 3/2015 | Whitfield et al. |
| 8,970,507 B2 | 3/2015 | Holbein et al. |
| 8,973,803 B2 | 3/2015 | Hall et al. |
| 8,973,804 B2 | 3/2015 | Hess et al. |
| 8,978,954 B2 | 3/2015 | Shelton, IV et al. |
| 8,978,955 B2 | 3/2015 | Aronhalt et al. |
| 8,978,956 B2 | 3/2015 | Schall et al. |
| 8,979,890 B2 | 3/2015 | Boudreaux |
| 8,982,195 B2 | 3/2015 | Claus et al. |
| 8,991,676 B2 | 3/2015 | Hess et al. |
| 8,991,677 B2 | 3/2015 | Moore et al. |
| 8,992,422 B2 | 3/2015 | Spivey et al. |
| 8,992,565 B2 | 3/2015 | Brisson et al. |
| 8,996,165 B2 | 3/2015 | Wang et al. |
| 8,998,058 B2 | 4/2015 | Moore et al. |
| 9,005,230 B2 | 4/2015 | Yates et al. |
| 9,011,471 B2 | 4/2015 | Timm et al. |
| 9,016,540 B2 | 4/2015 | Whitman et al. |
| 9,016,542 B2 | 4/2015 | Shelton, IV et al. |
| 9,017,331 B2 | 4/2015 | Fox |
| 9,017,371 B2 | 4/2015 | Whitman et al. |
| 9,023,014 B2 | 5/2015 | Chowaniec et al. |
| 9,028,494 B2 | 5/2015 | Shelton, IV et al. |
| 9,028,495 B2 | 5/2015 | Mueller et al. |
| 9,028,519 B2 | 5/2015 | Yates et al. |
| 9,033,203 B2 | 5/2015 | Woodard, Jr. et al. |
| 9,033,204 B2 | 5/2015 | Shelton, IV et al. |
| 9,038,881 B1 | 5/2015 | Schaller et al. |
| 9,039,690 B2 | 5/2015 | Kersten et al. |
| 9,039,720 B2 | 5/2015 | Madan |
| 9,043,027 B2 | 5/2015 | Durant et al. |
| 9,044,227 B2 | 6/2015 | Shelton, IV et al. |
| 9,044,228 B2 | 6/2015 | Woodard, Jr. et al. |
| 9,044,230 B2 | 6/2015 | Morgan et al. |
| 9,050,083 B2 | 6/2015 | Yates et al. |
| 9,050,084 B2 | 6/2015 | Schmid et al. |
| 9,050,100 B2 | 6/2015 | Yates et al. |
| 9,055,941 B2 | 6/2015 | Schmid et al. |
| 9,055,961 B2 | 6/2015 | Manzo et al. |
| 9,060,770 B2 | 6/2015 | Shelton, IV et al. |
| 9,072,515 B2 | 7/2015 | Hall et al. |
| 9,072,535 B2 | 7/2015 | Shelton, IV et al. |
| 9,072,536 B2 | 7/2015 | Shelton, IV et al. |
| 9,078,653 B2 | 7/2015 | Leimbach et al. |
| 9,084,601 B2 | 7/2015 | Moore et al. |
| 9,084,602 B2 | 7/2015 | Glieman |
| 9,086,875 B2 | 7/2015 | Harrat et al. |
| 9,089,330 B2 | 7/2015 | Widenhouse et al. |
| 9,095,339 B2 | 8/2015 | Moore et al. |
| 9,095,362 B2 | 8/2015 | Dachs, II et al. |
| 9,096,033 B2 | 8/2015 | Holop et al. |
| 9,099,863 B2 | 8/2015 | Smith et al. |
| 9,101,358 B2 | 8/2015 | Kerr et al. |
| 9,101,385 B2 | 8/2015 | Shelton, IV et al. |
| 9,107,663 B2 | 8/2015 | Swensgard |
| 9,113,862 B2 | 8/2015 | Morgan et al. |
| 9,113,864 B2 | 8/2015 | Morgan et al. |
| 9,113,865 B2 | 8/2015 | Shelton, IV et al. |
| 9,113,874 B2 | 8/2015 | Shelton, IV et al. |
| 9,113,880 B2 | 8/2015 | Zemlok et al. |
| 9,113,883 B2 | 8/2015 | Aronhalt et al. |
| 9,113,884 B2 | 8/2015 | Shelton, IV et al. |
| 9,119,657 B2 | 9/2015 | Shelton, IV et al. |
| 9,123,286 B2 | 9/2015 | Park |
| 9,125,654 B2 | 9/2015 | Aronhalt et al. |
| 9,125,662 B2 | 9/2015 | Shelton, IV |
| 9,131,940 B2 | 9/2015 | Huitema et al. |
| 9,131,957 B2 | 9/2015 | Sharbnik et al. |
| 9,138,225 B2 | 9/2015 | Huang et al. |
| 9,149,274 B2 | 10/2015 | Spivey et al. |
| 9,168,038 B2 | 10/2015 | Shelton, IV et al. |
| 9,179,911 B2 | 11/2015 | Morgan et al. |
| 9,179,912 B2 | 11/2015 | Yates et al. |

(56) References Cited

U.S. PATENT DOCUMENTS

| | | |
|---|---|---|
| 9,186,143 B2 | 11/2015 | Timm et al. |
| 9,192,380 B2 | 11/2015 | (Tarinelli) Racenet et al. |
| 9,192,384 B2 | 11/2015 | Bettuchi |
| 9,198,661 B2 | 12/2015 | Swensgard |
| 9,198,662 B2 | 12/2015 | Barton et al. |
| 9,204,877 B2 | 12/2015 | Whitman et al. |
| 9,204,878 B2 | 12/2015 | Hall et al. |
| 9,204,879 B2 | 12/2015 | Shelton, IV |
| 9,204,880 B2 | 12/2015 | Baxter, III et al. |
| 9,211,120 B2 | 12/2015 | Scheib et al. |
| 9,211,121 B2 | 12/2015 | Hall et al. |
| 9,211,122 B2 | 12/2015 | Hagerty et al. |
| 9,216,019 B2 | 12/2015 | Schmid et al. |
| 9,220,500 B2 | 12/2015 | Swayze et al. |
| 9,220,501 B2 | 12/2015 | Baxter, III et al. |
| 9,226,750 B2 | 1/2016 | Weir et al. |
| 9,226,751 B2 | 1/2016 | Shelton, IV et al. |
| 9,232,941 B2 | 1/2016 | Mandakolathur Vasudevan et al. |
| 9,232,945 B2 | 1/2016 | Zingman |
| 9,232,979 B2 | 1/2016 | Parihar et al. |
| 9,237,891 B2 | 1/2016 | Shelton, IV |
| 9,241,714 B2 | 1/2016 | Timm et al. |
| 9,259,274 B2 | 2/2016 | Prisco |
| 9,271,799 B2 | 3/2016 | Shelton, IV et al. |
| 9,272,406 B2 | 3/2016 | Aronhalt et al. |
| 9,277,919 B2 | 3/2016 | Timmer et al. |
| 9,282,962 B2 | 3/2016 | Schmid et al. |
| 9,282,966 B2 | 3/2016 | Shelton, IV et al. |
| 9,282,974 B2 | 3/2016 | Shelton, IV |
| 9,283,054 B2 | 3/2016 | Morgan et al. |
| 9,289,206 B2 | 3/2016 | Hess et al. |
| 9,289,210 B2 | 3/2016 | Baxter, III et al. |
| 9,289,212 B2 | 3/2016 | Shelton, IV et al. |
| 9,289,225 B2 | 3/2016 | Shelton, IV et al. |
| 9,289,256 B2 | 3/2016 | Shelton, IV et al. |
| 9,295,464 B2 | 3/2016 | Shelton, IV et al. |
| 9,301,752 B2 | 4/2016 | Mandakolathur Vasudevan et al. |
| 9,301,753 B2 | 4/2016 | Aldridge et al. |
| 9,301,755 B2 | 4/2016 | Shelton, IV et al. |
| 9,301,759 B2 | 4/2016 | Spivey et al. |
| 9,307,986 B2 | 4/2016 | Hall et al. |
| 9,307,988 B2 | 4/2016 | Shelton, IV |
| 2001/0025183 A1 | 9/2001 | Shahidi |
| 2001/0044637 A1 | 11/2001 | Jacobs et al. |
| 2002/0014510 A1 | 2/2002 | Richter et al. |
| 2002/0022836 A1 | 2/2002 | Goble et al. |
| 2002/0029036 A1 | 3/2002 | Goble et al. |
| 2002/0095175 A1 | 7/2002 | Brock et al. |
| 2002/0103494 A1 | 8/2002 | Pacey |
| 2002/0117534 A1 | 8/2002 | Green et al. |
| 2002/0127265 A1 | 9/2002 | Bowman et al. |
| 2002/0128552 A1 | 9/2002 | Nowlin et al. |
| 2002/0134811 A1 | 9/2002 | Napier et al. |
| 2002/0143340 A1 | 10/2002 | Kaneko |
| 2002/0165541 A1 | 11/2002 | Whitman |
| 2002/0193808 A1 | 12/2002 | Belef et al. |
| 2003/0023316 A1 | 1/2003 | Brown et al. |
| 2003/0078647 A1 | 4/2003 | Vallana et al. |
| 2003/0084983 A1 | 5/2003 | Rangachari et al. |
| 2003/0093103 A1 | 5/2003 | Malackowski et al. |
| 2003/0096158 A1 | 5/2003 | Takano et al. |
| 2003/0105478 A1 | 6/2003 | Whitman et al. |
| 2003/0130677 A1 | 7/2003 | Whitman et al. |
| 2003/0139741 A1 | 7/2003 | Goble et al. |
| 2003/0153908 A1 | 8/2003 | Goble et al. |
| 2003/0163085 A1 | 8/2003 | Tanner et al. |
| 2003/0181900 A1 | 9/2003 | Long |
| 2003/0195387 A1 | 10/2003 | Kortenbach et al. |
| 2003/0205029 A1 | 11/2003 | Chapolini et al. |
| 2003/0216732 A1 | 11/2003 | Truckai et al. |
| 2003/0220660 A1 | 11/2003 | Kortenbach et al. |
| 2003/0236505 A1 | 12/2003 | Bonadio et al. |
| 2004/0002726 A1 | 1/2004 | Nunez et al. |
| 2004/0006335 A1 | 1/2004 | Garrison |
| 2004/0006340 A1 | 1/2004 | Latterell et al. |
| 2004/0006372 A1 | 1/2004 | Racenet et al. |
| 2004/0006861 A1 | 1/2004 | Haytayan |
| 2004/0030333 A1 | 2/2004 | Goble |
| 2004/0034357 A1 | 2/2004 | Beane et al. |
| 2004/0034369 A1 | 2/2004 | Sauer et al. |
| 2004/0044364 A1 | 3/2004 | DeVries et al. |
| 2004/0068161 A1 | 4/2004 | Couvillon, Jr. |
| 2004/0068224 A1 | 4/2004 | Couvillon, Jr. et al. |
| 2004/0068307 A1 | 4/2004 | Goble |
| 2004/0070369 A1 | 4/2004 | Sakakibara |
| 2004/0073222 A1 | 4/2004 | Koseki |
| 2004/0078037 A1 | 4/2004 | Batchelor et al. |
| 2004/0093024 A1 | 5/2004 | Lousararian et al. |
| 2004/0094597 A1 | 5/2004 | Whitman et al. |
| 2004/0097987 A1 | 5/2004 | Pugsley et al. |
| 2004/0098040 A1 | 5/2004 | Taniguchi et al. |
| 2004/0101822 A1 | 5/2004 | Weisner et al. |
| 2004/0102783 A1 | 5/2004 | Sutterlin, III et al. |
| 2004/0108357 A1 | 6/2004 | Milliman et al. |
| 2004/0110439 A1 | 6/2004 | Chaikof et al. |
| 2004/0111081 A1 | 6/2004 | Whitman et al. |
| 2004/0115022 A1 | 6/2004 | Albertson et al. |
| 2004/0116952 A1 | 6/2004 | Sakurai et al. |
| 2004/0147909 A1 | 7/2004 | Johnston et al. |
| 2004/0164123 A1 | 8/2004 | Racenet et al. |
| 2004/0167572 A1 | 8/2004 | Roth et al. |
| 2004/0173659 A1 | 9/2004 | Green et al. |
| 2004/0181219 A1 | 9/2004 | Goble et al. |
| 2004/0186470 A1 | 9/2004 | Goble et al. |
| 2004/0193189 A1 | 9/2004 | Kortenbach et al. |
| 2004/0199181 A1 | 10/2004 | Knodel et al. |
| 2004/0222268 A1 | 11/2004 | Bilotti et al. |
| 2004/0225186 A1 | 11/2004 | Horne, Jr. et al. |
| 2004/0230214 A1 | 11/2004 | Donofrio et al. |
| 2004/0232201 A1 | 11/2004 | Wenchell et al. |
| 2004/0236352 A1 | 11/2004 | Wang et al. |
| 2004/0243147 A1 | 12/2004 | Lipow |
| 2004/0243151 A1 | 12/2004 | Demmy et al. |
| 2004/0243163 A1 | 12/2004 | Casiano et al. |
| 2004/0243176 A1 | 12/2004 | Hahnen et al. |
| 2004/0247415 A1 | 12/2004 | Mangone, Jr. |
| 2004/0254455 A1 | 12/2004 | Iddan |
| 2004/0254566 A1 | 12/2004 | Plicchi et al. |
| 2004/0254590 A1 | 12/2004 | Hoffman et al. |
| 2004/0254608 A1 | 12/2004 | Huitema et al. |
| 2004/0260315 A1 | 12/2004 | Dell et al. |
| 2004/0267310 A1 | 12/2004 | Racenet et al. |
| 2005/0010213 A1 | 1/2005 | Stad et al. |
| 2005/0032511 A1 | 2/2005 | Malone et al. |
| 2005/0033352 A1 | 2/2005 | Zeph et al. |
| 2005/0033357 A1 | 2/2005 | Braun |
| 2005/0054946 A1 | 3/2005 | Krzyzanowski |
| 2005/0059997 A1 | 3/2005 | Bauman et al. |
| 2005/0070929 A1 | 3/2005 | Dalessandro et al. |
| 2005/0075561 A1 | 4/2005 | Golden |
| 2005/0080454 A1 | 4/2005 | Drews et al. |
| 2005/0085693 A1 | 4/2005 | Belson et al. |
| 2005/0090817 A1 | 4/2005 | Phan |
| 2005/0096683 A1 | 5/2005 | Ellins et al. |
| 2005/0103819 A1 | 5/2005 | Racenet et al. |
| 2005/0107814 A1 | 5/2005 | Johnston et al. |
| 2005/0107824 A1 | 5/2005 | Hillstead et al. |
| 2005/0113820 A1 | 5/2005 | Goble et al. |
| 2005/0119525 A1 | 6/2005 | Takemoto |
| 2005/0119669 A1 | 6/2005 | Demmy |
| 2005/0124855 A1 | 6/2005 | Jaffe et al. |
| 2005/0125009 A1 | 6/2005 | Perry et al. |
| 2005/0125897 A1 | 6/2005 | Wyslucha et al. |
| 2005/0131173 A1 | 6/2005 | McDaniel et al. |
| 2005/0131211 A1 | 6/2005 | Bayley et al. |
| 2005/0131390 A1 | 6/2005 | Heinrich et al. |
| 2005/0131436 A1 | 6/2005 | Johnston et al. |
| 2005/0131437 A1 | 6/2005 | Johnston et al. |
| 2005/0131457 A1 | 6/2005 | Douglas et al. |
| 2005/0137454 A1 | 6/2005 | Saadat et al. |
| 2005/0137455 A1 | 6/2005 | Ewers et al. |
| 2005/0143759 A1 | 6/2005 | Kelly |
| 2005/0143769 A1 | 6/2005 | White et al. |
| 2005/0145675 A1 | 7/2005 | Hartwick et al. |

(56) References Cited

U.S. PATENT DOCUMENTS

| | | |
|---|---|---|
| 2005/0154258 A1 | 7/2005 | Tartaglia et al. |
| 2005/0154406 A1 | 7/2005 | Bombard et al. |
| 2005/0165419 A1 | 7/2005 | Sauer et al. |
| 2005/0165435 A1 | 7/2005 | Johnston et al. |
| 2005/0169974 A1 | 8/2005 | Tenerz et al. |
| 2005/0171522 A1 | 8/2005 | Christopherson |
| 2005/0177181 A1 | 8/2005 | Kagan et al. |
| 2005/0182298 A1 | 8/2005 | Ikeda et al. |
| 2005/0187545 A1 | 8/2005 | Hooven et al. |
| 2005/0187572 A1 | 8/2005 | Johnston et al. |
| 2005/0187576 A1 | 8/2005 | Whitman et al. |
| 2005/0189397 A1 | 9/2005 | Jankowski |
| 2005/0192609 A1 | 9/2005 | Whitman et al. |
| 2005/0192628 A1 | 9/2005 | Viola |
| 2005/0203550 A1 | 9/2005 | Laufer et al. |
| 2005/0216055 A1 | 9/2005 | Scirica et al. |
| 2005/0228224 A1 | 10/2005 | Okada et al. |
| 2005/0240178 A1 | 10/2005 | Morley et al. |
| 2005/0240222 A1 | 10/2005 | Shipp |
| 2005/0245965 A1 | 11/2005 | Orban, III et al. |
| 2005/0251128 A1 | 11/2005 | Amoah |
| 2005/0256452 A1 | 11/2005 | DeMarchi et al. |
| 2005/0256522 A1 | 11/2005 | Francischelli et al. |
| 2005/0261676 A1 | 11/2005 | Hall et al. |
| 2005/0261677 A1 | 11/2005 | Hall et al. |
| 2005/0263563 A1 | 12/2005 | Racenet et al. |
| 2005/0267455 A1 | 12/2005 | Eggers et al. |
| 2005/0274768 A1 | 12/2005 | Cummins et al. |
| 2005/0283188 A1 | 12/2005 | Loshakove et al. |
| 2006/0004407 A1 | 1/2006 | Hiles et al. |
| 2006/0008787 A1 | 1/2006 | Hayman et al. |
| 2006/0011699 A1 | 1/2006 | Olson et al. |
| 2006/0015009 A1 | 1/2006 | Jaffe et al. |
| 2006/0020247 A1 | 1/2006 | Kagan et al. |
| 2006/0020258 A1 | 1/2006 | Strauss et al. |
| 2006/0020336 A1 | 1/2006 | Liddicoat |
| 2006/0025811 A1 | 2/2006 | Shelton, IV |
| 2006/0025812 A1 | 2/2006 | Shelton, IV |
| 2006/0025813 A1 | 2/2006 | Shelton et al. |
| 2006/0041188 A1 | 2/2006 | Dirusso et al. |
| 2006/0047275 A1 | 3/2006 | Goble |
| 2006/0047303 A1 | 3/2006 | Ortiz et al. |
| 2006/0047307 A1 | 3/2006 | Ortiz et al. |
| 2006/0049229 A1 | 3/2006 | Milliman et al. |
| 2006/0052825 A1 | 3/2006 | Ransick et al. |
| 2006/0060630 A1 | 3/2006 | Shelton, IV et al. |
| 2006/0064086 A1 | 3/2006 | Odom |
| 2006/0079115 A1 | 4/2006 | Aranyi et al. |
| 2006/0079735 A1 | 4/2006 | Martone et al. |
| 2006/0085031 A1 | 4/2006 | Bettuchi |
| 2006/0085033 A1 | 4/2006 | Criscuolo et al. |
| 2006/0086032 A1 | 4/2006 | Valencic et al. |
| 2006/0087746 A1 | 4/2006 | Lipow |
| 2006/0089535 A1 | 4/2006 | Raz et al. |
| 2006/0100643 A1 | 5/2006 | Laufer et al. |
| 2006/0108393 A1 | 5/2006 | Heinrich et al. |
| 2006/0111711 A1 | 5/2006 | Goble |
| 2006/0111723 A1 | 5/2006 | Chapolini et al. |
| 2006/0122636 A1 | 6/2006 | Bailly et al. |
| 2006/0142772 A1 | 6/2006 | Ralph et al. |
| 2006/0149163 A1 | 7/2006 | Hibner et al. |
| 2006/0161185 A1 | 7/2006 | Saadat et al. |
| 2006/0167471 A1 | 7/2006 | Phillips |
| 2006/0173470 A1 | 8/2006 | Oray et al. |
| 2006/0178556 A1 | 8/2006 | Hasser et al. |
| 2006/0180634 A1 | 8/2006 | Shelton, IV et al. |
| 2006/0185682 A1 | 8/2006 | Marczyk |
| 2006/0200123 A1 | 9/2006 | Ryan |
| 2006/0201989 A1 | 9/2006 | Ojeda |
| 2006/0206100 A1 | 9/2006 | Eskridge et al. |
| 2006/0212069 A1 | 9/2006 | Shelton, IV |
| 2006/0217729 A1 | 9/2006 | Eskridge et al. |
| 2006/0226196 A1 | 10/2006 | Hueil et al. |
| 2006/0235368 A1 | 10/2006 | Oz |
| 2006/0235469 A1 | 10/2006 | Viola |
| 2006/0241655 A1 | 10/2006 | Viola |
| 2006/0241692 A1 | 10/2006 | McGuckin, Jr. et al. |
| 2006/0244460 A1 | 11/2006 | Weaver |
| 2006/0252993 A1 | 11/2006 | Freed et al. |
| 2006/0253069 A1 | 11/2006 | Li et al. |
| 2006/0258904 A1 | 11/2006 | Stefanchik et al. |
| 2006/0258910 A1 | 11/2006 | Stefanchik et al. |
| 2006/0259073 A1 | 11/2006 | Miyamoto et al. |
| 2006/0264927 A1 | 11/2006 | Ryan |
| 2006/0264929 A1 | 11/2006 | Goble et al. |
| 2006/0271042 A1 | 11/2006 | Latterell et al. |
| 2006/0271102 A1 | 11/2006 | Bosshard et al. |
| 2006/0278680 A1 | 12/2006 | Viola et al. |
| 2006/0278681 A1 | 12/2006 | Viola et al. |
| 2006/0284730 A1 | 12/2006 | Schmid et al. |
| 2006/0287576 A1 | 12/2006 | Tsuji et al. |
| 2006/0289602 A1 | 12/2006 | Wales et al. |
| 2006/0291981 A1 | 12/2006 | Viola et al. |
| 2007/0010838 A1 | 1/2007 | Shelton, IV et al. |
| 2007/0023476 A1 | 2/2007 | Whitman et al. |
| 2007/0023477 A1 | 2/2007 | Whitman et al. |
| 2007/0026039 A1 | 2/2007 | Drumheller et al. |
| 2007/0026040 A1 | 2/2007 | Crawley et al. |
| 2007/0027468 A1 | 2/2007 | Wales et al. |
| 2007/0027472 A1 | 2/2007 | Hiles et al. |
| 2007/0027551 A1 | 2/2007 | Farnsworth et al. |
| 2007/0034668 A1 | 2/2007 | Holsten et al. |
| 2007/0049951 A1 | 3/2007 | Menn |
| 2007/0049966 A1 | 3/2007 | Bonadio et al. |
| 2007/0051375 A1 | 3/2007 | Milliman |
| 2007/0055219 A1 | 3/2007 | Whitman et al. |
| 2007/0066981 A1 | 3/2007 | Meagher |
| 2007/0070574 A1 | 3/2007 | Nerheim et al. |
| 2007/0073341 A1 | 3/2007 | Smith |
| 2007/0078484 A1 | 4/2007 | Talarico et al. |
| 2007/0083193 A1 | 4/2007 | Werneth et al. |
| 2007/0084897 A1 | 4/2007 | Shelton, IV et al. |
| 2007/0093869 A1 | 4/2007 | Bloom et al. |
| 2007/0102472 A1 | 5/2007 | Shelton, IV |
| 2007/0106113 A1 | 5/2007 | Ravo |
| 2007/0106317 A1 | 5/2007 | Shelton, IV et al. |
| 2007/0118175 A1 | 5/2007 | Butler et al. |
| 2007/0129605 A1 | 6/2007 | Schaaf |
| 2007/0135686 A1 | 6/2007 | Pruitt, Jr. et al. |
| 2007/0135803 A1 | 6/2007 | Belson |
| 2007/0155010 A1 | 7/2007 | Farnsworth et al. |
| 2007/0158358 A1 | 7/2007 | Mason, II et al. |
| 2007/0170225 A1 | 7/2007 | Shelton, IV et al. |
| 2007/0173687 A1 | 7/2007 | Shima et al. |
| 2007/0173806 A1 | 7/2007 | Orszulak et al. |
| 2007/0173813 A1 | 7/2007 | Odom |
| 2007/0175950 A1 | 8/2007 | Shelton, IV et al. |
| 2007/0175951 A1 | 8/2007 | Shelton, IV et al. |
| 2007/0175955 A1 | 8/2007 | Shelton, IV et al. |
| 2007/0179528 A1 | 8/2007 | Soltz et al. |
| 2007/0181632 A1 | 8/2007 | Milliman |
| 2007/0190110 A1 | 8/2007 | Pameijer et al. |
| 2007/0191868 A1 | 8/2007 | Theroux et al. |
| 2007/0194079 A1 | 8/2007 | Hueil et al. |
| 2007/0194082 A1 | 8/2007 | Morgan et al. |
| 2007/0203510 A1 | 8/2007 | Bettuchi |
| 2007/0213750 A1 | 9/2007 | Weadock |
| 2007/0219571 A1 | 9/2007 | Balbierz et al. |
| 2007/0225562 A1 | 9/2007 | Spivey et al. |
| 2007/0233163 A1 | 10/2007 | Bombard et al. |
| 2007/0239028 A1 | 10/2007 | Houser et al. |
| 2007/0243227 A1 | 10/2007 | Gertner |
| 2007/0244471 A1 | 10/2007 | Malackowski |
| 2007/0246505 A1 | 10/2007 | Pace-Floridia et al. |
| 2007/0249999 A1 | 10/2007 | Sklar et al. |
| 2007/0260278 A1 | 11/2007 | Wheeler et al. |
| 2007/0270784 A1 | 11/2007 | Smith et al. |
| 2007/0270884 A1 | 11/2007 | Smith et al. |
| 2007/0275035 A1 | 11/2007 | Herman et al. |
| 2007/0276409 A1 | 11/2007 | Ortiz et al. |
| 2007/0279011 A1 | 12/2007 | Jones et al. |
| 2007/0286892 A1 | 12/2007 | Herzberg et al. |
| 2007/0287993 A1 | 12/2007 | Hinman et al. |
| 2007/0288044 A1 | 12/2007 | Jinno et al. |

(56) References Cited

U.S. PATENT DOCUMENTS

| | | |
|---|---|---|
| 2007/0299427 A1 | 12/2007 | Yeung et al. |
| 2008/0003196 A1 | 1/2008 | Jonn et al. |
| 2008/0015598 A1 | 1/2008 | Prommersberger |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0030170 A1 | 2/2008 | Dacquay et al. |
| 2008/0035701 A1 | 2/2008 | Racenet et al. |
| 2008/0041916 A1 | 2/2008 | Milliman et al. |
| 2008/0041917 A1 | 2/2008 | Racenet et al. |
| 2008/0051833 A1 | 2/2008 | Gramuglia et al. |
| 2008/0065153 A1 | 3/2008 | Allard et al. |
| 2008/0071328 A1 | 3/2008 | Haubrich et al. |
| 2008/0078802 A1 | 4/2008 | Hess et al. |
| 2008/0082114 A1 | 4/2008 | McKenna et al. |
| 2008/0082125 A1 | 4/2008 | Murray et al. |
| 2008/0082126 A1 | 4/2008 | Murray et al. |
| 2008/0083808 A1 | 4/2008 | Scirica |
| 2008/0083813 A1 | 4/2008 | Zemlok et al. |
| 2008/0085296 A1 | 4/2008 | Powell et al. |
| 2008/0086078 A1 | 4/2008 | Powell et al. |
| 2008/0091072 A1 | 4/2008 | Omori et al. |
| 2008/0114315 A1 | 5/2008 | Voegele et al. |
| 2008/0114385 A1 | 5/2008 | Byrum et al. |
| 2008/0128469 A1 | 6/2008 | Dalessandro et al. |
| 2008/0129253 A1 | 6/2008 | Shiue et al. |
| 2008/0140115 A1 | 6/2008 | Stopek |
| 2008/0154299 A1 | 6/2008 | Linvneh |
| 2008/0169328 A1 | 7/2008 | Shelton |
| 2008/0169332 A1 | 7/2008 | Shelton et al. |
| 2008/0169333 A1 | 7/2008 | Shelton et al. |
| 2008/0172087 A1 | 7/2008 | Fuchs et al. |
| 2008/0172088 A1 | 7/2008 | Smith et al. |
| 2008/0183193 A1 | 7/2008 | Omori et al. |
| 2008/0185419 A1 | 8/2008 | Smith et al. |
| 2008/0190989 A1 | 8/2008 | Crews et al. |
| 2008/0197167 A1 | 8/2008 | Viola et al. |
| 2008/0200762 A1 | 8/2008 | Stokes et al. |
| 2008/0200835 A1 | 8/2008 | Monson et al. |
| 2008/0200933 A1 | 8/2008 | Bakos et al. |
| 2008/0200949 A1 | 8/2008 | Hiles et al. |
| 2008/0228029 A1 | 9/2008 | Mikkaichi et al. |
| 2008/0245841 A1 | 10/2008 | Smith et al. |
| 2008/0251568 A1 | 10/2008 | Zemlok et al. |
| 2008/0251569 A1 | 10/2008 | Smith et al. |
| 2008/0255413 A1 | 10/2008 | Zemlok et al. |
| 2008/0255607 A1 | 10/2008 | Zemlok |
| 2008/0262654 A1 | 10/2008 | Omori et al. |
| 2008/0281171 A1 | 11/2008 | Fennell et al. |
| 2008/0283570 A1 | 11/2008 | Boyden et al. |
| 2008/0287944 A1 | 11/2008 | Pearson et al. |
| 2008/0287988 A1 | 11/2008 | Smith et al. |
| 2008/0290134 A1 | 11/2008 | Bettuchi et al. |
| 2008/0294179 A1 | 11/2008 | Balbierz et al. |
| 2008/0296346 A1 | 12/2008 | Shelton, IV et al. |
| 2008/0297287 A1 | 12/2008 | Shachar et al. |
| 2008/0308602 A1 | 12/2008 | Timm et al. |
| 2008/0308603 A1 | 12/2008 | Shelton, IV et al. |
| 2008/0308608 A1 | 12/2008 | Prommersberger |
| 2008/0314960 A1 | 12/2008 | Marczyk et al. |
| 2008/0315829 A1 | 12/2008 | Jones et al. |
| 2009/0001121 A1 | 1/2009 | Hess et al. |
| 2009/0001130 A1 | 1/2009 | Hess et al. |
| 2009/0004455 A1 | 1/2009 | Gravagna et al. |
| 2009/0005809 A1 | 1/2009 | Hess et al. |
| 2009/0012534 A1 | 1/2009 | Madhani et al. |
| 2009/0018553 A1 | 1/2009 | McLean et al. |
| 2009/0020958 A1 | 1/2009 | Soul |
| 2009/0047329 A1 | 2/2009 | Stucky et al. |
| 2009/0048589 A1 | 2/2009 | Takashino et al. |
| 2009/0048612 A1 | 2/2009 | Farritor et al. |
| 2009/0054908 A1 | 2/2009 | Zand et al. |
| 2009/0076506 A1 | 3/2009 | Baker |
| 2009/0078736 A1 | 3/2009 | Van Lue |
| 2009/0082789 A1 | 3/2009 | Milliman et al. |
| 2009/0088659 A1 | 4/2009 | Graham et al. |
| 2009/0088774 A1 | 4/2009 | Swarup et al. |
| 2009/0090763 A1 | 4/2009 | Zemlok et al. |
| 2009/0092651 A1 | 4/2009 | Shah et al. |
| 2009/0093728 A1 | 4/2009 | Hyde et al. |
| 2009/0099579 A1 | 4/2009 | Nentwick et al. |
| 2009/0099876 A1 | 4/2009 | Whitman |
| 2009/0108048 A1 | 4/2009 | Zemlok et al. |
| 2009/0112229 A1 | 4/2009 | Omori et al. |
| 2009/0114701 A1 | 5/2009 | Zemlok et al. |
| 2009/0119011 A1 | 5/2009 | Kondo et al. |
| 2009/0137952 A1 | 5/2009 | Ramamurthy et al. |
| 2009/0143805 A1 | 6/2009 | Palmer et al. |
| 2009/0143855 A1 | 6/2009 | Weber et al. |
| 2009/0149871 A9 | 6/2009 | Kagan et al. |
| 2009/0157067 A1 | 6/2009 | Kane et al. |
| 2009/0157087 A1 | 6/2009 | Wei et al. |
| 2009/0171147 A1 | 7/2009 | Lee et al. |
| 2009/0177226 A1 | 7/2009 | Reinprecht et al. |
| 2009/0188964 A1 | 7/2009 | Orlov |
| 2009/0198272 A1 | 8/2009 | Kerver et al. |
| 2009/0204108 A1 | 8/2009 | Steffen |
| 2009/0206125 A1 | 8/2009 | Huitema et al. |
| 2009/0206126 A1 | 8/2009 | Huitema et al. |
| 2009/0206131 A1 | 8/2009 | Weisenburgh, II et al. |
| 2009/0206133 A1 | 8/2009 | Morgan et al. |
| 2009/0206137 A1 | 8/2009 | Hall et al. |
| 2009/0206139 A1 | 8/2009 | Hall et al. |
| 2009/0206141 A1 | 8/2009 | Huitema et al. |
| 2009/0206142 A1 | 8/2009 | Huitema et al. |
| 2009/0213685 A1 | 8/2009 | Mak et al. |
| 2009/0234273 A1 | 9/2009 | Intoccia et al. |
| 2009/0242610 A1 | 10/2009 | Shelton, IV et al. |
| 2009/0247901 A1 | 10/2009 | Zimmer |
| 2009/0248038 A1 | 10/2009 | Blumenkranz et al. |
| 2009/0253959 A1 | 10/2009 | Yoshie et al. |
| 2009/0255974 A1 | 10/2009 | Viola |
| 2009/0255975 A1 | 10/2009 | Zemlok et al. |
| 2009/0255976 A1 | 10/2009 | Marczyk et al. |
| 2009/0255977 A1 | 10/2009 | Zemlok |
| 2009/0255978 A1 | 10/2009 | Viola et al. |
| 2009/0262078 A1 | 10/2009 | Pizzi |
| 2009/0270895 A1 | 10/2009 | Churchill et al. |
| 2009/0277949 A1 | 11/2009 | Viola et al. |
| 2009/0292283 A1 | 11/2009 | Odom |
| 2009/0308907 A1 | 12/2009 | Nalagatla et al. |
| 2010/0010511 A1 | 1/2010 | Harris et al. |
| 2010/0012704 A1 | 1/2010 | Tarinelli Racenet et al. |
| 2010/0016852 A1 | 1/2010 | Manzo et al. |
| 2010/0016888 A1 | 1/2010 | Calabrese et al. |
| 2010/0023024 A1 | 1/2010 | Zeiner et al. |
| 2010/0036370 A1 | 2/2010 | Mirel et al. |
| 2010/0049084 A1 | 2/2010 | Nock et al. |
| 2010/0057087 A1 | 3/2010 | Cha |
| 2010/0057107 A1 | 3/2010 | Sorrentino et al. |
| 2010/0069942 A1 | 3/2010 | Shelton, IV |
| 2010/0072254 A1 | 3/2010 | Aranyi et al. |
| 2010/0076483 A1 | 3/2010 | Imuta |
| 2010/0076489 A1 | 3/2010 | Stopek et al. |
| 2010/0087840 A1 | 4/2010 | Ebersole et al. |
| 2010/0094289 A1 | 4/2010 | Taylor et al. |
| 2010/0096431 A1 | 4/2010 | Smith et al. |
| 2010/0100124 A1 | 4/2010 | Calabrese et al. |
| 2010/0108740 A1 | 5/2010 | Pastorelli et al. |
| 2010/0108741 A1 | 5/2010 | Hessler et al. |
| 2010/0133317 A1 | 6/2010 | Shelton, IV et al. |
| 2010/0145146 A1 | 6/2010 | Melder |
| 2010/0147921 A1 | 6/2010 | Olson |
| 2010/0147922 A1 | 6/2010 | Olson |
| 2010/0147923 A1 | 6/2010 | D'Agostino et al. |
| 2010/0163598 A1 | 7/2010 | Belzer |
| 2010/0179022 A1 | 7/2010 | Shirokoshi |
| 2010/0179540 A1 | 7/2010 | Marczyk et al. |
| 2010/0180711 A1 | 7/2010 | Kilibarda et al. |
| 2010/0186219 A1 | 7/2010 | Smith |
| 2010/0193566 A1 | 8/2010 | Scheib et al. |
| 2010/0200637 A1 | 8/2010 | Beetel |
| 2010/0204717 A1 | 8/2010 | Knodel |

(56) References Cited

U.S. PATENT DOCUMENTS

| | | |
|---|---|---|
| 2010/0222901 A1 | 9/2010 | Swayze et al. |
| 2010/0230465 A1 | 9/2010 | Smith et al. |
| 2010/0243707 A1 | 9/2010 | Olson et al. |
| 2010/0243708 A1 | 9/2010 | Aranyi et al. |
| 2010/0249497 A1 | 9/2010 | Peine et al. |
| 2010/0249519 A1 | 9/2010 | Park et al. |
| 2010/0258611 A1 | 10/2010 | Smith et al. |
| 2010/0267662 A1 | 10/2010 | Fielder et al. |
| 2010/0268030 A1 | 10/2010 | Viola et al. |
| 2010/0274160 A1 | 10/2010 | Yachi et al. |
| 2010/0276471 A1 | 11/2010 | Whitman |
| 2010/0292540 A1 | 11/2010 | Hess et al. |
| 2010/0294827 A1 | 11/2010 | Boyden et al. |
| 2010/0298636 A1 | 11/2010 | Castro et al. |
| 2010/0312261 A1 | 12/2010 | Suzuki et al. |
| 2010/0320252 A1 | 12/2010 | Viola et al. |
| 2010/0331856 A1 | 12/2010 | Carlson et al. |
| 2010/0331880 A1 | 12/2010 | Stopek |
| 2011/0003528 A1 | 1/2011 | Lam |
| 2011/0006101 A1 | 1/2011 | Hall et al. |
| 2011/0011916 A1 | 1/2011 | Levine |
| 2011/0017799 A1 | 1/2011 | Whitman et al. |
| 2011/0022032 A1 | 1/2011 | Zemlok et al. |
| 2011/0024477 A1 | 2/2011 | Hall |
| 2011/0024478 A1 | 2/2011 | Shelton, IV |
| 2011/0034918 A1 | 2/2011 | Reschke |
| 2011/0036887 A1 | 2/2011 | Zemlok et al. |
| 2011/0036890 A1 | 2/2011 | Ma |
| 2011/0036891 A1 | 2/2011 | Zemlok et al. |
| 2011/0045047 A1 | 2/2011 | Bennett et al. |
| 2011/0046666 A1 | 2/2011 | Sorrentino et al. |
| 2011/0046667 A1 | 2/2011 | Culligan et al. |
| 2011/0060363 A1 | 3/2011 | Hess et al. |
| 2011/0084112 A1 | 4/2011 | Kostrzewski |
| 2011/0087276 A1 | 4/2011 | Bedi et al. |
| 2011/0087279 A1 | 4/2011 | Shah et al. |
| 2011/0095068 A1 | 4/2011 | Patel |
| 2011/0101065 A1 | 5/2011 | Milliman |
| 2011/0114697 A1 | 5/2011 | Baxter, III et al. |
| 2011/0118754 A1 | 5/2011 | Dachs, II et al. |
| 2011/0118778 A1 | 5/2011 | Burbank |
| 2011/0125176 A1 | 5/2011 | Yates et al. |
| 2011/0144640 A1 | 6/2011 | Heinrich et al. |
| 2011/0147433 A1 | 6/2011 | Shelton, IV et al. |
| 2011/0155786 A1 | 6/2011 | Shelton, IV |
| 2011/0155787 A1 | 6/2011 | Baxter, III et al. |
| 2011/0163146 A1 | 7/2011 | Ortiz et al. |
| 2011/0174099 A1 | 7/2011 | Ross et al. |
| 2011/0174861 A1 | 7/2011 | Shelton, IV et al. |
| 2011/0178536 A1 | 7/2011 | Kostrzewski |
| 2011/0184459 A1 | 7/2011 | Malkowski et al. |
| 2011/0192882 A1 | 8/2011 | Hess et al. |
| 2011/0208093 A1 | 8/2011 | Gross et al. |
| 2011/0210156 A1 | 9/2011 | Smith et al. |
| 2011/0253765 A1 | 10/2011 | Nicholas et al. |
| 2011/0264119 A1 | 10/2011 | Bayon et al. |
| 2011/0275901 A1 | 11/2011 | Shelton, IV |
| 2011/0276083 A1 | 11/2011 | Shelton, IV et al. |
| 2011/0278343 A1 | 11/2011 | Knodel et al. |
| 2011/0282446 A1 | 11/2011 | Schulte et al. |
| 2011/0290856 A1 | 12/2011 | Shelton, IV et al. |
| 2011/0293690 A1 | 12/2011 | Griffin et al. |
| 2011/0295269 A1 | 12/2011 | Swensgard et al. |
| 2011/0295295 A1 | 12/2011 | Shelton, IV et al. |
| 2011/0313894 A1 | 12/2011 | Dye et al. |
| 2011/0315413 A1 | 12/2011 | Fisher et al. |
| 2012/0004636 A1 | 1/2012 | Lo |
| 2012/0016413 A1 | 1/2012 | Timm et al. |
| 2012/0018326 A1 | 1/2012 | Racenet et al. |
| 2012/0022523 A1 | 1/2012 | Smith et al. |
| 2012/0022630 A1 | 1/2012 | Wübbeling |
| 2012/0029272 A1 | 2/2012 | Shelton, IV et al. |
| 2012/0033360 A1 | 2/2012 | Hsu |
| 2012/0046692 A1 | 2/2012 | Smith et al. |
| 2012/0074200 A1 | 3/2012 | Schmid et al. |
| 2012/0078071 A1 | 3/2012 | Bohm et al. |
| 2012/0078244 A1 | 3/2012 | Worrell et al. |
| 2012/0080336 A1 | 4/2012 | Shelton, IV et al. |
| 2012/0080340 A1 | 4/2012 | Shelton, IV et al. |
| 2012/0080344 A1 | 4/2012 | Shelton, IV |
| 2012/0080475 A1 | 4/2012 | Smith et al. |
| 2012/0080478 A1 | 4/2012 | Morgan et al. |
| 2012/0080498 A1 | 4/2012 | Shelton, IV et al. |
| 2012/0089131 A1 | 4/2012 | Zemlok et al. |
| 2012/0110810 A1 | 5/2012 | Houser et al. |
| 2012/0116265 A1 | 5/2012 | Houser et al. |
| 2012/0116395 A1 | 5/2012 | Madan et al. |
| 2012/0123203 A1 | 5/2012 | Riva |
| 2012/0125792 A1 | 5/2012 | Cassivi |
| 2012/0138658 A1 | 6/2012 | Ullrich et al. |
| 2012/0150192 A1 | 6/2012 | Dachs, II et al. |
| 2012/0175398 A1 | 7/2012 | Sandborn et al. |
| 2012/0187179 A1 | 7/2012 | Gleiman |
| 2012/0209289 A1 | 8/2012 | Duque et al. |
| 2012/0234895 A1 | 9/2012 | O'Connor et al. |
| 2012/0234897 A1 | 9/2012 | Shelton, IV et al. |
| 2012/0234899 A1 | 9/2012 | Scheib et al. |
| 2012/0241492 A1 | 9/2012 | Shelton, IV et al. |
| 2012/0241493 A1 | 9/2012 | Baxter, III et al. |
| 2012/0241498 A1 | 9/2012 | Gonzalez et al. |
| 2012/0241499 A1 | 9/2012 | Baxter, III et al. |
| 2012/0241502 A1 | 9/2012 | Aldridge et al. |
| 2012/0241505 A1 | 9/2012 | Alexander, III et al. |
| 2012/0248167 A1 | 10/2012 | Flanagan et al. |
| 2012/0248169 A1 | 10/2012 | Widenhouse et al. |
| 2012/0253298 A1 | 10/2012 | Henderson et al. |
| 2012/0253329 A1 | 10/2012 | Zemlok et al. |
| 2012/0265176 A1 | 10/2012 | Braun |
| 2012/0271285 A1 | 10/2012 | Sholev et al. |
| 2012/0273550 A1 | 11/2012 | Scirica |
| 2012/0283707 A1 | 11/2012 | Giordano et al. |
| 2012/0283748 A1 | 11/2012 | Ortiz et al. |
| 2012/0286021 A1 | 11/2012 | Kostrzewski et al. |
| 2012/0289979 A1 | 11/2012 | Eskaros et al. |
| 2012/0292367 A1 | 11/2012 | Morgan et al. |
| 2012/0296333 A1 | 11/2012 | Twomey |
| 2012/0298722 A1 | 11/2012 | Hess et al. |
| 2012/0310255 A1 | 12/2012 | Brisson et al. |
| 2012/0310256 A1 | 12/2012 | Brisson |
| 2012/0312860 A1 | 12/2012 | Ming et al. |
| 2012/0318842 A1 | 12/2012 | Anim et al. |
| 2012/0318843 A1 | 12/2012 | Henderson et al. |
| 2012/0318844 A1 | 12/2012 | Shelton, IV et al. |
| 2012/0325892 A1 | 12/2012 | Kostrzewski |
| 2013/0012983 A1 | 1/2013 | Kleyman |
| 2013/0018361 A1 | 1/2013 | Bryant |
| 2013/0020375 A1 | 1/2013 | Shelton, IV et al. |
| 2013/0020376 A1 | 1/2013 | Shelton, IV et al. |
| 2013/0023861 A1 | 1/2013 | Shelton, IV et al. |
| 2013/0026208 A1 | 1/2013 | Shelton, IV et al. |
| 2013/0026210 A1 | 1/2013 | Shelton, IV et al. |
| 2013/0032626 A1 | 2/2013 | Smith et al. |
| 2013/0037596 A1 | 2/2013 | Bear et al. |
| 2013/0048697 A1 | 2/2013 | Shelton, IV et al. |
| 2013/0060278 A1 | 3/2013 | Bozung et al. |
| 2013/0062391 A1 | 3/2013 | Boudreaux et al. |
| 2013/0075446 A1 | 3/2013 | Wang et al. |
| 2013/0079814 A1 | 3/2013 | Hess et al. |
| 2013/0087597 A1 | 4/2013 | Shelton, IV et al. |
| 2013/0087599 A1 | 4/2013 | Krumanaker et al. |
| 2013/0087602 A1 | 4/2013 | Olson et al. |
| 2013/0090534 A1 | 4/2013 | Burns et al. |
| 2013/0098970 A1 | 4/2013 | Racenet et al. |
| 2013/0103024 A1 | 4/2013 | Monson et al. |
| 2013/0116668 A1 | 5/2013 | Shelton, IV et al. |
| 2013/0116669 A1 | 5/2013 | Shelton, IV et al. |
| 2013/0119108 A1 | 5/2013 | Altman et al. |
| 2013/0123822 A1 | 5/2013 | Wellman et al. |
| 2013/0126582 A1 | 5/2013 | Shelton, IV et al. |
| 2013/0131651 A1 | 5/2013 | Strobl et al. |
| 2013/0146641 A1 | 6/2013 | Shelton, IV et al. |
| 2013/0146642 A1 | 6/2013 | Shelton, IV et al. |
| 2013/0150832 A1 | 6/2013 | Belson et al. |
| 2013/0153633 A1 | 6/2013 | Casasanta, Jr. et al. |

(56) References Cited

U.S. PATENT DOCUMENTS

| | | |
|---|---|---|
| 2013/0153634 A1 | 6/2013 | Carter et al. |
| 2013/0153636 A1 | 6/2013 | Shelton, IV et al. |
| 2013/0153638 A1 | 6/2013 | Carter et al. |
| 2013/0153641 A1 | 6/2013 | Shelton, IV et al. |
| 2013/0161374 A1 | 6/2013 | Swayze et al. |
| 2013/0168431 A1 | 7/2013 | Zemlok et al. |
| 2013/0172929 A1 | 7/2013 | Hess et al. |
| 2013/0175317 A1 | 7/2013 | Yates et al. |
| 2013/0175322 A1 | 7/2013 | Yates et al. |
| 2013/0181033 A1 | 7/2013 | Shelton, IV et al. |
| 2013/0181034 A1 | 7/2013 | Shelton, IV et al. |
| 2013/0184718 A1 | 7/2013 | Smith et al. |
| 2013/0184719 A1 | 7/2013 | Shelton, IV et al. |
| 2013/0186932 A1 | 7/2013 | Shelton, IV et al. |
| 2013/0186933 A1 | 7/2013 | Shelton, IV et al. |
| 2013/0186936 A1 | 7/2013 | Shelton, IV |
| 2013/0190733 A1 | 7/2013 | Giordano et al. |
| 2013/0190757 A1 | 7/2013 | Yates et al. |
| 2013/0193188 A1 | 8/2013 | Shelton, IV et al. |
| 2013/0193189 A1 | 8/2013 | Swensgard et al. |
| 2013/0197556 A1 | 8/2013 | Shelton, IV et al. |
| 2013/0214025 A1 | 8/2013 | Zemlok et al. |
| 2013/0214030 A1 | 8/2013 | Aronhalt et al. |
| 2013/0221059 A1 | 8/2013 | Racenet et al. |
| 2013/0221063 A1 | 8/2013 | Aronhalt et al. |
| 2013/0221064 A1 | 8/2013 | Aronhalt et al. |
| 2013/0221065 A1 | 8/2013 | Aronhalt et al. |
| 2013/0233906 A1 | 9/2013 | Hess et al. |
| 2013/0233908 A1 | 9/2013 | Knodel et al. |
| 2013/0238021 A1 | 9/2013 | Gross et al. |
| 2013/0248576 A1 | 9/2013 | Laurent et al. |
| 2013/0256365 A1 | 10/2013 | Shelton, IV et al. |
| 2013/0256366 A1 | 10/2013 | Shelton, IV et al. |
| 2013/0256369 A1 | 10/2013 | Schmid et al. |
| 2013/0256371 A1 | 10/2013 | Shelton, IV |
| 2013/0256373 A1 | 10/2013 | Schmid et al. |
| 2013/0256374 A1 | 10/2013 | Shelton, IV et al. |
| 2013/0256375 A1 | 10/2013 | Shelton, IV et al. |
| 2013/0256377 A1 | 10/2013 | Schmid et al. |
| 2013/0256378 A1 | 10/2013 | Schmid et al. |
| 2013/0256379 A1 | 10/2013 | Schmid et al. |
| 2013/0256380 A1 | 10/2013 | Schmid et al. |
| 2013/0256382 A1 | 10/2013 | Swayze et al. |
| 2013/0256383 A1 | 10/2013 | Aronhalt et al. |
| 2013/0261648 A1 | 10/2013 | Laurent et al. |
| 2013/0270322 A1 | 10/2013 | Scheib et al. |
| 2013/0277412 A1 | 10/2013 | Gresham et al. |
| 2013/0310873 A1 | 11/2013 | Stopek (nee Prommersberger) et al. |
| 2013/0313303 A1 | 11/2013 | Shelton, IV et al. |
| 2013/0313304 A1 | 11/2013 | Shelton, IV et al. |
| 2013/0313306 A1 | 11/2013 | Shelton, IV et al. |
| 2013/0319706 A1 | 12/2013 | Nicholas et al. |
| 2013/0324981 A1 | 12/2013 | Smith et al. |
| 2013/0324982 A1 | 12/2013 | Smith et al. |
| 2013/0327809 A1 | 12/2013 | Shelton, IV et al. |
| 2013/0327810 A1 | 12/2013 | Swayze et al. |
| 2013/0334283 A1 | 12/2013 | Swayze et al. |
| 2013/0334284 A1 | 12/2013 | Swayze et al. |
| 2013/0334285 A1 | 12/2013 | Swayze et al. |
| 2013/0334286 A1 | 12/2013 | Swayze et al. |
| 2013/0334287 A1 | 12/2013 | Shelton, IV |
| 2013/0334288 A1 | 12/2013 | Shelton, IV |
| 2013/0341374 A1 | 12/2013 | Shelton, IV et al. |
| 2014/0001231 A1 | 1/2014 | Shelton, IV et al. |
| 2014/0001234 A1 | 1/2014 | Shelton, IV et al. |
| 2014/0001235 A1 | 1/2014 | Shelton, IV |
| 2014/0001236 A1 | 1/2014 | Shelton, IV et al. |
| 2014/0001237 A1 | 1/2014 | Shelton, IV et al. |
| 2014/0001238 A1 | 1/2014 | Shelton, IV et al. |
| 2014/0001239 A1 | 1/2014 | Shelton, IV et al. |
| 2014/0001240 A1 | 1/2014 | Shelton, IV et al. |
| 2014/0005640 A1 | 1/2014 | Shelton, IV et al. |
| 2014/0005678 A1 | 1/2014 | Shelton, IV et al. |
| 2014/0005693 A1 | 1/2014 | Shelton, IV et al. |
| 2014/0005694 A1 | 1/2014 | Shelton, IV et al. |
| 2014/0005702 A1 | 1/2014 | Timm et al. |
| 2014/0005703 A1 | 1/2014 | Stulen et al. |
| 2014/0005718 A1 | 1/2014 | Shelton, IV et al. |
| 2014/0008414 A1 | 1/2014 | Shelton, IV et al. |
| 2014/0012237 A1 | 1/2014 | Pribanic et al. |
| 2014/0014705 A1 | 1/2014 | Baxter, III |
| 2014/0015782 A1 | 1/2014 | Kim et al. |
| 2014/0018832 A1 | 1/2014 | Shelton, IV |
| 2014/0042205 A1 | 2/2014 | Baxter, III et al. |
| 2014/0048580 A1 | 2/2014 | Merchant et al. |
| 2014/0061279 A1 | 3/2014 | Laurent et al. |
| 2014/0061280 A1 | 3/2014 | Ingmanson et al. |
| 2014/0100558 A1 | 4/2014 | Schmitz et al. |
| 2014/0103093 A1 | 4/2014 | Koch, Jr. et al. |
| 2014/0107640 A1 | 4/2014 | Yates et al. |
| 2014/0110455 A1 | 4/2014 | Ingmanson et al. |
| 2014/0128850 A1 | 5/2014 | Kerr et al. |
| 2014/0151431 A1 | 6/2014 | Hodgkinson et al. |
| 2014/0151433 A1 | 6/2014 | Shelton, IV et al. |
| 2014/0166722 A1 | 6/2014 | Hess et al. |
| 2014/0166724 A1 | 6/2014 | Schellin et al. |
| 2014/0166725 A1 | 6/2014 | Schellin et al. |
| 2014/0166726 A1 | 6/2014 | Schellin et al. |
| 2014/0171966 A1 | 6/2014 | Giordano et al. |
| 2014/0175152 A1 | 6/2014 | Hess et al. |
| 2014/0175154 A1 | 6/2014 | Shelton, IV et al. |
| 2014/0175155 A1 | 6/2014 | Shelton, IV et al. |
| 2014/0191014 A1 | 7/2014 | Shelton, IV |
| 2014/0191015 A1 | 7/2014 | Shelton, IV |
| 2014/0203061 A1 | 7/2014 | Hodgkinson |
| 2014/0205637 A1 | 7/2014 | Widenhouse et al. |
| 2014/0207166 A1 | 7/2014 | Shelton, IV et al. |
| 2014/0224686 A1 | 8/2014 | Aronhalt et al. |
| 2014/0224857 A1 | 8/2014 | Schmid |
| 2014/0230595 A1 | 8/2014 | Butt et al. |
| 2014/0236184 A1 | 8/2014 | Leimbach et al. |
| 2014/0239036 A1 | 8/2014 | Zerkle et al. |
| 2014/0243865 A1 | 8/2014 | Swayze et al. |
| 2014/0246471 A1 | 9/2014 | Jaworek et al. |
| 2014/0246472 A1 | 9/2014 | Kimsey et al. |
| 2014/0246473 A1 | 9/2014 | Auld |
| 2014/0246474 A1 | 9/2014 | Hall et al. |
| 2014/0246475 A1 | 9/2014 | Hall et al. |
| 2014/0246477 A1 | 9/2014 | Koch, Jr. et al. |
| 2014/0246478 A1 | 9/2014 | Baber et al. |
| 2014/0246479 A1 | 9/2014 | Baber et al. |
| 2014/0249557 A1 | 9/2014 | Koch, Jr. et al. |
| 2014/0252066 A1 | 9/2014 | Shelton, IV et al. |
| 2014/0252068 A1 | 9/2014 | Shelton, IV et al. |
| 2014/0259591 A1 | 9/2014 | Shelton, IV et al. |
| 2014/0263537 A1 | 9/2014 | Leimbach et al. |
| 2014/0263538 A1 | 9/2014 | Leimbach et al. |
| 2014/0263539 A1 | 9/2014 | Leimbach et al. |
| 2014/0263541 A1 | 9/2014 | Leimbach et al. |
| 2014/0263542 A1 | 9/2014 | Leimbach et al. |
| 2014/0263543 A1 | 9/2014 | Leimbach et al. |
| 2014/0263551 A1 | 9/2014 | Hall et al. |
| 2014/0263552 A1 | 9/2014 | Hall et al. |
| 2014/0263553 A1 | 9/2014 | Leimbach et al. |
| 2014/0263554 A1 | 9/2014 | Leimbach et al. |
| 2014/0263558 A1 | 9/2014 | Hausen et al. |
| 2014/0263562 A1 | 9/2014 | Patel et al. |
| 2014/0263564 A1 | 9/2014 | Leimbach et al. |
| 2014/0263565 A1 | 9/2014 | Lytle, IV et al. |
| 2014/0263572 A1 | 9/2014 | Shelton, IV et al. |
| 2014/0277017 A1 | 9/2014 | Leimbach et al. |
| 2014/0284371 A1 | 9/2014 | Morgan et al. |
| 2014/0284373 A1 | 9/2014 | Shelton, IV et al. |
| 2014/0291378 A1 | 10/2014 | Shelton, IV et al. |
| 2014/0291379 A1 | 10/2014 | Schellin et al. |
| 2014/0291380 A1 | 10/2014 | Weaner et al. |
| 2014/0291381 A1 | 10/2014 | Weaner et al. |
| 2014/0291382 A1 | 10/2014 | Lloyd et al. |
| 2014/0291383 A1 | 10/2014 | Spivey et al. |
| 2014/0296873 A1 | 10/2014 | Morgan et al. |
| 2014/0296874 A1 | 10/2014 | Morgan et al. |
| 2014/0299648 A1 | 10/2014 | Shelton, IV et al. |
| 2014/0303645 A1 | 10/2014 | Morgan et al. |

(56) References Cited

U.S. PATENT DOCUMENTS

| | | |
|---|---|---|
| 2014/0303646 A1 | 10/2014 | Morgan et al. |
| 2014/0305987 A1 | 10/2014 | Parihar et al. |
| 2014/0305988 A1 | 10/2014 | Boudreaux et al. |
| 2014/0305989 A1 | 10/2014 | Parihar et al. |
| 2014/0305990 A1 | 10/2014 | Shelton, IV et al. |
| 2014/0305991 A1 | 10/2014 | Parihar et al. |
| 2014/0305992 A1 | 10/2014 | Kimsey et al. |
| 2014/0305994 A1 | 10/2014 | Parihar et al. |
| 2014/0309665 A1 | 10/2014 | Parihar et al. |
| 2014/0309666 A1 | 10/2014 | Shelton, IV et al. |
| 2014/0330161 A1 | 11/2014 | Swayze et al. |
| 2014/0339286 A1 | 11/2014 | Motooka et al. |
| 2014/0352463 A1 | 12/2014 | Parihar |
| 2014/0353358 A1 | 12/2014 | Shelton, IV et al. |
| 2014/0367447 A1 | 12/2014 | Woodard, Jr. et al. |
| 2014/0378950 A1 | 12/2014 | Chiu |
| 2015/0008248 A1 | 1/2015 | Giordano et al. |
| 2015/0034696 A1 | 2/2015 | Shelton, IV et al. |
| 2015/0038986 A1 | 2/2015 | Swensgard et al. |
| 2015/0041518 A1 | 2/2015 | Shelton, IV et al. |
| 2015/0053737 A1 | 2/2015 | Leimbach et al. |
| 2015/0053738 A1 | 2/2015 | Morgan et al. |
| 2015/0053739 A1 | 2/2015 | Morgan et al. |
| 2015/0053740 A1 | 2/2015 | Shelton, IV |
| 2015/0053741 A1 | 2/2015 | Shelton, IV et al. |
| 2015/0053742 A1 | 2/2015 | Shelton, IV et al. |
| 2015/0053743 A1 | 2/2015 | Yates et al. |
| 2015/0053744 A1 | 2/2015 | Swayze et al. |
| 2015/0053745 A1 | 2/2015 | Yates et al. |
| 2015/0053746 A1 | 2/2015 | Shelton, IV et al. |
| 2015/0053748 A1 | 2/2015 | Yates et al. |
| 2015/0053749 A1 | 2/2015 | Shelton, IV et al. |
| 2015/0060518 A1 | 3/2015 | Shelton, IV et al. |
| 2015/0060519 A1 | 3/2015 | Shelton, IV et al. |
| 2015/0060520 A1 | 3/2015 | Shelton, IV et al. |
| 2015/0060521 A1 | 3/2015 | Weisenburgh, II et al. |
| 2015/0076207 A1 | 3/2015 | Boudreaux et al. |
| 2015/0076208 A1 | 3/2015 | Shelton, IV |
| 2015/0076209 A1 | 3/2015 | Shelton, IV et al. |
| 2015/0076210 A1 | 3/2015 | Shelton, IV et al. |
| 2015/0076212 A1 | 3/2015 | Shelton, IV |
| 2015/0080868 A1 | 3/2015 | Kerr |
| 2015/0083780 A1 | 3/2015 | Shelton, IV et al. |
| 2015/0083781 A1 | 3/2015 | Giordano et al. |
| 2015/0083782 A1 | 3/2015 | Scheib et al. |
| 2015/0083783 A1 | 3/2015 | Shelton, IV et al. |
| 2015/0090759 A1 | 4/2015 | Spivey et al. |
| 2015/0090760 A1 | 4/2015 | Giordano et al. |
| 2015/0090761 A1 | 4/2015 | Giordano et al. |
| 2015/0090762 A1 | 4/2015 | Giordano et al. |
| 2015/0090763 A1 | 4/2015 | Murray et al. |
| 2015/0108199 A1 | 4/2015 | Shelton, IV et al. |
| 2015/0122869 A1 | 5/2015 | Aronhalt et al. |
| 2015/0136830 A1 | 5/2015 | Baxter, III et al. |
| 2015/0136831 A1 | 5/2015 | Baxter, III et al. |
| 2015/0136832 A1 | 5/2015 | Baxter, III et al. |
| 2015/0136833 A1 | 5/2015 | Shelton, IV et al. |
| 2015/0136835 A1 | 5/2015 | Shelton, IV et al. |
| 2015/0173744 A1 | 6/2015 | Shelton, IV et al. |
| 2015/0173745 A1 | 6/2015 | Baxter, III et al. |
| 2015/0173746 A1 | 6/2015 | Baxter, III et al. |
| 2015/0173747 A1 | 6/2015 | Baxter, III et al. |
| 2015/0173749 A1 | 6/2015 | Shelton, IV et al. |
| 2015/0173750 A1 | 6/2015 | Shelton, IV et al. |
| 2015/0173751 A1 | 6/2015 | Shelton, IV et al. |
| 2015/0173755 A1 | 6/2015 | Baxter, III et al. |
| 2015/0173756 A1 | 6/2015 | Baxter, III et al. |
| 2015/0173760 A1 | 6/2015 | Shelton, IV et al. |
| 2015/0173761 A1 | 6/2015 | Shelton, IV et al. |
| 2015/0173762 A1 | 6/2015 | Shelton, IV et al. |
| 2015/0173789 A1 | 6/2015 | Baxter, III et al. |
| 2015/0182220 A1 | 7/2015 | Yates et al. |
| 2015/0182222 A1 | 7/2015 | Swayze et al. |
| 2015/0196295 A1 | 7/2015 | Shelton, IV et al. |
| 2015/0196296 A1 | 7/2015 | Swayze et al. |
| 2015/0196299 A1 | 7/2015 | Swayze et al. |
| 2015/0196347 A1 | 7/2015 | Yates et al. |
| 2015/0196348 A1 | 7/2015 | Yates et al. |
| 2015/0201932 A1 | 7/2015 | Swayze et al. |
| 2015/0201935 A1 | 7/2015 | Weisenburgh, II et al. |
| 2015/0201936 A1 | 7/2015 | Swayze et al. |
| 2015/0201937 A1 | 7/2015 | Swayze et al. |
| 2015/0201938 A1 | 7/2015 | Swayze et al. |
| 2015/0201939 A1 | 7/2015 | Swayze et al. |
| 2015/0201940 A1 | 7/2015 | Swayze et al. |
| 2015/0201941 A1 | 7/2015 | Swayze et al. |
| 2015/0209031 A1 | 7/2015 | Shelton, IV et al. |
| 2015/0209038 A1 | 7/2015 | Shelton, IV et al. |
| 2015/0209039 A1 | 7/2015 | Shelton, IV et al. |
| 2015/0223809 A1 | 8/2015 | Scheib et al. |
| 2015/0223816 A1 | 8/2015 | Morgan et al. |
| 2015/0230783 A1 | 8/2015 | Shelton, IV et al. |
| 2015/0230784 A1 | 8/2015 | Shelton, IV et al. |
| 2015/0231409 A1 | 8/2015 | Racenet et al. |
| 2015/0238185 A1 | 8/2015 | Schellin et al. |
| 2015/0238186 A1 | 8/2015 | Aronhalt et al. |
| 2015/0238187 A1 | 8/2015 | Schellin et al. |
| 2015/0238188 A1 | 8/2015 | Vendely et al. |
| 2015/0238191 A1 | 8/2015 | Schellin et al. |
| 2015/0239180 A1 | 8/2015 | Schellin et al. |
| 2015/0265276 A1 | 9/2015 | Huitema et al. |
| 2015/0265357 A1 | 9/2015 | Shelton, IV et al. |
| 2015/0272557 A1 | 10/2015 | Overmyer et al. |
| 2015/0272569 A1 | 10/2015 | Leimbach et al. |
| 2015/0272570 A1 | 10/2015 | Lytle, IV et al. |
| 2015/0272571 A1 | 10/2015 | Leimbach et al. |
| 2015/0272572 A1 | 10/2015 | Overmyer et al. |
| 2015/0272574 A1 | 10/2015 | Leimbach et al. |
| 2015/0272575 A1 | 10/2015 | Leimbach et al. |
| 2015/0272578 A1 | 10/2015 | Leimbach et al. |
| 2015/0272579 A1 | 10/2015 | Leimbach et al. |
| 2015/0272580 A1 | 10/2015 | Leimbach et al. |
| 2015/0272581 A1 | 10/2015 | Leimbach et al. |
| 2015/0272582 A1 | 10/2015 | Leimbach et al. |
| 2015/0272583 A1 | 10/2015 | Leimbach et al. |
| 2015/0277471 A1 | 10/2015 | Leimbach et al. |
| 2015/0280384 A1 | 10/2015 | Leimbach et al. |
| 2015/0280424 A1 | 10/2015 | Leimbach et al. |
| 2015/0282809 A1 | 10/2015 | Shelton, IV et al. |
| 2015/0282810 A1 | 10/2015 | Shelton, IV et al. |
| 2015/0289870 A1 | 10/2015 | Shelton, IV et al. |
| 2015/0289873 A1 | 10/2015 | Shelton, IV et al. |
| 2015/0289874 A1 | 10/2015 | Leimbach et al. |
| 2015/0297210 A1 | 10/2015 | Widenhouse et al. |
| 2015/0297217 A1 | 10/2015 | Huitema et al. |
| 2015/0297218 A1 | 10/2015 | Shelton, IV et al. |
| 2015/0297219 A1 | 10/2015 | Shelton, IV et al. |
| 2015/0297221 A1 | 10/2015 | Kerr et al. |
| 2015/0297222 A1 | 10/2015 | Huitema et al. |
| 2015/0297223 A1 | 10/2015 | Huitema et al. |
| 2015/0297224 A1 | 10/2015 | Hall et al. |
| 2015/0297225 A1 | 10/2015 | Huitema et al. |
| 2015/0297226 A1 | 10/2015 | Hall et al. |
| 2015/0297227 A1 | 10/2015 | Huitema et al. |
| 2015/0297228 A1 | 10/2015 | Huitema et al. |
| 2015/0297229 A1 | 10/2015 | Schellin et al. |
| 2015/0297230 A1 | 10/2015 | Schellin et al. |
| 2015/0297231 A1 | 10/2015 | Huitema et al. |
| 2015/0297232 A1 | 10/2015 | Huitema et al. |
| 2015/0297233 A1 | 10/2015 | Huitema et al. |
| 2015/0297234 A1 | 10/2015 | Schellin et al. |
| 2015/0297235 A1 | 10/2015 | Harris et al. |
| 2015/0297236 A1 | 10/2015 | Harris et al. |
| 2015/0305744 A1 | 10/2015 | Moore et al. |
| 2015/0305745 A1 | 10/2015 | Baxter, III et al. |
| 2015/0313591 A1 | 11/2015 | Baxter, III et al. |
| 2015/0313594 A1 | 11/2015 | Shelton, IV et al. |
| 2015/0327853 A1 | 11/2015 | Aronhalt et al. |
| 2015/0335328 A1 | 11/2015 | Shelton, IV et al. |
| 2015/0335329 A1 | 11/2015 | Shelton, IV et al. |
| 2015/0342606 A1 | 12/2015 | Schmid et al. |
| 2015/0342607 A1 | 12/2015 | Shelton, IV et al. |
| 2015/0351755 A1 | 12/2015 | Shelton, IV et al. |
| 2015/0359536 A1 | 12/2015 | Cropper et al. |

(56) References Cited

U.S. PATENT DOCUMENTS

| | | |
|---|---|---|
| 2015/0374367 A1 | 12/2015 | Hall et al. |
| 2015/0374368 A1 | 12/2015 | Swayze et al. |
| 2015/0374369 A1 | 12/2015 | Yates et al. |
| 2015/0374374 A1 | 12/2015 | Shelton, IV et al. |
| 2015/0374375 A1 | 12/2015 | Shelton, IV et al. |
| 2015/0374376 A1 | 12/2015 | Shelton, IV |
| 2015/0374377 A1 | 12/2015 | Shelton, IV |
| 2015/0374378 A1 | 12/2015 | Giordano et al. |
| 2015/0374379 A1 | 12/2015 | Shelton, IV |
| 2016/0000430 A1 | 1/2016 | Ming et al. |
| 2016/0000431 A1 | 1/2016 | Giordano et al. |
| 2016/0000432 A1 | 1/2016 | Huang et al. |
| 2016/0000437 A1 | 1/2016 | Giordano et al. |
| 2016/0000438 A1 | 1/2016 | Swayze et al. |
| 2016/0000439 A1 | 1/2016 | Weisenburgh, II et al. |
| 2016/0000440 A1 | 1/2016 | Weisenburgh, II et al. |
| 2016/0000441 A1 | 1/2016 | Shelton, IV et al. |
| 2016/0000442 A1 | 1/2016 | Shelton, IV |
| 2016/0000452 A1 | 1/2016 | Yates et al. |
| 2016/0000453 A1 | 1/2016 | Yates et al. |
| 2016/0000513 A1 | 1/2016 | Shelton, IV et al. |
| 2016/0007992 A1 | 1/2016 | Yates et al. |
| 2016/0008023 A1 | 1/2016 | Yates et al. |
| 2016/0015390 A1 | 1/2016 | Timm et al. |
| 2016/0015391 A1 | 1/2016 | Shelton, IV et al. |
| 2016/0051257 A1 | 2/2016 | Shelton, IV et al. |
| 2016/0058443 A1 | 3/2016 | Yates et al. |
| 2016/0066909 A1 | 3/2016 | Baber et al. |
| 2016/0066910 A1 | 3/2016 | Baber et al. |
| 2016/0066911 A1 | 3/2016 | Baber et al. |
| 2016/0066912 A1 | 3/2016 | Baber et al. |
| 2016/0066913 A1 | 3/2016 | Swayze et al. |
| 2016/0066914 A1 | 3/2016 | Baber et al. |
| 2016/0066915 A1 | 3/2016 | Baber et al. |
| 2016/0066916 A1 | 3/2016 | Overmyer et al. |
| 2016/0074038 A1 | 3/2016 | Leimbach et al. |
| 2016/0074040 A1 | 3/2016 | Widenhouse et al. |
| 2016/0089137 A1 | 3/2016 | Hess et al. |
| 2016/0089141 A1 | 3/2016 | Harris et al. |
| 2016/0089142 A1 | 3/2016 | Harris et al. |
| 2016/0089143 A1 | 3/2016 | Harris et al. |
| 2016/0089146 A1 | 3/2016 | Harris et al. |
| 2016/0089147 A1 | 3/2016 | Harris et al. |
| 2016/0089148 A1 | 3/2016 | Harris et al. |
| 2016/0089149 A1 | 3/2016 | Harris et al. |
| 2016/0100837 A1 | 4/2016 | Huang et al. |
| 2016/0106426 A1 | 4/2016 | Shelton, IV et al. |
| 2016/0106427 A1 | 4/2016 | Shelton, IV et al. |
| 2016/0106431 A1 | 4/2016 | Shelton, IV et al. |
| 2016/0174969 A1 | 6/2016 | Kerr |
| 2016/0174970 A1 | 6/2016 | Shelton, IV |
| 2016/0174971 A1 | 6/2016 | Baxter, III |
| 2016/0174972 A1 | 6/2016 | Shelton, IV |
| 2016/0174973 A1 | 6/2016 | Shelton, IV |
| 2016/0174975 A1 | 6/2016 | Shelton, IV |
| 2016/0174976 A1 | 6/2016 | Morgan |
| 2016/0174977 A1 | 6/2016 | Lytle, IV |
| 2016/0174978 A1 | 6/2016 | Overmyer |
| 2016/0174983 A1 | 6/2016 | Shelton, IV |

FOREIGN PATENT DOCUMENTS

| | | |
|---|---|---|
| AU | 2012200178 B2 | 7/2013 |
| CA | 2458946 A1 | 3/2003 |
| CA | 2477181 A1 | 4/2004 |
| CA | 2512960 A1 | 1/2006 |
| CA | 2514274 A1 | 1/2006 |
| CA | 2639177 A1 | 2/2009 |
| CN | 2488482 Y | 5/2002 |
| CN | 1523725 A | 8/2004 |
| CN | 1545154 A | 11/2004 |
| CN | 1634601 A | 7/2005 |
| CN | 2716900 Y | 8/2005 |
| CN | 2738962 Y | 11/2005 |
| CN | 1726874 A | 2/2006 |
| CN | 1868411 A | 11/2006 |
| CN | 1915180 A | 2/2007 |
| CN | 2868212 Y | 2/2007 |
| CN | 1960679 A | 5/2007 |
| CN | 101011286 A | 8/2007 |
| CN | 101095621 A | 1/2008 |
| CN | 101541251 A | 9/2009 |
| CN | 101675898 A | 3/2010 |
| CN | 101683280 A | 3/2010 |
| CN | 201949071 U | 8/2011 |
| CN | 102188270 A | 9/2011 |
| CN | 101534723 B | 1/2012 |
| CN | 101507633 B | 2/2013 |
| CN | 101023879 B | 3/2013 |
| CN | 101401736 B | 6/2013 |
| DE | 273689 C | 5/1914 |
| DE | 1775926 A | 1/1972 |
| DE | 3212828 A1 | 11/1982 |
| DE | 3709067 A1 | 9/1988 |
| DE | 9412228 U | 9/1994 |
| DE | 19509116 A1 | 9/1996 |
| DE | 19851291 A1 | 1/2000 |
| DE | 19924311 A1 | 11/2000 |
| DE | 69328576 T2 | 1/2001 |
| DE | 10052679 A1 | 5/2001 |
| DE | 20112837 U1 | 10/2001 |
| DE | 20121753 U1 | 4/2003 |
| DE | 10314827 B3 | 4/2004 |
| DE | 10314072 A1 | 10/2004 |
| EP | 0000756 A1 | 2/1979 |
| EP | 0122046 A1 | 10/1984 |
| EP | 0070230 B1 | 10/1985 |
| EP | 0156774 A2 | 10/1985 |
| EP | 0033548 B1 | 5/1986 |
| EP | 0077262 B1 | 8/1986 |
| EP | 0129442 B1 | 11/1987 |
| EP | 0276104 A2 | 7/1988 |
| EP | 0379721 B1 | 8/1990 |
| EP | 0178940 B1 | 1/1991 |
| EP | 0178941 B1 | 1/1991 |
| EP | 0169044 B1 | 6/1991 |
| EP | 0248844 B1 | 1/1993 |
| EP | 0539762 A1 | 5/1993 |
| EP | 0545029 A1 | 6/1993 |
| EP | 0548998 A1 | 6/1993 |
| EP | 0277959 B1 | 10/1993 |
| EP | 0591946 A1 | 10/1993 |
| EP | 0233940 B1 | 11/1993 |
| EP | 0261230 B1 | 11/1993 |
| EP | 0639349 A2 | 2/1994 |
| EP | 0324636 B1 | 3/1994 |
| EP | 0593920 A1 | 4/1994 |
| EP | 0594148 A1 | 4/1994 |
| EP | 0427949 B1 | 6/1994 |
| EP | 0523174 B1 | 6/1994 |
| EP | 0600182 A2 | 6/1994 |
| EP | 0310431 B1 | 11/1994 |
| EP | 0375302 B1 | 11/1994 |
| EP | 0376562 B1 | 11/1994 |
| EP | 0630612 A1 | 12/1994 |
| EP | 0630614 A1 | 12/1994 |
| EP | 0634144 A1 | 1/1995 |
| EP | 0646356 A2 | 4/1995 |
| EP | 0646357 A1 | 4/1995 |
| EP | 0505036 B1 | 5/1995 |
| EP | 0653189 A2 | 5/1995 |
| EP | 0669104 A1 | 8/1995 |
| EP | 0387980 B1 | 10/1995 |
| EP | 0511470 B1 | 10/1995 |
| EP | 0674876 A2 | 10/1995 |
| EP | 0679367 A2 | 11/1995 |
| EP | 0392547 B1 | 12/1995 |
| EP | 0685204 A1 | 12/1995 |
| EP | 0364216 B1 | 1/1996 |
| EP | 0699418 A1 | 3/1996 |
| EP | 0702937 A1 | 3/1996 |
| EP | 0488768 B1 | 4/1996 |
| EP | 0705571 A1 | 4/1996 |
| EP | 0711611 A2 | 5/1996 |

(56) References Cited

FOREIGN PATENT DOCUMENTS

| | | |
|---|---|---|
| EP | 0484677 B2 | 6/1996 |
| EP | 0541987 B1 | 7/1996 |
| EP | 0667119 B1 | 7/1996 |
| EP | 0737446 A1 | 10/1996 |
| EP | 0748614 A1 | 12/1996 |
| EP | 0708618 B1 | 3/1997 |
| EP | 0770355 A1 | 5/1997 |
| EP | 0503662 B1 | 6/1997 |
| EP | 0447121 B1 | 7/1997 |
| EP | 0621009 B1 | 7/1997 |
| EP | 0625077 B1 | 7/1997 |
| EP | 0633749 B1 | 8/1997 |
| EP | 0710090 B1 | 8/1997 |
| EP | 0578425 B1 | 9/1997 |
| EP | 0621006 B1 | 10/1997 |
| EP | 0625335 B1 | 11/1997 |
| EP | 0552423 B1 | 1/1998 |
| EP | 0592244 B1 | 1/1998 |
| EP | 0648476 B1 | 1/1998 |
| EP | 0649290 B1 | 3/1998 |
| EP | 0598618 B1 | 9/1998 |
| EP | 0676173 B1 | 9/1998 |
| EP | 0678007 B1 | 9/1998 |
| EP | 0869104 A1 | 10/1998 |
| EP | 0603472 B1 | 11/1998 |
| EP | 0605351 B1 | 11/1998 |
| EP | 0878169 A1 | 11/1998 |
| EP | 0879742 A1 | 11/1998 |
| EP | 0695144 B1 | 12/1998 |
| EP | 0722296 B1 | 12/1998 |
| EP | 0760230 B1 | 2/1999 |
| EP | 0623316 B1 | 3/1999 |
| EP | 0650701 B1 | 3/1999 |
| EP | 0537572 B1 | 6/1999 |
| EP | 0923907 A1 | 6/1999 |
| EP | 0640317 A1 | 9/1999 |
| EP | 0843906 B1 | 3/2000 |
| EP | 0552050 B1 | 5/2000 |
| EP | 0833592 B1 | 5/2000 |
| EP | 0832605 B1 | 6/2000 |
| EP | 0830094 B1 | 9/2000 |
| EP | 1034747 A1 | 9/2000 |
| EP | 1034748 A1 | 9/2000 |
| EP | 0694290 B1 | 11/2000 |
| EP | 1050278 A1 | 11/2000 |
| EP | 1053719 A1 | 11/2000 |
| EP | 1053720 A1 | 11/2000 |
| EP | 1055399 A1 | 11/2000 |
| EP | 1055400 A1 | 11/2000 |
| EP | 1058177 A1 | 12/2000 |
| EP | 1080694 A1 | 3/2001 |
| EP | 1090592 A1 | 4/2001 |
| EP | 1095627 A1 | 5/2001 |
| EP | 1256318 B1 | 5/2001 |
| EP | 0806914 B1 | 9/2001 |
| EP | 0768840 B1 | 12/2001 |
| EP | 0908152 B1 | 1/2002 |
| EP | 0717959 B1 | 2/2002 |
| EP | 0872213 B1 | 5/2002 |
| EP | 0862386 B1 | 6/2002 |
| EP | 0949886 B1 | 9/2002 |
| EP | 1238634 A2 | 9/2002 |
| EP | 0858295 B1 | 12/2002 |
| EP | 0656188 B1 | 1/2003 |
| EP | 0717960 B1 | 2/2003 |
| EP | 1284120 A1 | 2/2003 |
| EP | 1287788 A1 | 3/2003 |
| EP | 0717966 B1 | 4/2003 |
| EP | 0869742 B1 | 5/2003 |
| EP | 0829235 B1 | 6/2003 |
| EP | 0887046 B1 | 7/2003 |
| EP | 1323384 A2 | 7/2003 |
| EP | 0852480 B1 | 8/2003 |
| EP | 0891154 B1 | 9/2003 |
| EP | 0813843 B1 | 10/2003 |
| EP | 0873089 B1 | 10/2003 |
| EP | 0856326 B1 | 11/2003 |
| EP | 1374788 A1 | 1/2004 |
| EP | 0741996 B1 | 2/2004 |
| EP | 0814712 B1 | 2/2004 |
| EP | 1402837 A1 | 3/2004 |
| EP | 0705570 B1 | 4/2004 |
| EP | 0959784 B1 | 4/2004 |
| EP | 1407719 A2 | 4/2004 |
| EP | 1086713 B1 | 5/2004 |
| EP | 0996378 B1 | 6/2004 |
| EP | 1426012 A1 | 6/2004 |
| EP | 0833593 B2 | 7/2004 |
| EP | 1442694 A1 | 8/2004 |
| EP | 0888749 B1 | 9/2004 |
| EP | 0959786 B1 | 9/2004 |
| EP | 1459695 A1 | 9/2004 |
| EP | 1254636 B1 | 10/2004 |
| EP | 1473819 A1 | 11/2004 |
| EP | 1477119 A1 | 11/2004 |
| EP | 1479345 A1 | 11/2004 |
| EP | 1479347 A1 | 11/2004 |
| EP | 1479348 A1 | 11/2004 |
| EP | 0754437 B2 | 12/2004 |
| EP | 1025807 B1 | 12/2004 |
| EP | 1001710 B1 | 1/2005 |
| EP | 1496805 A2 | 1/2005 |
| EP | 1520521 A1 | 4/2005 |
| EP | 1520522 A1 | 4/2005 |
| EP | 1520523 A1 | 4/2005 |
| EP | 1520525 A1 | 4/2005 |
| EP | 1522264 A1 | 4/2005 |
| EP | 1523942 A2 | 4/2005 |
| EP | 1550408 A1 | 7/2005 |
| EP | 1557129 A1 | 7/2005 |
| EP | 1064883 B1 | 8/2005 |
| EP | 1067876 B1 | 8/2005 |
| EP | 0870473 B1 | 9/2005 |
| EP | 1157666 B1 | 9/2005 |
| EP | 0880338 B1 | 10/2005 |
| EP | 1158917 B1 | 11/2005 |
| EP | 1344498 B1 | 11/2005 |
| EP | 0906764 B1 | 12/2005 |
| EP | 1330989 B1 | 12/2005 |
| EP | 0771176 B2 | 1/2006 |
| EP | 1621138 A2 | 2/2006 |
| EP | 1621139 A2 | 2/2006 |
| EP | 1621141 A2 | 2/2006 |
| EP | 1621145 A2 | 2/2006 |
| EP | 1621151 A2 | 2/2006 |
| EP | 1034746 B1 | 3/2006 |
| EP | 1201196 B1 | 3/2006 |
| EP | 1632191 A2 | 3/2006 |
| EP | 1647231 A1 | 4/2006 |
| EP | 1065981 B1 | 5/2006 |
| EP | 1082944 B1 | 5/2006 |
| EP | 1230899 B1 | 5/2006 |
| EP | 1652481 A2 | 5/2006 |
| EP | 1382303 B1 | 6/2006 |
| EP | 1253866 B1 | 7/2006 |
| EP | 1032318 B1 | 8/2006 |
| EP | 1045672 B1 | 8/2006 |
| EP | 1617768 B1 | 8/2006 |
| EP | 1693015 A2 | 8/2006 |
| EP | 1400214 B1 | 9/2006 |
| EP | 1702567 A2 | 9/2006 |
| EP | 1129665 B1 | 11/2006 |
| EP | 1400206 B1 | 11/2006 |
| EP | 1721568 A1 | 11/2006 |
| EP | 1256317 B1 | 12/2006 |
| EP | 1285633 B1 | 12/2006 |
| EP | 1728473 A1 | 12/2006 |
| EP | 1728475 A2 | 12/2006 |
| EP | 1736105 A1 | 12/2006 |
| EP | 1011494 B1 | 1/2007 |
| EP | 1479346 B1 | 1/2007 |
| EP | 1484024 B1 | 1/2007 |
| EP | 1749485 A1 | 2/2007 |
| EP | 1754445 A2 | 2/2007 |

(56) References Cited

FOREIGN PATENT DOCUMENTS

| | | | |
|---|---|---|---|
| EP | 1759812 | A1 | 3/2007 |
| EP | 1767157 | A1 | 3/2007 |
| EP | 1767163 | A1 | 3/2007 |
| EP | 1563792 | B1 | 4/2007 |
| EP | 1769756 | A1 | 4/2007 |
| EP | 1769758 | A1 | 4/2007 |
| EP | 1581128 | B1 | 5/2007 |
| EP | 1780825 | A1 | 5/2007 |
| EP | 1785097 | A2 | 5/2007 |
| EP | 1790293 | A2 | 5/2007 |
| EP | 1790294 | A1 | 5/2007 |
| EP | 1563793 | B1 | 6/2007 |
| EP | 1800610 | A1 | 6/2007 |
| EP | 1300117 | B1 | 8/2007 |
| EP | 1813199 | A1 | 8/2007 |
| EP | 1813200 | A2 | 8/2007 |
| EP | 1813201 | A1 | 8/2007 |
| EP | 1813202 | A1 | 8/2007 |
| EP | 1813203 | A2 | 8/2007 |
| EP | 1813207 | A1 | 8/2007 |
| EP | 1813209 | A1 | 8/2007 |
| EP | 1815950 | A1 | 8/2007 |
| EP | 1330991 | B1 | 9/2007 |
| EP | 1806103 | B1 | 9/2007 |
| EP | 1837041 | A1 | 9/2007 |
| EP | 0922435 | B1 | 10/2007 |
| EP | 1487359 | B1 | 10/2007 |
| EP | 1599146 | B1 | 10/2007 |
| EP | 1839596 | A1 | 10/2007 |
| EP | 2110083 | A2 | 10/2007 |
| EP | 1679096 | B1 | 11/2007 |
| EP | 1857057 | A2 | 11/2007 |
| EP | 1402821 | B1 | 12/2007 |
| EP | 1872727 | A1 | 1/2008 |
| EP | 1550410 | B1 | 2/2008 |
| EP | 1671593 | B1 | 2/2008 |
| EP | 1897502 | A1 | 3/2008 |
| EP | 1611856 | B1 | 4/2008 |
| EP | 1908417 | A2 | 4/2008 |
| EP | 1917929 | A1 | 5/2008 |
| EP | 1330201 | B1 | 6/2008 |
| EP | 1702568 | B1 | 7/2008 |
| EP | 1943955 | A2 | 7/2008 |
| EP | 1943957 | A2 | 7/2008 |
| EP | 1943959 | A1 | 7/2008 |
| EP | 1943962 | A2 | 7/2008 |
| EP | 1943964 | A1 | 7/2008 |
| EP | 1943976 | A2 | 7/2008 |
| EP | 1593337 | B1 | 8/2008 |
| EP | 1970014 | A1 | 9/2008 |
| EP | 1974678 | A2 | 10/2008 |
| EP | 1980213 | A2 | 10/2008 |
| EP | 1980214 | A2 | 10/2008 |
| EP | 1759645 | B1 | 11/2008 |
| EP | 1987780 | A2 | 11/2008 |
| EP | 1990014 | A2 | 11/2008 |
| EP | 1552795 | B1 | 12/2008 |
| EP | 1693008 | B1 | 12/2008 |
| EP | 1759640 | B1 | 12/2008 |
| EP | 1997439 | A2 | 12/2008 |
| EP | 2000101 | A2 | 12/2008 |
| EP | 2000102 | A2 | 12/2008 |
| EP | 2005894 | A2 | 12/2008 |
| EP | 2005897 | A2 | 12/2008 |
| EP | 2005901 | A1 | 12/2008 |
| EP | 2008595 | A2 | 12/2008 |
| EP | 1736104 | B1 | 3/2009 |
| EP | 1749486 | B1 | 3/2009 |
| EP | 1782743 | B1 | 3/2009 |
| EP | 2039302 | A2 | 3/2009 |
| EP | 2039308 | A2 | 3/2009 |
| EP | 2039316 | A2 | 3/2009 |
| EP | 1721576 | B1 | 4/2009 |
| EP | 1733686 | B1 | 4/2009 |
| EP | 2044890 | A1 | 4/2009 |
| EP | 2055243 | A2 | 5/2009 |
| EP | 1550409 | B1 | 6/2009 |
| EP | 1550413 | B1 | 6/2009 |
| EP | 1719461 | B1 | 6/2009 |
| EP | 1834594 | B1 | 6/2009 |
| EP | 1709911 | B1 | 7/2009 |
| EP | 2077093 | A2 | 7/2009 |
| EP | 1745748 | B1 | 8/2009 |
| EP | 2090231 | A1 | 8/2009 |
| EP | 2090237 | A1 | 8/2009 |
| EP | 2090241 | A1 | 8/2009 |
| EP | 2090244 | B1 | 8/2009 |
| EP | 2090245 | A1 | 8/2009 |
| EP | 2090254 | A1 | 8/2009 |
| EP | 2090256 | A2 | 8/2009 |
| EP | 2095777 | A2 | 9/2009 |
| EP | 2098170 | A2 | 9/2009 |
| EP | 2110082 | A1 | 10/2009 |
| EP | 2110084 | A2 | 10/2009 |
| EP | 2111803 | A2 | 10/2009 |
| EP | 1762190 | B8 | 11/2009 |
| EP | 1813208 | B1 | 11/2009 |
| EP | 1908426 | B1 | 11/2009 |
| EP | 2116195 | A1 | 11/2009 |
| EP | 2116197 | A2 | 11/2009 |
| EP | 1607050 | B1 | 12/2009 |
| EP | 1815804 | B1 | 12/2009 |
| EP | 1875870 | B1 | 12/2009 |
| EP | 1878395 | B1 | 1/2010 |
| EP | 2151204 | A1 | 2/2010 |
| EP | 1813211 | B1 | 3/2010 |
| EP | 2165656 | A2 | 3/2010 |
| EP | 2165660 | A2 | 3/2010 |
| EP | 1566150 | B1 | 4/2010 |
| EP | 1813206 | B1 | 4/2010 |
| EP | 1769754 | B1 | 6/2010 |
| EP | 1854416 | B1 | 6/2010 |
| EP | 1911408 | B1 | 6/2010 |
| EP | 2198787 | A1 | 6/2010 |
| EP | 1647286 | B1 | 9/2010 |
| EP | 1825821 | B1 | 9/2010 |
| EP | 1535565 | B1 | 10/2010 |
| EP | 1702570 | B1 | 10/2010 |
| EP | 1785098 | B1 | 10/2010 |
| EP | 2005896 | B1 | 10/2010 |
| EP | 2030578 | B1 | 11/2010 |
| EP | 2036505 | B1 | 11/2010 |
| EP | 2245993 | A2 | 11/2010 |
| EP | 2253280 | A1 | 11/2010 |
| EP | 1627605 | B1 | 12/2010 |
| EP | 2027811 | B1 | 12/2010 |
| EP | 2130498 | B1 | 12/2010 |
| EP | 2263568 | A2 | 12/2010 |
| EP | 1994890 | B1 | 1/2011 |
| EP | 2005900 | B1 | 1/2011 |
| EP | 2283780 | A2 | 2/2011 |
| EP | 2286738 | A2 | 2/2011 |
| EP | 1690502 | B1 | 3/2011 |
| EP | 1884201 | B1 | 3/2011 |
| EP | 2292153 | A1 | 3/2011 |
| EP | 1769755 | B1 | 4/2011 |
| EP | 2090240 | B1 | 4/2011 |
| EP | 2305135 | A1 | 4/2011 |
| EP | 2308388 | A1 | 4/2011 |
| EP | 2314254 | A2 | 4/2011 |
| EP | 2316345 | A1 | 5/2011 |
| EP | 2316366 | A2 | 5/2011 |
| EP | 1813205 | B1 | 6/2011 |
| EP | 2090243 | B1 | 6/2011 |
| EP | 2329773 | A1 | 6/2011 |
| EP | 2090239 | B1 | 7/2011 |
| EP | 2340771 | A2 | 7/2011 |
| EP | 2353545 | A1 | 8/2011 |
| EP | 2361562 | A1 | 8/2011 |
| EP | 1836986 | B1 | 11/2011 |
| EP | 1908414 | B1 | 11/2011 |
| EP | 2153781 | B1 | 11/2011 |
| EP | 2389928 | A2 | 11/2011 |
| EP | 1847225 | B1 | 12/2011 |

(56) References Cited

FOREIGN PATENT DOCUMENTS

| | | | |
|---|---|---|---|
| EP | 2399538 A2 | 12/2011 |
| EP | 1785102 B1 | 1/2012 |
| EP | 2090253 B1 | 3/2012 |
| EP | 2430986 A2 | 3/2012 |
| EP | 2446834 A1 | 5/2012 |
| EP | 2455007 A2 | 5/2012 |
| EP | 2457519 A1 | 5/2012 |
| EP | 2462878 A1 | 6/2012 |
| EP | 2462880 A2 | 6/2012 |
| EP | 1813204 B1 | 7/2012 |
| EP | 2189121 B1 | 7/2012 |
| EP | 2248475 B1 | 7/2012 |
| EP | 2005895 B1 | 8/2012 |
| EP | 2090248 B1 | 8/2012 |
| EP | 2481359 A1 | 8/2012 |
| EP | 2486862 A2 | 8/2012 |
| EP | 1908412 B1 | 9/2012 |
| EP | 1935351 B1 | 9/2012 |
| EP | 2497431 A1 | 9/2012 |
| EP | 1550412 B2 | 10/2012 |
| EP | 1616549 B1 | 10/2012 |
| EP | 2030579 B1 | 10/2012 |
| EP | 2090252 B1 | 10/2012 |
| EP | 2517637 A1 | 10/2012 |
| EP | 2517638 A1 | 10/2012 |
| EP | 2517642 A2 | 10/2012 |
| EP | 2517645 A2 | 10/2012 |
| EP | 2517649 A2 | 10/2012 |
| EP | 2517651 A2 | 10/2012 |
| EP | 2526877 A1 | 11/2012 |
| EP | 2526883 A1 | 11/2012 |
| EP | 1884206 B1 | 3/2013 |
| EP | 2090238 B1 | 4/2013 |
| EP | 2586380 A1 | 5/2013 |
| EP | 1982657 B1 | 7/2013 |
| EP | 2614782 A2 | 7/2013 |
| EP | 2090234 B1 | 9/2013 |
| EP | 2633830 A1 | 9/2013 |
| EP | 2644124 A1 | 10/2013 |
| EP | 2644209 A2 | 10/2013 |
| EP | 2649948 A1 | 10/2013 |
| EP | 2649949 A1 | 10/2013 |
| EP | 2700367 A1 | 2/2014 |
| EP | 1772105 B1 | 5/2014 |
| EP | 2759267 A2 | 7/2014 |
| EP | 2446835 B1 | 1/2015 |
| EP | 2923660 A2 | 9/2015 |
| ES | 2396594 T3 | 2/2013 |
| FR | 1112936 A | 3/1956 |
| FR | 2598905 A1 | 11/1987 |
| FR | 2765794 A | 1/1999 |
| FR | 2815842 A1 | 10/2000 |
| GB | 939929 A | 10/1963 |
| GB | 1210522 A | 10/1970 |
| GB | 1217159 A | 12/1970 |
| GB | 1339394 A | 12/1973 |
| GB | 2024012 A | 1/1980 |
| GB | 2109241 A | 6/1983 |
| GB | 2272159 A | 5/1994 |
| GB | 2284242 A | 5/1995 |
| GB | 2286435 A | 8/1995 |
| GB | 2336214 A | 10/1999 |
| GB | 2425903 A | 11/2006 |
| GB | 2423199 B | 5/2009 |
| GR | 930100110 A | 11/1993 |
| JP | S 58500053 A | 1/1983 |
| JP | S 58-501360 A | 8/1983 |
| JP | S 59-174920 A | 3/1984 |
| JP | 60-100955 A | 6/1985 |
| JP | 61-98249 A | 5/1986 |
| JP | S 61502036 A | 9/1986 |
| JP | S 63-59764 A | 3/1988 |
| JP | S 63-147449 A | 6/1988 |
| JP | 63-203149 A | 8/1988 |
| JP | H 02-279149 A | 11/1990 |
| JP | 3-12126 A | 1/1991 |
| JP | H 04-215747 A | 8/1992 |
| JP | H 05-084252 A | 4/1993 |
| JP | H 05-123325 A | 5/1993 |
| JP | 5-212039 A | 8/1993 |
| JP | 6007357 A | 1/1994 |
| JP | H 6-30945 A | 2/1994 |
| JP | H 06-54857 A | 3/1994 |
| JP | H 06-63054 A | 3/1994 |
| JP | H 06-26812 U | 4/1994 |
| JP | H 6-121798 A | 5/1994 |
| JP | H 6-125913 A | 5/1994 |
| JP | H 06-197901 A | 7/1994 |
| JP | H 06-237937 A | 8/1994 |
| JP | H 06-327684 A | 11/1994 |
| JP | 7-31623 A | 2/1995 |
| JP | 7051273 A | 2/1995 |
| JP | H 7-47070 A | 2/1995 |
| JP | 7-124166 A | 5/1995 |
| JP | H 7-163574 A | 6/1995 |
| JP | 07-171163 A | 7/1995 |
| JP | 7-255735 A | 10/1995 |
| JP | H 7-285089 A | 10/1995 |
| JP | 8-33642 A | 2/1996 |
| JP | 8033641 A | 2/1996 |
| JP | 8-164141 A | 6/1996 |
| JP | H 08-182684 A | 7/1996 |
| JP | H 08-507708 A | 8/1996 |
| JP | 8229050 A | 9/1996 |
| JP | H08-289895 A | 11/1996 |
| JP | H 8-336540 A | 12/1996 |
| JP | H 08-336544 A | 12/1996 |
| JP | H 09-501081 A | 2/1997 |
| JP | H 09-501577 A | 2/1997 |
| JP | H 09-164144 A | 6/1997 |
| JP | H 10-113352 A | 5/1998 |
| JP | H 10-118090 A | 5/1998 |
| JP | 10-512469 A | 12/1998 |
| JP | 2000-14632 A | 1/2000 |
| JP | 2000033071 A | 2/2000 |
| JP | 2000-112002 A | 4/2000 |
| JP | 2000-166932 A | 6/2000 |
| JP | 2000171730 A | 6/2000 |
| JP | 2000287987 A | 10/2000 |
| JP | 2000325303 A | 11/2000 |
| JP | 2001-046384 A | 2/2001 |
| JP | 2001-87272 A | 4/2001 |
| JP | 2001-514541 A | 9/2001 |
| JP | 2001-276091 A | 10/2001 |
| JP | 2001-517473 A | 10/2001 |
| JP | 2001286477 A | 10/2001 |
| JP | 2002-51974 A | 2/2002 |
| JP | 2002-085415 A | 3/2002 |
| JP | 2002143078 A | 5/2002 |
| JP | 2002-204801 A | 7/2002 |
| JP | 2002-528161 A | 9/2002 |
| JP | 2002-314298 A | 10/2002 |
| JP | 2002369820 A | 12/2002 |
| JP | 2003-500153 A | 1/2003 |
| JP | 2003000603 A | 1/2003 |
| JP | 2003-504104 A | 2/2003 |
| JP | 2003-135473 A | 5/2003 |
| JP | 2003-148903 A | 5/2003 |
| JP | 2003-164066 A | 6/2003 |
| JP | 2003-521301 A | 7/2003 |
| JP | 2003-523251 A | 8/2003 |
| JP | 2003-523254 A | 8/2003 |
| JP | 2004-147701 A | 5/2004 |
| JP | 2004-162035 A | 6/2004 |
| JP | 2004-229976 A | 8/2004 |
| JP | 2004-524076 A | 8/2004 |
| JP | 2004-531280 A | 10/2004 |
| JP | 2004-532084 A | 10/2004 |
| JP | 2004-532676 A | 10/2004 |
| JP | 2004-329624 A | 11/2004 |
| JP | 2004-337617 A | 12/2004 |
| JP | 2004-344662 A | 12/2004 |
| JP | 2004-344663 A | 12/2004 |
| JP | 2005-028147 A | 2/2005 |

(56) References Cited

FOREIGN PATENT DOCUMENTS

| | | |
|---|---|---|
| JP | 2005-28148 A | 2/2005 |
| JP | 2005-028149 A | 2/2005 |
| JP | 2005-505309 A | 2/2005 |
| JP | 2005-505334 A | 2/2005 |
| JP | 2005505322 T | 2/2005 |
| JP | 2005-80702 A | 3/2005 |
| JP | 2005-103280 A | 4/2005 |
| JP | 2005-103281 A | 4/2005 |
| JP | 2005103293 A | 4/2005 |
| JP | 2005-511131 A | 4/2005 |
| JP | 2005-511137 A | 4/2005 |
| JP | 2005131163 A | 5/2005 |
| JP | 2005131164 A | 5/2005 |
| JP | 2005131173 A | 5/2005 |
| JP | 2005131211 A | 5/2005 |
| JP | 2005131212 A | 5/2005 |
| JP | 2005-137919 A | 6/2005 |
| JP | 2005-144183 A | 6/2005 |
| JP | 2005-516714 A | 6/2005 |
| JP | 2005137423 A | 6/2005 |
| JP | 2005152416 A | 6/2005 |
| JP | 2005-521109 A | 7/2005 |
| JP | 2005-523105 A | 8/2005 |
| JP | 4461008 B2 | 8/2005 |
| JP | 2005524474 A | 8/2005 |
| JP | 2005-296412 A | 10/2005 |
| JP | 2005-328882 A | 12/2005 |
| JP | 2005-335432 A | 12/2005 |
| JP | 2005-342267 A | 12/2005 |
| JP | 2006-034975 A | 2/2006 |
| JP | 2006-34977 A | 2/2006 |
| JP | 2006-034978 A | 2/2006 |
| JP | 2006-034980 A | 2/2006 |
| JP | 2006-506106 A | 2/2006 |
| JP | 2006-510879 A | 3/2006 |
| JP | 2006-187649 A | 7/2006 |
| JP | 2006-218297 A | 8/2006 |
| JP | 2006-223872 A | 8/2006 |
| JP | 2006-281405 A | 10/2006 |
| JP | 2006-289064 A | 10/2006 |
| JP | 2006-334412 A | 12/2006 |
| JP | 2006-334417 A | 12/2006 |
| JP | 2006-346445 A | 12/2006 |
| JP | 2007-000634 A | 1/2007 |
| JP | 2007-050253 A | 3/2007 |
| JP | 2007-61628 A | 3/2007 |
| JP | 2007-083051 A | 4/2007 |
| JP | 2007-098130 A | 4/2007 |
| JP | 2007-105481 A | 4/2007 |
| JP | 3906843 B2 | 4/2007 |
| JP | 2007-117725 A | 5/2007 |
| JP | 2007-130471 A | 5/2007 |
| JP | 2007-130479 A | 5/2007 |
| JP | 2007-222615 A | 6/2007 |
| JP | 3934161 B2 | 6/2007 |
| JP | 2007-203049 A | 8/2007 |
| JP | 2007-203051 A | 8/2007 |
| JP | 2007-203057 A | 8/2007 |
| JP | 2007-524435 A | 8/2007 |
| JP | 2007-229448 A | 9/2007 |
| JP | 2007-252916 A | 10/2007 |
| JP | 4001860 B2 | 10/2007 |
| JP | 2007-307373 A | 11/2007 |
| JP | 2007-325922 A | 12/2007 |
| JP | 2008-68073 A | 3/2008 |
| JP | 2008-206967 A | 9/2008 |
| JP | 2008-212637 A | 9/2008 |
| JP | 2008-212638 A | 9/2008 |
| JP | 2008-220956 A | 9/2008 |
| JP | 2008-259860 A | 10/2008 |
| JP | 2008-264535 A | 11/2008 |
| JP | 2008-283459 A | 11/2008 |
| JP | 2009-006137 A | 1/2009 |
| JP | 2009-502351 A | 1/2009 |
| JP | 2009-022742 A | 2/2009 |
| JP | 2009-506799 A | 2/2009 |
| JP | 2009-72599 A | 4/2009 |
| JP | 2009-090113 A | 4/2009 |
| JP | 2009-106752 A | 5/2009 |
| JP | 2009-189836 A | 8/2009 |
| JP | 2009-189837 A | 8/2009 |
| JP | 2009-189838 A | 8/2009 |
| JP | 2009-201998 A | 9/2009 |
| JP | 2009-536082 A | 10/2009 |
| JP | 2009-261944 A | 11/2009 |
| JP | 2009-268908 A | 11/2009 |
| JP | 2009-539420 A | 11/2009 |
| JP | 2009-291604 A | 12/2009 |
| JP | 2010-504808 A | 2/2010 |
| JP | 2010-504809 A | 2/2010 |
| JP | 2010-504846 A | 2/2010 |
| JP | 2010-505524 A | 2/2010 |
| JP | 2010-069310 A | 4/2010 |
| JP | 2010-088876 A | 4/2010 |
| JP | 2010-098844 A | 4/2010 |
| JP | 4549018 B2 | 9/2010 |
| JP | 2010-540192 A | 12/2010 |
| JP | 4783373 B2 | 7/2011 |
| JP | 5140421 B2 | 2/2013 |
| JP | 5162595 B2 | 3/2013 |
| JP | 2013-128791 A | 7/2013 |
| JP | 5333899 B2 | 11/2013 |
| KR | 20110003229 A | 1/2011 |
| RU | 2008830 C1 | 3/1994 |
| RU | 2052979 C1 | 1/1996 |
| RU | 2141279 C1 | 11/1999 |
| RU | 2144791 C1 | 1/2000 |
| RU | 2181566 C2 | 4/2002 |
| RU | 2187249 C2 | 8/2002 |
| RU | 2189091 C2 | 9/2002 |
| RU | 32984 U1 | 10/2003 |
| RU | 2225170 C2 | 3/2004 |
| RU | 42750 U1 | 12/2004 |
| RU | 61114 U1 | 2/2007 |
| SU | 189517 A | 1/1967 |
| SU | 328636 A | 9/1972 |
| SU | 886900 A1 | 12/1981 |
| SU | 1009439 A | 4/1983 |
| SU | 1022703 A1 | 6/1983 |
| SU | 1333319 A2 | 8/1987 |
| SU | 1377053 A1 | 2/1988 |
| SU | 1561964 A1 | 5/1990 |
| SU | 1722476 A1 | 3/1992 |
| SU | 1814161 A1 | 5/1993 |
| WO | WO 82/02824 A1 | 9/1982 |
| WO | WO 86/02254 A1 | 4/1986 |
| WO | WO 91/15157 A1 | 10/1991 |
| WO | WO 92/20295 A1 | 11/1992 |
| WO | WO 92/21300 A1 | 12/1992 |
| WO | WO 93/08755 A1 | 5/1993 |
| WO | WO 93/13718 A1 | 7/1993 |
| WO | WO 93/14690 A1 | 8/1993 |
| WO | WO 93/15648 A1 | 8/1993 |
| WO | WO 93/15850 A1 | 8/1993 |
| WO | WO 93/19681 A1 | 10/1993 |
| WO | WO 94/00060 A1 | 1/1994 |
| WO | WO 94/11057 A1 | 5/1994 |
| WO | WO 94/12108 A1 | 6/1994 |
| WO | WO 94/18893 A1 | 9/1994 |
| WO | WO 94/20030 A1 | 9/1994 |
| WO | WO 94/22378 A1 | 10/1994 |
| WO | WO 94/23659 A1 | 10/1994 |
| WO | WO 94/24943 A1 | 11/1994 |
| WO | WO 94/24947 A1 | 11/1994 |
| WO | WO 95/02369 A1 | 1/1995 |
| WO | WO 95/03743 A1 | 2/1995 |
| WO | WO 95/06817 A1 | 3/1995 |
| WO | WO 95/09576 A1 | 4/1995 |
| WO | WO 95/09577 A1 | 4/1995 |
| WO | WO 95/14436 A1 | 6/1995 |
| WO | WO 95/17855 A1 | 7/1995 |
| WO | WO 95/18383 A1 | 7/1995 |
| WO | WO 95/18572 A1 | 7/1995 |
| WO | WO 95/19739 A1 | 7/1995 |

(56) References Cited

FOREIGN PATENT DOCUMENTS

| | | |
|---|---|---|
| WO | WO 95/20360 A1 | 8/1995 |
| WO | WO 95/23557 A1 | 9/1995 |
| WO | WO 95/24865 A1 | 9/1995 |
| WO | WO 95/25471 A3 | 9/1995 |
| WO | WO 95/26562 A1 | 10/1995 |
| WO | WO 95/29639 A1 | 11/1995 |
| WO | WO 96/04858 A1 | 2/1996 |
| WO | WO 96/18344 A2 | 6/1996 |
| WO | WO 96/19151 A1 | 6/1996 |
| WO | WO 96/19152 A1 | 6/1996 |
| WO | WO 96/20652 A1 | 7/1996 |
| WO | WO 96/21119 A1 | 7/1996 |
| WO | WO 96/22055 A1 | 7/1996 |
| WO | WO 96/23448 A1 | 8/1996 |
| WO | WO 96/24301 A1 | 8/1996 |
| WO | WO 96/27337 A1 | 9/1996 |
| WO | WO 96/31155 A1 | 10/1996 |
| WO | WO 96/35464 A1 | 11/1996 |
| WO | WO 96/39085 A1 | 12/1996 |
| WO | WO 96/39086 A1 | 12/1996 |
| WO | WO 96/39087 A1 | 12/1996 |
| WO | WO 96/39088 A1 | 12/1996 |
| WO | WO 96/39089 A1 | 12/1996 |
| WO | WO 97/00646 A1 | 1/1997 |
| WO | WO 97/00647 A1 | 1/1997 |
| WO | WO 97/01989 A1 | 1/1997 |
| WO | WO 97/06582 A1 | 2/1997 |
| WO | WO 97/10763 A1 | 3/1997 |
| WO | WO 97/10764 A1 | 3/1997 |
| WO | WO 97/11648 A2 | 4/1997 |
| WO | WO 97/11649 A1 | 4/1997 |
| WO | WO 97/15237 A1 | 5/1997 |
| WO | WO 97/24073 A1 | 7/1997 |
| WO | WO 97/24993 A1 | 7/1997 |
| WO | WO 97/30644 A1 | 8/1997 |
| WO | WO 97/34533 A1 | 9/1997 |
| WO | WO 97/37598 A1 | 10/1997 |
| WO | WO 97/39688 A2 | 10/1997 |
| WO | WO 98/01080 A1 | 1/1998 |
| WO | WO 98/17180 A1 | 4/1998 |
| WO | WO 98/22154 A2 | 5/1998 |
| WO | WO 98/27880 A1 | 7/1998 |
| WO | WO 98/30153 A1 | 7/1998 |
| WO | WO 98/47436 A1 | 10/1998 |
| WO | WO 98/58589 A1 | 12/1998 |
| WO | WO 99/02090 A1 | 1/1999 |
| WO | WO 99/03407 A1 | 1/1999 |
| WO | WO 99/03408 A1 | 1/1999 |
| WO | WO 99/03409 A1 | 1/1999 |
| WO | WO 99/12483 A1 | 3/1999 |
| WO | WO 99/12487 A1 | 3/1999 |
| WO | WO 99/12488 A1 | 3/1999 |
| WO | WO 99/15086 A1 | 4/1999 |
| WO | WO 99/15091 A1 | 4/1999 |
| WO | WO 99/23933 A2 | 5/1999 |
| WO | WO 99/23959 A1 | 5/1999 |
| WO | WO 99/25261 A1 | 5/1999 |
| WO | WO 99/29244 A1 | 6/1999 |
| WO | WO 99/34744 A1 | 7/1999 |
| WO | WO 99/45849 A1 | 9/1999 |
| WO | WO 99/48430 A1 | 9/1999 |
| WO | WO 99/51158 A1 | 10/1999 |
| WO | WO 00/24322 A1 | 5/2000 |
| WO | WO 00/24330 A1 | 5/2000 |
| WO | WO 00/41638 A1 | 7/2000 |
| WO | WO 00/48506 A1 | 8/2000 |
| WO | WO 00/53112 A2 | 9/2000 |
| WO | WO 00/54653 A1 | 9/2000 |
| WO | WO 00/57796 A1 | 10/2000 |
| WO | WO 00/64365 A1 | 11/2000 |
| WO | WO 00/72762 A1 | 12/2000 |
| WO | WO 00/72765 A1 | 12/2000 |
| WO | WO 00/78222 A1 | 12/2000 |
| WO | WO 01/03587 A1 | 1/2001 |
| WO | WO 01/05702 A1 | 1/2001 |
| WO | WO 01/10482 A1 | 2/2001 |
| WO | WO 01/35845 A1 | 5/2001 |
| WO | WO 01/54594 A1 | 8/2001 |
| WO | WO 01/58371 A1 | 8/2001 |
| WO | WO 01/62158 A2 | 8/2001 |
| WO | WO 01/62161 A1 | 8/2001 |
| WO | WO 01/62162 A1 | 8/2001 |
| WO | WO 01/62163 A1 | 8/2001 |
| WO | WO 01/62164 A2 | 8/2001 |
| WO | WO 01/62169 A2 | 8/2001 |
| WO | WO 01/78605 A2 | 10/2001 |
| WO | WO 01/80757 A2 | 11/2001 |
| WO | WO 01/91646 A1 | 12/2001 |
| WO | WO 02/00121 A1 | 1/2002 |
| WO | WO 02/07608 A2 | 1/2002 |
| WO | WO 02/07618 A1 | 1/2002 |
| WO | WO 02/17799 A1 | 3/2002 |
| WO | WO 02/19920 A1 | 3/2002 |
| WO | WO 02/19932 A1 | 3/2002 |
| WO | WO 02/26143 A1 | 4/2002 |
| WO | WO 02/30297 A2 | 4/2002 |
| WO | WO 02/32322 A2 | 4/2002 |
| WO | WO 02/36028 A1 | 5/2002 |
| WO | WO 02/43571 A2 | 6/2002 |
| WO | WO 02/058568 A1 | 8/2002 |
| WO | WO 02/060328 A1 | 8/2002 |
| WO | WO 02/065933 A2 | 8/2002 |
| WO | WO 02/067785 A2 | 9/2002 |
| WO | WO 02/080781 A2 | 10/2002 |
| WO | WO 02/085218 A2 | 10/2002 |
| WO | WO 02/087586 A1 | 11/2002 |
| WO | WO 02/098302 A1 | 12/2002 |
| WO | WO 03/000138 A2 | 1/2003 |
| WO | WO 03/001329 A2 | 1/2003 |
| WO | WO 03/001986 A2 | 1/2003 |
| WO | WO 03/013363 A1 | 2/2003 |
| WO | WO 03/013372 A2 | 2/2003 |
| WO | WO 03/015604 A2 | 2/2003 |
| WO | WO 03/020106 A2 | 3/2003 |
| WO | WO 03/020139 A2 | 3/2003 |
| WO | WO 03/024339 A1 | 3/2003 |
| WO | WO 03/079909 A3 | 3/2003 |
| WO | WO 03/030743 A2 | 4/2003 |
| WO | WO 03/037193 A1 | 5/2003 |
| WO | WO 03/047436 A3 | 6/2003 |
| WO | WO 03/055402 A1 | 7/2003 |
| WO | WO 03/057048 A1 | 7/2003 |
| WO | WO 03/057058 A1 | 7/2003 |
| WO | WO 03/063694 A1 | 8/2003 |
| WO | WO 03/077769 A1 | 9/2003 |
| WO | WO 03/079911 A1 | 10/2003 |
| WO | WO 03/082126 A1 | 10/2003 |
| WO | WO 03/086206 A1 | 10/2003 |
| WO | WO 03/088845 A2 | 10/2003 |
| WO | WO 03/090630 A2 | 11/2003 |
| WO | WO 03/094743 A1 | 11/2003 |
| WO | WO 03/094745 A1 | 11/2003 |
| WO | WO 03/094746 A1 | 11/2003 |
| WO | WO 03/094747 A1 | 11/2003 |
| WO | WO 03/101313 A1 | 12/2003 |
| WO | WO 03/105698 A2 | 12/2003 |
| WO | WO 03/105702 A2 | 12/2003 |
| WO | WO 2004/006980 A2 | 1/2004 |
| WO | WO 2004/011037 A2 | 2/2004 |
| WO | WO 2004/014238 A2 | 2/2004 |
| WO | WO 2004/019769 A1 | 3/2004 |
| WO | WO 2004/019803 A1 | 3/2004 |
| WO | WO 2004/021868 A2 | 3/2004 |
| WO | WO 2004/028585 A2 | 4/2004 |
| WO | WO 2004/030554 A1 | 4/2004 |
| WO | WO 2004/032754 A2 | 4/2004 |
| WO | WO 2004/032760 A2 | 4/2004 |
| WO | WO 2004/032762 A1 | 4/2004 |
| WO | WO 2004/032763 A2 | 4/2004 |
| WO | WO 2004/032783 A1 | 4/2004 |
| WO | WO 2004/034875 A2 | 4/2004 |
| WO | WO 2004/047626 A1 | 6/2004 |
| WO | WO 2004/047653 A2 | 6/2004 |
| WO | WO 2004/049956 A2 | 6/2004 |

(56) References Cited

FOREIGN PATENT DOCUMENTS

| | | |
|---|---|---|
| WO | WO 2004/050971 A2 | 6/2004 |
| WO | WO 2004/052426 A2 | 6/2004 |
| WO | WO 2004/056276 A1 | 7/2004 |
| WO | WO 2004/056277 A1 | 7/2004 |
| WO | WO 2004/062516 A1 | 7/2004 |
| WO | WO 2004/064600 A2 | 8/2004 |
| WO | WO 2004/078050 A2 | 9/2004 |
| WO | WO 2004/078051 A2 | 9/2004 |
| WO | WO 2004/078236 A2 | 9/2004 |
| WO | WO 2004/086987 A1 | 10/2004 |
| WO | WO 2004/096015 A2 | 11/2004 |
| WO | WO 2004/096057 A2 | 11/2004 |
| WO | WO 2004/103157 A2 | 12/2004 |
| WO | WO 2004/105593 A1 | 12/2004 |
| WO | WO 2004/105621 A1 | 12/2004 |
| WO | WO 2004/112618 A2 | 12/2004 |
| WO | WO 2004/112652 A2 | 12/2004 |
| WO | WO 2005/027983 A2 | 3/2005 |
| WO | WO 2005/037329 A2 | 4/2005 |
| WO | WO 2005/042041 A1 | 5/2005 |
| WO | WO 2005/044078 A2 | 5/2005 |
| WO | WO 2005/055846 A1 | 6/2005 |
| WO | WO 2005/072634 A2 | 8/2005 |
| WO | WO 2005/078892 A1 | 8/2005 |
| WO | WO 2005/079675 A2 | 9/2005 |
| WO | WO 2005/087128 A1 | 9/2005 |
| WO | WO 2005/096954 A2 | 10/2005 |
| WO | WO 2005/112806 A2 | 12/2005 |
| WO | WO 2005/112808 A1 | 12/2005 |
| WO | WO 2005/115251 A1 | 12/2005 |
| WO | WO 2005/115253 A2 | 12/2005 |
| WO | WO 2005/117735 A1 | 12/2005 |
| WO | WO 2005/122936 A1 | 12/2005 |
| WO | WO 2006/023486 A1 | 3/2006 |
| WO | WO 2006/023578 A2 | 3/2006 |
| WO | WO 2006/027014 A1 | 3/2006 |
| WO | WO 2006/028314 A1 | 3/2006 |
| WO | WO 2006/044490 A2 | 4/2006 |
| WO | WO 2006/044581 A2 | 4/2006 |
| WO | WO 2006/044810 A2 | 4/2006 |
| WO | WO 2006/049852 A2 | 5/2006 |
| WO | WO 2006/051252 A1 | 5/2006 |
| WO | WO 2006/059067 A1 | 6/2006 |
| WO | WO 2006/083748 A1 | 8/2006 |
| WO | WO 2006/085389 A1 | 8/2006 |
| WO | WO 2006/092563 A1 | 9/2006 |
| WO | WO 2006/092565 A1 | 9/2006 |
| WO | WO 2006/115958 A1 | 11/2006 |
| WO | WO 2006/125940 A1 | 11/2006 |
| WO | WO 2006/132992 A2 | 12/2006 |
| WO | WO 2007/002180 A2 | 1/2007 |
| WO | WO 2007/016290 A2 | 2/2007 |
| WO | WO 2007/018898 A2 | 2/2007 |
| WO | WO 2007/059233 A2 | 5/2007 |
| WO | WO 2007/074430 A2 | 7/2007 |
| WO | WO 2007/089603 A2 | 8/2007 |
| WO | WO 2007/098220 A2 | 8/2007 |
| WO | WO 2007/121579 A1 | 11/2007 |
| WO | WO 2007/129121 A1 | 11/2007 |
| WO | WO 2007/131110 A2 | 11/2007 |
| WO | WO 2007/137304 A2 | 11/2007 |
| WO | WO 2007/139734 A2 | 12/2007 |
| WO | WO 2007/142625 A2 | 12/2007 |
| WO | WO 2007/145825 A2 | 12/2007 |
| WO | WO 2007/146987 A2 | 12/2007 |
| WO | WO 2007/147439 A1 | 12/2007 |
| WO | WO 2008/020964 A2 | 2/2008 |
| WO | WO 2008/021969 A2 | 2/2008 |
| WO | WO 2008/039249 A1 | 4/2008 |
| WO | WO 2008/039270 A1 | 4/2008 |
| WO | WO 2008/045383 A2 | 4/2008 |
| WO | WO 2008/057281 A2 | 5/2008 |
| WO | WO 2008/070763 A1 | 6/2008 |
| WO | WO 2008/089404 A2 | 7/2008 |
| WO | WO 2008/101080 A1 | 8/2008 |
| WO | WO 2008/101228 A2 | 8/2008 |
| WO | WO 2008/103797 A2 | 8/2008 |
| WO | WO 2008/109125 A1 | 9/2008 |
| WO | WO 2008/124748 A1 | 10/2008 |
| WO | WO 2009/022614 A1 | 2/2009 |
| WO | WO 2009/023851 A1 | 2/2009 |
| WO | WO 2009/033057 A2 | 3/2009 |
| WO | WO 2009/039506 A1 | 3/2009 |
| WO | WO 2009/046394 A1 | 4/2009 |
| WO | WO 2009/067649 A2 | 5/2009 |
| WO | WO 2009/091497 A2 | 7/2009 |
| WO | WO 2009/120944 A2 | 10/2009 |
| WO | WO 2009/137761 A2 | 11/2009 |
| WO | WO 2009/143092 A1 | 11/2009 |
| WO | WO 2009/143331 A1 | 11/2009 |
| WO | WO 2009/150650 A2 | 12/2009 |
| WO | WO 2010/028332 A2 | 3/2010 |
| WO | WO 2010/030434 A1 | 3/2010 |
| WO | WO 2010/050771 A2 | 5/2010 |
| WO | WO 2010/054404 A1 | 5/2010 |
| WO | WO 2010/056714 A1 | 5/2010 |
| WO | WO 2010/063795 A1 | 6/2010 |
| WO | WO 2010/090940 A1 | 8/2010 |
| WO | WO 2010/093333 A1 | 8/2010 |
| WO | WO 2010/098871 A2 | 9/2010 |
| WO | WO 2011/008672 A2 | 1/2011 |
| WO | WO 2011/013103 A1 | 2/2011 |
| WO | WO 2011/044343 A2 | 4/2011 |
| WO | WO 2011/060311 A2 | 5/2011 |
| WO | WO 2012/006306 A2 | 1/2012 |
| WO | WO 2012/021671 A1 | 2/2012 |
| WO | WO 2012/040438 A1 | 3/2012 |
| WO | WO 2012/044551 A1 | 4/2012 |
| WO | WO 2012/044554 A1 | 4/2012 |
| WO | WO 2012/044597 A1 | 4/2012 |
| WO | WO 2012/044606 A2 | 4/2012 |
| WO | WO 2012/044820 A1 | 4/2012 |
| WO | WO 2012/044844 A2 | 4/2012 |
| WO | WO 2012/044853 A1 | 4/2012 |
| WO | WO 2012/058213 A2 | 5/2012 |
| WO | WO 2012/068156 A2 | 5/2012 |
| WO | WO 2012/127462 A1 | 9/2012 |
| WO | WO 2012/135705 A1 | 10/2012 |
| WO | WO 2012/143913 A2 | 10/2012 |
| WO | WO 2012/148667 A2 | 11/2012 |
| WO | WO 2012/148703 A2 | 11/2012 |
| WO | WO 2012/160163 A1 | 11/2012 |
| WO | WO 2013/009699 A2 | 1/2013 |
| WO | WO 2013/036409 A1 | 3/2013 |
| WO | WO 2013/043707 A2 | 3/2013 |
| WO | WO 2013/043717 A1 | 3/2013 |
| WO | WO 2013/043721 A2 | 3/2013 |
| WO | WO 2013/062978 A2 | 5/2013 |
| WO | WO 2013/148762 A2 | 10/2013 |
| WO | WO 2013/167427 A1 | 11/2013 |
| WO | WO 2014/004199 A1 | 1/2014 |

OTHER PUBLICATIONS

C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20, pp. 1744-1748.

B.R. Coolman, DVM, MS et al., "Comparison of Skin Staples With Sutures for Anastomosis of the Small Intestine in Dogs," Abstract; http://www.blackwell-synergy.com/doi/abs/10.1053/jvet.2000. 7539?cookieSet=1&journalCode=vsu which redirects to http://www3.interscience.wiley.com/journal/119040681/abstract?CRETRY=1&SRETRY=0; [online] accessed: Sep. 22, 2008 (2 pages).

The Sodem Aseptic Battery Transfer Kit, Sodem Systems, (2000), 3 pages.

"Biomedical Coatings," Fort Wayne Metals, Research Products Corporation, obtained online at www.fwmetals.com on Jun. 21, 2010 (1 page).

Van Meer et al., "A Disposable Plastic Compact Wrist for Smart Minimally Invasive Surgical Tools," LAAS/CNRS (Aug. 2005).

(56) References Cited

OTHER PUBLICATIONS

Breedveld et al., "A New, Easily Miniaturized Sterrable Endoscope," IEEE Engineering in Medicine and Biology Magazine (Nov./Dec. 2005).
D. Tuite, Ed., "Get the Lowdown on Ultracapacitors," Nov. 15, 2007; [online] URL: http://electronicdesign.com/Articles/Print.cfm?ArticleID=17465, accessed Jan. 15, 2008 (5 pages).
Datasheet for Panasonic TK Relays Ultra Low Profile 2 A Polarized Relay, Copyright Matsushita Electric Works, Ltd. (Known of at least as early as Aug. 17, 2010), 5 pages.
ASTM procedure D2240-00, "Standard Test Method for Rubber Property-Durometer Hardness," (Published Aug. 2000).
ASTM procedure D2240-05, "Standard Test Method for Rubber Property-Durometer Hardness," (Published Apr. 2010).
Covidien Brochure, "Endo GIA™ Reloads with Tri-Staple™ Technology," (2010), 1 page.
Covidien Brochure, "Endo GIA™ Reloads with Tri-Staple™ Technology and Endo GIA™ Ultra Universal Staplers," (2010), 2 pages.
Covidien Brochure, "Endo GIA™ Black Reload with Tri-Staple™ Technology," (2012), 2 pages.
Covidien Brochure, "Endo GIA™ Curved Tip Reload with Tri-Staple™ Technology," (2012), 2 pages.
Covidien Brochure, "Endo GIA™ Reloads with Tri-Staple™ Technology," (2010), 2 pages.
Covidien Brochure, "Endo GIA™ Ultra Universal Stapler," (2010), 2 pages.
Miyata et al., "Biomolecule-Sensitive Hydrogels," Advanced Drug Delivery Reviews, 54 (2002) pp. 79-98.
Jeong et al., "Thermosensitive Sol-Gel Reversible Hydrogels," Advanced Drug Delivery Reviews, 54 (2002) pp. 37-51.
Byrne et al., "Molecular Imprinting Within Hydrogels," Advanced Drug Delivery Reviews, 54 (2002) pp. 149-161.
Qiu et al., "Environment-Sensitive Hydrogels for Drug Delivery," Advanced Drug Delivery Reviews, 53 (2001) pp. 321-339.
Hoffman, "Hydrogels for Biomedical Applications," Advanced Drug Delivery Reviews, 43 (2002) pp. 3-12.
Hoffman, "Hydrogels for Biomedical Applications," Advanced Drug Delivery Reviews, 54 (2002) pp. 3-12.
Peppas, "Physiologically Responsive Hydrogels," Journal of Bioactive and Compatible Polymers, vol. 6 (Jul. 1991) pp. 241-246.
Ebara, "Carbohydrate-Derived Hydrogels and Microgels," Engineered Carbohydrate-Based Materials for Biomedical Applications: Polymers, Surfaes, Dendrimers, Nanoparticles, and Hydrogels, Edited by Ravin Narain, 2011, pp. 337-345.
Peppas, Editor "Hydrogels in Medicine and Pharmacy," vol. I, Fundamentals, CRC Press, 1986.
Matsuda, "Thermodynamics of Formation of Porous Polymeric Membrane from Solutions," Polymer Journal, vol. 23, No. 5, pp. 435-444 (1991).
Young, "Microcellular foams via phase separation," Journal of Vacuum Science & Technology A 4(3), (May/Jun. 1986).
Chen et al., "Elastomeric Biomaterials for Tissue Engineering," Progress in Polymer Science 38 (2013), pp. 584-671.
Pitt et al., "Attachment of Hyaluronan to Metallic Surfaces," J. Biomed. Mater. Res. 68A: pp. 95-106, 2004.
Schellhammer et al., "Poly-Lactic-Acid for Coating of Endovascular Stents: Preliminary Results in Canine Experimental Av-Fistulae," Mat.-wiss. u. Werkstofftech., 32, pp. 193-199 (2001).
Solorio et al., "Gelatin Microspheres Crosslinked with Genipin for Local Delivery of Growth Factors," J. Tissue Eng. Regen. Med. (2010), 4(7): pp. 514-523.
http://ninpgan.net/publications/51-100/89.pdf; 2004, Ning Pan, On Uniqueness of Fibrous Materials, Design & Nature II. Eds: Colins, M. And Brebbia, C. WIT Press, Boston, 493-504.
Covidien iDrive™ Ultra in Service Reference Card, "iDrive™ Ultra Powered Stapling Device," (4 pages).
Covidien iDrive™ Ultra Powered Stapling System ibrochure, "The Power of iDrive™ Ultra Powered Stapling System and Tri-Staple™ Technology," (23 pages).
Seils et al., Covidien Summary: Clinical Study "UCONN Biodynamics: Final Report on Results," (2 pages).
Covidien "iDrive™ Ultra Powered Stapling System, A Guide for Surgeons," (6 pages).
Covidien "iDrive™ Ultra Powered Stapling System, Cleaning and Sterilization Guide," (2 pages).
Covidien brochure "iDrive™ Ultra Powered Stapling System," (6 pages).
"Indian Standard: Automotive Vehicles—Brakes and Braking Systems (IS 11852-1:2001)", Mar. 1, 2001.
Fast, Versatile Blackfin Processors Handle Advanced RFID Reader Applications; Analog Dialogue: vol. 40—Sep. 2006; http://www.analog.com/library/analogDialogue/archives/40-09/rfid.pdf; Wayback Machine to Feb. 15, 2012.
Serial Communication Protocol; Michael Lemmon Feb. 1, 2009; http://www3.nd.edu/~lemmon/courses/ee224/web-manual/web-manual/lab12/node2.html; Wayback Machine to Apr. 29, 2012.
European Search Report for Application No. 15162018.4, dated Oct. 28, 2015 (9 pages).
European Search Report for Application No. 08250104.0, dated Jul. 27, 2012 (9 pages).

\* cited by examiner

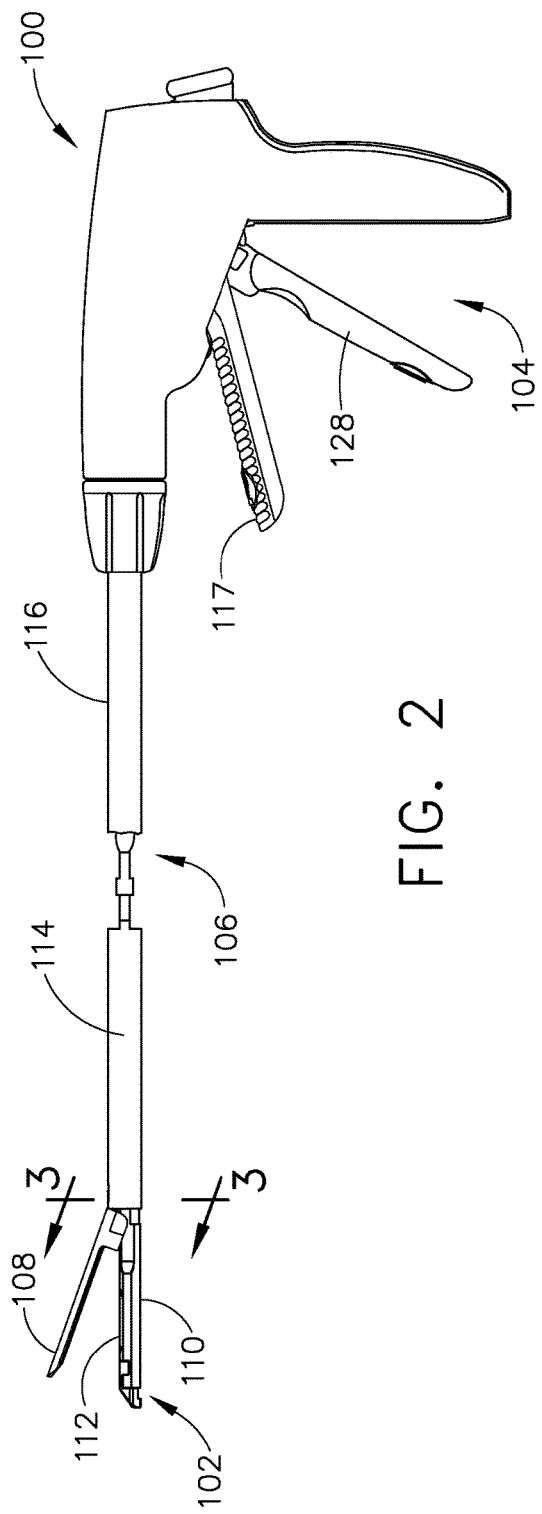
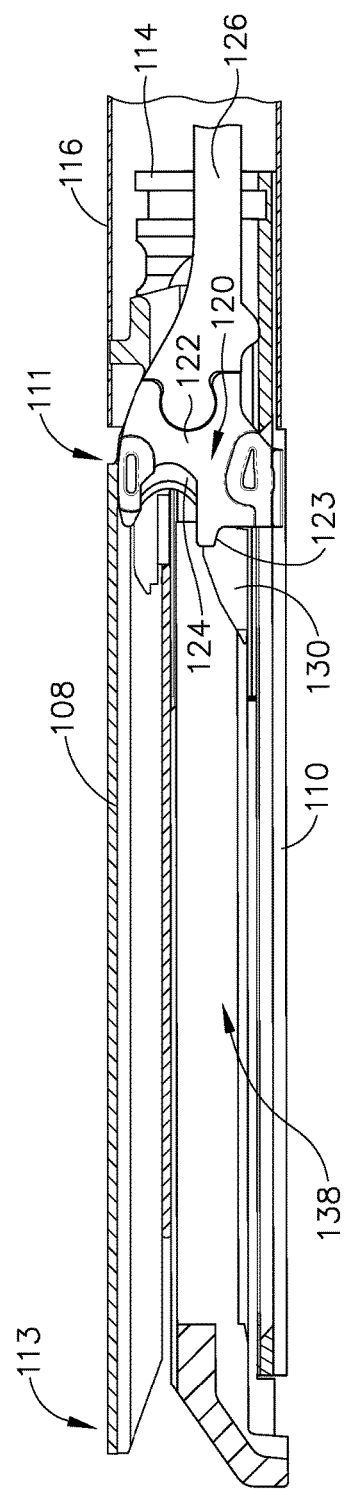
FIG. 2
FIG. 3

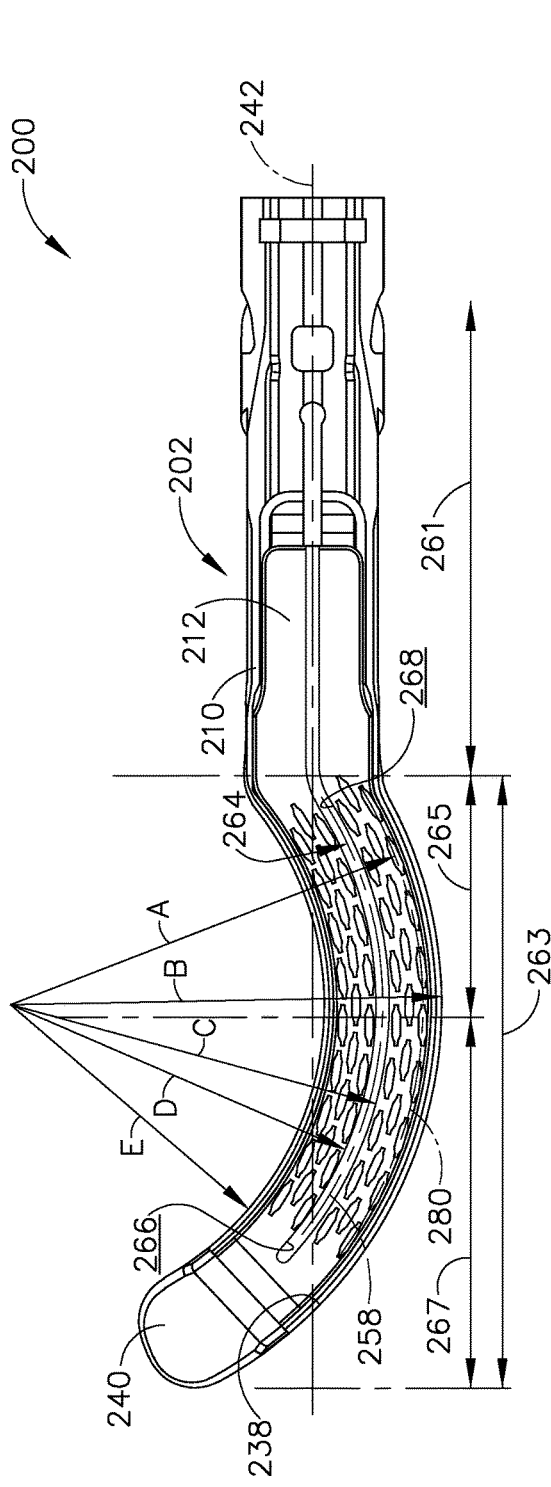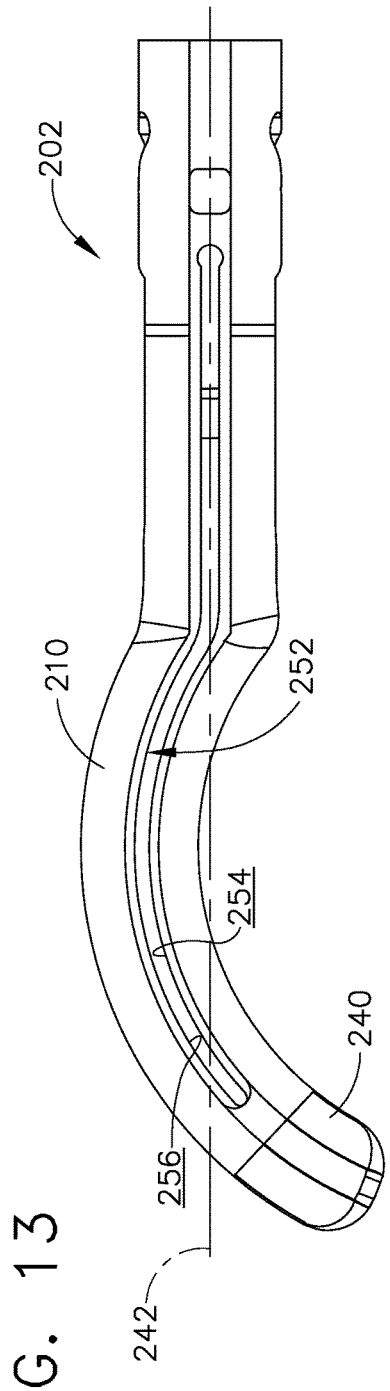
FIG. 13
FIG. 14

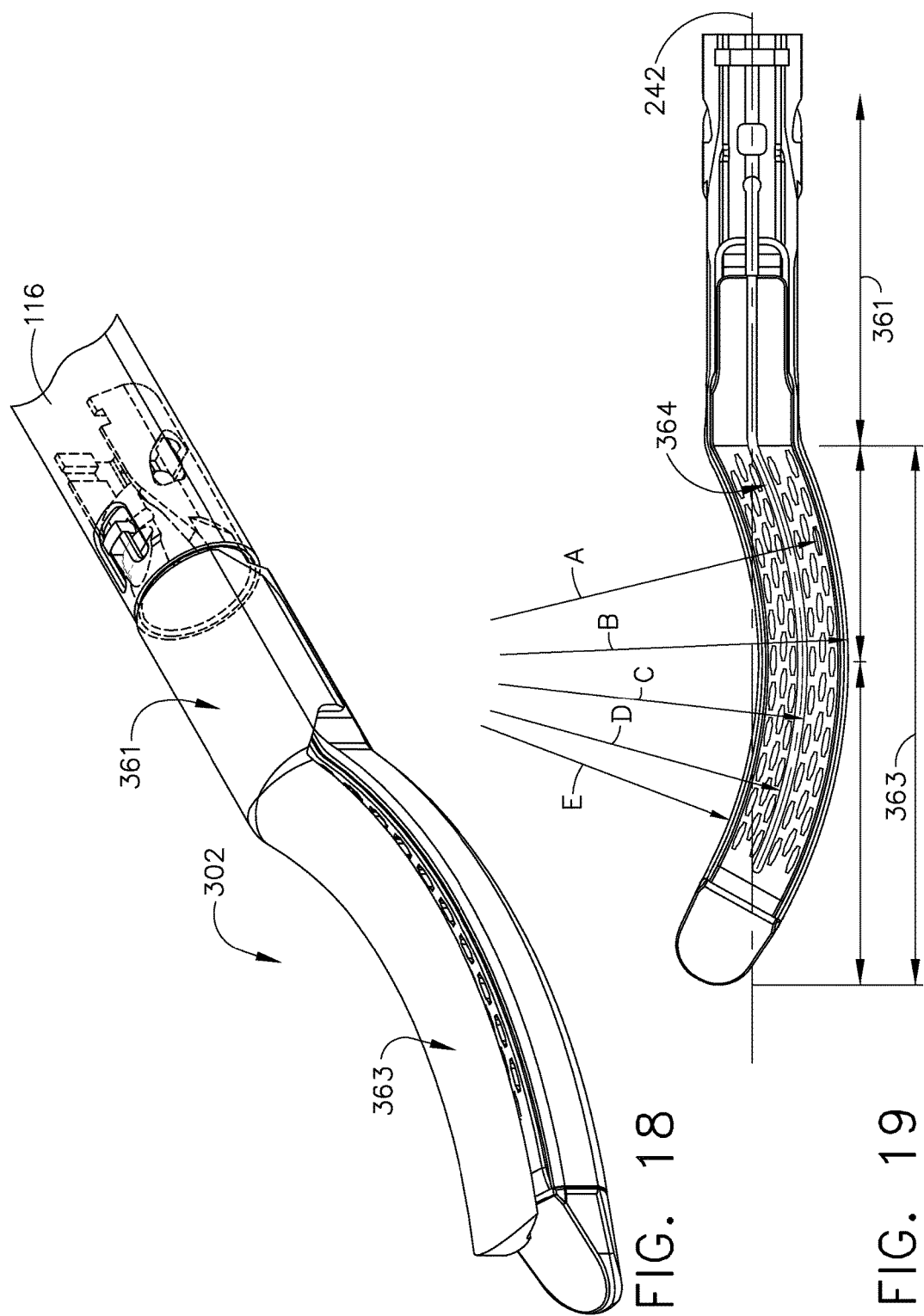

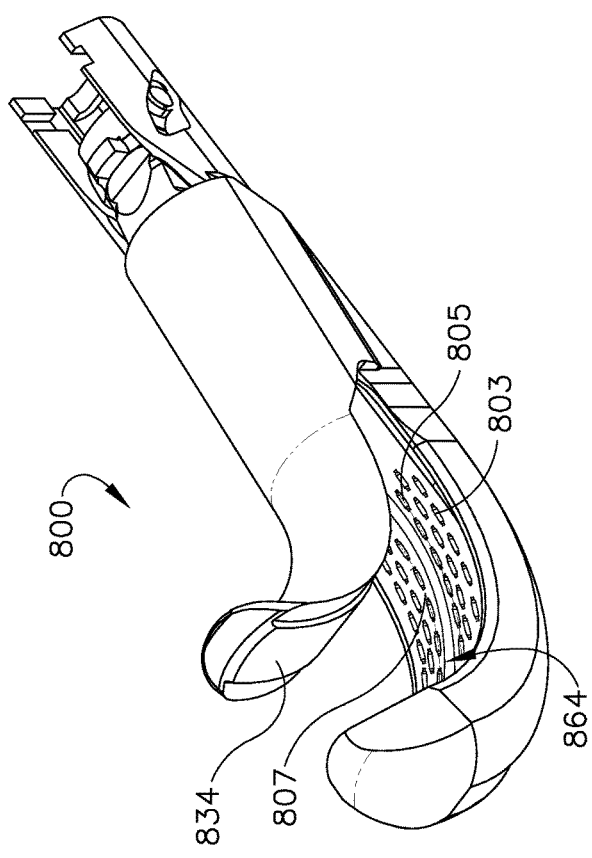
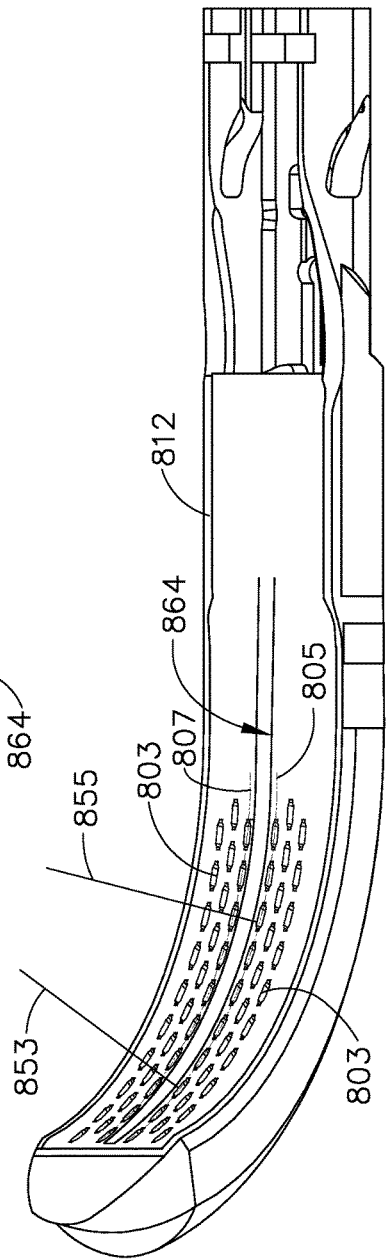
FIG. 38
FIG. 39

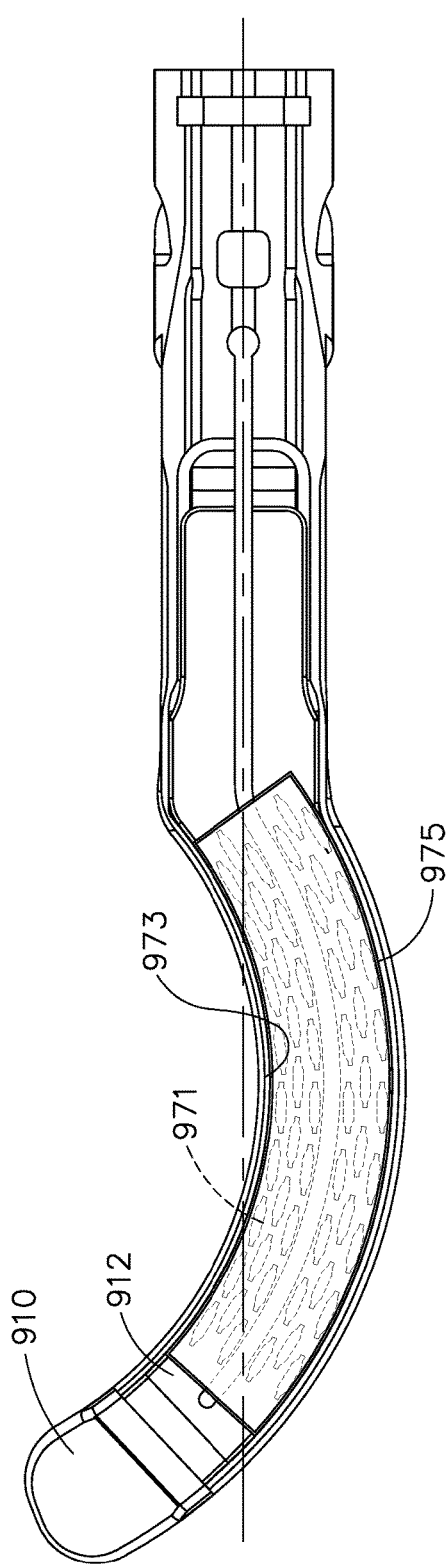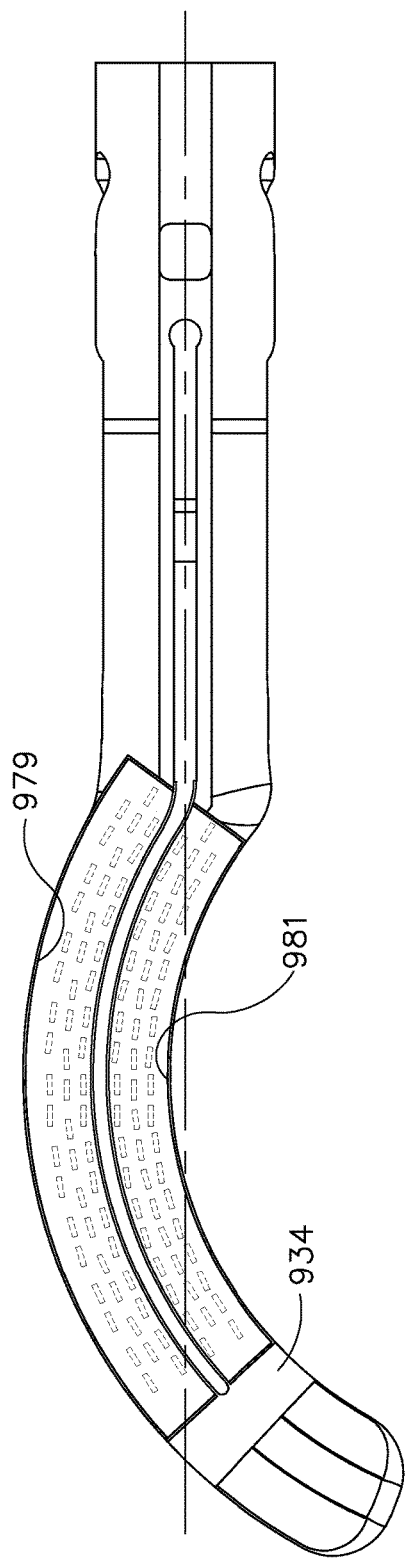
FIG. 45
FIG. 46

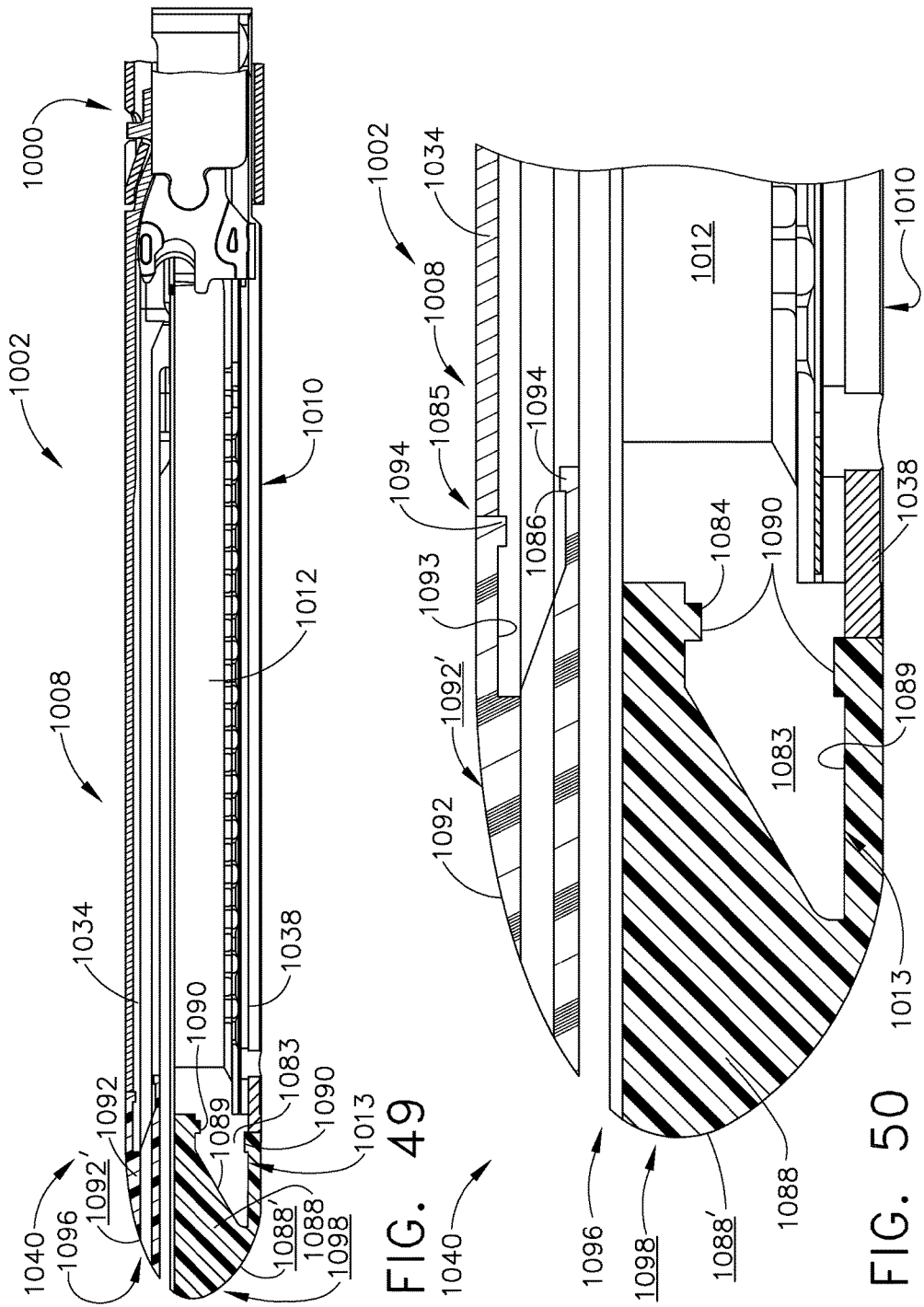

SURGICAL STAPLING DEVICE WITH A CURVED STAPLE CARTRIDGE

CROSS REFERENCE TO RELATED APPLICATIONS

The present application is a continuation application under 35 U.S.C. §120 of co-pending U.S. patent application Ser. No. 11/652,169, filed on Jan. 11, 2007, entitled SURGICAL STAPLING DEVICE WITH A CURVED CUTTING MEMBER, now U.S. Patent Application Publication No. 2008/0169332, the disclosure of which is incorporated herein by reference in its entirety.

The subject application is also related to six co-pending and commonly-owned applications filed on Jan. 11, 2007, the disclosure of each is hereby incorporated by reference in their entirety, these six applications being respectively entitled:

(1) U.S. patent application Ser. No. 11/652,166, entitled "Surgical Stapling Device Having Supports for a Flexible Drive Mechanism" to Frederick E. Shelton, IV, and Jerome R. Morgan, now U.S. Patent Application Publication No. 2008/0169331;

(2) U.S. patent application Ser. No. 11/652,165, entitled "Surgical Stapling Device With a Curved End Effector" to Frederick E. Shelton, IV, Jerome R. Morgan, and Stephen J. Balek, now U.S. Patent Application Publication No. 2008/0169330;

(3) U.S. patent application Ser. No. 11/652,188, entitled "Apparatus for Closing a Curved Anvil of a Surgical Stapling Device" to Frederick E. Shelton, IV, and Jerome R. Morgan, now U.S. Pat. No. 7,434,717;

(4) U.S. patent application Ser. No. 11/652,164, entitled "Improved Curved End Effector for a Surgical Stapling Device" to Frederick E. Shelton, IV, Jerome R. Morgan, Stephen J. Balek, and Douglas Siebenaler, now U.S. Patent Application Publication No. 2008/0169329;

(5) U.S. patent application Ser. No. 11/652,423, entitled "Improved Buttress Material For Use With a Surgical Stapler" to Frederick E. Shelton, IV, now U.S. Patent Application Publication No. 2008/0169328; and (6) U.S. patent application Ser. No. 11/652,170, entitled "Surgical Stapler End Effector With Tapered Distal End" to Frederick E. Shelton, IV, and Jerome R. Morgan, now U.S. Patent Application Publication No. 2008/0169333.

BACKGROUND

1. Field of the Invention

The present invention generally relates to surgical staplers, and, more particularly, to surgical staplers having a curved end-effector and to surgical techniques for using the same.

2. Description of the Related Art

As known in the art, surgical staplers are often used to deploy staples into soft tissue to reduce or eliminate bleeding from the soft tissue, especially as the tissue is being transected, for example. Surgical staplers, such as an endocutter, for example, often comprise an end-effector which is configured to secure the soft tissue between first and second jaw members. The first jaw member often includes a staple cartridge which is configured to removably store staples therein and the second jaw member often includes an anvil. In use, the staples are typically deployed from the staple cartridge by a driver which traverses a channel in the staple cartridge. The driver causes the staples to be deformed against the anvil and secure layers of the soft tissue together. Often, as known in the art, the staples are deployed in several staple lines, or rows, in order to more reliably secure the layers of tissue together. The end-effector may also include a cutting member, such as a knife, for example, which is advanced between two rows of the staples to resect the soft tissue after the layers of the soft tissue have been stapled together.

The end-effectors of previous endocutters are often configured to deploy staples in straight lines. During many surgical techniques, such as the resection of stomach tissue, for example, such a linear deployment is often preferred. During these techniques, the end-effector is typically inserted through a cannula to access the surgical site and, as a result, it is often desirable for the end-effector to have a linear configuration that can be aligned with an axis of the cannula before the end-effector is inserted therethrough. However, in some circumstances, end-effectors having such a linear configuration are somewhat difficult to use. More particularly, for example, when the end-effector must be placed adjacent to or against a cavity wall, such as the thoracic cavity wall, for example, it is often difficult for the surgeon to position a jaw of the end effector behind delicate or fragile tissue which is proximal to and/or attached to the cavity wall. Furthermore, even if the surgeon is successful in positioning a jaw behind the tissue, owing to the linear configuration of the end-effector, the surgeon may not be able to see the distal end of the end-effector.

In some circumstances, endocutters having a curved end-effector have been used for accessing, stapling and transecting tissue. These end-effectors typically include curved anvils and staple cartridges which co-operate to deploy the staples in curved rows. To deploy the staples in this manner, the staple driver and the cutting member can be moved through a curved path by a flexible drive member. However, owing to the amount of force that is typically transmitted through the flexible drive member, the drive member may buckle or otherwise deform in an unsuitable manner. Furthermore, previous curved end-effectors are configured such that the distal ends of the jaw members are the last portions of the jaw members to contact the soft tissue. As a result, tissue may escape from between the jaw members before the jaw members are completely closed. What is needed is an improvement over the foregoing.

SUMMARY

In various embodiments, an end effector for use with a surgical instrument is disclosed comprising a curved staple cartridge comprising a first curved row of staple cavities, a second curved row of staple cavities, a plurality of staples, wherein a first quantity of staples are ejectably stored in the staple cavities of the first curved row of staple cavities, and wherein a second quantity of staples are ejectably stored in the staple cavities of the second curved row of staple cavities, and a curved slot positioned intermediate the first curved row of staple cavities and the second curved row of staple cavities, wherein the curved slot extends along a curved path between a proximal portion of the curved staple cartridge and a distal portion of the curved staple cartridge. The end effector further comprises a sled configured to translate along the slot and eject the staples from the staple cavities during a firing stroke. The sled comprises a first permanently curved camming wedge, a second permanently curved camming wedge, and a permanently curved connector extending between the first permanently curved camming wedge and the second permanently curved camming wedge, wherein the permanently curved connector connects the first permanently curved camming wedge and the second permanently curved camming wedge within the curved staple cartridge, wherein the permanently curved connector comprises a permanent curvature that corresponds to the curved path of the curved slot.

In various embodiments, a replaceable end effector for cutting and stapling tissue is disclosed comprising a first jaw, a second jaw, and a longitudinally curved staple cartridge comprising a plurality of staple cavities, wherein the staple cavities are arranged along a plurality of longitudinally curved axes, a plurality of staples removably stored in the staple cavities, and a longitudinally curved slot comprising a radius of curvature. The end effector further comprises a longitudinally curved sled configured to translate through at least a portion of the longitudinally curved staple cartridge, wherein the longitudinally curved sled comprises a plurality of longitudinally curved camming wedges, wherein each longitudinally curved camming wedge comprises an inflexible radius of curvature, wherein the longitudinally curved sled further comprises a longitudinally curved connector flanked by the longitudinally curved camming wedges, wherein the longitudinally curved connector connects the longitudinally curved camming wedges within the longitudinally curved staple cartridge, wherein the longitudinally curved connector comprises an inflexible radius of curvature, and wherein the inflexible radius of curvature of the longitudinally curved connector corresponds to the radius of curvature of the longitudinally curved slot.

In various embodiments, an end effector for cutting and stapling tissue is disclosed comprising a curved staple cartridge comprising a plurality of curved rows of staple cavities, a plurality of staples, wherein the staples are ejectably positioned in the staple cavities of the plurality of curved rows of staple cavities, and a slot extending between a proximal portion of the curved staple cartridge and a distal portion of the curved staple cartridge, wherein the slot defines a curved trajectory within the curved staple cartridge. The end effector further comprises a curved sled configured to translate through at least a portion of the curved staple cartridge during a firing stroke. The curved sled comprises a plurality of staple-ejecting cams, a connector extending between a pair of the staple-ejecting cams, wherein the connector connects the pair of staple-ejecting cams within the curved staple cartridge, wherein the connector comprises an irreversible radius of curvature that corresponds to the curved trajectory of the slot, and a curved trajectory that is fixed prior to the firing stroke, wherein the curved trajectory of the curved sled matches the curved trajectory of the slot.

In various embodiments, an end effector for use with a surgical instrument is disclosed comprising a curved staple cartridge comprising a plurality of curved rows of staple cavities, a plurality of staples removably positioned in the staple cavities of the plurality of curved rows of staple cavities, and a curved slot extending along a curved path between a proximal portion of the curved staple cartridge and a distal portion of the curved staple cartridge. The end effector further comprises an irreversibly curved sled configured to eject staples from the staple cavities during a firing stroke, wherein the irreversibly curved sled comprises a plurality of irreversibly curved ramps and an irreversibly curved connector flanked by the irreversibly curved ramps, wherein the irreversibly curved connector connects the irreversibly curved ramps within the curved staple cartridge, wherein the irreversibly curved connector comprises an irreversible curvature, wherein the irreversibly curved connector is configured to translate along the curved path of the curved slot, and wherein the irreversible curvature corresponds to the curved path.

In various embodiments, a disposable end effector for cutting and stapling tissue is disclosed comprising a staple cartridge comprising a plurality of staples removably positioned in staple cavities and a slot extending from a proximal portion of the staple cartridge to a distal portion of the staple cartridge, wherein the slot comprises a radius of curvature between the proximal portion of the staple cartridge and the distal portion of the staple cartridge. The end effector further comprises a staple-ejecting sled comprising a first ramp, a second ramp, and a central section intermediate the first ramp and the second ramp, wherein the central section connects the first ramp and the second ramp within the staple cartridge, wherein the central section comprises an inflexible radius of curvature, and wherein the inflexible radius of curvature relates to the radius of curvature of the slot, and wherein the central section is configured to translate along at least a portion of the slot.

In various embodiments, an end effector for a surgical stapler is disclosed comprising a staple cartridge comprising a plurality of staples removably positioned in staple cavities, wherein the staples are removed from the staple cavities during a firing stroke, and a curved slot extending along a curved path between a proximal portion of the staple cartridge and a distal portion of the staple cartridge. The end effector further comprises a permanently curved sled configured to translate along the curved slot during the firing stroke, wherein the permanently curved sled comprises a ramp and a connector comprising a permanent curvature that corresponds to the curved path of the curved slot, wherein the connector is connected to the ramp within the staple cartridge.

In various embodiments, a surgical end effector is disclosed comprising a staple cartridge comprising a plurality staple cavities, a plurality of staples removably positioned in the staple cavities, and a slot extending between a proximal portion of the staple cartridge and a distal portion of the staple cartridge, wherein the slot defines a curved trajectory between the proximal portion of the staple cartridge and the distal portion of the staple cartridge. The end effector further comprises a staple-ejecting sled comprising a ramp configured to translate between the proximal portion of the staple cartridge and the distal portion of the staple cartridge during a firing stroke, wherein the ramp defines a predefined trajectory that is defined pre-firing stroke, wherein the predefined trajectory is coextensive with the curved trajectory of the slot, wherein the staple-electing sled further comprises a central section configured to translate in the slot, wherein the central section is connected to the ramp within the staple cartridge, and wherein the central section comprises a permanent curvature that corresponds to the curved trajectory of the slot.

In various embodiments, an end effector for use with a surgical instrument is disclosed comprising a staple cartridge comprising a plurality of staple cavities arranged in staple cavity rows, a plurality of staples ejectably stored in the staple cavities, and a slot comprising a longitudinal curvature. The end effector further comprises a staple-ejecting sled configured to translate along the slot during a firing stroke, wherein the staple-ejecting sled comprises a ramp and an irreversibly curved guide, wherein the irreversibly curved guide is connected to the ramp within the staple cartridge and wherein the irreversibly curved guide comprises a longitudinal curvature that matches the longitudinal curvature of the slot.

In various embodiments, a disposable end effector for cutting and stapling tissue is disclosed comprising a first jaw, a second jaw, and a staple cartridge comprising a plurality of staples removably positioned in a plurality of staple cavities and a slot extending between a proximal portion of the staple cartridge and a distal portion of the staple cartridge, wherein the slot comprises a curvature between the proximal portion of the staple cartridge and the distal portion of the staple cartridge. The end effector further comprises a staple-firing sled configured to translate at least partially through the staple cartridge during a firing stroke. The staple-firing sled comprises a staple-camming body comprising a proximal end and a distal end, a central section configured to translate along the slot, wherein the central section is connected to the staple-camming body within the staple cartridge, and wherein the central section comprises a permanent radius of curvature that corresponds to the curvature of the slot, and a pre-defined radius of curvature between the proximal end and the distal end of the staple-camming body, wherein the pre-defined radius of curvature is defined pre-firing stroke.

BRIEF DESCRIPTION OF THE FIGURES

The above-mentioned and other features and advantages of this invention, and the manner of attaining them, will become more apparent and the invention itself will be better understood by reference to the following description of embodiments of the invention taken in conjunction with the accompanying drawings, wherein:

FIG. 2 is a partial cut-away view of the endocutter of FIG. 1;

FIG. 3 is a partial cross-sectional view of the endocutter of FIG. 2 taken along line 3-3 in FIG. 2;

FIG. 13 is a top view of the staple cartridge of the end-effector of FIG. 12;

FIG. 14 is a bottom view of the jaw configured to support the staple cartridge of FIG. 13;

FIG. 18 is a perspective view of an endocutter having a curved end-effector in accordance with an alternative embodiment of the present invention;

FIG. 19 is a top view of the staple cartridge of the end-effector of FIG. 18;

FIG. 38 is a perspective view of an endocutter having a curved end-effector in accordance with an alternative embodiment of the present invention;

FIG. 39 is a perspective view of the staple cartridge of the end-effector of FIG. 38;

FIG. 45 is a top view of the staple cartridge of FIG. 44 illustrating a piece of buttress material positioned thereon;

FIG. 46 is a bottom view of the anvil of FIG. 44 illustrating two pieces of buttress material positioned thereon;

FIG. 49 is a cross-sectional view of the end effector of FIG. 48 taken along line 49-49 in FIG. 48; and FIG. 50 is an enlarged cross-sectional view of the distal end of the end effector of FIG. 49.

Figure 1:
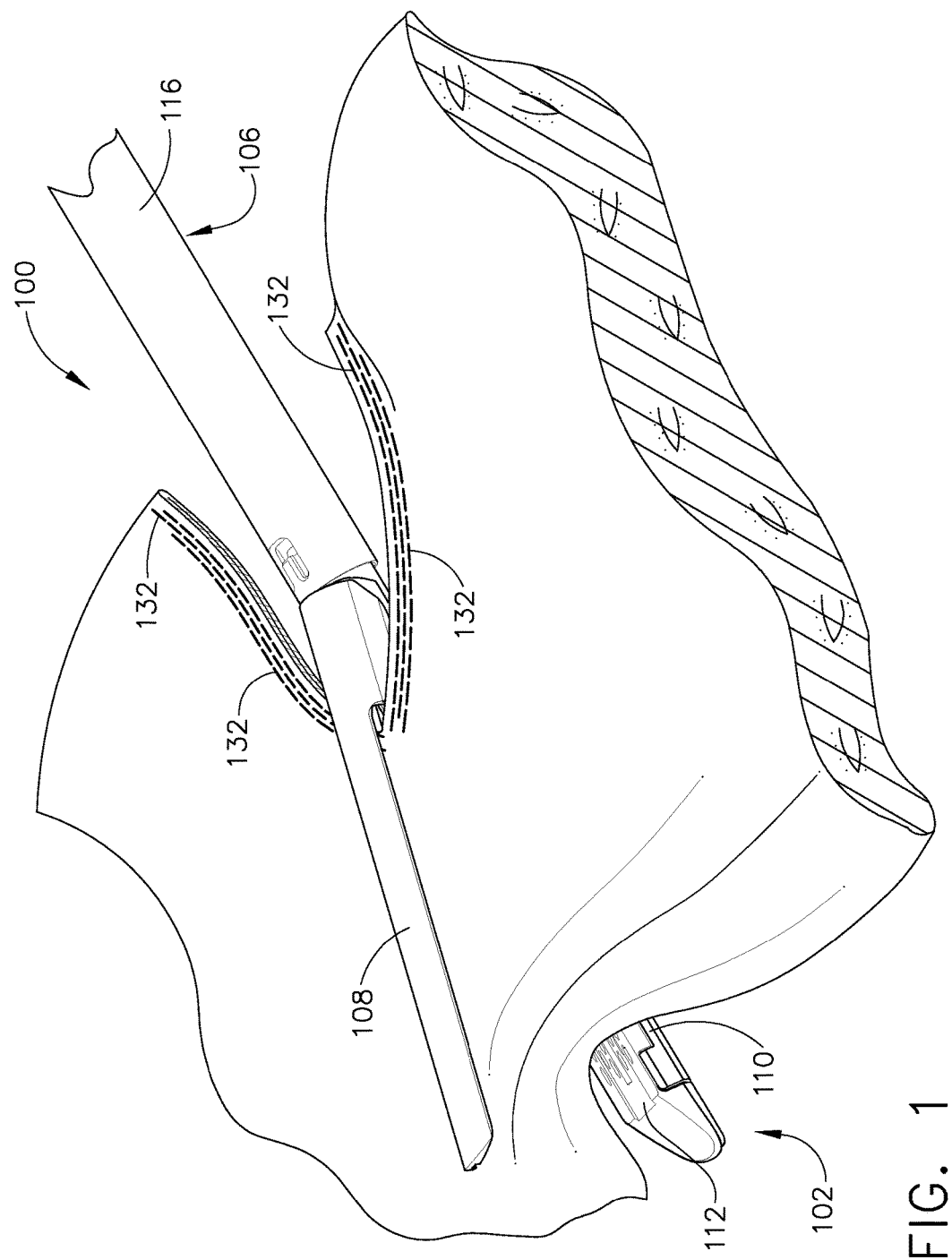
FIG. 1 is a schematic of an endocutter being used to transect and staple tissue.
Figure 4:
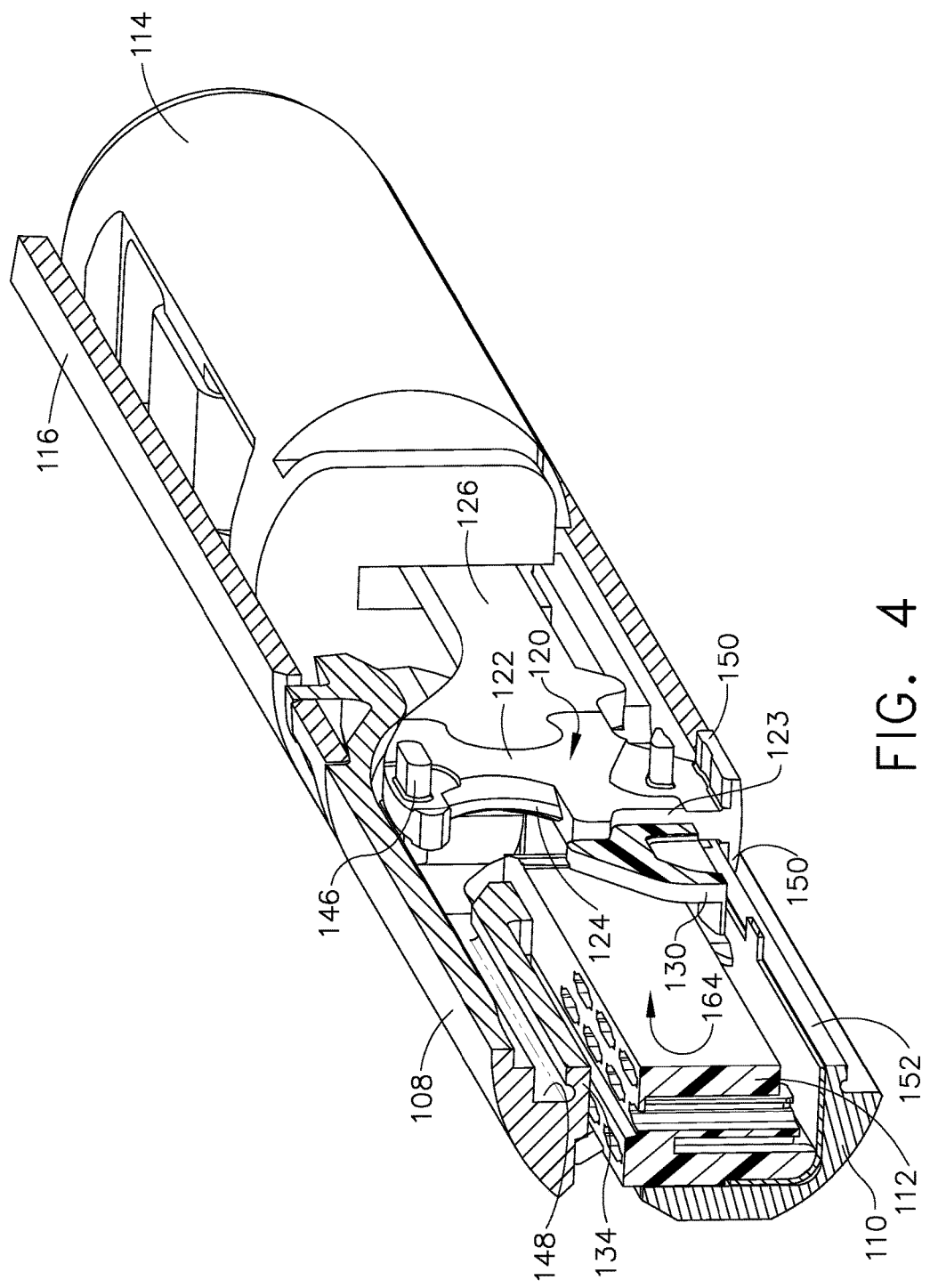
FIG. 4 is a perspective cut-away view of the endocutter of FIG. 2.

Corresponding reference characters indicate corresponding parts throughout the several views. The exemplifications set out herein illustrate preferred embodiments of the invention, in various forms, and such exemplifications are not to be construed as limiting the scope of the invention in any manner.

DETAILED DESCRIPTION

As known in the art, it is often necessary to resect tissue from a patient after the tissue has become necrotic or cancerous, for example. Frequently, blood vessels within the tissue are transected as the tissue is being cut. As a result, blood may flow from the blood vessels and complicate the surgery or endanger the patient. Often, a surgical stapler is used to secure and compress several layers of tissue together in order to substantially close the blood vessels. For example, referring to FIG. 1, a surgical stapler, such as an endocutter, can include devices which staple and then cut the tissue. As a result, the blood vessels can be substantially closed by the staples before the tissue is cut, thereby reducing bleeding therefrom.

Referring to FIGS. 1 and 2, endocutters, such as endocutter 100, for example, typically include an end-effector 102, a handle portion 104 (FIG. 2), and a shaft 106 extending therebetween. End-effector 102 includes first jaw 108 and second jaw 110 which can be configured in one of an open or a closed configuration. In their open configuration, jaws 108 and 110 can be configured to receive soft tissue therebetween, for example, allowing jaws 108 and 110 to be placed on opposite sides thereof. To close the jaws and secure the tissue therebetween, at least one of the jaws is moved against the tissue such that it holds the tissue against the opposing jaw. In the illustrated embodiment, jaw 108 is moved relative to jaw 110. Once closed, as known in the art, an anti-firing mechanism can be released allowing cutting member 120 to be advanced toward the tissue. Thereafter, as described in greater detail below, staples 132 can be deployed from staple cartridge 112 in jaw 110 to secure the layers of tissue together. Such mechanisms are described in greater detail in U.S. Pat. No. 7,000,818, the disclosure of which is hereby incorporated by reference herein.

Figure 5:
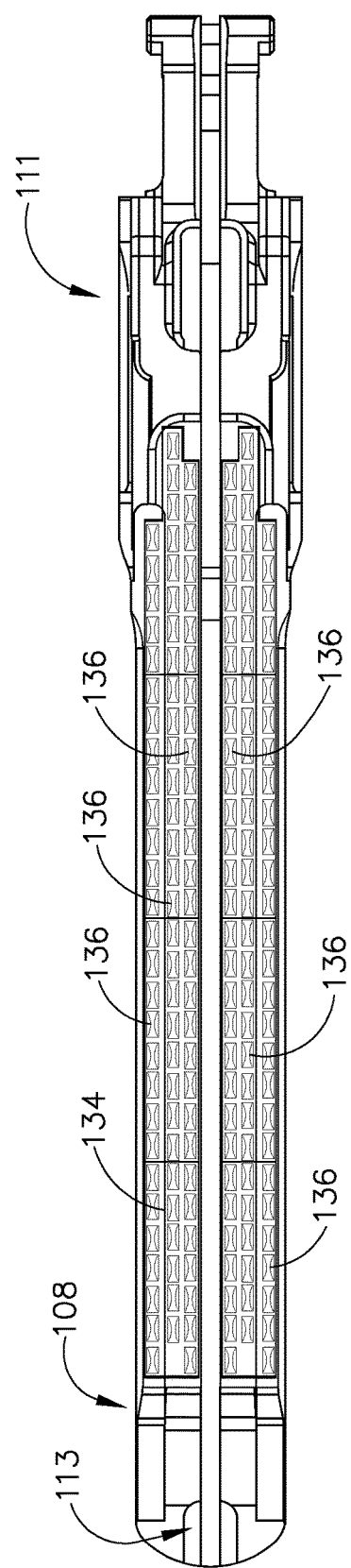
FIG. 5 is a bottom view of the anvil of the endocutter of FIG. 2.
Figure 6:
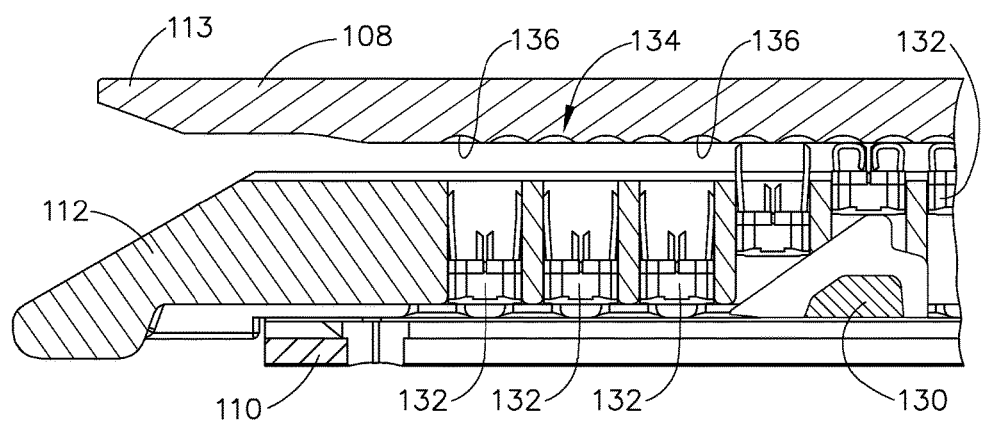
FIG. 6 is a schematic view of staples being deployed from the staple cartridge of the endocutter of FIG. 2 by a staple driver.
Figure 7:
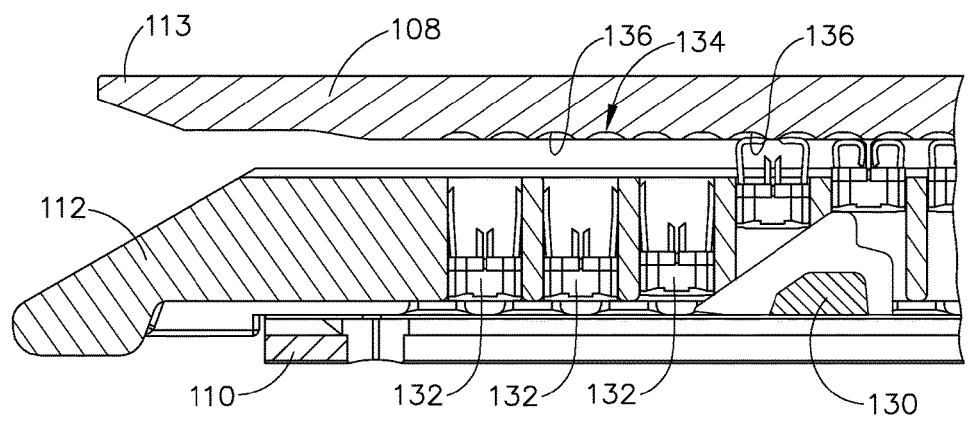
FIG. 7 is a schematic view of staples being deployed from the staple cartridge of FIG. 2 where the staple driver has been advanced within the staple cartridge with respect to its position in FIG. 6.
Figure 8:
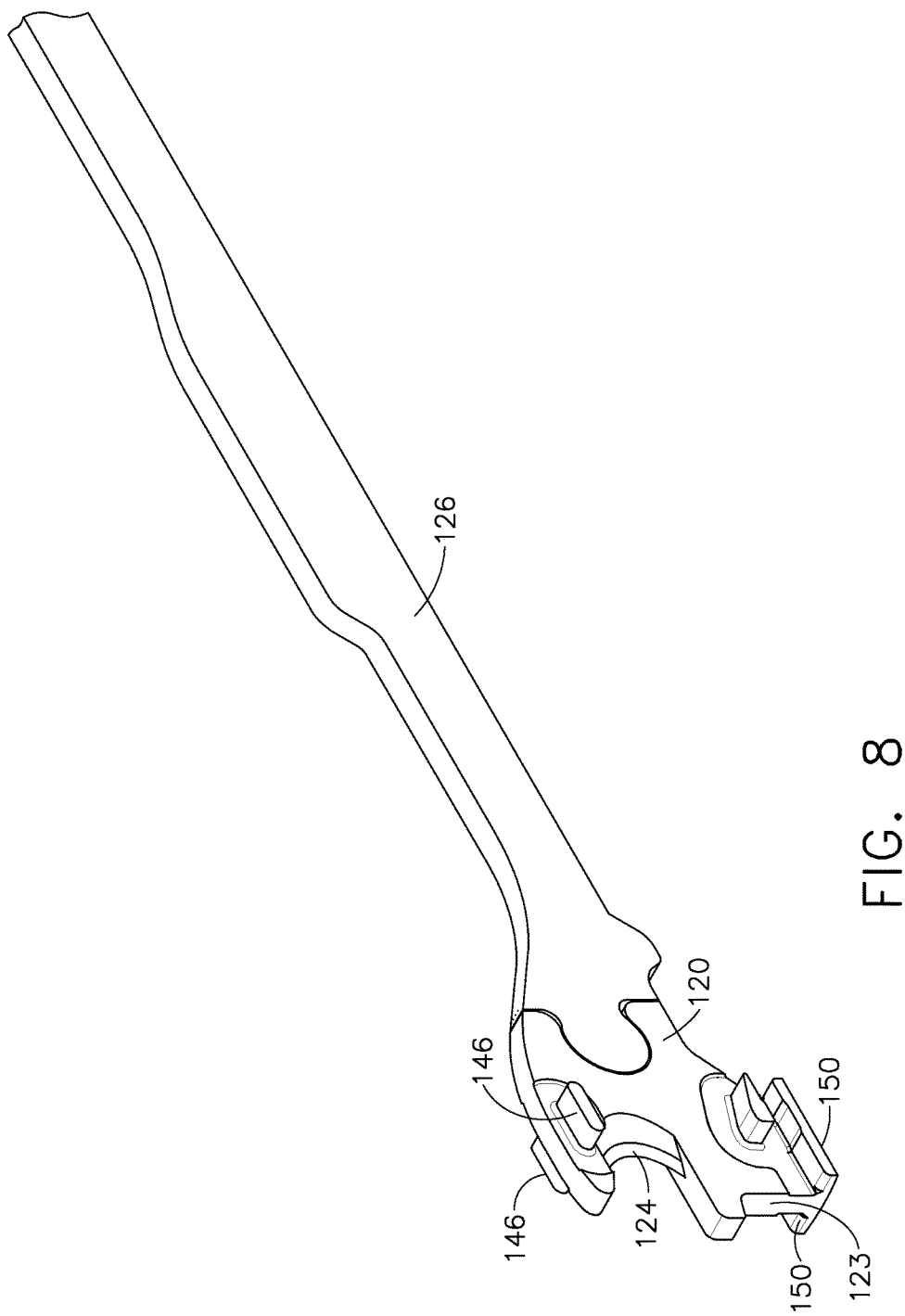
FIG. 8 is a perspective view of the cutting member and drive bar of the endocutter of FIG. 2.

Referring to FIGS. 3-4 and 6-8, cutting member 120 includes body 122 and cutting surface 124. Cutting member 120 is operably engaged with firing trigger 128 of handle portion 104 via drive bar 126 wherein the actuation of firing trigger 128 advances drive bar 126 and cutting member 120 toward the distal ends of jaws 108 and 110. In various embodiments, firing trigger 128 can activate a firing drive system which may be manually, electrically, or pneumatically driven. Cutting member body 122 further includes distal portion 123 which is configured to engage a staple driver 130 commonly supported within staple cartridge 112 and advance staple driver 130 therein. As staple driver 130 is advanced, staples 132 are lifted by driver 130 toward anvil 134. Referring to FIG. 5, anvil 134 includes pockets 136 which are configured to deform the legs of staples 132 and capture the layers of tissue therein in a known manner. In the present embodiment, as staple driver 130 is advanced, cutting member 120 is also advanced to resect the tissue after it has been stapled. In other embodiments, cutting member 120 can be configured to resect the tissue during or before the tissue has been stapled.

Figure 9:
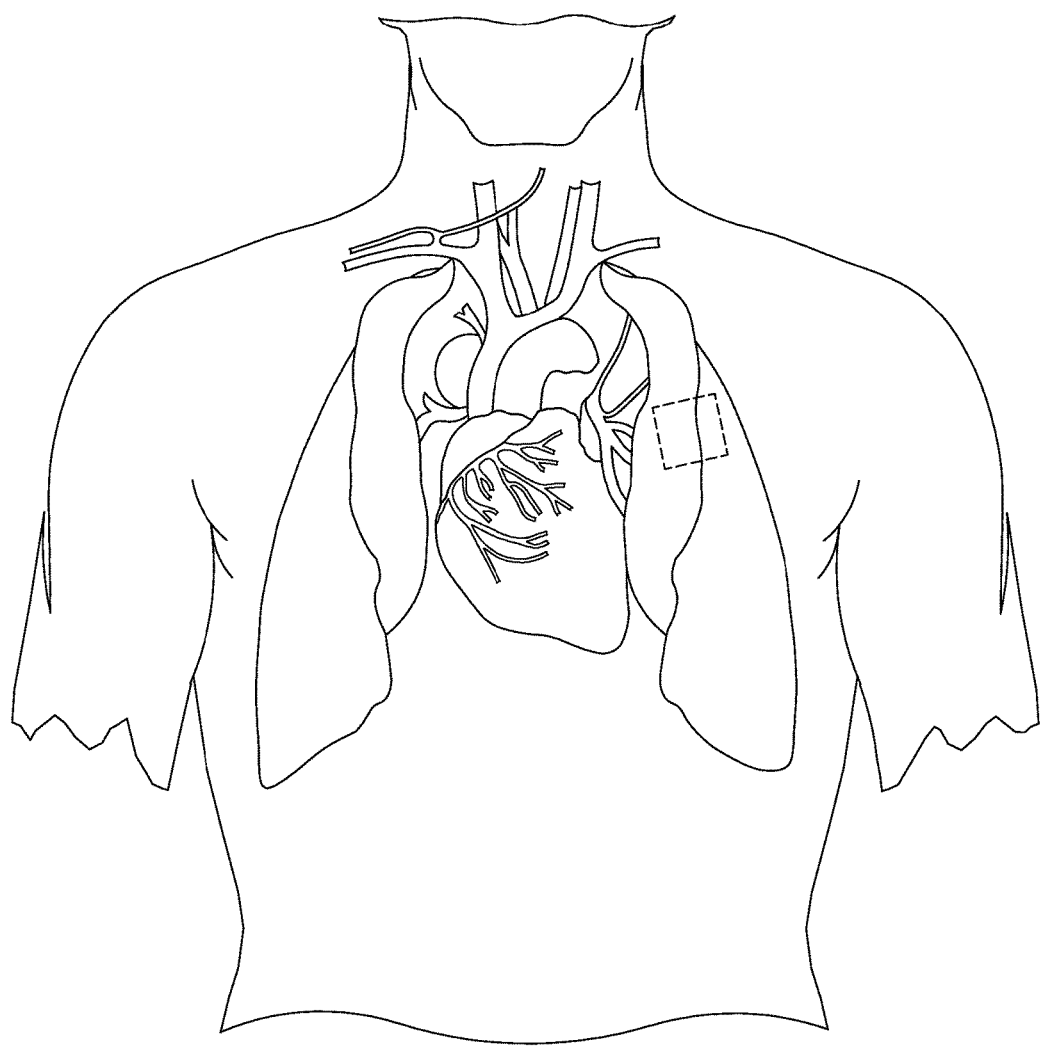
FIG. 9 is a schematic of an opened thoracic cavity.

Referring to FIGS. 1-7, the end-effector of many typical endocutters is linear, i.e., it is configured to deploy staples in straight lines. In these endocutters, drive bar 126 is configured to move cutting member 120 in a straight line and, accordingly, drive bar 126 is rigid such that it does not substantially deflect when the force to deploy the staples and transect the tissue is transmitted therethrough. In addition to the above, a variety of other drive arrangements are known for deploying staples in straight lines while resecting the tissue located between opposite lines of staples. However, it is often difficult to position such linear end-effectors in a surgical site. During at least one surgical technique, referring to FIGS. 9 and 10, an endocutter is used to transect and staple a pulmonary artery (PA) during a partial or total pneumonectomy. During this technique, the end-effector is typically placed against the wall of the thoracic cavity (TCW) such that jaw 110, and staple cartridge 112, are positioned behind the pulmonary artery. However, as the wall of the thoracic cavity is typically curved, it is often difficult to position linear jaw 110 behind the pulmonary artery. Furthermore, even if the surgeon is successful in positioning a jaw behind the pulmonary artery, the surgeon, owing to the linear configuration of the end-effector, cannot readily see the end of the jaw as it is typically hidden behind the pulmonary artery. As a result, it is difficult for the surgeon to readily determine whether the end of the jaw extends beyond the pulmonary artery, i.e., whether the pulmonary artery is entirely captured between the jaws of the end-effector.

Figure 10:
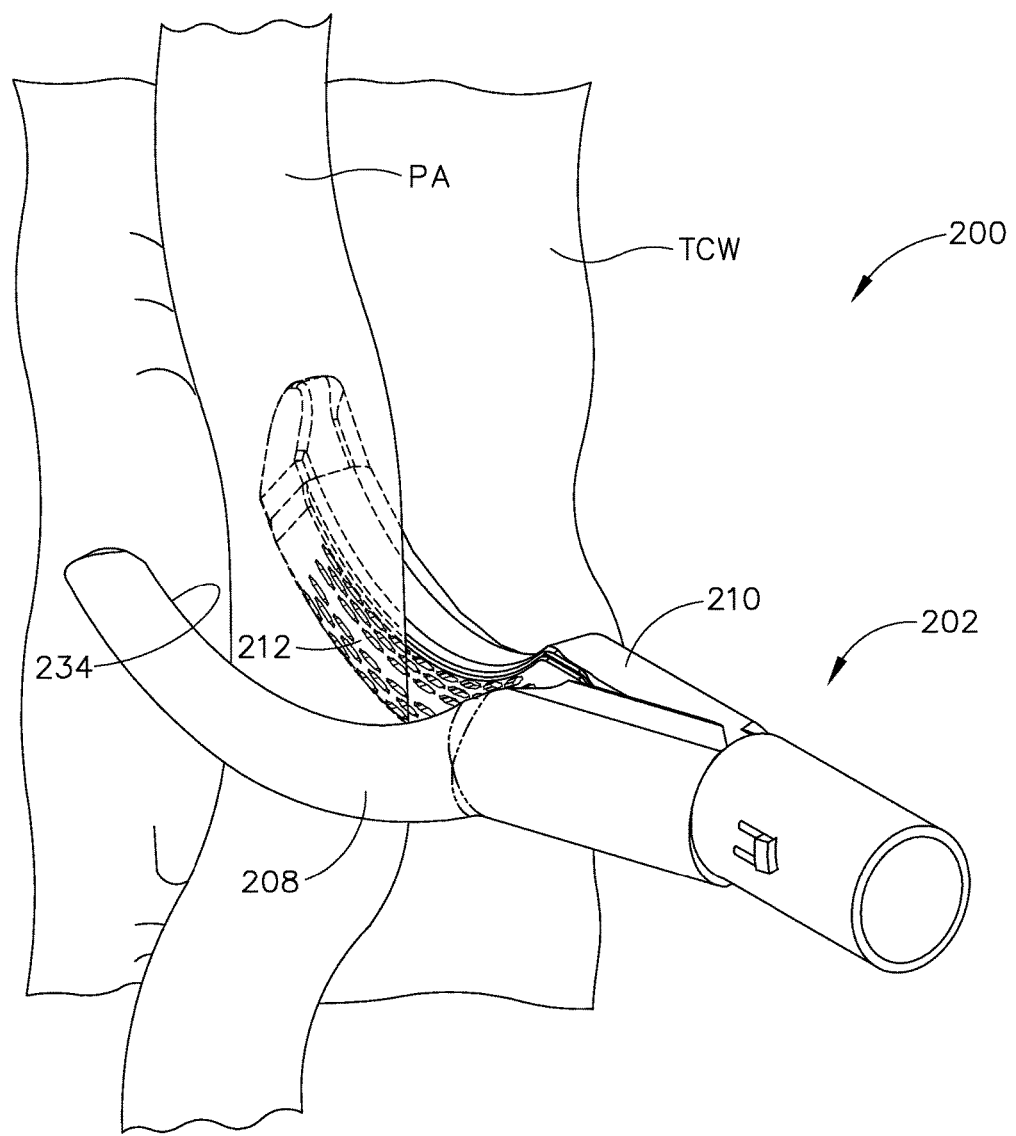
FIG. 10 is a schematic of an endocutter having a curved end-effector in accordance with an embodiment of the present invention being positioned against the side wall of a thoracic cavity.
Figure 11:
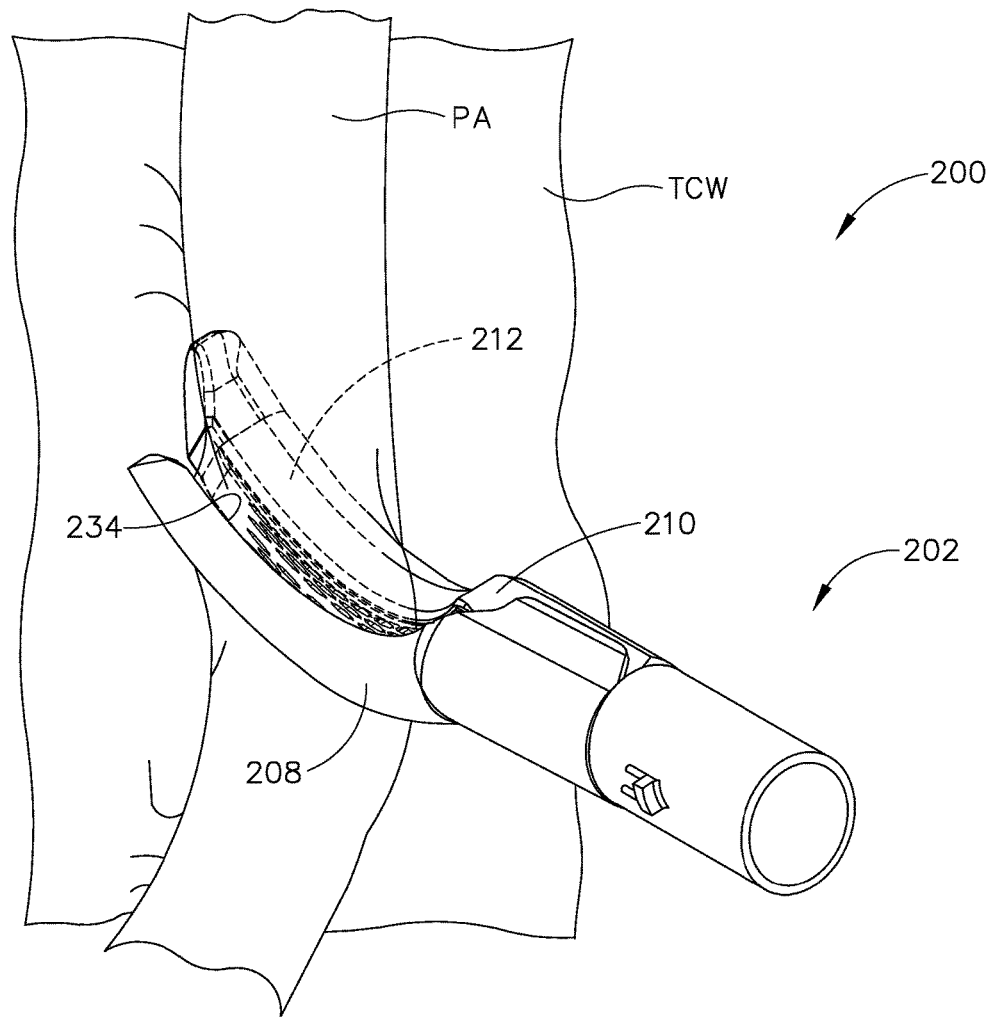
FIG. 11 is a perspective view of the endocutter of FIG. 10 illustrated in a closed configuration and positioned about a pulmonary artery.
Figure 12:
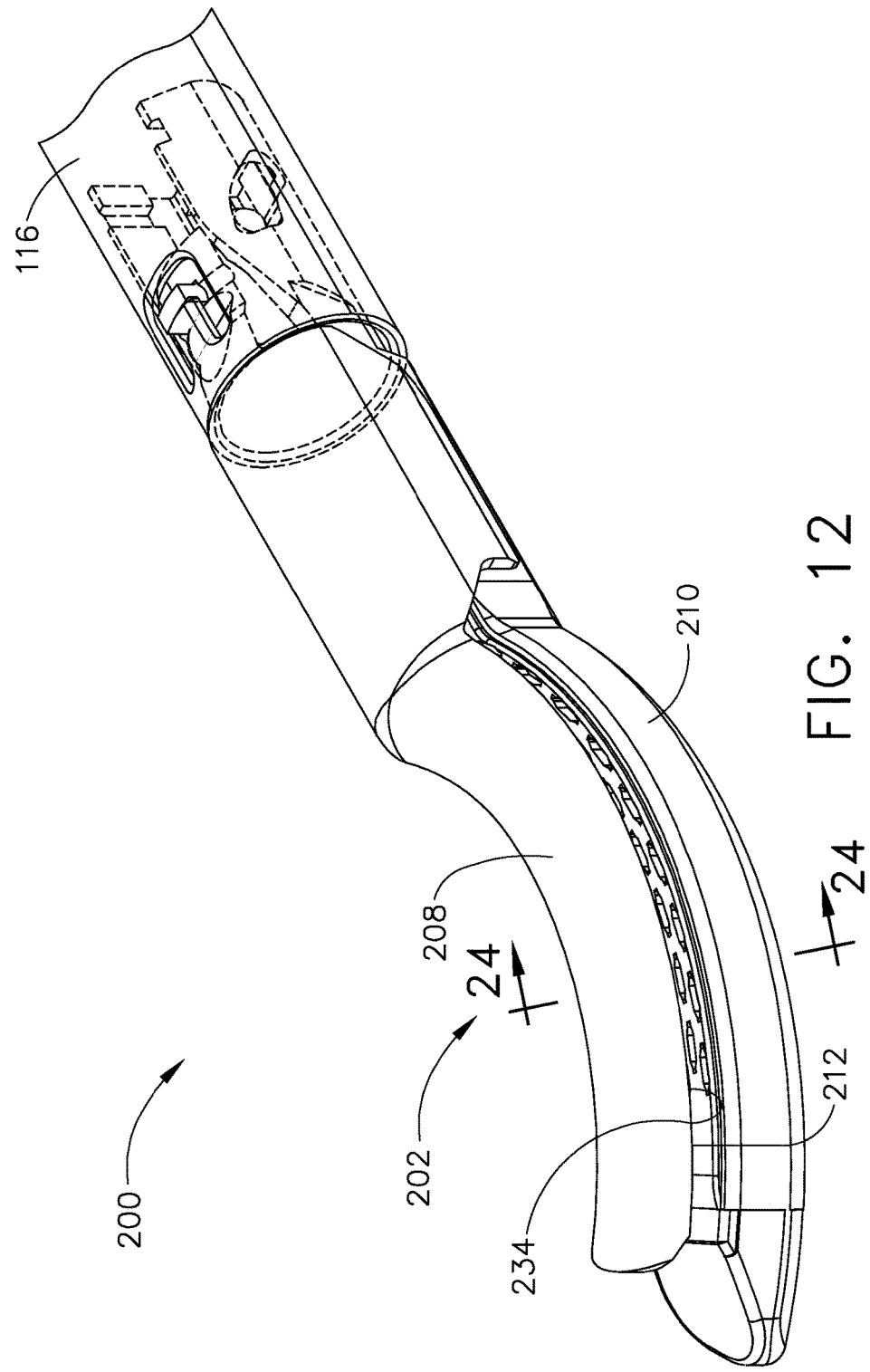
FIG. 12 is a perspective view of the end-effector of the endocutter of FIG. 11.

In various embodiments of the present invention, referring to FIG. 10, the end-effector of the endocutter is curved. A curved end-effector allows a surgeon to more easily position the end-effector against the curved wall of the thoracic cavity, for example. In at least one embodiment, the curvature of the end-effector can be configured to substantially match the contour of a typical thoracic cavity wall. In these embodiments, the curvature of several thoracic cavity walls can be measured and statistically analyzed to determine the optimum profile of the curved end-effector. This profile can include several arcuate portions and, in addition, several linear portions. In other embodiments, referring to endocutter 200 of FIGS. 10-14, the curvature of the thoracic cavity wall can be approximated by a single radius of curvature. Such embodiments can be simpler and less expensive to manufacture. In at least one embodiment, this radius of curvature is 1.2". In other various embodiments, the curvature of the end-effector can be configured to match the profile of the lower rectum, pelvis, or lower abdomen.

In order to transect the pulmonary artery PA, as mentioned above, a surgeon typically positions one of jaws 208 and 210 behind the pulmonary artery PA against the thoracic cavity wall TCW. Once positioned, referring to FIGS. 10 and 11, closure trigger 117 is actuated to pivot jaw 208 with respect to jaw 210 such that anvil 234 contacts the pulmonary artery and compresses the pulmonary artery between anvil 234 and staple cartridge 212. Unlike previous linear end-effectors, the curved profile of end-effector 202 assists the surgeon in locating the distal end of the end-effector with respect to the pulmonary artery. More particularly, referring to FIGS. 13 and 14, end 240 of jaw 210 can extend to one side of a centerline, or axis 242, defined by the distal end of shaft 106. As a result of this offset, the surgeon may be able to more readily see distal end 240 and evaluate whether the pulmonary artery is completely captured within the end-effector, for example.

Figure 15:
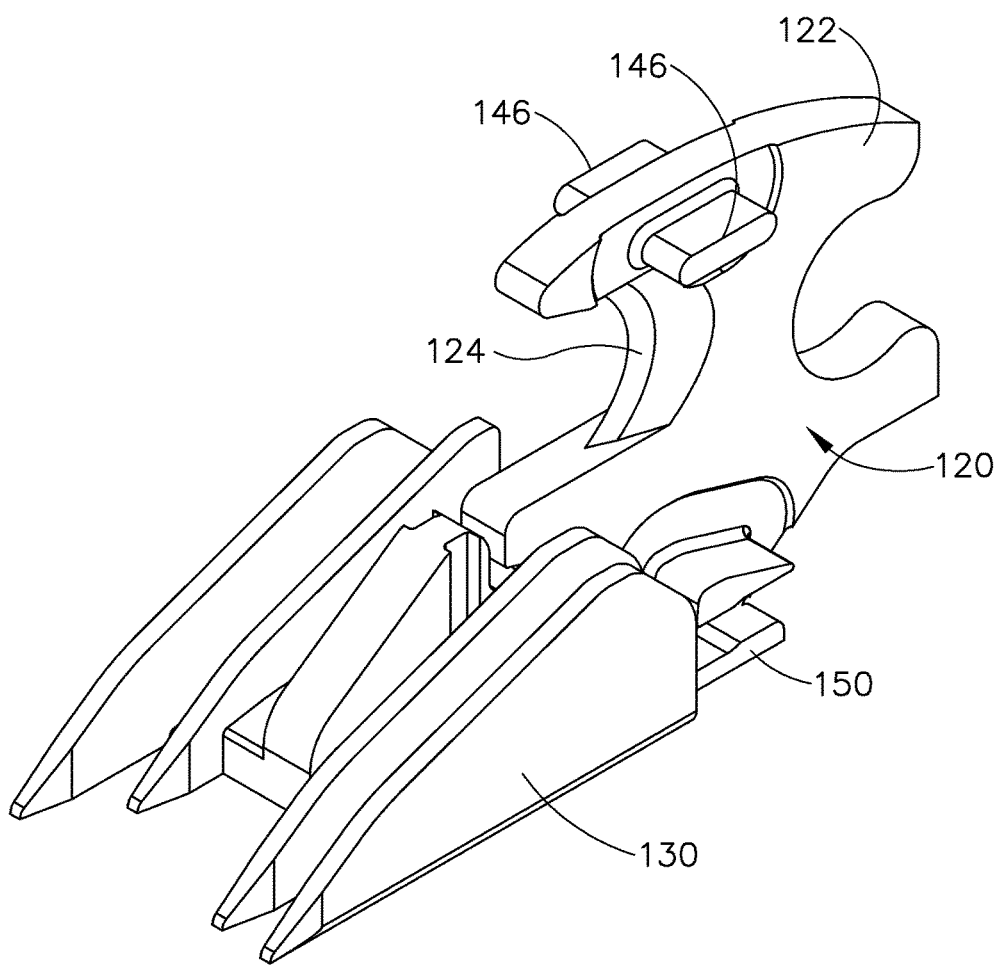
FIG. 15 is a perspective view of the cutting member and staple driver of the endocutter of FIG. 2.
Figure 16:
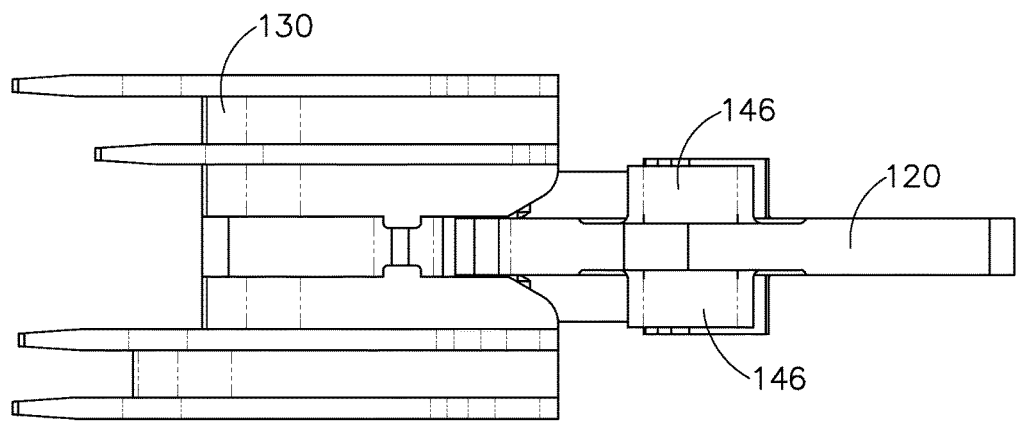
FIG. 16 is a top view of the cutting member and staple driver of FIG. 15.

Once the jaws of the endocutter have been closed, the cutting member of the endocutter can be advanced toward the tissue, as described above. In previous endocutters, referring to FIGS. 4, 15 and 16, cutting member 120 is configured to travel within linear slots defined by staple cartridge 112, staple cartridge channel 138, and anvil 134. Similarly, staple driver 130 is configured to travel within at least one linear slot defined by staple cartridge 112. As a result of these linear slots, cutting member 120 and staple driver 130 are moved in a straight line between the proximal and distal ends of the end-effector. For example, referring to FIG. 4, cutting member 120 includes first projections 146 extending from body 122 which are sized and configured to fit within slot 148 of anvil 134. Cutting member 120 further includes second projections 150 extending from body 122 which are sized and configured to retain cutting member body 122 within slot 164 of staple cartridge 112 and slot 152 of jaw 110. Accordingly, as cutting member 120 is advanced from the proximal end of the end-effector to the distal end, linear slots 148, 152 and 164 define a linear path for cutting member 120.

In various embodiments of the present invention, referring to FIGS. 13 and 14, staple cartridge 212, staple cartridge channel 238 and anvil 234 can include curved slots for controlling the movement of cutting member 120 and staple driver 130 along a curved path. These curved slots can include several arcuate portions and several linear portions. In various embodiments, the curved slots can be defined by one radius of curvature. In the embodiment illustrated in FIGS. 13 and 14, staple cartridge 212 and staple cartridge channel 238 can include curved slots 264 and 252, respectively. Similar to the above, curved slots 264 and 252 can be configured to receive a portion of cutting member 120 and guide cutting member 120 along a path defined by slots 264 and 252. However, owing to the substantially linear configuration of cutting member 120, cutting member 120 may, in some circumstances, become misaligned or stuck within curved slots 264 and 252, or a corresponding curved slot in anvil 234.

Figure 17:
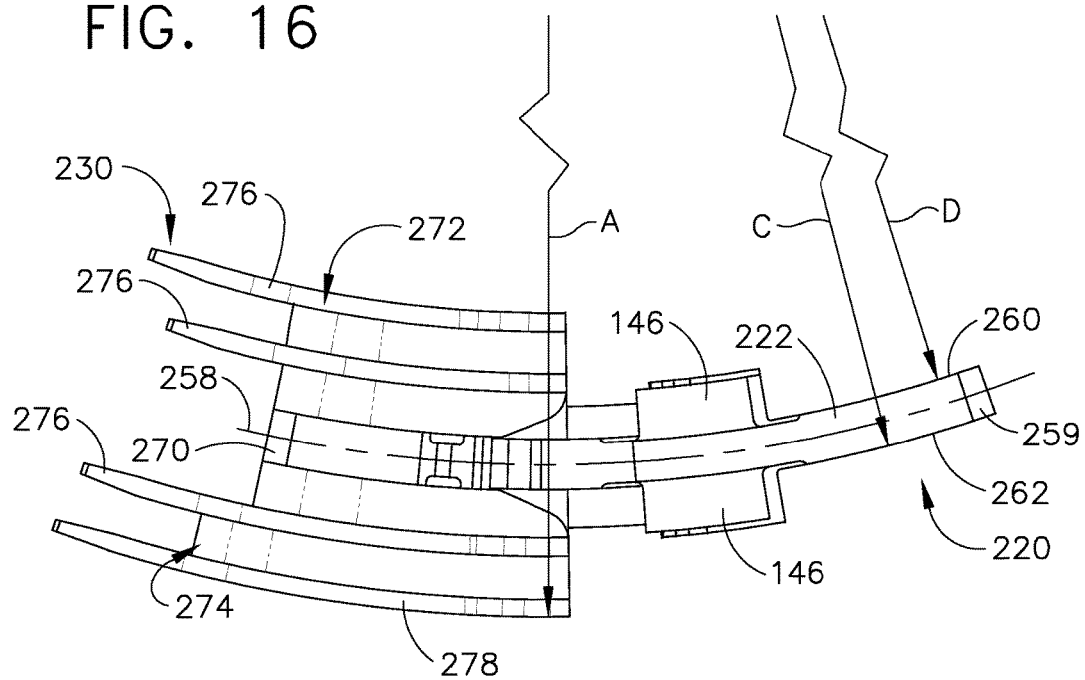
FIG. 17 is a top view of a cutting member and staple driver in accordance with an embodiment of the present invention.
Figure 20:
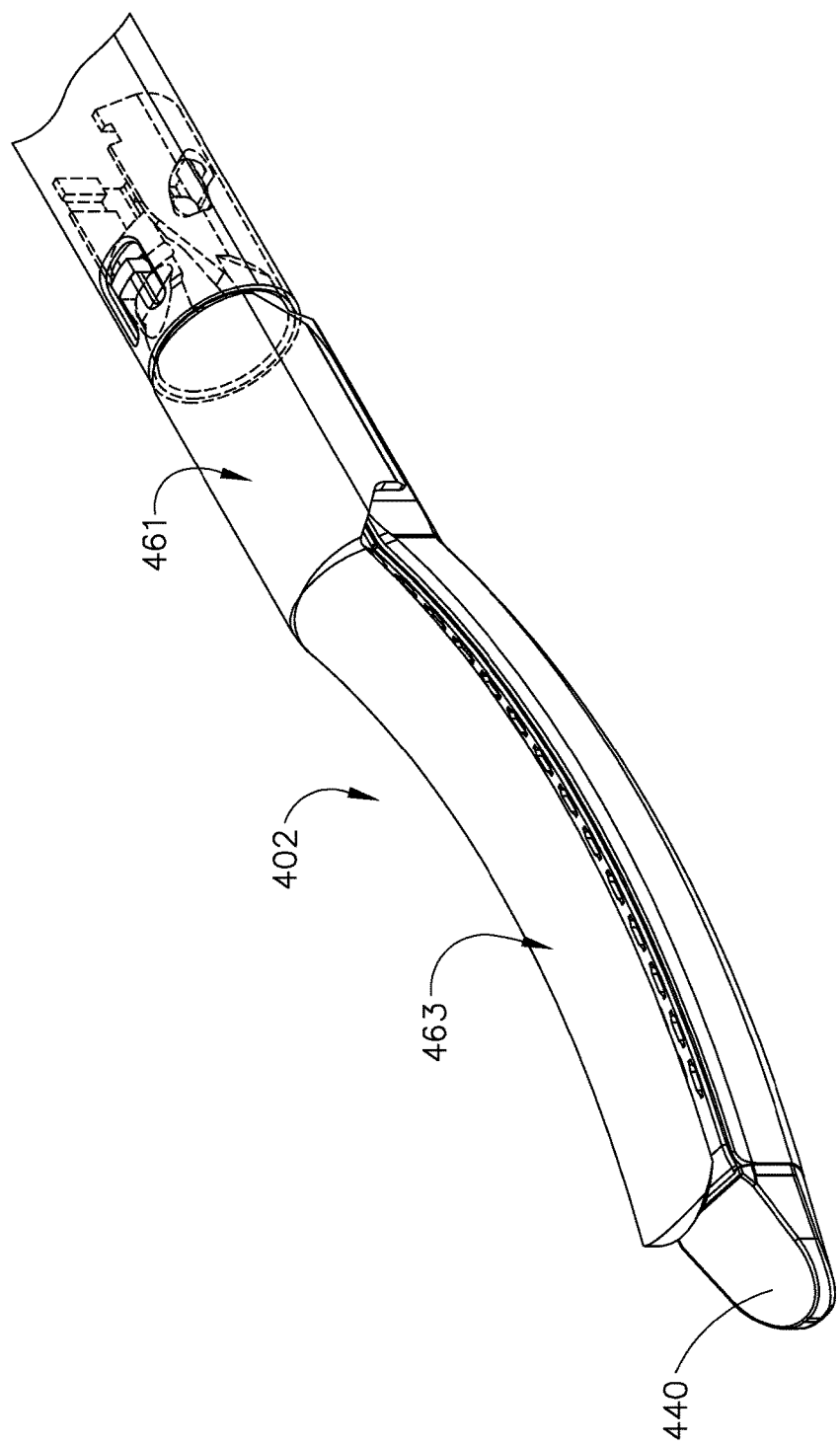
FIG. 20 is a perspective view of an endocutter having a curved end-effector in accordance with an alternative embodiment of the present invention.
Figure 21:
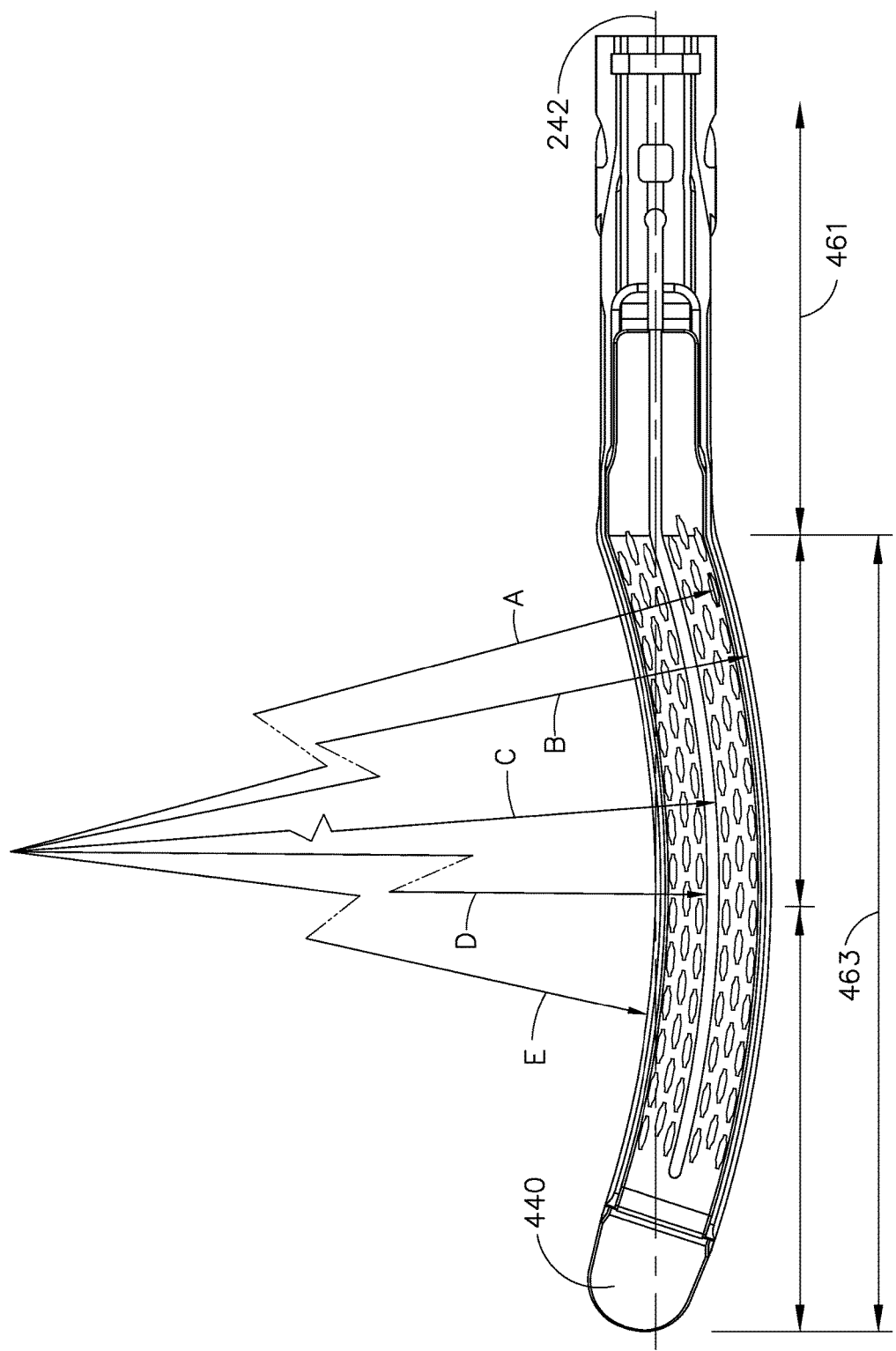
FIG. 21 is a top view of the staple cartridge of the end-effector of FIG. 20.

To ameliorate the above-described problem, at least a portion of the cutting member and staple driver can be curved. In at least one embodiment, the cutting member and staple driver can be configured to substantially match the curvature of the path defined by curved slots 264 and 252, i.e., path 258. More particularly, referring to FIGS. 13 and 17, cutting member body 222 can include a center portion which is configured to match the radius of curvature of path 258, and a curved inner portion 260 and a curved outer portion 262 which are configured to co-operate with the sidewalls of curved slots 264 and 252. For example, curved cartridge channel slot 252 can include inner surface 254 and outer surface 256 and curved staple cartridge slot 264 can include inner surface 266 and outer surface 268 where, in the present embodiment, inner surfaces 254 and 266 are substantially defined by radius of curvature D, which is smaller than the radius of curvature of path 258, and outer surfaces 256 and 268 are substantially defined by radius of curvature C, which is larger than the radius of curvature of path 258. As illustrated in FIG. 17, inner portion 260 of cutting member 220 can be configured to closely parallel the profile of inner surfaces 254 and 266, and outer portion 262 of cutting member 220 can be configured to closely parallel the profile of outer surfaces 256 and 268. Furthermore, although not illustrated, anvil 234 can include a curved slot which, similar to slots 264 and 252, co-operates with curved cutting member 220 to guide cutting member along path 258. As a result of the above, the likelihood of cutting member 220 becoming misaligned or stuck within curved path 252 can be reduced.

Alternatively, although not illustrated, the cutting member can include slots which are configured to co-operate with features on the anvil and/or staple cartridge and guide the cutting member along a curved path. More particularly, the anvil and/or staple cartridge can each include an elongate, arcuate projection, or a plurality of projections, which define a curved, or curvilinear, path for the cutting member. The slots of the cutting member can be configured to receive the projections and guide the cutting member along the curved path. In one embodiment, one of the anvil and staple cartridge can include such a projection, or a plurality of projections, and the other of the anvil and staple cartridge can include a slot configured to receive a portion of the cutting member, as described above.

Similar to the above, at least a portion of staple driver 230 can be configured to substantially match the curvature of path 258. More particularly, referring to FIG. 17, staple driver 230 can include a center arcuate portion 270 which is configured to match the radius of curvature of path 258, and an inner arcuate portion 272 and an outer arcuate portion 274 which are configured to co-operate with the sidewalls of slots, or channels, within staple cartridge 212. Similar to staple driver 130, staple driver 230 can include ramps which are configured to lift, or deploy, staples 132 against anvil 234 positioned opposite staple cartridge 212. However, in the present embodiment, ramps 276 of staple driver 230 can be curved to deploy staples 132 along a curved staple line. More particularly, for example, the ramps can be defined by a radius of curvature which substantially matches the radius of curvature of a staple line. For example, ramp 278 is defined by a radius of curvature which substantially matches the radius of curvature of staple line 280, i.e., radius of curvature A.

Although the path of the cutting member has been described above as being defined by a single radius of curvature, the invention is not so limited. In various embodiments, referring to FIGS. 13 and 14, end-effector 202 of endocutter 200 can include curved portion 263 and, in addition, linear portion 261 which is substantially collinear with an axis defined by the distal portion of shaft 116, i.e., axis 242. In at least one embodiment, curved portion 263 can further include first portion 265 and second portion 267. Referring to FIG. 13, first portion 265 can include a proximal end connected to linear portion 261 positioned along axis 242 and a distal end spaced from axis 242 wherein second portion 267 can include a proximal end connected to the distal end of first portion 265 and extend toward axis 242. Stated another way, first portion 265 can define an arcuate portion which extends away from axis 242 and second portion 267 can define an arcuate portion which extends toward axis 242. As described above, an end-effector having such a profile may facilitate the positioning of the end-effector against the wall of the thoracic cavity, for example.

Referring to FIGS. 18-21, the end-effector of other various embodiments of the present invention can include other advantageous profiles. For example, referring to FIGS. 18 and 19, end-effector 302 can include linear portion 361 and curved portion 363 wherein the distal end of slot 364 can be positioned along axis 242. As a result, although the cutting member progresses along an arcuate path offset with respect to axis 242, the cutting member will stop at a point along axis 242. Thus, as long as the surgeon is able to discern the orientation of axis 242, the surgeon will know that the cutting member will not progress beyond axis 242 and can thereby gauge the point at which the tissue will no longer be transected. In another embodiment, referring to FIGS. 20 and 21, end-effector 402 can include linear portion 461 and curved portion 463 wherein distal tip 440 of the end-effector lies along axis 242 although at least a portion of the end-effector is offset with respect to axis 242. In this embodiment, as long as the surgeon is able to discern the orientation of axis 242, the surgeon can gauge the location of the distal end of the end-effector when moving or dissecting tissue.

Figure 22:
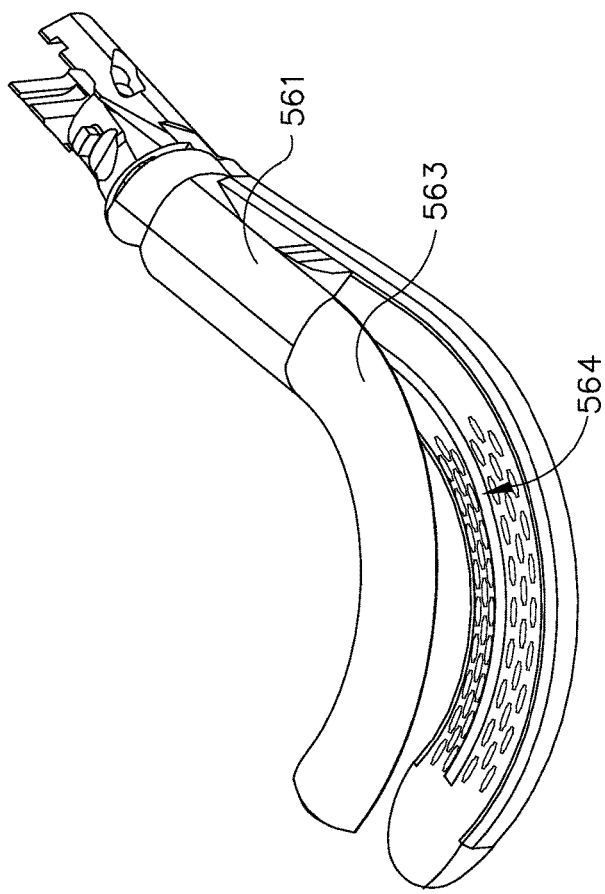
FIG. 22 is a perspective view of an endocutter having a curved end-effector in accordance with an alternative embodiment of the present invention.
Figure 23:
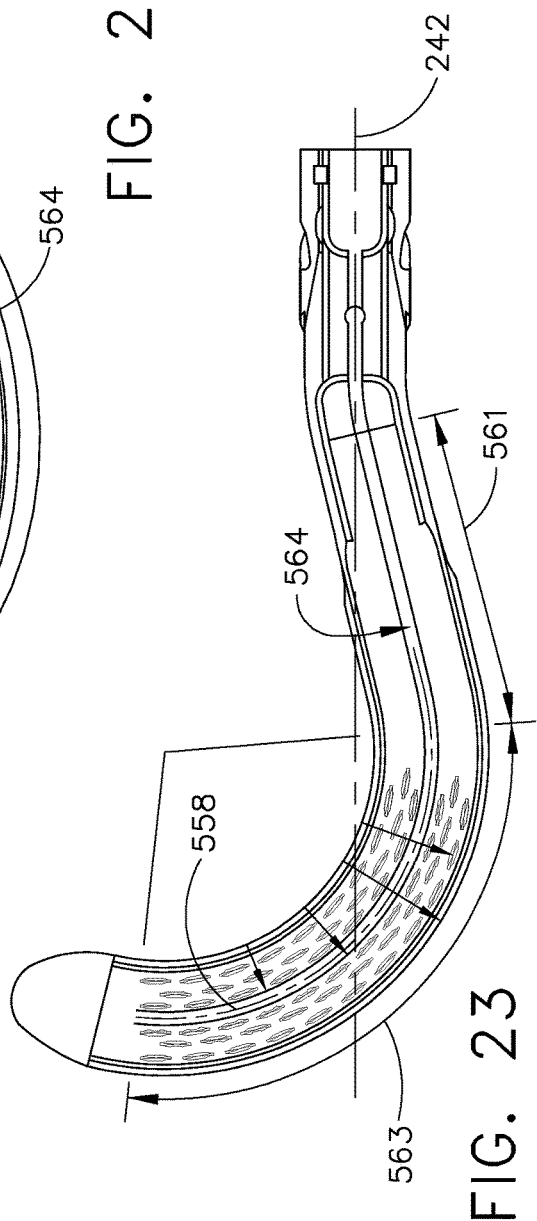
FIG. 23 is a top view of the staple cartridge of the end-effector of FIG. 22.

In other various embodiments, referring to FIGS. 22 and 23, the end-effector can define an arcuate path for the cutting member that is defined by an angle that is greater than or equal to 90 degrees. More particularly, for example, path 558 can include linear portion 561 and curved portion 563 wherein curved portion 563 is defined by a radius of curvature that spans an arc corresponding to an approximately 110 degree angle. As a result of the significant curvature of curved portion 563, a surgeon can position a pulmonary artery, for example, entirely within curved portion 563. In various embodiments, referring to FIG. 26, staples 132 may only be positioned within cavities in curved portion 563, and not linear portion 561. In these embodiments, the staple lines can be comprised of continuous, curved rows without abrupt changes in direction within the staple line. As known in the art, abrupt changes in a staple line may provide a leak path for blood to flow therethrough. As a result of the above embodiments, the likelihood of such a leak path is reduced.

As described above, the anvil and staple cartridge can include curved slots for receiving and guiding the cutting member. In many embodiments, the anvil and the staple cartridge can be configured such that their features parallel the curved slots therein. For example, referring to FIGS. 13 and 14, curved portion 263 of staple cartridge 212 can include an inner radius of curvature and an outer radius of curvature which parallel the radius of curvature of curved slot 264. More particularly, referring to FIG. 13, the inner surface of staple cartridge 212 can be defined by radius of curvature E and the outer surface of staple cartridge 212 can be defined by radius of curvature B, wherein curvatures B and E share a substantially common radial point with radius of curvatures C and D which, as described above, substantially define the inner and outer surfaces of slot 264. However, in various embodiments, although not illustrated, the inner and outer surfaces of the anvil and/or staple cartridge, or any other features thereof, may be non-parallel to the curved slot. In these embodiments, the anvil and staple cartridge, and the jaws surrounding them, may be configured to achieve any suitable configuration or purpose.

In previous endocutters, as described above and referring to FIGS. 4 and 8, linear drive bar 126 is configured to advance cutting member 120 along a linear path and, as a result, drive bar 126 is constructed such that is rigid and does not substantially deflect. After cutting member 120 has been advanced into slots 148, 164 and 152 of anvil 134, staple cartridge 112, and staple cartridge channel 138, respectively, at least a portion of drive bar 126 can enter into slots 148, 164 and 152. However, although cutting member 120 is guided and supported within slots 148, 164, and 152, drive bar 126, in these previous devices, is unsupported within slots 148, 164, and 152. As a result, drive bar 126 may deflect or buckle in an uncontrollable and undesirable manner when load is transmitted therethrough.

Figure 24:
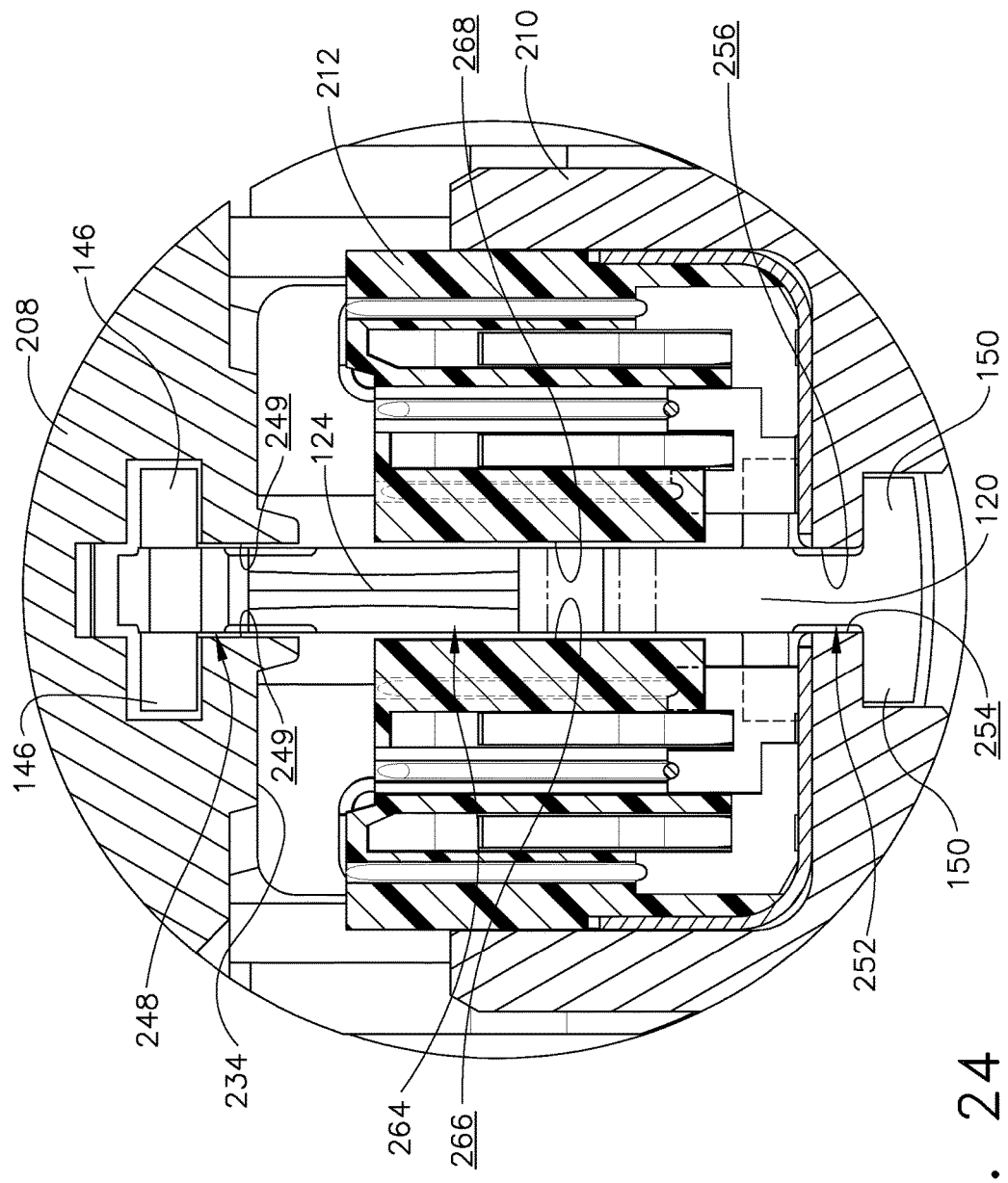
FIG. 24 is a cross-sectional view of the end-effector of FIG. 12 taken along line 24-24 in FIG. 12.
Figure 25:
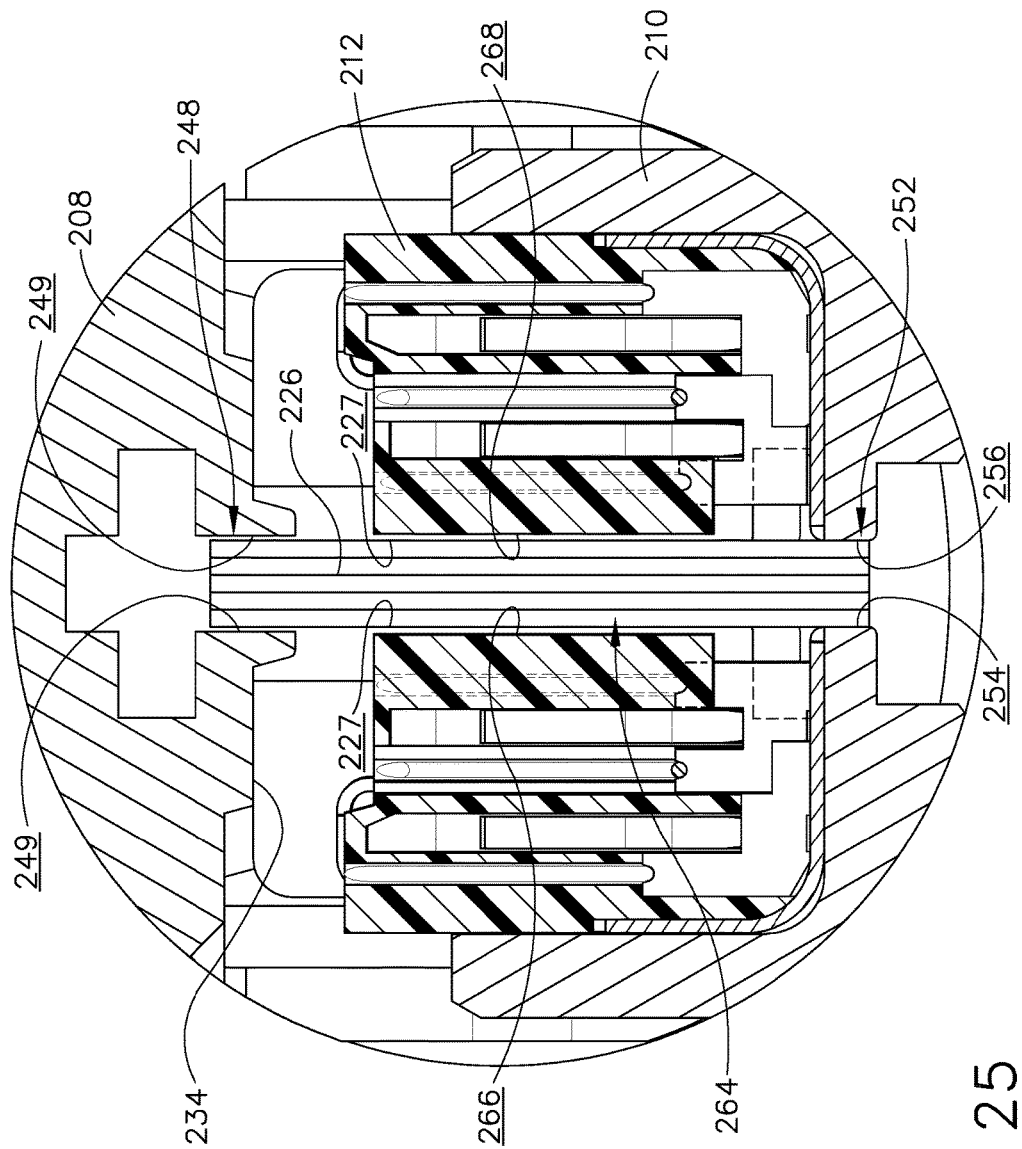
FIG. 25 is a cross-sectional view of the end-effector of FIG. 12 after the drive bar has been advanced into the end-effector.

In various embodiments of the present invention, a flexible drive bar can be used to advance the cutting member within the end-effector. More particularly, in order for the drive bar to be advanced into and translate within the curved slots of the end-effector, the drive bar can deflect to closely parallel the curvature of the curved slots of the end-effector. In various embodiments, unlike previous endocutters, the slots within the anvil and staple cartridge can be configured to support the flexible driver bar. More particularly, referring generally to FIGS. 24-26, after cutting member 120 has been at least partially advanced within slots 248, 264, and 252, referring to FIG. 25, at least a portion of drive bar 226 can enter slots 248, 264, and 252. Slot 248 can include support surfaces 249 which are configured to abut, or be positioned closely adjacent to, side surfaces 227 of drive bar 226. Similarly, surfaces 254 and 256 of slot 252 and surfaces 266 and 268 of slot 264 can also support the drive bar. While these features are particularly advantageous when used with curved end-effectors, they can also be used in linear end-effectors. In these embodiments, even though the slots may be linear, the slots can support the driver, whether rigid or flexible, and prevent it from buckling in the event that it is overloaded, for example.

Although flexible drive bar 226 can be used to advance linear cutting member 120 and linear staple driver 130 within a curved end-effector, as described above, flexible drive bar 226 can also be used to advance curved cutting members and staple drivers, such as cutting member 220 and staple driver 230, for example, within a curved end-effector. Furthermore, although not illustrated, one of the anvil and staple cartridge can include a slot configured to receive and guide the cutting member and the other of the anvil and staple cartridge can include a slot configured to receive and support the drive bar. In these embodiments, the slot which is configured to receive the cutting member can have a different geometry than the slot which is configured to receive the drive bar. Accordingly, the cutting member and the drive bar can have different thicknesses, for example.

In various embodiments, the support surfaces of slots 248, 264 and 252 may be continuous, i.e., they may be configured to contact drive bar 226 continuously along the length thereof, or, alternatively, slots 248, 264 and 252 may be configured to contact drive bar 226 at various, spaced-apart locations. In these embodiments, projections may extend from the slot walls to define the path of the cutting member and the drive bar. In various embodiments, drive bar 226 may be comprised of a flexible, unitary material such as plastic, for example. Alternatively, referring to FIGS. 25 and 26, drive bar 226 may be comprised of a laminated material, i.e., a material comprised of two or more materials bonded together. In these embodiments, two or more strips of material may be glued together where the strips have the same cross-sectional geometry, or, alternatively, different cross-sectional geometries. Furthermore, the strips may be comprised of the same material or different materials. The cross-sectional geometries and materials of the above-described embodiments may be selected such that the drive bar is more flexible when deflected in one direction and less flexible when deflected in a different direction.

As described above, the curvature of an end-effector can be selected such that it facilitates the placement of the end-effector in a particular surgical site. In various embodiments, referring to FIGS. 35-37 and 38-40, the end-effector can be curved in a downward or upward direction, i.e., it can be curved in a plane that is substantially parallel to planes defined by the staple lines. More particularly, referring to FIGS. 38 and 39, staple cavities 803, which are configured to store staples 132 therein, are positioned along staple lines 805 and 807, for example, such that staples 132, when they are deployed from staple cartridge 812, are deployed in substantially parallel planes which are at least partially defined by staple lines 805 and 807.

Figure 35:
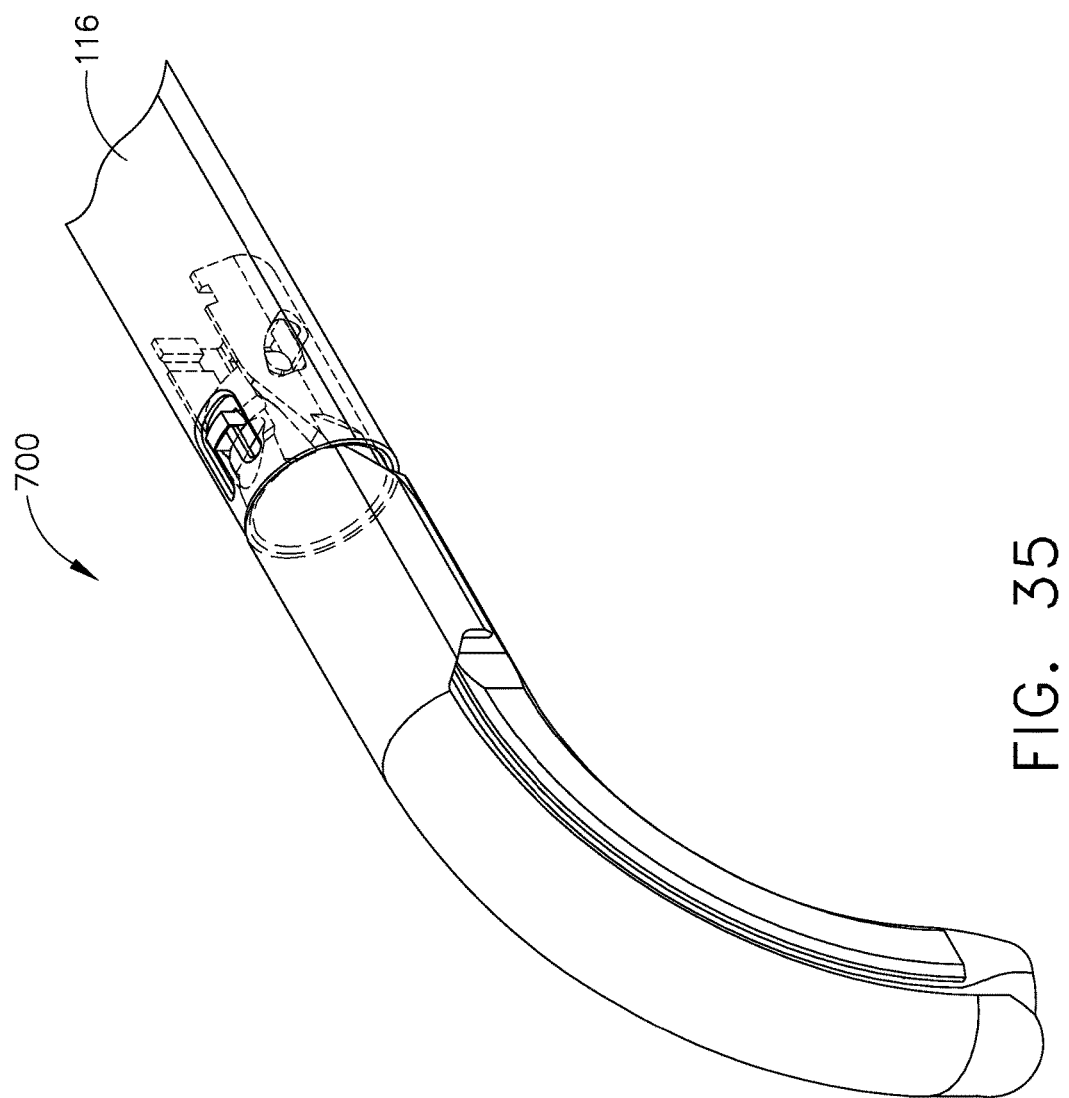
FIG. 35 is a perspective view of an endocutter having a curved end-effector in accordance with an alternative embodiment of the present invention.
Figure 36:
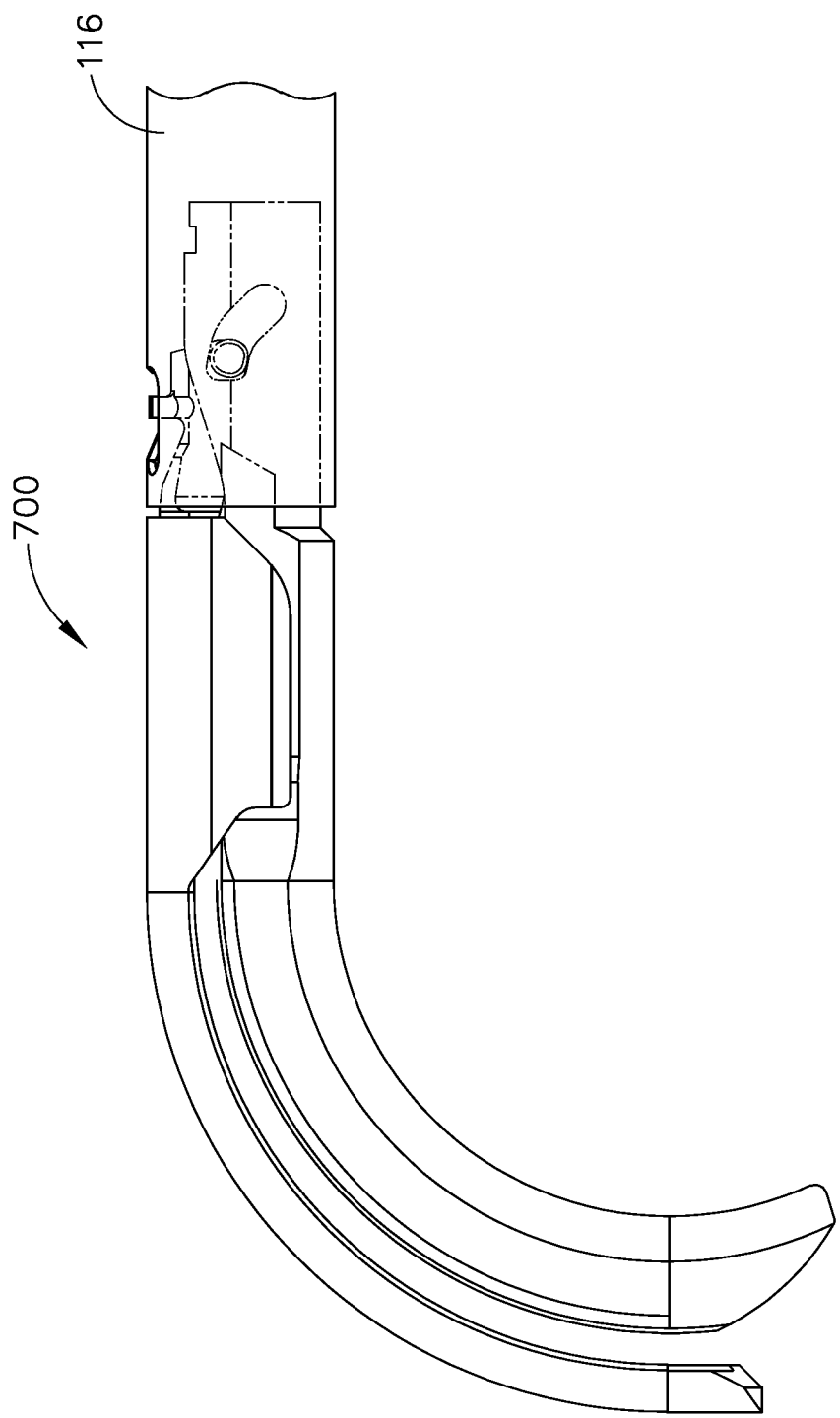
FIG. 36 is a side view of the endocutter of FIG. 35.
Figure 37:
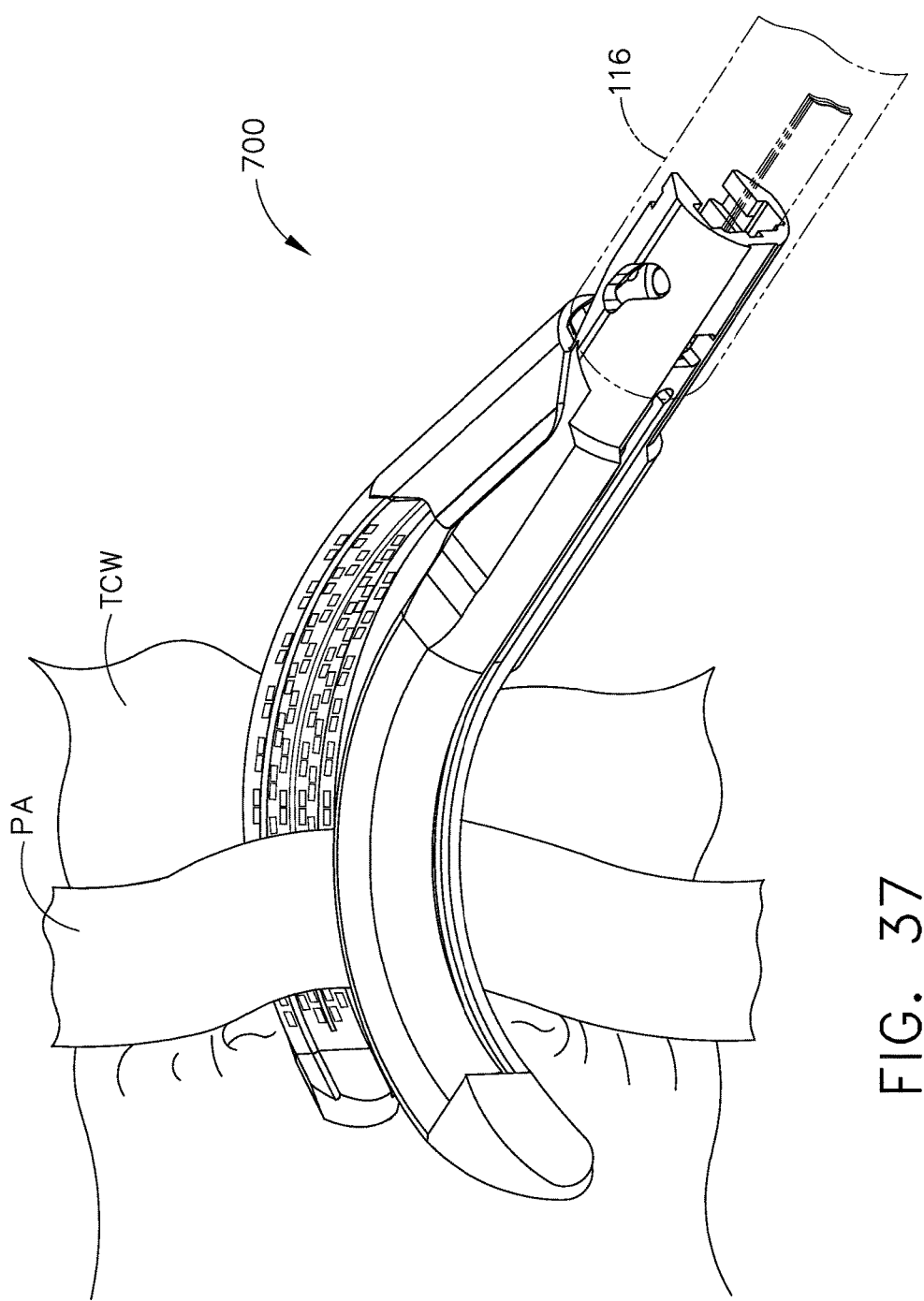
FIG. 37 is a schematic of the endocutter of FIG. 35 being used to transect a pulmonary artery.
Figure 40:
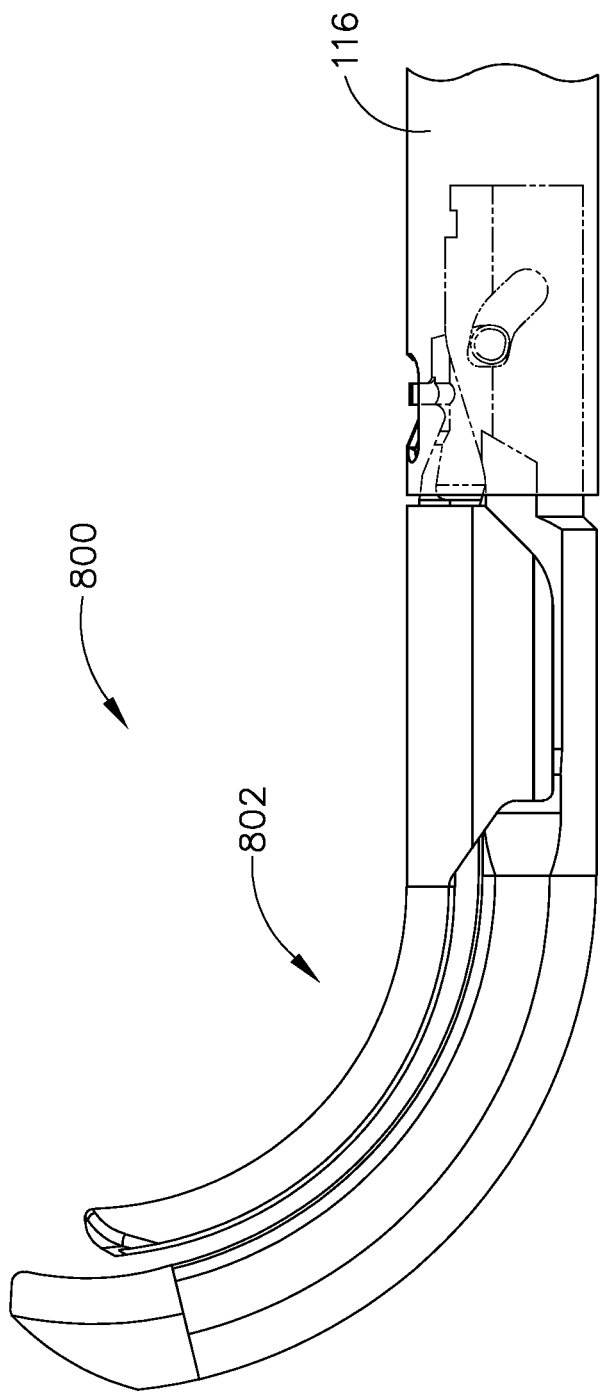
FIG. 40 is a side view of the end-effector of the endocutter of FIG. 39.

For each parallel plane described above, as a result of these upward and/or downward curvatures, staples 132 can be deployed along axes which are co-planar, but not parallel. More particularly, referring to FIG. 39, a first staple 132 (not illustrated in FIG. 39) can be deployed from its staple cavity 803 along axis 853 and a second staple 132 can be deployed from its staple cavity 803 along axis 855. While axis 853 and axis 855 can be co-planar, as illustrated in FIG. 39, axis 853 and axis 855 are not parallel. In some embodiments, the axes defined by staple cavities 803 can converge, as illustrated in FIGS. 38 and 39, or diverge, as illustrated in FIGS. 35-37. In various embodiments, the staple deployment axes can define an angle therebetween which is greater than or equal to 30 degrees. In other various embodiments, the axes can be substantially perpendicular and, in further embodiments, the axes can define an angle that is greater than ninety degrees.

Figure 26:
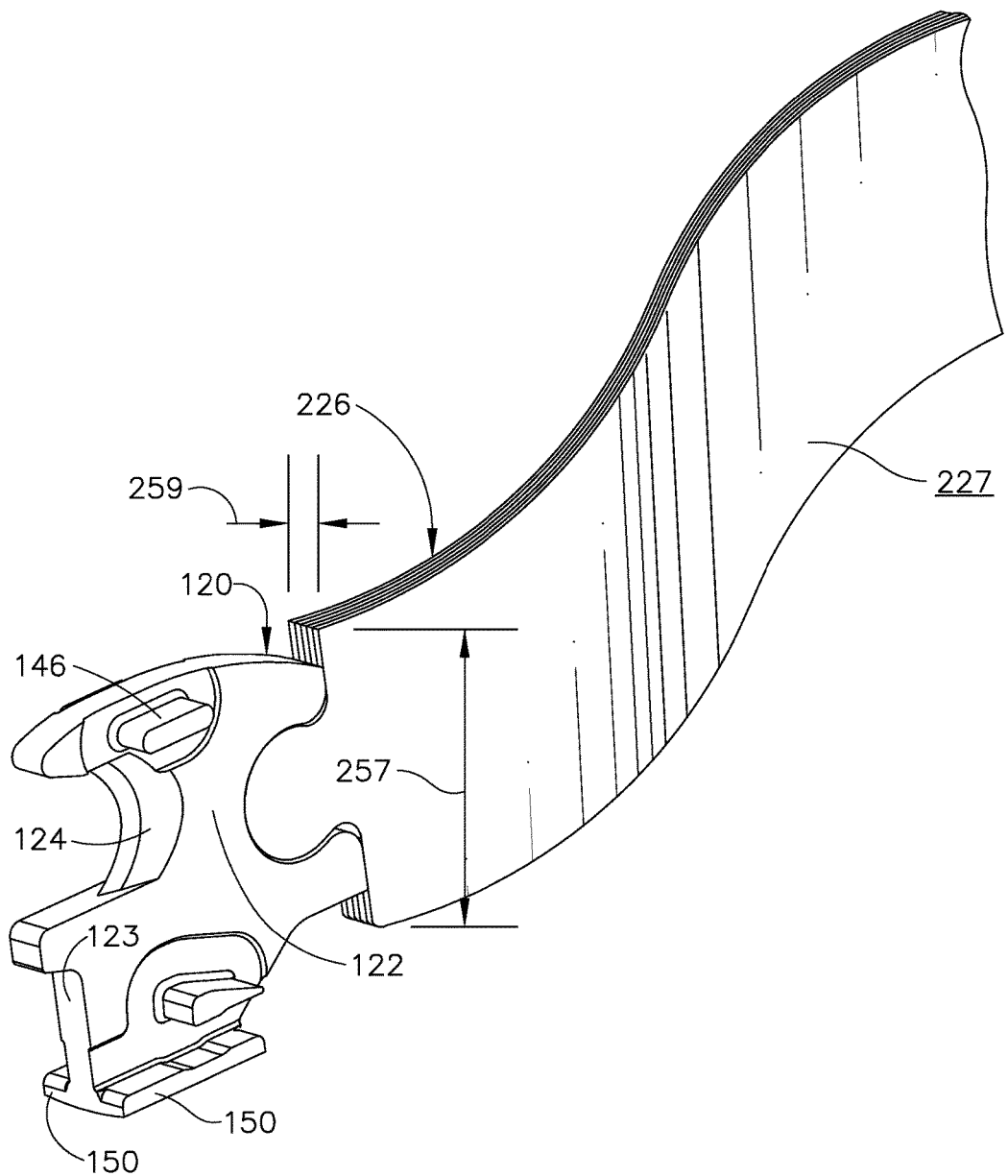
FIG. 26 is a schematic of the cutting member and drive bar of the endocutter of FIGS. 24 and 25.

As described above, an endocutter in accordance with an embodiment of the present invention can include a cutting member which is advanced through and guided by curved slots in the staple cartridge and/or anvil. For example, referring to FIGS. 38-43, staple cartridge 812 can include slot 864 which is configured to receive and guide cutting member 120. Similar to the above, endocutter 800 can further include a drive bar for advancing cutting member 120 within slot 864 of staple cartridge 812, however, owing to the direction and degree of the curvature of staple cartridge 812, some drive bars may be largely unsuitable for use with endocutter 700 or 800, for example. More particularly, the illustrated drive bars 126 and 226 in FIGS. 4 and 24, respectively, owing to their cross-sectional geometries, may not be particularly well-suited to flex in a substantially downward or substantially upward direction as required by endocutters 700 and 800, respectively. Referring to FIG. 26, for example, the illustrated cross-section of drive bar 226 is substantially rectangular and is defined by height 257 and width 259. As illustrated in FIG. 26, height 257 is substantially greater than width 259 and, as a result, the cross-section of the illustrated drive bar 226 has a moment of inertia with respect to height 257 that is substantially greater than the moment of inertia with respect to width 259. Accordingly, the illustrated drive bar 226 is substantially less flexible with respect to height 257 than width 259 and may not be able to sufficiently bend in the substantially downward and upward directions described above. It is important to note that drive bars 126 and 226 are not limited to the configurations described above. On the contrary, drive bars 126 and 226 can have cross-sections in which the width is greater than the height. Any reference in this paragraph to drive bars 126 and 226 are references to the particular drive bars 126 and 226 that happen to be illustrated in FIGS. 4 and 24, respectively.

Figure 41:
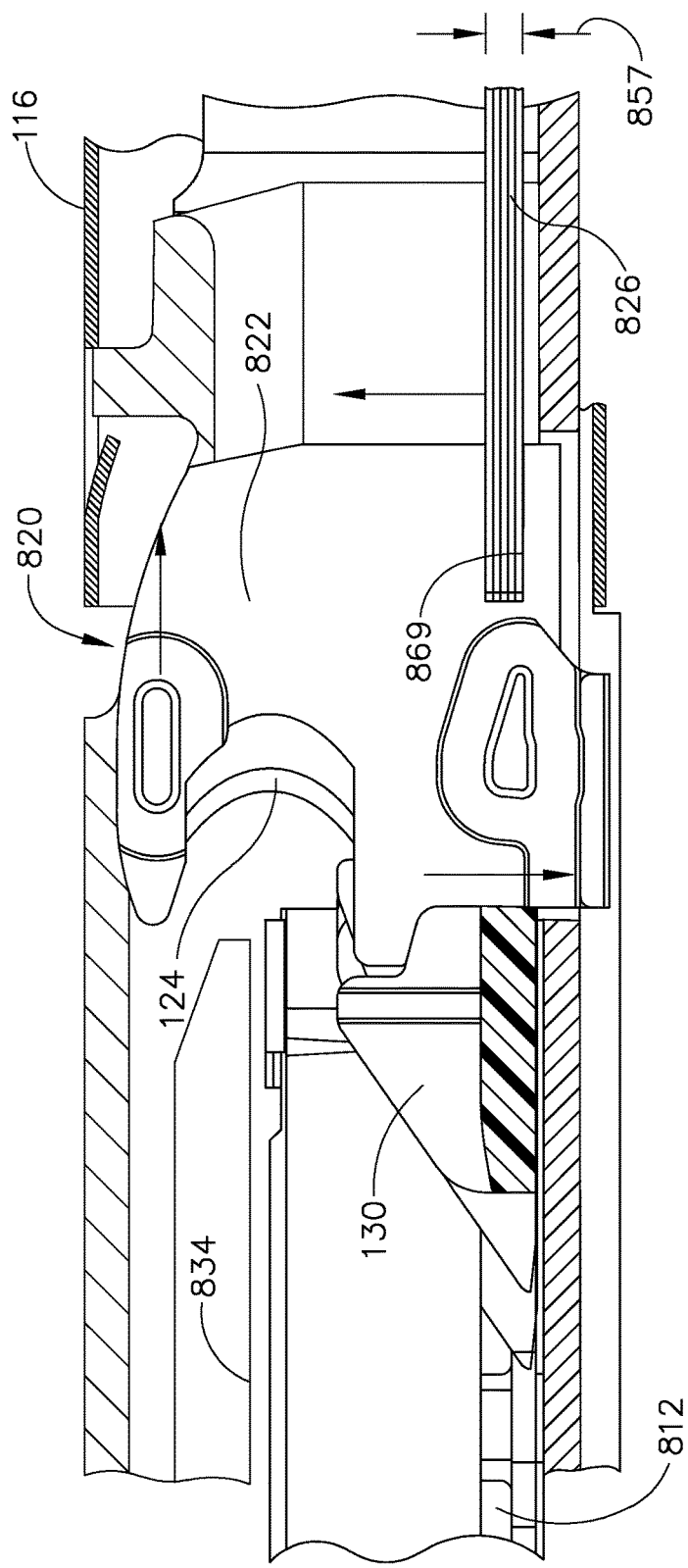
FIG. 41 is a partial cross-sectional view of the end-effector of the endocutter of FIG. 38.
Figure 42:
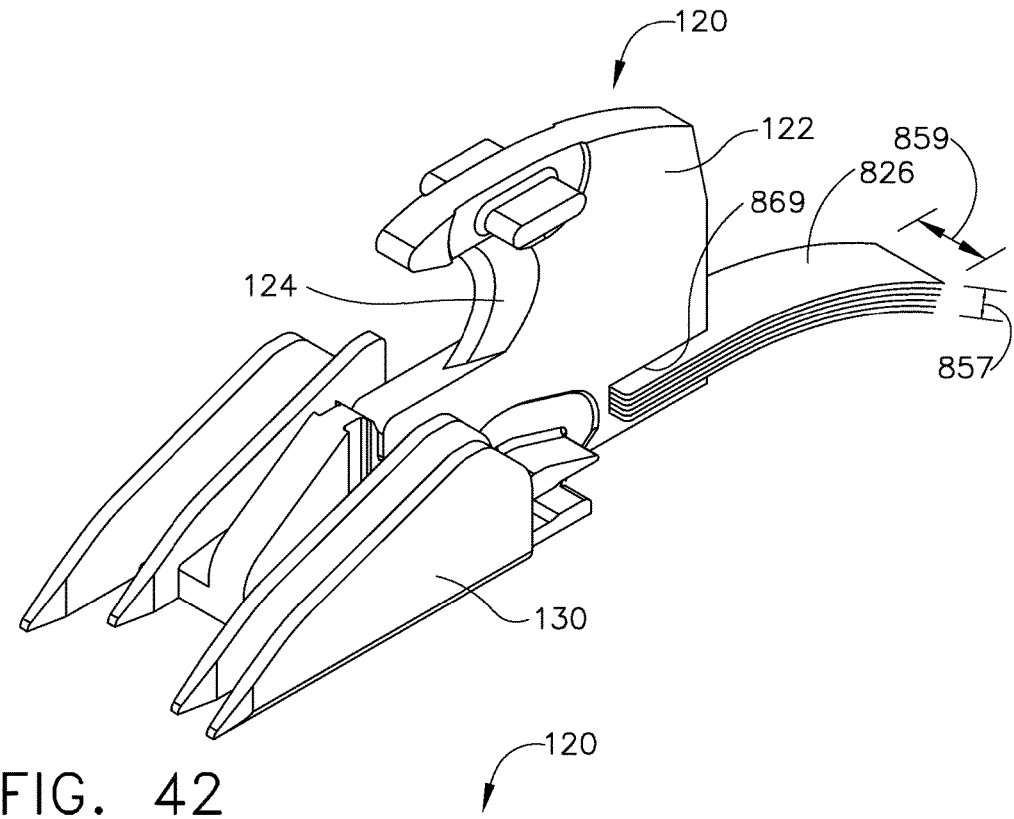
FIG. 42 is a perspective view of the staple driver, cutting member and drive bar of FIG. 41.
Figure 43:
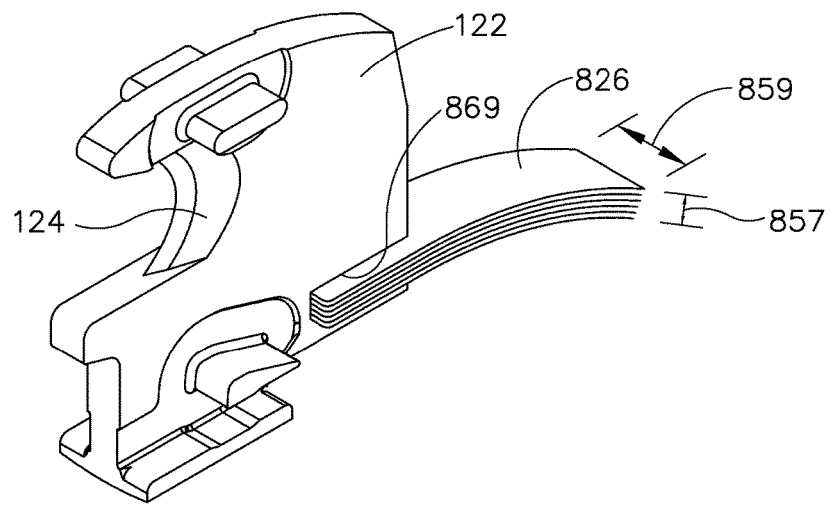
FIG. 43 is a perspective view of the cutting member and drive bar of FIG. 41.
Figure 44:
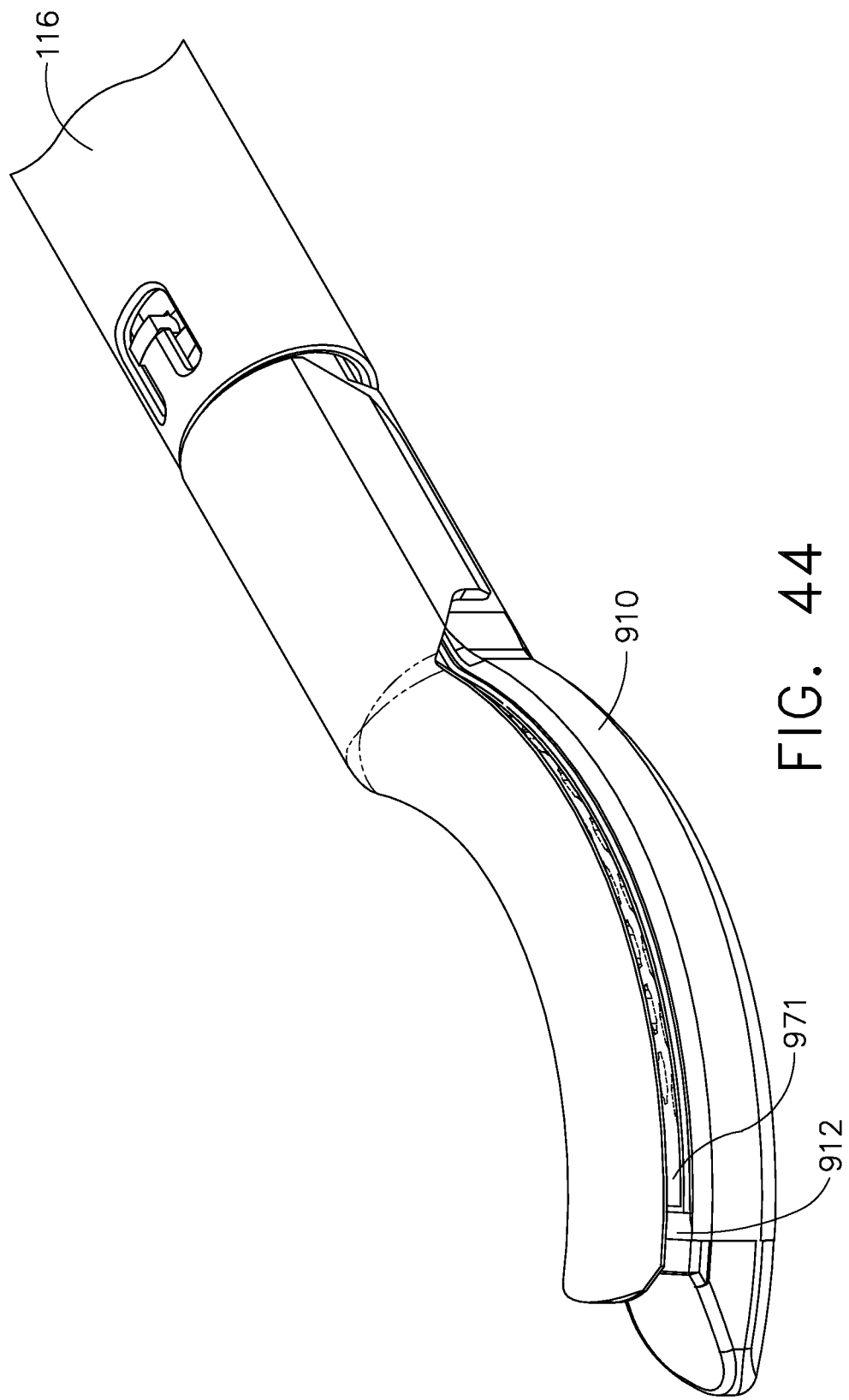
FIG. 44 is a perspective view of an endocutter having a curved staple cartridge and a curved anvil configured to retain buttress material thereon in accordance with an embodiment of the present invention.

Referring to FIGS. 41-43, endocutter 800 can include drive bar 826 which, similar to drive bar 226, is configured to advance cutting member 120, or a curved cutting member, through curved slots in an end-effector. In various embodiments, drive bar 826 can include a cross-sectional geometry having a width 859 that is greater than its height 857. In these embodiments, the moment of inertia of the cross-section with respect to height 857 is less than the moment of inertia with respect to width 859. As a result, drive bar 826 can be more flexible with respect to height 857, i.e., in the upward and downward directions, than with respect to width 859. In at least one embodiment, width 859 can be approximately 0.12" and height 857 can be approximately 0.05". Although drive bar 826 is illustrated as having a rectangular cross-section, the invention is not so limited. On the contrary, the cross-section of drive bar 826 can include various embodiments in which the width of the drive bar cross-section is greater than its height. In at least one embodiment, drive bar 826 can include a cross-section defined by a width and a height wherein the width is greater than the height, and wherein the width defines an axis that is not parallel to an axis defined by cutting edge 124 of cutting member 120. In various embodiments, as known in the art, cutting edge 124 can include a knife edge or a wire configured to conduct current therethrough. Furthermore, in various embodiments, the drive bar can be asymmetric with respect to centerline 224 of the distal end of shaft 116, for example. In these embodiments, as a result, drive bar 826 can be predisposed to bending in a pre-determined direction.

Similar to drive bar 226, drive bar 826 can be comprised of one material or, alternatively, several layers of material bonded together. As above, the flexibility of drive bar 826 can be pre-determined by the types of materials used and the arrangement of the layers within the drive bar. Referring to FIG. 41, cutting member body 822 can include slot 869 which is configured to receive the distal end of drive bar 826. In the present embodiment, slot 869 is configured to receive drive bar 826 in a press-fit relationship, however, other means, such as adhesive or fasteners, can be used to secure drive bar 826 to cutting member 820. Similar to the above, staple cartridge 812 can include a slot configured to receive and support drive bar 826 when it enters into staple cartridge 812. In various embodiments, although not illustrated, anvil 834 could be configured to receive and support drive bar 826.

As described above, the jaws of an endocutter can be placed on opposite sides of several layers of tissue, for example, and then closed onto the tissue. In the illustrated embodiments, referring to FIG. 4, jaw 108 can be pivoted between opened and closed positions with respect to jaw 110 via the interaction of inner portion 114 and outer sleeve 116 of shaft 106 in a known manner. Although not illustrated, jaw 108 is connected to jaw 110 via a pivot connection such that when inner portion 114 moves jaw 108 relative to outer sleeve 116, jaw 108 is pivoted toward jaw 110. Throughout the movement of jaw 108, the proximal portion of jaw 108, i.e., proximal portion 111, is positioned closer to jaw 110 than its distal portion, i.e., distal portion 113, until jaw 108 is brought into its final position opposite staple cartridge 112. In this final, closed position, distal portion 113 and proximal portion 111 can be substantially equidistant from staple cartridge 112. However, as a result of distal portion 113 being the last portion of jaw 108 to reach its final position, a portion of the tissue, or an artery, for example, can escape from between jaws 108 and 110 before distal portion 113 is moved into its final position. Accordingly, the surgeon may have to reopen the jaws and reposition the end-effector in an attempt to properly capture the tissue, or artery, therebetween.

As detailed below, an end-effector in accordance with an embodiment of the present invention can be configured to capture the tissue, or an artery, between the distal and proximal portions of the end-effector before the jaws are moved into their final position. In at least one embodiment, referring to FIGS. 27-34, jaw 608 can be pivotally connected to jaw 610 via pivot connection 609. Pivot connection 609 can include first trunnion 615 and second trunnion 617 extending from jaw 608, and, in addition, first slot 619 and second slot 621 in jaw 610. Trunnions 615 and 617 can be sized and configured to fit within slots 619 and 621, respectively, such that pivot connection 609 allows for relative rotational and translation movement between jaw 608 and jaw 610. In other alternative embodiments, jaw 608 may include slots 619 and 621 and jaw 610 may include trunnions 615 and 617, or any other combination thereof.

Figure 27:
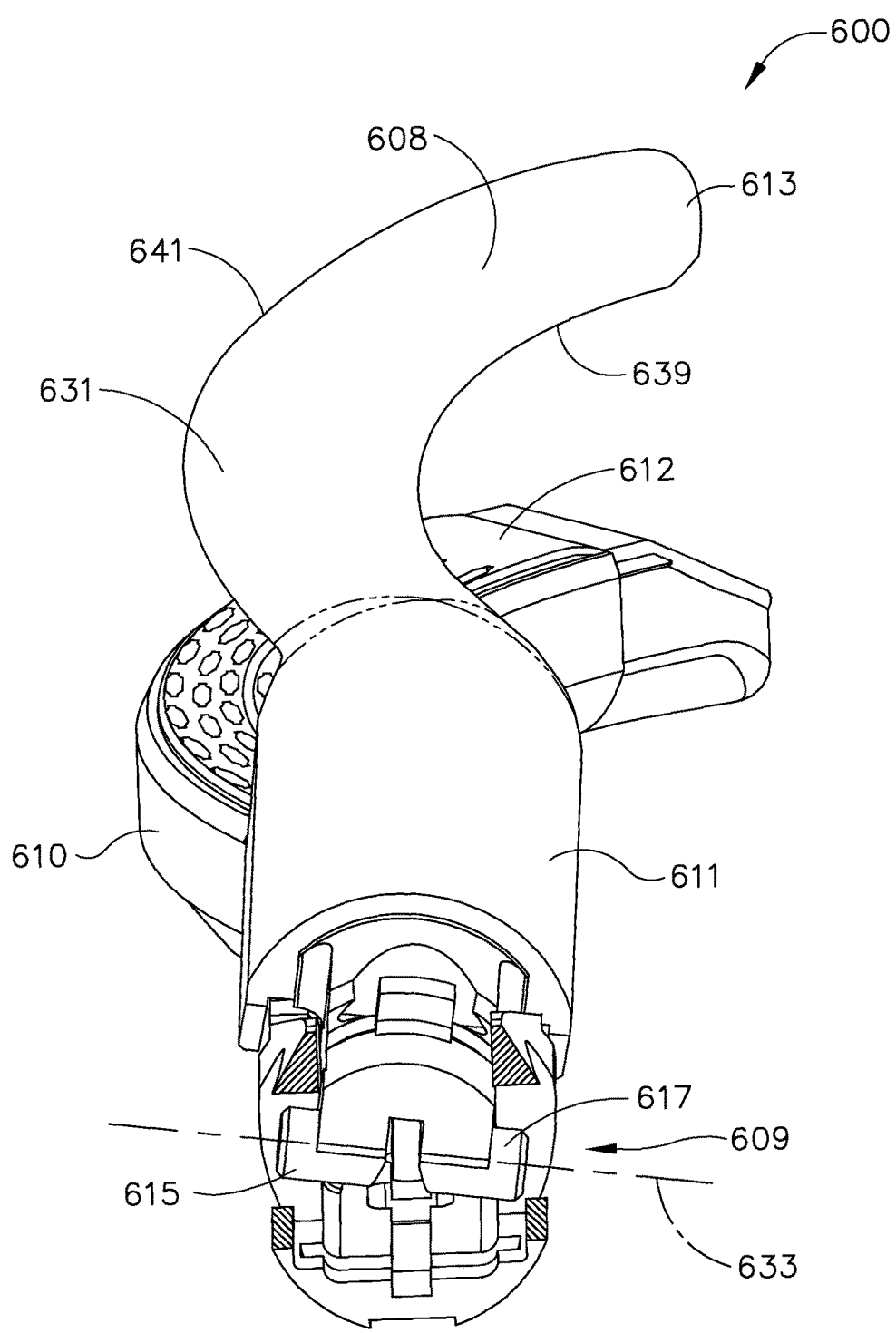
FIG. 27 is a perspective view of an endocutter having a curved end-effector configured to close in an asymmetric manner in accordance with an embodiment of the present invention.
Figure 28:
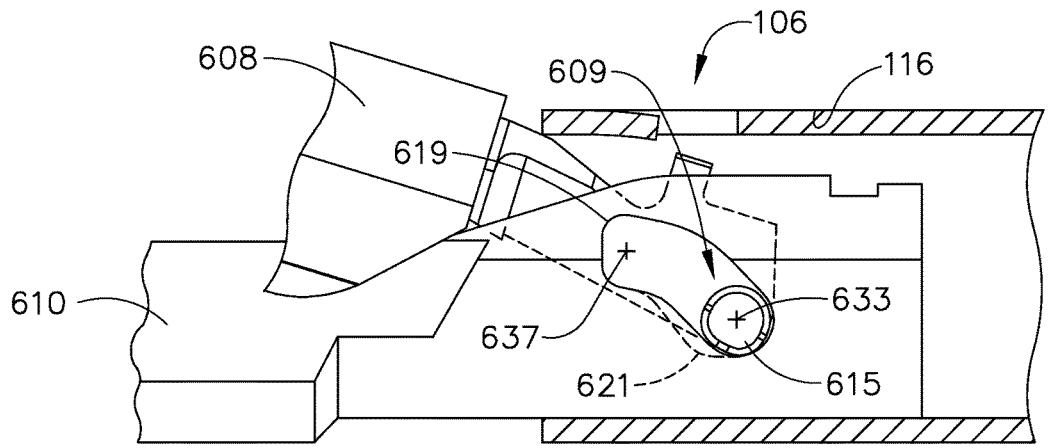
FIG. 28 is a cross-sectional view of the hinge connection between the jaws of the curved end-effector of FIG. 27 wherein the jaws are in an open configuration.
Figure 29:
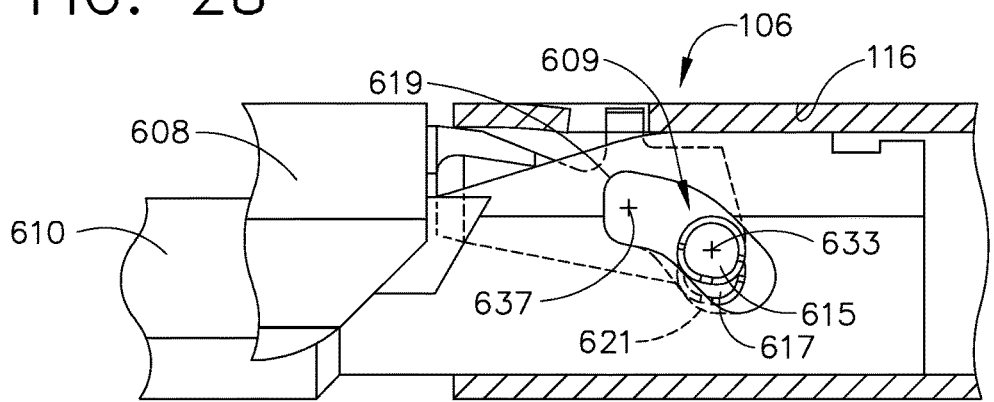
FIG. 29 is a cross-sectional view of the hinge connection of FIG. 28 wherein the jaws are in a partially closed configuration.
Figure 31:
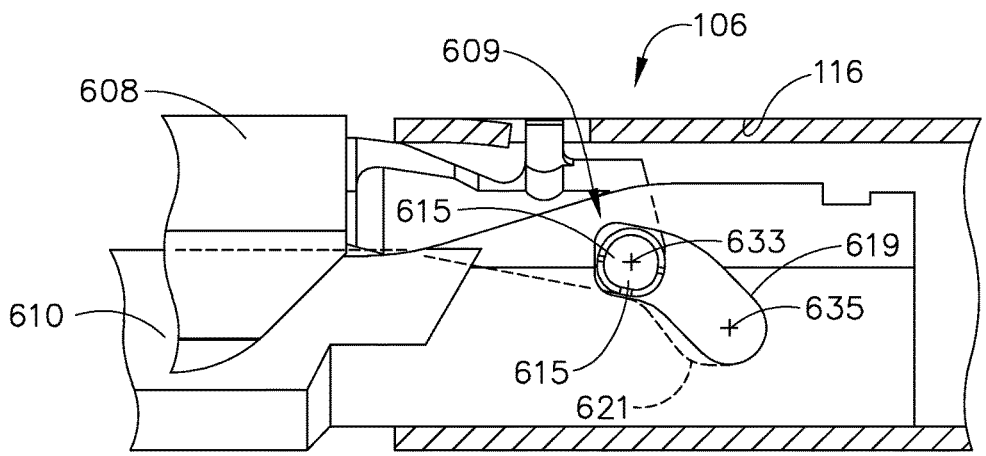
FIG. 31 is a cross-sectional view of the hinge connection of FIG. 28 wherein the end-effector is in a closed configuration.
Figure 30:
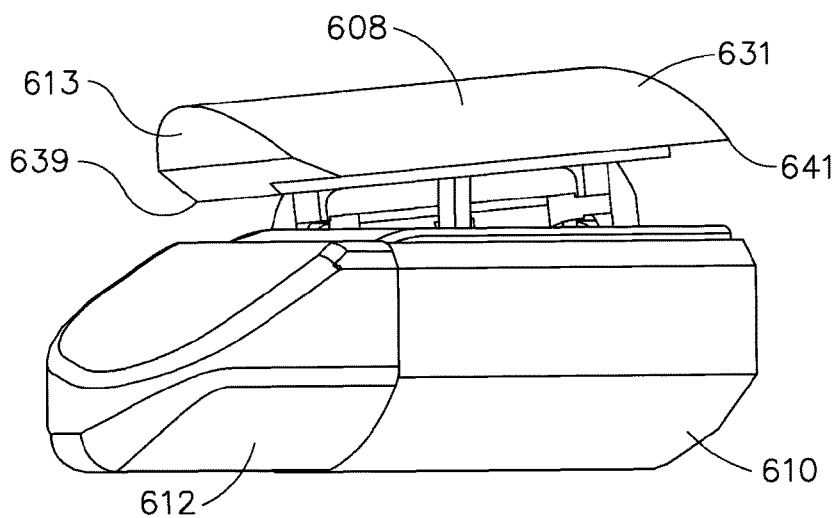
FIG. 30 is an end view of the curved end-effector of FIG. 27 illustrated in a partially closed configuration.

Referring to FIGS. 28, 29 and 31 which schematically illustrate slot 619 in solid and slot 621 in dashes, trunnions 615 and 617 are configured to travel within slots 619 and 621, respectively, and define the relative movement between jaws 608 and 610. In the present embodiment, slots 619 and 621 define two different arcuate paths for trunnions 615 and 617. More particularly, referring to FIGS. 33 and 34, slot 619 includes first portion 623, second portion 625, and intermediate portion 627 extending therebetween wherein slot 621 also includes first portion 623 and second portion 625, however, slot 621 includes an intermediate portion, i.e., portion 629, which is different than intermediate portion 627. Referring to FIG. 27, as a result of slots 619 and 621 having different intermediate portions, slots 619 and 621 can cause jaw 608 to tilt, or otherwise move in a non-symmetrical manner, with respect to jaw 610 as it is opened and closed. Advantageously, referring to FIGS. 30 and 32, such an asymmetric motion, or tilting, can allow distal portion 613 of jaw 608 to be placed in close proximity to staple cartridge 612 before the intermediate portion of jaw 608, i.e., portion 631, is moved into its final position illustrated in FIG. 32. As a result, referring to FIG. 30, an end-effector in accordance with the above can be used to capture tissue, or an artery, between proximal end 611 and distal end 613 before intermediate portion 631 is moved into its final, or closed, position. As a result, the possibility of a portion of the tissue, or artery, escaping from between jaws 608 and 610 is reduced. In addition to the above, the distal ends of jaws 608 and 610 can be brought into close opposition to each other in order to grip delicate tissue, for example, without having to completely close the end-effector.

As outlined above, slots 619 and 621 can define different paths for trunnions 615 and 617, respectively, when jaw 608 is moved between an open and a closed position. When jaw 608 is in its open position, referring to FIG. 28, trunnions 615 and 617 are positioned within first portions 623 of slots 619 and 621. In this position, axis 633, which is defined by trunnions 615 and 617, is substantially collinear with axis 635 defined between first portions 623 of slots 619 and 621. Thereafter, jaw 608 can be moved distally such that trunnions 615 and 617 move upward through slots 619 and 621. Owing to the asymmetric configurations of slots 619 and 621, referring to FIG. 27 which illustrates jaw 108 in a partially closed position, trunnion 615 is elevated to a relatively higher position with respect to trunnion 617, as evidenced by the tilting of axis 633. In this position, an inner edge of jaw 608, i.e., edge 639, can be in closer proximity to staple cartridge 612 than an outer edge of jaw 608, i.e., edge 641. Advantageously, as a result, inner edge 639 can be brought into contact against the tissue, or an artery, for example, allowing the surgeon to evaluate the position of the end-effector with respect to the tissue, or artery, without having to bring the entire anvil 634 of jaw 608 against the tissue. This feature may be particularly advantageous when the end-effector is positioned around a pulmonary artery as pulmonary arteries are especially susceptible to rupture.

Figure 32:
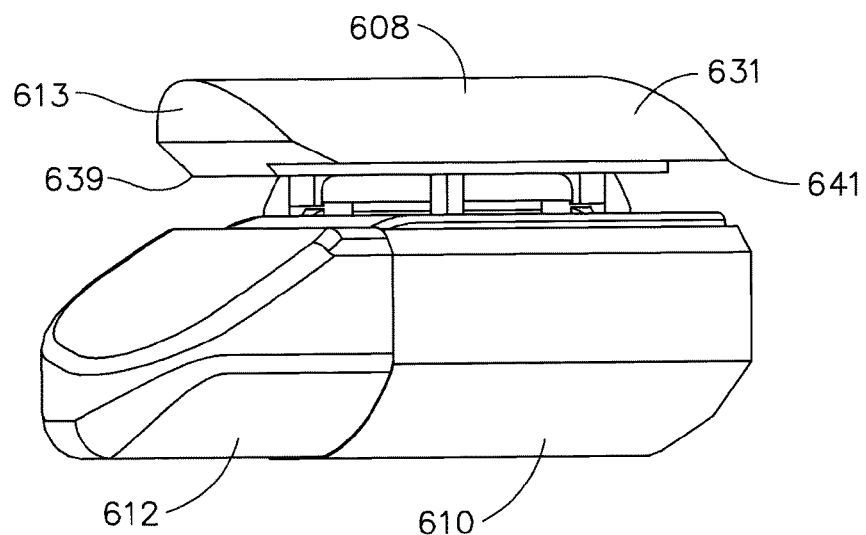
FIG. 32 is an end view of the curved end-effector of FIG. 27 illustrated in a closed configuration.
Figure 33:
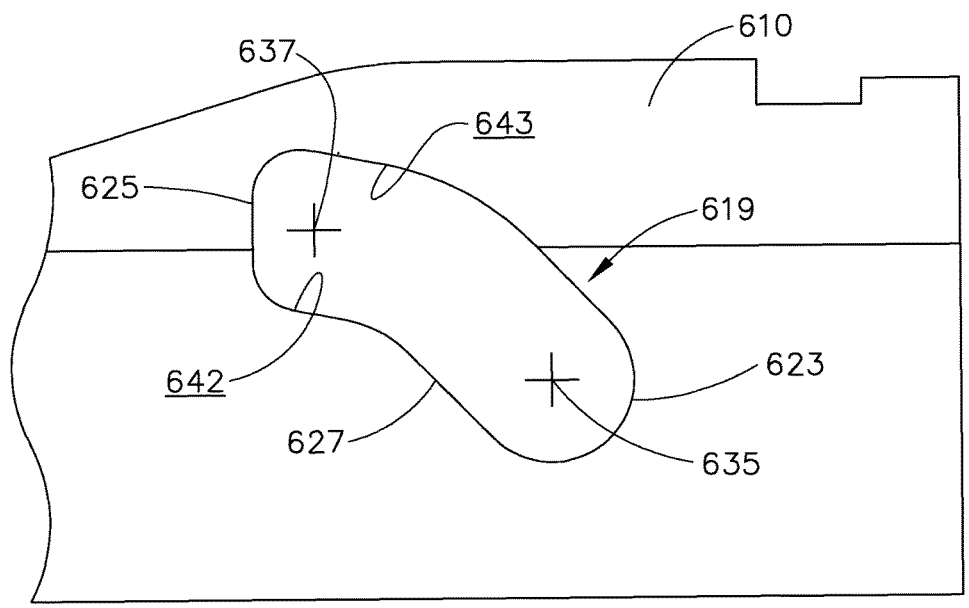
FIG. 33 is a detail view of a first slot of the hinge connection of FIG. 28 that is configured to receive a first projection extending from the anvil and is also configured to define a first path for relative movement therebetween.
Figure 34:
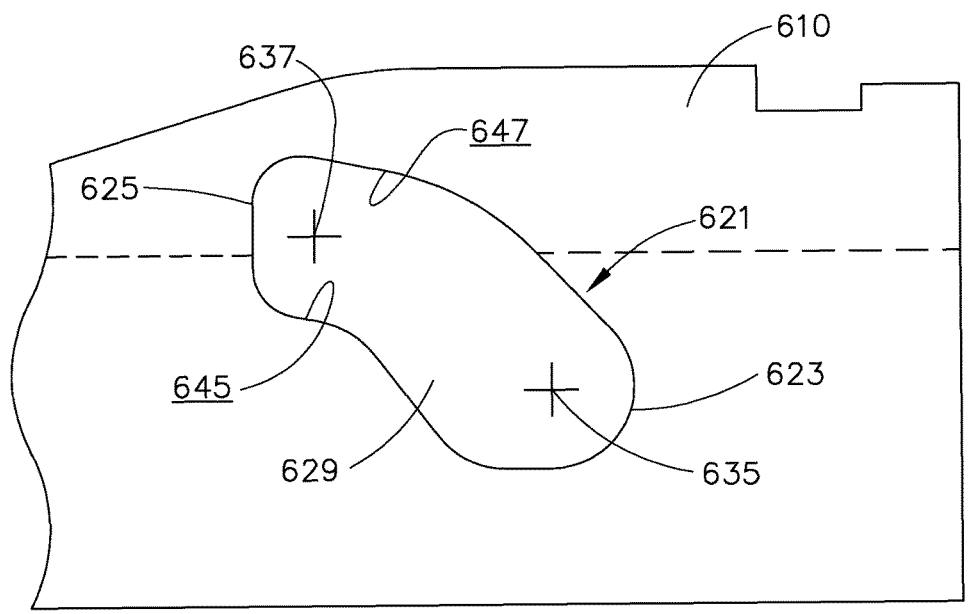
FIG. 34 is a detail view of a second slot of the hinge connection of FIG. 28 that is configured to receive a second projection extending from the anvil and is also configured to define a path for relative movement therebetween that is different than the first path.

After the tissue, or artery, has been captured between the proximal and distal ends of the end-effector, referring to FIGS. 31 and 32, jaw 608 can be moved into its final, or closed, position with respect to staple cartridge 612. In this position, axis 633, which is defined by trunnions 615 and 617, can be substantially collinear with axis 637 defined between second portions 625 of slots 619 and 621. Furthermore, in this final position, intermediate portion 631, distal portion 613 and proximal portion 611 can be equidistant from staple cartridge 612. Similarly, outer edge 641 and inner edge 639 can also be positioned equidistant with respect to staple cartridge 612. In this final position, tissue, or an artery, for example, can be securely retained between jaws 608 and 610. Although the above-described embodiments include a curved end-effector, the invention is not so limited. On the contrary, the above features can be utilized with a linear end-effector, for example, to achieve the advantages described above.

In various embodiments, slots 619 and 621 can define paths having different centerlines wherein each centerline can be defined as the line equidistant from the top and bottom surfaces of each slot. For example, referring to FIGS. 33 and 34, slot 619 can include bottom surface 642 and top surface 643 which define a centerline therebetween that is different than the centerline defined by bottom surface 645 and top surface 647 of slot 621. In these embodiments, slots 619 and 621 can be configured to closely retain trunnions 615 and 617 between these top and bottom surfaces such that axis 633 of trunnions 615 and 617 substantially travels along the centerlines of slots 619 and 621. In various embodiments, jaws 608 and 610 can be configured such that trunnions 615 and 617 contact bottom surfaces 642 and 645 of slots 619 and 621. In these embodiments, jaw 608 can be biased by a spring, for example, such that trunnions 615 and 617 are positioned against bottom surfaces 642 and 645 throughout the movement of jaw 608. Owing to different profiles for bottom surfaces 642 and 645, the advantages described above can be achieved.

As described above, once the jaws of the end-effector are closed onto the layers of tissue, for example, staples can be deployed into the tissue. However, oftentimes, the layers of tissue are very thin and the staples may not properly capture the tissue therein. To ameliorate this problem, as known in the art, buttress material can be placed on one or both sides of the tissue to support the tissue as it is being stapled. In such embodiments, the purchase of the staples is improved and the clamping force of the staples may be spread more evenly across the buttress material. In various embodiments, the buttress material can be comprised of a bioabsorbable material such that it can dissolve away during the healing process. Previously, however, the buttress material has been provided in linear strips which are configured to accommodate linear staple lines and end-effectors. Such linear strips may be unsuitable for use with endocutters having a curved end-effector configured to deploy staples in curved staple lines.

Figure 47:
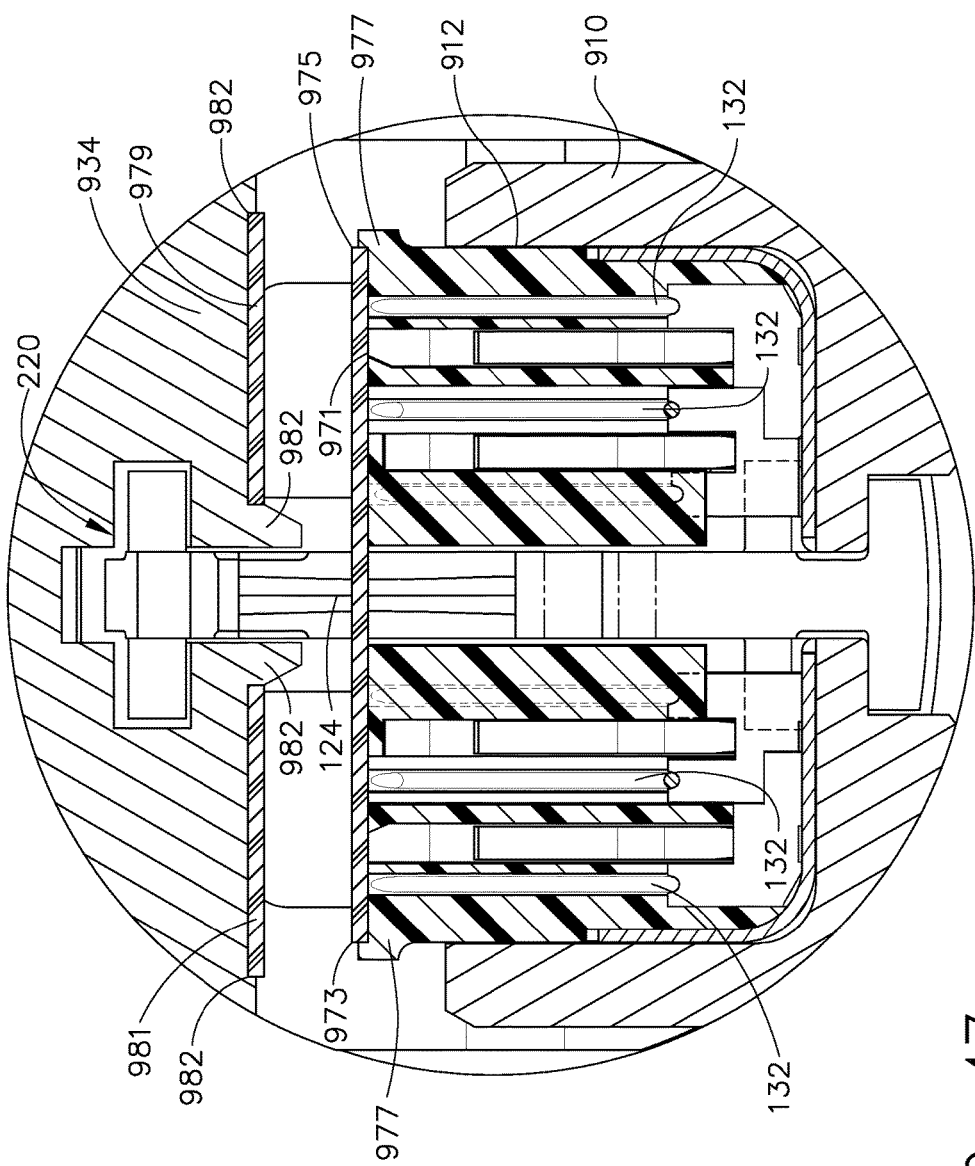
FIG. 47 is a cross-sectional view of the end-effector of the endocutter of FIG. 44 taken along line 47-47 in FIG. 44.

In accordance with an embodiment of the present invention, referring to FIGS. 44-47, curved staple cartridge 912 can be configured to receive a curved piece, or pieces, of buttress material thereon, such as buttress material 971. Curved buttress material 971 can include inner edge 973 which can be configured to substantially parallel the inner radius of curvature of jaw 910, and, in addition, outer edge 975 which can be configured to substantially parallel the outer radius of curvature of jaw 910. In some embodiments, referring to FIG. 47, staple cartridge 912 can include lip 977 extending therefrom which is configured to retain buttress material 971 on staple cartridge 912. More particularly, lip 977, as illustrated, can be configured to limit lateral movement of buttress material 971 with respect to staple cartridge 912 and, although not illustrated, lip 977 can also be configured to extend distal to and/or proximal to the ends of the buttress material to limit relative axial movement between buttress material 977 and staple cartridge 912. Similar to the above, curved anvil 934 can be configured to receive a piece, or pieces, of curved buttress material thereon, such as buttress material 979 and 981, for example. Referring to FIG. 47, anvil 934 can include several lips 982 which are configured to limit relative movement between buttress material 979 and 981 and anvil 934. In various embodiments, an adhesive, such as cyanoacrilate, for example, can be applied to the buttress material, anvil and/or staple cartridge to further limit the movement of the buttress material or otherwise prevent the mobilization thereof.

As a result of the above, a surgeon may be able to position the end-effector into a surgical site without the buttress material falling off or moving relative to the staple cartridge and/or anvil. Once positioned, cutting member 120 can be advanced to cut buttress material 971. More specifically, referring to FIG. 47, cutting edge 124 can be aligned with buttress material 971 such that it cuts the buttress material as cutting member 920 is advanced through staple cartridge 912. However, in some circumstances, the cutting member may at least partially dislodge the buttress material relative to the staple cartridge. This relative movement may especially occur when the buttress material is thick, or, the cutting member must cut more than one piece of buttress material at a time. To ameliorate this problem, the buttress material may include a series of perforations, for example, positioned along the path in which the cutting member will cut the buttress material. In these embodiments, these perforations may be formed along a radius of curvature which is parallel to and positioned intermediate two curved staple rows. In other various embodiments, the buttress material may include other features which disrupt the cross-sectional thickness of the buttress material to facilitate the cutting of the buttress material. As a result of the above, less force may be required to cut the buttress material and, accordingly, it is less likely the buttress material may slide, for example, when it is cut.

Figure 48:
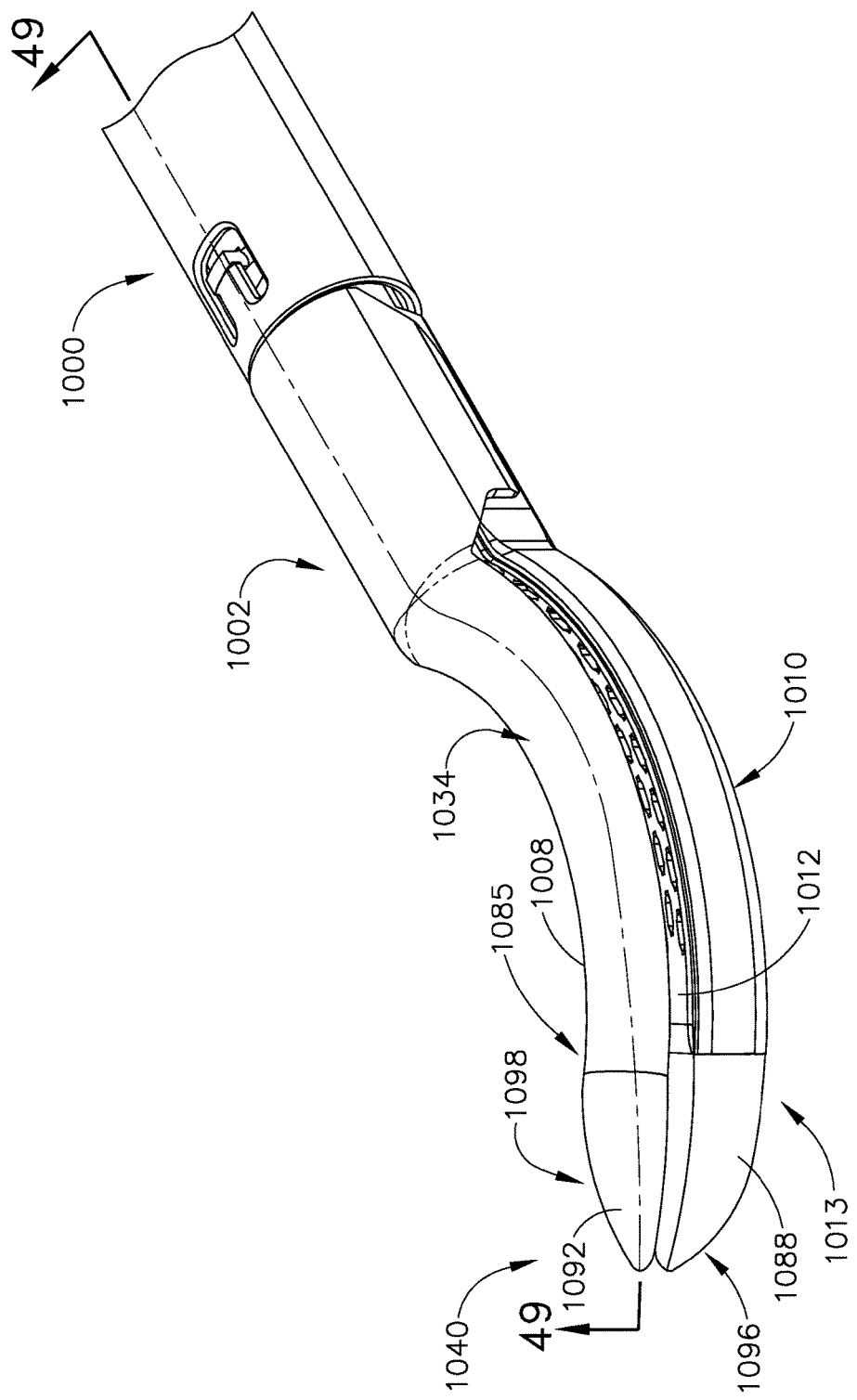
FIG. 48 is a perspective view of an endocutter in accordance with an embodiment of the present invention.

FIGS. 48-50 illustrate another surgical instrument of the present invention. As can be seen in these Figures, the surgical instrument 1000 includes an end-effector 1002 that has a first jaw 1008 and a second jaw 1010. The second jaw 1010 may comprise a channel 1038 that is configured to operably support a staple cartridge 1012 therein. Staple cartridge 1012 may be removably supported in the channel 1038 or, in various embodiments, staple cartridge 1012 may form an integral part of the second jaw 1010. The surgical instrument 1000 further includes a movable anvil 1034 that may be movably coupled to the lower jaw 1010 in the various manners described above or in other manners that are known in the art.

In the embodiment depicted in FIGS. 48-50, the end effector 1002 has a distal end generally designated as 1040. As can further be seen in those Figures, the staple cartridge 1012 has a blunt first tip portion 1088 thereon. The first tip portion 1088 may be integrally formed (molded, machined, etc.) on the distal end 1013 of the staple cartridge 1012 or it may comprise a separate piece that may be formed with a cavity 1089 (FIG. 50) configured to receive a nose 1083 of a conventional staple cartridge 1012. The first tip portion 1088 can include snap features 1090 (FIG. 50) or other suitable retainer portions formed therein to retainingly mate with complementary retention grooves 1084 formed in the nose 1083. In addition, or in the alternative, the first tip portion 1088 may be affixed to the cartridge 1012 by adhesive such as, for example, cyanoacrylates, light-curable acrylics, polyurethanes, silicones, epoxies, and ultra-violet curable adhesives such as Henkel Loctite®. In other embodiments, a combination of snap features and grooves may be provided in both the staple cartridge 1012 and the first tip portion 1088. Still other forms of fasteners and fastener arrangements may be used to affix the first tip portion 1088 to the staple cartridge 1012. In other embodiments, the first tip portion 1088 may be affixed to the channel 1038. As can be seen in FIG. 50, the first tip portion 1088 has a first upwardly extending curved outer surface.

Similarly, in this embodiment, the anvil 1034 may be equipped with a second tip portion 1092. The second tip portion 1092 may be integrally formed (molded, machined, etc.) on the distal end 1085 of the anvil 1034 or it may comprise a separate piece that may be formed with a cavity 1093 configured to receive an end portion of a conventional anvil 1034 with snap features 1094 or other suitable retainer portions formed therein to retainingly mate with complementary retention grooves 1086 formed in distal end 1085. In addition, or in the alternative, the second tip portion 1092 may be affixed to the anvil 1034 by adhesive such as, for example, cyanoacrylates, light-curable acrylics, polyurethanes, silicones, epoxies, and ultra-violet curable adhesives such as Henkel Loctite®. In other embodiments, a combination of snap features and grooves may be provided in both distal end 1085 and the second tip portion 1092. Still other forms of fasteners may be used to affix the second tip portion 1092 to the anvil 1034. As can be seen in FIG. 50, the second tip portion 1092 has a downwardly extending substantially curved outer surface.

In various embodiments, the first tip portion 1088 and the second tip portion 1092 may be fabricated from a variety of different materials that may be identical to or different from the materials from which the staple cartridge 1012 and anvil 1034 are manufactured. For example, the first tip portion 1088 and the second tip portion 1092 may be manufactured from soft plastic, rubber, etc. The first tip portion 1088 and the second tip portion 1092 may be fabricated from the same or different materials.

In various embodiments, the first tip portion 1088 and the second tip portion 1092 are shaped such that their respective outer surfaces 1088', 1092' cooperate to substantially form a substantially blunt end effector nose generally designated as 1096 that, in one exemplary embodiment, has a paraboloid surface 1098 when the anvil 1034 is in the closed position as shown in FIG. 50. As used herein, the term "paraboloid surface" means a surface having parabolic sections parallel to a single coordinate axis and elliptic sections perpendicular to that axis. Those of ordinary skill in the art will appreciate that when employing various embodiments of the instrument 1000, as long as the surgeon can see one or the other of the first tip portion or second tip portion, the surgeon will know where the other tip portion is, even if it is behind tissue or other structures. In addition, the unique and novel tip configurations permit the surgeon to pass the anvil and/or channel around tissue without great risk of incidental trauma to adjacent tissues. Furthermore, when in the closed orientation as depicted in FIGS. 49 and 50, these embodiments are particularly well suited for use as a dissector for separating and manipulating tissues.

The first tip portion and the second tip portion have been described and depicted in the Figures as being used in connection with a curved end effector. Those of ordinary skill in the art will readily appreciate, however, that the first and second tip portions may be used in connection with a variety of different end effector configurations such as linear endocutters and other types of end effectors without departing from the spirit and scope of the present invention. Thus, the first and second tip portions described above should not be limited solely to use in connection with curved endocutters/staplers.

As was described above, the first tip portion may be constructed for attachment to the distal end of a conventional staple cartridge or it may be integrally formed on the end of the staple cartridge. In still other embodiments, the first tip portion may be constructed for attachment to a distal end of the channel or it may be integrally formed on the distal end of the channel. Similarly, the second tip portion may be constructed for attachment to a conventional endocutter anvil or it may be integrally formed on the distal end of the anvil. In those applications wherein the first tip portion and/or second tip portion are fabricated separately from the cartridge and anvil, respectively, the tip portions may be supplied as a kit for retrofitting onto the cartridge and anvil by the end user. For example, in such arrangements, the tip portions may be presterilized and packaged and be configured to snap onto or otherwise attach to the staple cartridge and anvil or channel and anvil, whichever the case may be.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

While this invention has been described as having exemplary designs, the present invention may be further modified within the spirit and scope of the disclosure. This application is therefore intended to cover any variations, uses, or adaptations of the invention using its general principles. Further, this application is intended to cover such departures from the present disclosure as come within known or customary practice in the art to which this invention pertains.

What is claimed is:

1. An end effector for use with a surgical instrument, the end effector comprising:
   a curved staple cartridge, comprising:
      a first curved row of staple cavities;
      a second curved row of staple cavities;
      a plurality of staples, wherein a first quantity of said staples are ejectably stored in the staple cavities of said first curved row of staple cavities, and wherein a second quantity of said staples are ejectably stored in the staple cavities of said second curved row of staple cavities; and
      a curved slot positioned intermediate said first curved row of staple cavities and said second curved row of staple cavities, wherein said curved slot extends along a curved path between a proximal portion of said curved staple cartridge and a distal portion of said curved staple cartridge; and
   a sled configured to translate along said slot and eject said staples from said staple cavities during a firing stroke, wherein said sled comprises:
      a first permanently curved camming wedge; and
      a second permanently curved camming wedge; and
      a permanently curved connector extending between said first permanently curved camming wedge and said second permanently curved camming wedge, wherein said permanently curved connector connects said first permanently curved camming wedge and said second permanently curved camming wedge within said curved staple cartridge, wherein said permanently curved connector comprises a permanent curvature that corresponds to said curved path of said curved slot.

2. The end effector of claim 1, wherein said first permanently curved camming wedge is configured to translate along a first curved axis defined by said first curved row of staple cavities during the firing stroke, and wherein said second permanently curved camming wedge is configured to translate along a second curved axis defined by said second curved row of staple cavities during the firing stroke.

3. The end effector of claim 1, further comprising:
   a first plurality of curved rows of staple cavities on a first side of said curved slot, wherein said first plurality of curved rows of staple cavities comprises said first curved row of staple cavities; and
   a second plurality of curved rows of staple cavities on a second side of said curved slot, wherein said second plurality of curved rows of staple cavities comprises said second curved row of staple cavities.

4. The end effector of claim 3, wherein said sled further comprises:
   a permanently curved guide, wherein said curved slot is configured to received said permanently curved guide;
   a first plurality of permanently curved camming wedges on a first side of said permanently curved guide, wherein said first plurality of permanently curved camming wedges comprises said first permanently curved camming wedge; and a second plurality of permanently curved camming wedges on a second side of said permanently curved guide, wherein said second plurality of permanently curved camming wedges comprises said second permanently curved camming wedge.

5. A replaceable end effector for cutting and stapling tissue, the end effector comprising:
a first jaw;
a second jaw;
a longitudinally curved staple cartridge, comprising:
a plurality of staple cavities, wherein said staple cavities are arranged along a plurality of longitudinally curved axes;
a plurality of staples removably stored in said staple cavities; and
a longitudinally curved slot comprising a radius of curvature; and
a longitudinally curved sled configured to translate through at least a portion of said longitudinally curved staple cartridge, wherein said longitudinally curved sled comprises a plurality of longitudinally curved camming wedges, wherein each said longitudinally curved camming wedge comprises an inflexible radius of curvature, wherein said longitudinally curved sled further comprises a longitudinally curved connector flanked by said longitudinally curved camming wedges, wherein said longitudinally curved connector connects said longitudinally curved caroming wedges within said longitudinally curved staple cartridge, wherein said longitudinally curved connector comprises an inflexible radius of curvature, and wherein said inflexible radius of curvature of said longitudinally curved connector corresponds to said radius of curvature of said longitudinally curved slot.

6. The replaceable end effector of claim 5, wherein said inflexible radius of curvature of each said longitudinally curved camming wedge matches said radius of curvature of said longitudinally curved slot.

7. The replaceable end effector of claim 5, wherein each longitudinally curved camming wedge is configured to translate along a longitudinally curved axis to remove said staples from said staple cavities arranged along the longitudinally curved axis.

8. An end effector for cutting and stapling tissue, the end effector comprising:
a curved staple cartridge, comprising:
a plurality of curved rows of staple cavities;
a plurality of staples, wherein said staples are ejectably positioned in the staple cavities of said plurality of curved rows of staple cavities; and
a slot extending between a proximal portion of said curved staple cartridge and a distal portion of said curved staple cartridge, wherein said slot defines a curved trajectory within said curved staple cartridge; and
a curved sled configured to translate through at least a portion of said curved staple cartridge during a firing stroke, wherein said curved sled comprises:
a plurality of staple-ejecting cams;
a connector extending between a pair of said staple-ejecting cams, wherein said connector connects said pair of staple-electing cams within said curved staple cartridge, wherein said connector comprises an irreversible radius of curvature that corresponds to said curved trajectory of said slot; and a curved trajectory that is fixed prior to the firing stroke, wherein said curved trajectory of said curved sled matches said curved trajectory of said slot.

9. The end effector of claim 8, wherein said staples are ejectably positioned in the staple cavities.

10. The end effector of claim 9, further comprising a plurality of staple drivers, wherein said staple drivers are positioned in the staple cavities.

11. An end effector for use with a surgical instrument, the end effector comprising:
a curved staple cartridge, comprising:
a plurality of curved rows of staple cavities;
a plurality of staples removably positioned in the staple cavities of said plurality of curved rows of staple cavities; and
a curved slot extending along a curved path between a proximal portion of said curved staple cartridge and a distal portion of said curved staple cartridge; and
an irreversibly curved sled configured to eject staples from said staple cavities during a firing stroke, wherein said irreversibly curved sled comprises a plurality of irreversibly curved ramps and an irreversibly curved connector flanked by said irreversibly curved ramps, wherein said irreversibly curved connector connects said irreversibly curved ramps within said curved staple cartridge, wherein said irreversibly curved connector comprises an irreversible curvature, wherein said irreversibly curved connector is configured to translate along said curved path of said curved slot, and wherein said irreversible curvature corresponds to said curved path.

12. The end effector of claim 11, wherein said irreversibly curved sled comprises a sled radius of curvature, wherein said curved staple cartridge comprises a cartridge radius of curvature, and wherein said sled radius of curvature matches said cartridge radius of curvature pre-firing stroke.

13. A disposable end effector for cutting and stapling tissue, the disposable end effector comprising:
a staple cartridge, comprising:
a plurality of staples removably positioned in staple cavities; and
a slot extending from a proximal portion of said staple cartridge to a distal portion of said staple cartridge, wherein said slot comprises a radius of curvature between the proximal portion of said staple cartridge and the distal portion of said staple cartridge; and
a staple-ejecting sled comprising a first ramp, a second ramp, and a central section intermediate said first ramp and said second ramp, wherein said central section connects said first ramp and said second ramp within said staple cartridge, wherein said central section comprises an inflexible radius of curvature, and wherein said inflexible radius of curvature relates to said radius of curvature of said slot, and wherein said central section is configured to translate along at least a portion of said slot.

14. The disposable end effector of claim 13, wherein said sled further comprises a plurality of ramps, wherein said plurality of ramps comprises said first ramp and said second ramp, and wherein each said ramp comprises an inflexible radius of curvature.

15. The disposable end effector of claim 14, further comprising a plurality of staple cavities arranged along a plurality of curved axes, wherein each said ramp is configured to translate along a curved axis to eject said staples from said staple cavities arranged along the curved axis.

16. An end effector for a surgical stapler, the end effector comprising:
a staple cartridge, comprising:
a plurality of staples removably positioned in staple cavities, wherein said staples are removed from said staple cavities during a firing stroke; and
a curved slot extending along a curved path between a proximal portion of said staple cartridge and a distal portion of said staple cartridge; and
a permanently curved sled configured to translate along said curved slot during the firing stroke, wherein said permanently curved sled comprises a ramp and a connector comprising a permanent curvature that corresponds to said curved path of said curved slot, wherein said connector is connected to said ramp within said staple cartridge.

17. The end effector of claim 16, wherein said permanently curved sled comprises a plurality of permanently curved camming wedges, wherein said plurality of permanently curved camming wedges comprises a first permanently curved camming wedge and a second permanently curved camming wedge, and wherein said connector extends between said first permanently curved camming wedge and said second permanently curved camming wedge.

18. A surgical end effector, comprising:
a staple cartridge, comprising:
a plurality staple cavities;
a plurality of staples removably positioned in said staple cavities; and
a slot extending between a proximal portion of said staple cartridge and a distal portion of said staple cartridge, wherein said slot defines a curved trajectory between the proximal portion of said staple cartridge and the distal portion of said staple cartridge; and
a staple-ejecting sled comprising a ramp configured to translate between the proximal portion of said staple cartridge and the distal portion of said staple cartridge during a firing stroke, wherein said ramp defines a predefined trajectory that is defined pre-firing stroke, wherein said predefined trajectory is coextensive with said curved trajectory of said slot, wherein said staple-ejecting sled further comprises a central section configured to translate in said slot, wherein said central section is connected to said ramp within said staple cartridge, and wherein said central section comprises a permanent curvature that corresponds to said curved trajectory of said slot.

19. An end effector for use with a surgical instrument, the end effector comprising:
a staple cartridge, comprising:
a plurality of staple cavities arranged in staple cavity rows;
a plurality of staples ejectably stored in said staple cavities; and
a slot comprising a longitudinal curvature;
a staple-ejecting sled configured to translate along said slot during a firing stroke, wherein said staple-ejecting sled comprises a ramp and an irreversibly curved guide, wherein said irreversibly curved guide is connected to said ramp within said staple cartridge and wherein said irreversibly curved guide comprises a longitudinal curvature that matches said longitudinal curvature of said slot.

20. The end effector of claim 19, wherein said staple-ejecting sled comprises a plurality of irreversibly curved wedges, and wherein an irreversibly curved wedge is configured to translate along a curved axis defined by a staple cavity row during a firing stroke.

21. A disposable end effector for cutting and stapling tissue, the end effector comprising:
a first jaw;
a second jaw;
a staple cartridge, comprising:
a plurality of staples removably positioned in a plurality of staple cavities; and
a slot extending between a proximal portion of said staple cartridge and a distal portion of said staple cartridge, wherein said slot comprises a curvature between the proximal portion of said staple cartridge and the distal portion of said staple cartridge; and
a staple-firing sled configured to translate at least partially through said staple cartridge during a firing stroke, wherein said staple-firing sled comprises:
a staple-camming body comprising a proximal end and a distal end;
a central section configured to translate along said slot, wherein said central section is connected to said staple-camming body within said staple cartridge, and wherein said central section comprises a permanent radius of curvature that corresponds to said curvature of said slot; and
a pre-defined radius of curvature between the proximal end and the distal end of said staple-camming body, wherein said pre-defined radius of curvature is defined pre-firing stroke.

* * * * *